United States Patent
Levy et al.

(10) Patent No.: US 7,723,471 B2
(45) Date of Patent: *May 25, 2010

(54) PANCREATIC POLYPEPTIDE FAMILY MOTIFS, POLYPEPTIDES AND METHODS COMPRISING THE SAME

(75) Inventors: Odile Esther Levy, San Diego, CA (US); Carolyn M. Jodka, Encinitas, CA (US); Soumitra S. Ghosh, San Diego, CA (US); David G. Parkes, Del Mar, CA (US); Richard A. Pittner, San Diego, CA (US); Lawrence J. D'Souza, Del Mar, CA (US); John S. Ahn, San Diego, CA (US); Kathryn S. Prickett, San Diego, CA (US); Jonathan David Roth, San Diego, CA (US); Sean H. Adams, Davis, CA (US)

(73) Assignee: Amylin Pharmaceuticals, Inc., San Diego, CA (US)

( * ) Notice: Subject to any disclaimer, the term of this patent is extended or adjusted under 35 U.S.C. 154(b) by 657 days.

This patent is subject to a terminal disclaimer.

(21) Appl. No.: 11/301,744

(22) Filed: Dec. 12, 2005

(65) Prior Publication Data
US 2006/0135747 A1 Jun. 22, 2006

Related U.S. Application Data

(60) Provisional application No. 60/635,897, filed on Dec. 13, 2004, provisional application No. 60/543,406, filed on Feb. 11, 2004, provisional application No. 60/543,407, filed on Feb. 11, 2004.

(51) Int. Cl.
*A61K 38/00* (2006.01)

(52) U.S. Cl. .................................................... 530/324

(58) Field of Classification Search .................. None
See application file for complete search history.

(56) References Cited

U.S. PATENT DOCUMENTS

| | | | |
|---|---|---|---|
| 4,265,884 A | 5/1981 | Kofod | |
| 4,353,888 A | 10/1982 | Sefton | |
| 4,391,909 A | 7/1983 | Lim | |
| 4,533,494 A | 8/1985 | Uchiyama et al. | |
| 4,683,195 A | 7/1987 | Mullis et al. | |
| 4,683,202 A | 7/1987 | Mullis | |
| 4,839,343 A | 6/1989 | Waeber et al. | |
| 4,891,357 A | 1/1990 | Kala | |
| 4,892,538 A | 1/1990 | Aebischer et al. | |
| 5,106,627 A | 4/1992 | Aebischer et al. | |
| 5,308,701 A | 5/1994 | Cohen et al. | |
| 5,459,039 A | 10/1995 | Modrich et al. | |
| 5,498,531 A | 3/1996 | Jarrell | |
| 5,574,010 A | 11/1996 | McFadden | |
| 5,604,203 A | 2/1997 | Balsubramanian | |
| 5,696,093 A | 12/1997 | Tseng | |
| 5,824,778 A | 10/1998 | Ishikawa et al. | |
| 5,824,784 A | 10/1998 | Kinstler et al. | |
| 5,912,227 A | 6/1999 | Croom, Jr. et al. | |
| 5,939,462 A | 8/1999 | Connell et al. | |
| 5,968,819 A | 10/1999 | Gerald et al. | |
| 5,980,945 A | 11/1999 | Ruiz | |
| 6,013,622 A | 1/2000 | Bruno et al. | |
| 6,315,203 B1 | 11/2001 | Ikeda et al. | |
| 6,355,478 B1 | 3/2002 | Baez et al. | |
| 6,391,343 B1 | 5/2002 | Yen | |
| 6,420,532 B1 | 7/2002 | Gerald et al. | |
| 6,506,724 B1 | 1/2003 | Hiles et al. | |
| 6,558,708 B1 | 5/2003 | Lin | |
| 6,569,832 B1 | 5/2003 | Knudsen et al. | |
| 6,734,166 B1 | 5/2004 | Croom, Jr. et al. | |
| 2002/0094346 A1 | 7/2002 | Lin | |
| 2002/0141985 A1 | 10/2002 | Pittner et al. | |
| 2003/0224983 A1 | 12/2003 | Nielsen | |
| 2004/0115135 A1 | 6/2004 | Quay | |
| 2004/0228846 A1 | 11/2004 | Pang et al. | |

FOREIGN PATENT DOCUMENTS

| | | |
|---|---|---|
| EA | 004791 B1 | 8/2004 |
| EP | 0992239 | 3/2003 |
| JP | 06133731 | 5/1994 |
| WO | WO 83/04056 | 11/1983 |
| WO | WO 89/01967 | 3/1989 |
| WO | WO 90/02580 | 3/1990 |
| WO | WO 90/15637 | 12/1990 |
| WO | WO 91/10425 | 7/1991 |
| WO | WO 91/10470 | 7/1991 |
| WO | WO 94/16101 | 7/1994 |
| WO | WO96/40196 A1 | 12/1996 |
| WO | WO97/26321 A2 | 7/1997 |
| WO | WO 98/20885 | 5/1998 |
| WO | WO98/28427 A1 | 7/1998 |

(Continued)

OTHER PUBLICATIONS

Kofod, "Secretin and the Endocrine Pancreas", Acta Endocrinologica 126 (Suppl. 1.): 8-41 (1992).

(Continued)

*Primary Examiner*—Cecilia Tsang
*Assistant Examiner*—Thomas S Heard

(57) ABSTRACT

The present invention provides novel Pancreatic Polypeptide Family ("PPF") polypeptides and methods for their use.

53 Claims, 57 Drawing Sheets

FOREIGN PATENT DOCUMENTS

| | | |
|---|---|---|
| WO | WO 99/07404 | 2/1999 |
| WO | WO 99/15516 | 4/1999 |
| WO | WO 99/25727 | 5/1999 |
| WO | WO 99/25728 | 5/1999 |
| WO | WO 00/47219 | 8/2000 |
| WO | WO 00/68197 | 11/2000 |
| WO | WO 01/62737 | 8/2001 |
| WO | WO 01/76631 | 10/2001 |
| WO | WO02/46227 A2 | 6/2002 |
| WO | WO 03/026591 | 4/2003 |
| WO | WO 03/057235 | 5/2003 |
| WO | WO 03/105736 | 12/2003 |
| WO | WO 2004/089279 | 10/2004 |
| WO | WO 2005/077094 | 8/2005 |

OTHER PUBLICATIONS

Geoghegan and Pappas, "Clinical Uses of Gut Peptides", Annals of Surgery 225 (2) 145-154 (1997).
Nicholl et al., "The Hormonal Regulation of Food Intake, Digestion and Absorption", Ann. Rev. Nutr. 5: 213-239 (1995).
Nishitani et al., "Transcriptional Regulation of Secretin Gene Expression", J. Clin. Gastroenterology 2 (Suppl. 1.) : S50-S55 (1995).
Townsend et al., "Gastrointestinal Hormones and Cell Proliferation", Surgery Today (Jpn J Surg) 24 : 772-777 (1984).
Ulrich II et al., "Secretin and Vasoactive Intestinal Peptide Receptors:Members of a Unique Family of G Protein-Coupled Receptors", Gastroenterology 114: 382-397 (1998).
Funakoshi et al., "Changes in Insulin Secretion After Secretin Administration and the Implication in Diabetes Mellitus", Endocrinologica Japonoca 32 (4): 473-479 (1985).
Kofod et al., "Secretin and Its C-terminal Hexapeptide Potentiates Insulin Release in Mouse Islets", American Journal of Psychology, 250:E107-E113 (1986).
Lerner et al., "Augmentation by Secretin of Glucose Stimulated Insulin Responses in diabetes Subjects", Clinical Research 25: 126A (1997).
McCrea et al., 2-36[K, RYYSA]PP a novel Y5-receptor preferring ligand with strong stimulatory effect on food intake, Regulatory Peptides 87 (2000) 47-58.
Adrian, T.E., et al., Gastroenterology (1985) 89, 1070-1077.
Adrian, T.E.,et al. Digestion (1981) 21, 214-218.
Ahren, B. et al., Eur J Endocrinol (1996) 134, 362-365.
Allen, J.M., et al., Digestion (1984) 30, 255-262.
Ando, R., et al., Eur J Pharmacol (2001) 427, 53-59.
Andres, C.J., et al., Bioorg Med Chem Lett (2003) 13, 2883-2885.
Aponte, G.W., et al. FASEB J (1989) 3, 1949-55.
Asakawa, A., et al., Peptides (1999) 20, 1445-1448.
Bader, R., et al., Biochemistry (2002) 41, 8031-8042.
Balasubramaniam, A., et al., Peptides (1993) 14, 1011-1016.
Balasubramaniam, A., et al., Int J Pept Protein Res (1987) 29, 78-83.
Balasubramaniam, A., et al., Pept Res(1988) 1, 32-35.
Balasubramaniam, A., et al., Peptides (2002) 23, 1485-1490.
Balasubramaniam, A., et al., J Med Chem (2000) 43, 3420-3427.
Balasubramaniam, A. Peptides (1997) 18, 445-457.
Barany, F. Proc Natl Acad Sci U S A (1991) 88, 189-193.
Bartlett PA, et al. Bioorg Chem. 1986;14:356-377.
Batterham, R.L., et al., N Engl J Med (2003) 349, 941-948.
Batterham, R.L., et al., Nature (2002) 418, 650-654.
Beck, A., et al., FEBS Lett (1989) 244, 119-122.
Beck-Sickinger, A.G., et al., J Recept Res (1993) 13, 215-228.
Beltowski, J. et al., Pol J Pharmacol (2004) 56, 5-27.
Berge, S.M., et al., J Pharm Sci (1977) 66, 1-19.
Berglund, M.M., et al., Exp Biol Med (Maywood) (2003) 228, 217-244.
Bertrand, G., et al., Pancreas (1992) 7, 595-600.
Birdsall, N.J.M. et al., Trends Pharmacol Sci (1983) 4, 459-463.
Bischoff, A. et al., Trends Pharmacol Sci (1999) 20, 104-106.
Bonaz, B., et al., Neurosci Lett (1993) 163, 77-80.
Bottcher, G., et al., Pancreas (1989) 4, 282-288.
Boublik, J.H., et al., J Med Chem (1989) 32, 597-601.
Bourguet E, et al., Bioorg Med Chem Lett. (2003) 13:1561-1564.
Brown, K.K., et al., Diabetes (1999) 48, 1415-1424.
Cabrele, C. et al., J Pept Sci (2000) 6, 97-122.
Cabrele, C., et al., J Biol Chem (2000) 275, 36043-36048.
Cabrele, C., et al., Biochemistry (2002) 41, 8043-8049.
Cabrele, C., Peptides (2001) 22, 365-378.
Camilleri, M., et al., Gut (1981) 22, 14-18.
Campfield, L.A., et al., Science (1995) 269, 546-549.
Chen, C.H.et al., Am J Physiol (1995) 269, R787-R792.
Chen, C.H., et al., Regul Pept (1996) 61, 95-98.
Chen, C.H., et al., Neurogastroenterol Motil (1997) 9, 109-116.
Chen, M.H., et al., Gastroenterology (1984) 87, 1332-1338.
Chen, Z., et al., FEBS Lett (2001) 492, 119-122.
Clark, J.T., et al., Endocrinology (1984) 115, 427-429.
Clark, J.T., et al., Regul Pept (1987) 17, 31-39.
Conlon, J.M. Peptides (2002) 23, 269-278.
Cook, D.L. et al., Nature (1984) 311, 271-273.
Corp, E.S., et al., Peptides (2001) 22, 493-499.
Corp, E.S., et al., Am J Physiol (1990) 259, R317-R323.
Coruzzi, G., et al., Arch Int Pharmacodyn Ther (1989) 302, 232-241.
Cotton, R.G. Mutat Res (1993) 285, 125-144.
Cotton, R.G., et al., Proc Natl Acad Sci U S A (1988) 85, 4397-4401.
Cox, H.M. et al., Br J Pharmacol (1990) 101, 247-252.
Cox, H.M., et al., J Physiol (1988) 398, 65-80.
Cox, H.M., et al., Regul Pept (1998) 75-76, 3-8.
Dea, D., et al., Gastroenterology (1989) 96, 695-703.
Deng, X., et al., Dig Dis Sci (2001) 46, 156-165.
Dox, I.G., et al., Definition of 'islet'. In: Anonymous The HarperCollins Illustrated Medical Dictionary, (1993) 1st edn. pp. 227 New York: HarperCollins Publishers, Inc.
Dumont, Y., et al., Brain Res Mol Brain Res (1994) 26, 320-324.
Dumont, Y., et al., Eur J Pharmacol (1993) 238, 37-45.
Dumont Y, et al., Society for Neuroscience Abstracts. 1993;19:726. Abstract 299.8.
Eberlein, G.A., et al., Peptides (1989) 10, 797-803.
Ebert, R. Z Gastroenterol Verh (1988) 23, 165-170.
Eto, B., et al., Peptides (1995) 16, 1403-1409.
Fackelmann USA Today, Health and Science Gut hormone could curb urge to overeat. (Aug. 7, 2002).
Feinstein, R.D., et al., J Med Chem (1992) 35, 2836-2843.
Ferber, S., et al., Journal of Biological Chemistry (1994) 269, 11523-11529.
Fournier, A., et al., Mol Pharmacol (1994) 45, 93-101.
Freshney, R.I. Freshney, R.I., (Ed.) Culture of Animal Cells: A Manual of Basic Technique, (1983) pp. 4 New York: Alan R. Liss, Inc.
Garlicki, J., et al., Am J Physiol (1990) 258, E40-E45.
Gedulin, B., et al., Gastroenterology (1995) 108, A604.
Gehlert, D.R. Proc Soc Exp Biol Med (1998) 218, 7-22.
Gibbs, R.A., et al., Nucleic Acids Res (1989) 17, 2437-2448.
Gobbi, M., et al., J Neurochem (1999) 72, 1663-1670.
Gold, G., et al., Diabetes (1981) 30, 77-82.
Gordon, E.A., et al., Neurosci Lett (1990) 119, 187-190.
Gomez, G., et al., Am J Physiol (1995) 268, G71-G81.
Grandt, D., et al., Regul Pept (1994) 51, 151-159.
Grandt, D., et al Biochem Biophys Res Commun (1992) 186, 1299-1306.
Greeley, G.H et al., Proc Soc Exp Biol Med (1988) 189, 325-328.
Greeley, G.H. et al., Am J Physiol (1988) 254, E513-E517.
Grieco P, et al., Tetrahedron Lett. 2002;43:6297-6299.
Groth, C.G., et, al. Transplant Proc (1992) 24, 972-973.
Grouzmann, E., et al., Endocrine Society Program & Abstracts 75th Annual Meeting, Las Vegas, NV, Jun. 9-12, 1993 180. Abstract 519B.
Grundemar, L., et al. Regul Pept (1996) 62, 131-136.
Gu X, et al., Tetrahedron Lett. 2003;44:5863-5866.
Gue, M., et al., Br J Pharmacol (1996) 118, 237-242.
Gustavsson, S., et al., Scand J Gastroenterol (1977) 12, 993-997.
Hagan, M.M. et al., Pharmacol Biochem Behav (1993) 45, 941-944.
Halaas, J.L., et al., Science (1995) 269, 543-546.
Halatchev, I.G., et al., Endocrinology (2004) 145, 2585-2590.
Hanessian S, et al., Tetrahedron. 1997;53:12789-12854.
Harding, R.K. et al., Peptides (1989) 10, 21-24.
Haynes, J.M., et al., Br J Pharmacol (1997) 122, 1530-1536.

Henry, M.et al., Obes Res (2005) 13, 36-47.
Hoentjen, F., et al., Scand J Gastroenterol (2000) 35, 166-171.
Holliday, N.D. et al., Br J Pharmacol (1996) 119, 321-329.
Hsu, I.C., et al., Carcinogenesis (1994) 15, 1657-1662.
Hu, Y., et al., J Biol Chem (1996) 271, 26315-26319.
Hughes, S.D., et al., Proceedings of the National Academy of Sciences of the United States of America (1992) 89, 688-692.
Inui, A. Trends Pharmacol Sci (1999) 20, 43-46.
Iyengar, S., et al., J Pharmacol Exp Ther (1999) 289, 1031-1040.
Jackerott, M. et al., Endocrinology (1997) 138, 5013-5018.
Jackerott, M., et al., J Histochem Cytochem (1996) 44, 809-817.
Johnson, J.H., et al., Science (1990) 250, 546-549.
Jones, P.M. et al., Endocr Rev (1998) 19, 429-461.
Kanatani, A., et al., Biochem Biophys Res Commun (2000) 272, 169-173.
Kanatani, A., et al., Biochem Biophys Res Commun (1999) 266, 88-91.
Kanatani, A., et al., Endocrinology (2000) 141, 1011-1016.
Karlsson S, et al., Acta Physiol Scand. 1996;157:305-306.
Kato, K., et al., Peptides (1995) 16, 1257-1262.
Kawakubo, K., et al., (2000) Brain Res 854, 30-34.
Keire, D.A., et al., Peptides (2002) 23, 305-321.
Keire, D.A., et al., Biochemistry (2000) 39, 9935-9942.
Keire, D.A., et al., Am J Physiol (2000) 279, G126-G131.
Kimmel, J.R., et al., Endocrinology (1968) 83, 1323-1330.
Kirby, D.A., et al., J Med Chem (1993) 36, 3802-3808.
Kirby, D.A., et al., J Med Chem (1995) 38, 4579-4586.
Kopelman, P.G. Nature (2000) 404, 635-643.
Korsgren, O., et al., Transplantation (1988) 45, 509-514.
Krasinski, S.D., et al., Mol Endocrinol (1991) 5, 433-440.
Krstenansky, J.L., et al., Proc Natl Acad Sci (1989) U S A 86, 4377-4381.
Krstenansky, J.L., et al., Neuropeptides (1990) 17, 117-120.
Kruger, D.F., et al., Diabetes Educ (1999) 25, 389-397; quiz 398.
Kumagai Braesch, M., et, al., Transplant Proc (1992) 24, 679-680.
Kushi, A., et al., Proc Natl Acad Sci U S A (1998) 95, 15659-15664.
Lacy, P.E., et al., Science (1991) 254, 1782-1784.
Landegren, U., et al., Science (1988) 241, 1077-1080.
Leban, J.J., et al., J Med Chem (1995) 38, 1150-1157.
Leibowitz, S.F. et al., Peptides (1991) 12, 1251-1260.
Liu, C.D., et al., J Gastrointest Surg (2001) 5, 147-152.
Liu, X.M., et al., Diabetes (1991) 40, 858-66.
Lloyd, K.C.K., et al., Am J Physiol (1996) 270, G123-G127.
Lundberg, J.M., et al., Proc Natl Acad Sci U S A (1982) 79, 4471-4475.
Lyznicki JM, et al., Am Fam Physician. 2001;63:2185-2196.
Makimura, H. et al., Obesity Poster Abstract No. 118 Adrenalectomy stimulated hypothalamic proopiomelanocortin mRNA but does not correct obesity in diet-induced obese mice.
Malaisse-Lagae, F., et al., Experientia (1977) 33, 915–917.
Markison S., et al., Obesity Poster Abstract No. 119 "Selective melanin-concentrating hormone receptor antagonists decrease feeding in rodents."
Marsh, D.J., et al., Nat Med (1998) 4, 718-721.
Martin, J.R. Brain Res (2004) 1002, 11-20.
Mashiko, S., et al., Endocrinology(2003) 144, 1793-1801.
Mashiko et al., Obesity Poster Abstract No. 120 "Characterization of neuropeptide Y Y5 receptor mediated obesity in mice."
Maxam, A.M., et al., Proc Natl Acad Sci U S A (1977) 74, 560-564.
Mazelin L, et al., J Auton Nerv Syst. 1998;73:38-45.
Medeiros, M.D. et al., Endocrinology (1994) 134, 2088-2094.
Michel, M.C., et al., Pharmacol Rev (1998) 50, 143-150.
Morley, J.E. Neuropsychobiology (1989) 21, 22-30.
Morley, J.E. et al., Life Sci (1987) 41, 2157-2165.
Morley, J.E., et al., Am J Physiol (1994) 267, R178-R184.
Morley, J.E., et al., Brain Res (1985) 341, 200-203.
Morris GP, et al., Gastroenterology. (1989);96:795-803.
Mulder, H., et al., Microscopy Research and Technique (1998) 43, 313-321.
Mullins, D., et al., Mol Pharmacol (2001) 60, 534-540.
Munson, P.J. et al., Anal Biochem (1980) 107, 220-239.
Murakami, Y., et al., J Med Chem (1999) 42, 2621-2632.
Murase, S., et al., J Biochem (Tokyo) (1996) 119, 37-41.

Myers, R.M., et al., Science (1985) 230, 1242-1246.
Myers, R.M., et al., Nature (1985) 313, 495-498.
Naeve, C.W., et al., Biotechniques (1995) 19, 448-453.
Nakajima, M., et al., J Pharmacol Exp Ther (1994) 268, 1010-1014.
Nakazawa, H., et al., Proc Natl Acad Sci U S A (1994) 91, 360-364.
Naslund, E., et al., Int J Obes Relat Metab Disord (1999) 23, 304-311.
Ngo, J.T. et al., The protein folding problem and tertiary structure prediction, (1994) pp. 491-495. Boston: Birkhauser.
Nieuwenhuizen, A.G., et al., Diabetologia (1994) 37, 871-878.
Nightingale, J.M., et al., Gut (1996) 39, 267-272.
Odagiri, H., et al., J Biol Chem (1996) 271, 1909-1915.
Okada, S., et al., Endocrine Society Program & Abstracts 75th Annual Meeting, Las Vegas, NV, Jun. 9-12, 1993 180. Abstract 520B.
Okumura, T., et al., Neuroscience Letters(1994) 178, 167-170.
Orita, M., et al., Proc Natl Acad Sci U S A (1989) 86, 2766-2770.
Otonkoski, T., et al., Diabetes (1988) 37, 286-291.
Pappas, T.N., et al., Gastroenterology (1986) 91, 1386-1389.
Pappas, T.N., et al., Am J Physiol (1985) 248, G118-G123.
Parker, E.M., et al., Eur J Pharmacol (1998) 349, 97-105.
Parker, E.M., et al., Peptides (2000) 21, 393-399.
Parker, S.L. et al., Can J Physiol Pharmacol (2000) 78, 150-161.
Pelleymounter, M.A., et al., Science (1995) 269, 540-543.
Pheng, L.H., et al., Br J Pharmacol (2003) 139, 695-704.
Pironi, L., et al., Gastroenterology (1993) 105, 733-739.
Pokrovsky, V.I. (1996) Nephrotomy: renal insufficiency. In: Academician of RAMS, (Ed.) Small Medical Encyclopedia, pp. 59-62. Moscow: Meditisina Publishers] (w/ trnsltn.
Potter, E.K., et al., Eur J Pharmacol (1994) 267, 253-262.
Randle, P.J. Diabetes Metab Rev(1998) 14, 263-283.
Renshaw, D. et al., Curr Drug Targets (2005) 6, 171-179.
Rhodes, C.J. et al., J Cell Biol (1987) 105, 145-153.
Rico, L. et al., Obesity Poster Abstract No. 117 Early and dissociated leptin and insulin resistance in transgenic mice overexpressing leptin from keratinocytes.
Rissanen, A., et al., BMJ (1990) 301, 835-837.
Rist, B., et al., Eur J Biochem (1997) 247, 1019-1028.
Rist, B., et al., FEBS Lett (1996) 394, 169-173.
Robbins, L.S., et al., The Endocrine Pancreas. In: Robbins, L.S., Cotran, R.S. and Kumar, V., (Eds.) Pathologic Basis of Disease, (1984) 3rd edn. pp. 972-990. Philadelphia.
Saiki, R.K., et al., Nature (1986) 324, 163-166.
Wahoff, D.C., et al., Transplant Proc (1994) 26, 804.
Walker, M.W., et al., J Neurosci (1988) 8, 2438-2446.
Walker, M.W., et al., Peptides (1997) 18, 609-612.
Wang, Z.L., et al., Endocrine Society Program & Abstracts 75th Annual Meeting, Las Vegas, NV, Jun. 9-12, 1993 180. Abstract 518B.
Weinberg, D.H., et al., J Biol Chem (1996) 271, 16435-16438.
Wells, J.A. Biochemistry (1990) 29, 8509-8517.
Widdowson, P.S., et al., Brain Res (1997) 778, 242-250.
Wilding, J.P. Diabet Med (2002) 19, 619-627.
Wiley, J.W., et al., Gastroenterology (1991) 100, 865-872.
Wilson, J.D., et al., Diabetes (1989) 38 Suppl 1, 217-219.
Wimalawansa, S.J. Crit Rev Neurobiol (1997) 11, 167-239.
Yang, H., et al., Br J Pharmacol (1998) 123, 1549-1554.
Yoshinaga, K., et al Am J Physiol (1992) 263, G695-G701.
Ang, H. et al., Am J Physiol (1995) 268, G943-G948.
Young, A.A. et al., Program and Abstracts, 10th International Congress of Endocrinology (1996) 419 (poster P2-58).
Young, A.A., et al., Metabolism (1996) 45, 1-3.
Zai, H., et al., Regul Pept (1996) 61, 181-188.
Hyperdictionary—definition of "Structure Activity Relationship".
On-Line Medical Dictionary. Dept. of Oncology, U. Newcastle upon tyne. Cancerweb Project © 1997-2004 (defs of "hyperlipoproteinaemia"; "hyperlipidemia" and "hyperlipidaemia").
Aponte, G.W. (2002) Peptides 23, 367-376.
Bousquet-Melou, A., et al. (1995) J Lipid Res 36, 451-461.
Pi-Sunyer, F.X. (2002) Obes Surg 12 Suppl 1, 6S-11S.
St-Onge, M.P. et al., (2002) J Nutr 132, 329-332.
Valet, P., et al., (1990) J Clin Invest 85, 291-295.
Towfigh et al., Surgical Forum vol. 50: 25-27 (1999).
Saiki, R.K., et al., Proc Natl Acad Sci U S A (1989) 86, 6230-6234.
Sainsbury, A.,et al., Genes Dev (2002) 16, 1077-1088.

Saleeba, J.A. et al., Methods Enzymol (1993) 217, 286-295.
Sander, M., et al., Proc Natl Acad Sci U S A (1998) 95, 11572-11577.
Sanger, F., et al., Proc Natl Acad Sci U S A (1977) 74, 5463-5467.
Sato, N., et al., J Med Chem (2003) 46, 666-669.
Savage, A.P., et al., Gut (1987) 28, 166-170.
Scatchard, G. Ann NY Acad Sci (1949) 51, 660.
Scheen, A.J. Drugs (1997) 54, 355-368.
Schuit, F.C. Horm Res (1996) 46, 99-106.
Schwartz, M.W., et al., Nature (2000) 404, 661-671.
Servin, A.L., et al., Endocrinology (1989) 124, 692-700.
Shan, L., et al., Science (2002) 297, 2275-2279.
Sheikh, S.P. Am J Physiol (1991) 261, G701-G715.
Silva, A.P., et al., Clin Chim Acta (2002) 326, 3-25.
Simeonovic, C.J. et al., Aust J Exp Biol Med Sci (1982) 60 Pt 4, 383-390.
Slack, J.M. Development (1995) 121, 1569-1580.
Small, C.J., et al., Proc Natl Acad Sci U S A (1997) 94, 11686-11691.
SoII, R.M., et al., Eur J Biochem (2001) 268, 2828-2837.
Souers AJ, et al., Tetrahedron. 2001;57:7431-7448.
Stanley, B.G., et al., Peptides (1985) 6, 1205-1211.
Sullivan, S.J., et al., Science (1991) 252, 718-721.
Surwit, R.S., et al., Metabolism—Clinical and Experimental (1995) 44, 645-651.
Suzuki, T., et al., Gastroenterology (1983) 85, 114-121.
Taniguchi, H., et al., Eur J Pharmacol(1996) 312, 227-233.
Tatemoto, K. Proc Natl Acad Sci U S A (1982) 79, 2514-2518.
Tatemoto, K. Proc Natl Acad Sci U S A (1982) 79, 5485-5489.
Tatemoto, K., et al., Nature (1982) 296, 659-660.
Tatemoto, K., et al., Proc Natl Acad Sci U S A (1992) 89, 1174-1178.
Tatemoto, K., et al., Biochem Biophys Res Commun (1988) 157, 713-717.
Taylor, I.L. J Dairy Sci (1993) 76, 2094-2101.
Taylor, I.L. Am J Physiol (1985) 248, G277-G28.
Teyssen, S., et al., Pancreas (1996) 13, 80-88.
Thorens, B,et al., Proceedings of the National Academy of Sciences of the United States of America (1990) 87, 6492-6496.
Thum, A., et al., Exp Clin Endocrinol Diabetes (2002) 110, 113-118.
Tito JM, et al., Am J Surg. 1993;165:690-696.
Totheroh, G., "Science Offers Promising Treatment for an Overweight Nation" CBN News (Sep. 4, 2003).
Tsai JH, et al., Bioorg Med Chem. 1999;7:29-38.
Tschop, M., et al., Nature (2004) 430, 1 p following 165; discussion 2 p following 165.
Tseng, W.W. et al., Peptides (2002) 23, 389-395.
Tuch, B.E., et al., J Endocrinol (1992) 132, 159-167.
Turnbull, A.V., et al., Diabetes (2002) 51, 2441-2449.
Ueno, N., et al., Gastroenterology (1999) 117, 1427-1432.
Upchurch, B.H., et al., Development (1994) 120, 245-252.
Valera, A., et al., J Biol Chem (1994) 269, 28543-28546.
van Santbrink, E.J. et al., J Clin Endocrinol Metab (1997) 82, 3597-602.
Verchere, C.B., et al., Endocrine Society Program & Abstracts 75th Annual Meeting, Las Vegas, NV, Jun. 9-12, 1993 180. Abstract 517B.
Virgilio AA, et al., Tetrahedron. 1997;53:6635-6644.
Voisin, T., et al., J Biol Chem (1993) 268, 20547-20554.
Wager-Page, S.A., et al., Can J Physiol Pharmacol (1993) 71, 768-775.
Conlon, J.M., "Neuropeptide Y-Related Peptides From the Pancreas of a Teleostean Eel Holostean Bowfin and Elasmobranch Skate Fish," Peptides, 1991, 221-226, vol. 12, No. 2.
Bork, Peer, "Powers and Pitfalls in Sequence Analysis: The 70% Hurdle." Genome Research, 10:398-400, 2000.
Bork, Peer, "Go hunting in sequence databases but watch out for traps." Trends in Genetics, vol. 12. No. 10. pp. 425-427, 1996.
Brenner, S.E., "Errors in genome annotation." Trends in Genetics, vol. 15. No. 4. pp. 132-133, 1999.
Doerks, Tobias, Protein annotation: detective work for function prediction. Trends in Genetics, vol. 14. No. 6. pp. 248-250, 1998.
Ngo, Thomas J., "Computational Complexity, Protein Structure Prediction and the Levinthal Paradox." In Merz and Le Grand (Eds.) The Protein Folding Problem and Tertiary Structure Predication, Birkhauser Boston, pp. 492-495, 1992.
Skolnick, Jeffrey et al., "From genes to protein structure and function: novel applications of computational approaches in the genomic era." Tibtech, vol. 18. No. 1. pp. 248-250, 1998.
Smith, Temple F. et al., "The challenges of genome sequence annotation or The devil is in the details". Nature Biotechnology, vol. 15. pp. 1222-1223, 1997.
Wells, J.A., "Additivity of Mutational Effects in Proteins." Biochemistry, vol. 29. No. 37. pp. 8509-8517, 1990.
Halford, Jason, et al. "The Psychopharmacology of Appetite: Targets for Potential Anti-Obesity Agents"; Central Nervous System Agents in Medicinal Chemistry, Bentham Science Publishers Ltd.; vol. 3, No. 4:pp. 283-310 (2003).
Howl, John, et al.: "Chimeric Strategies for the RTational Design of Bioactive Analogs of Small Peptide Hormones" FASEB Journal, Fed. of American Soc. for Experimental Biology;vol. 11, No. 7: pp. 582-590; (2007).
Chasrzad, Montrose-Rafizadeh, et al.: "High Potency Antagonishts of The Pancreatic Glucagon-like Peptide-1 Receptor"; Journal of Biological Chemistry, American Soc. of Biochemical Biologists; vol. 272, No. 34; pp. 21201-21206 (1997).
Pollock, H.G., et al., "Isolation and Structures of Alligator Gar (*Lepisosteus spatula*) Insulin and Pancreatic Polypeptide," General and Comparative Endocrinology (1987), 67(3), 375-82 .

Food Intake Assay, Mouse, Dose: 10 nmol/kg i.p.

PPF Polypeptide Shows efficacy in *in-vivo* Assays
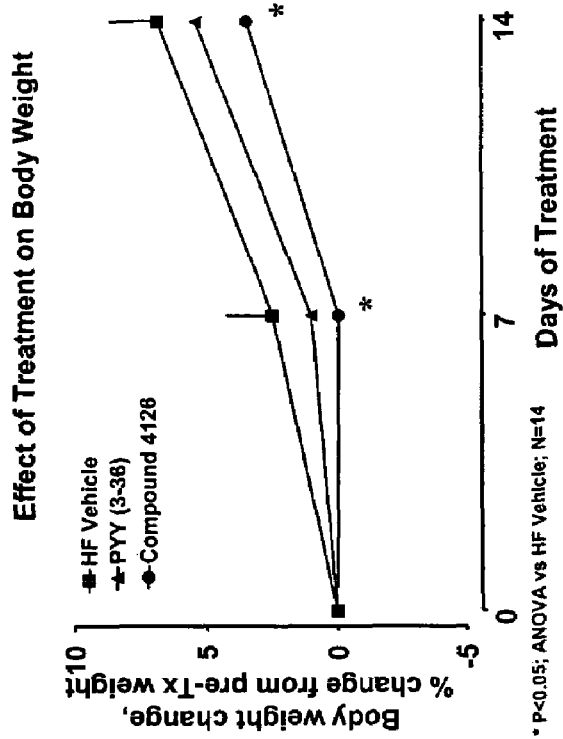
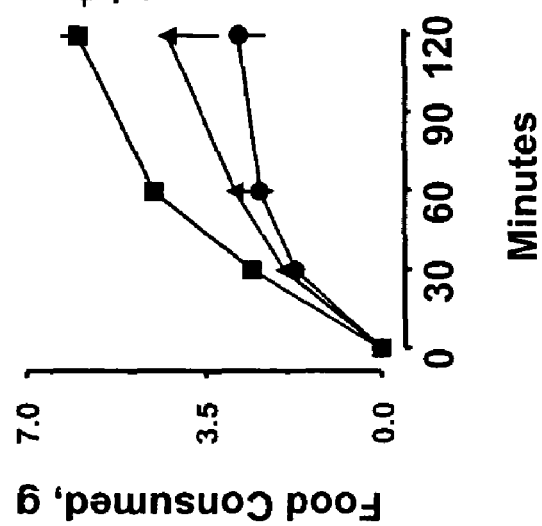
FIG. 8

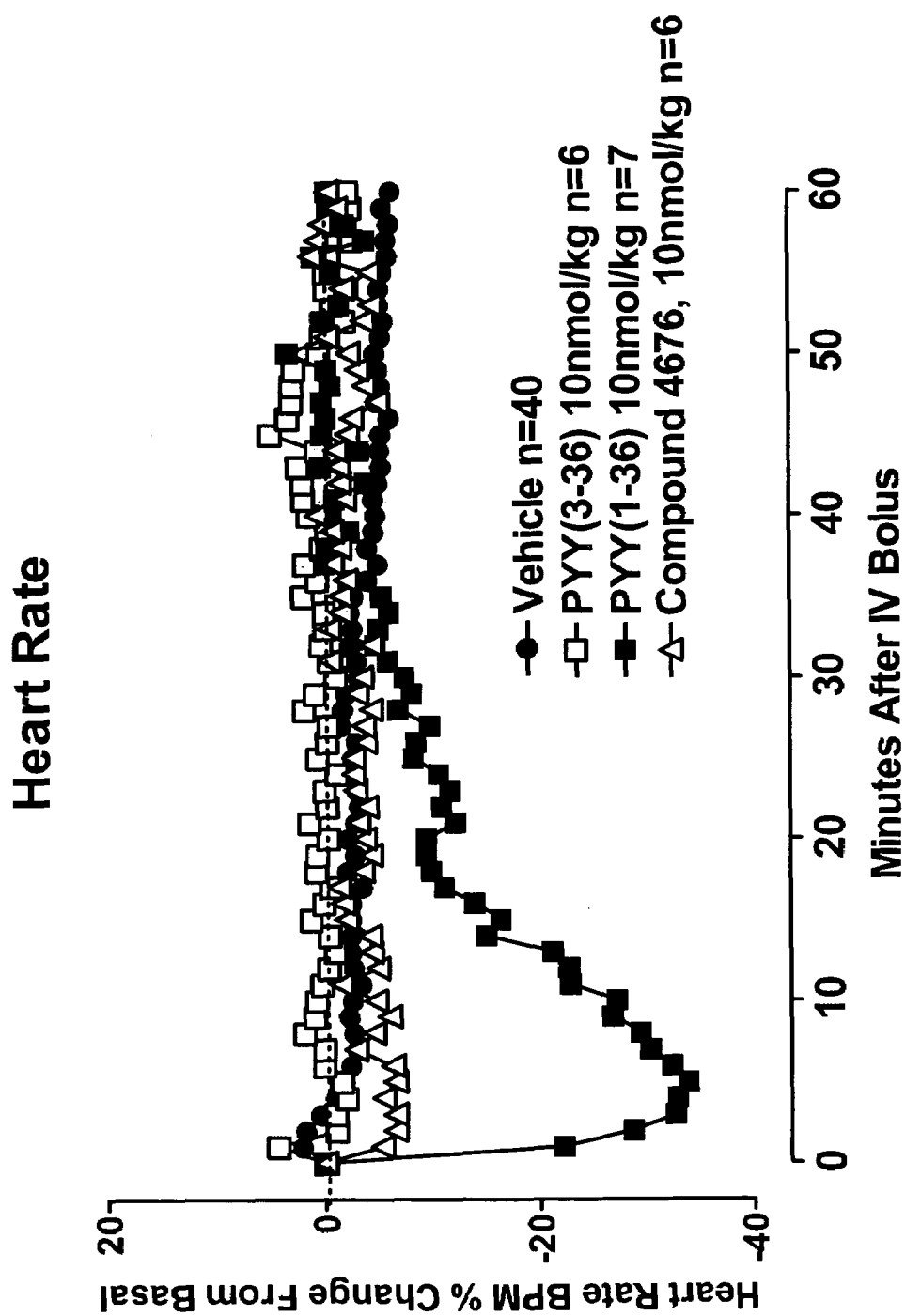
FIG. 9-A

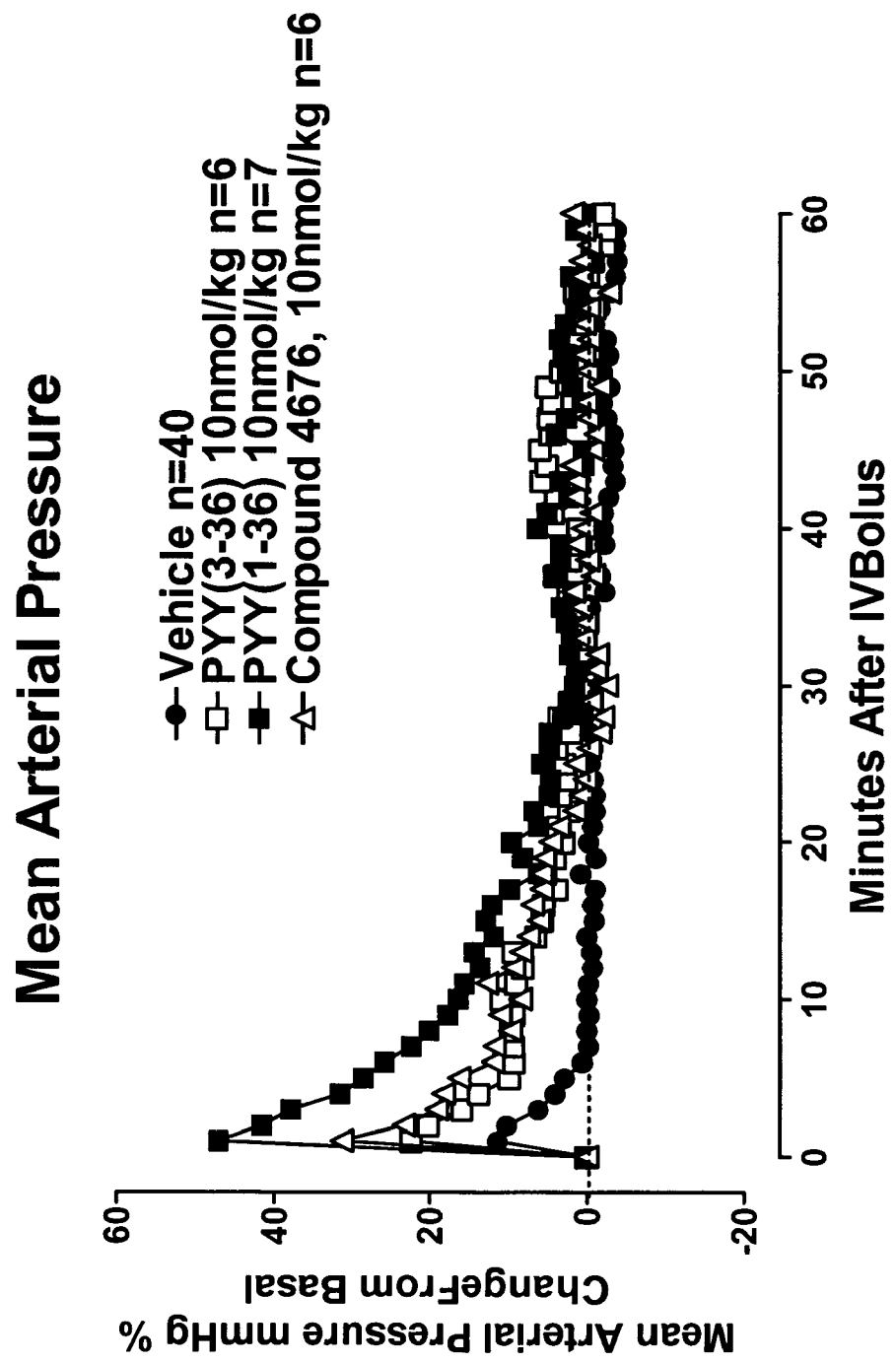
FIG. 9-B

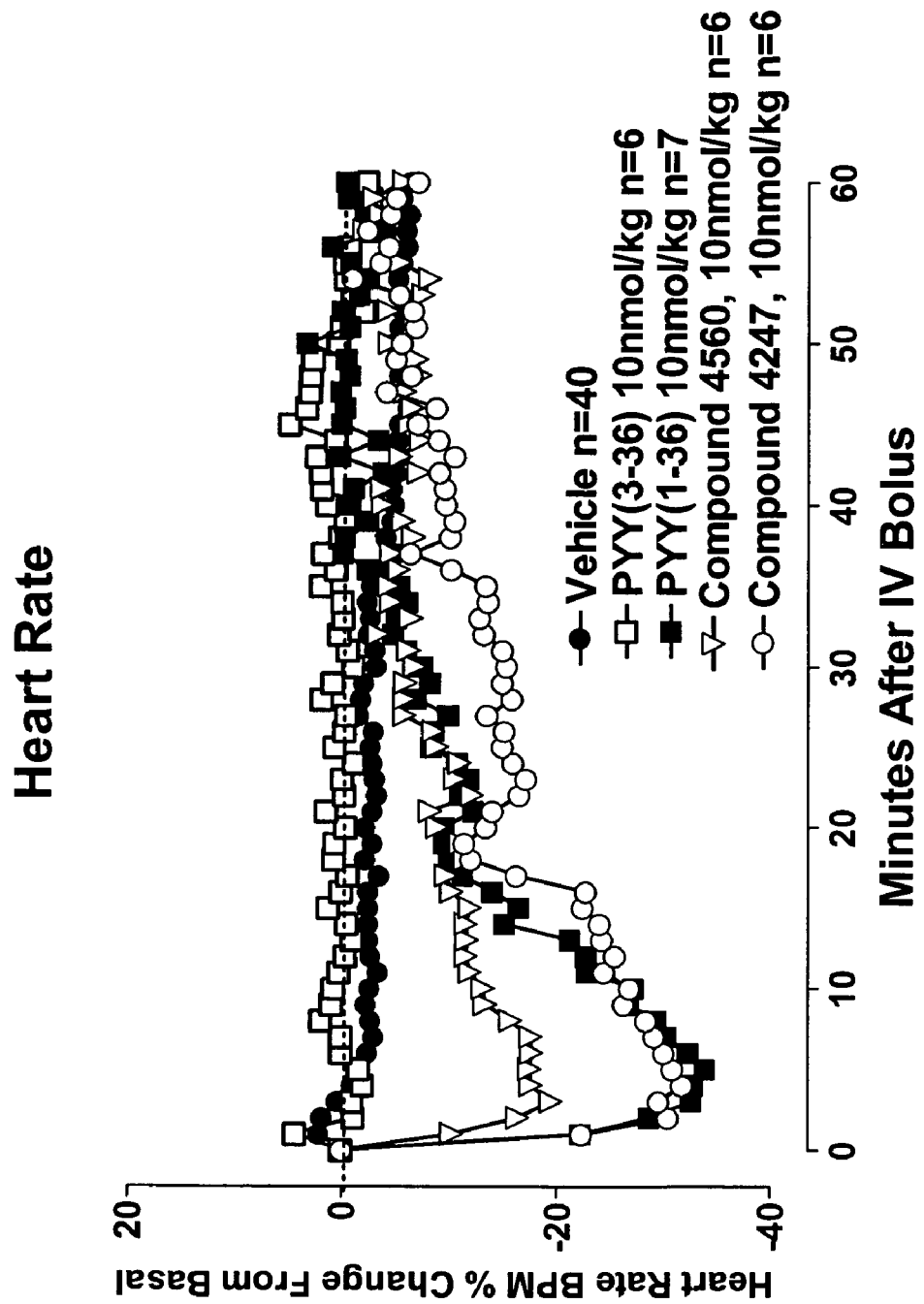
FIG. 9-C

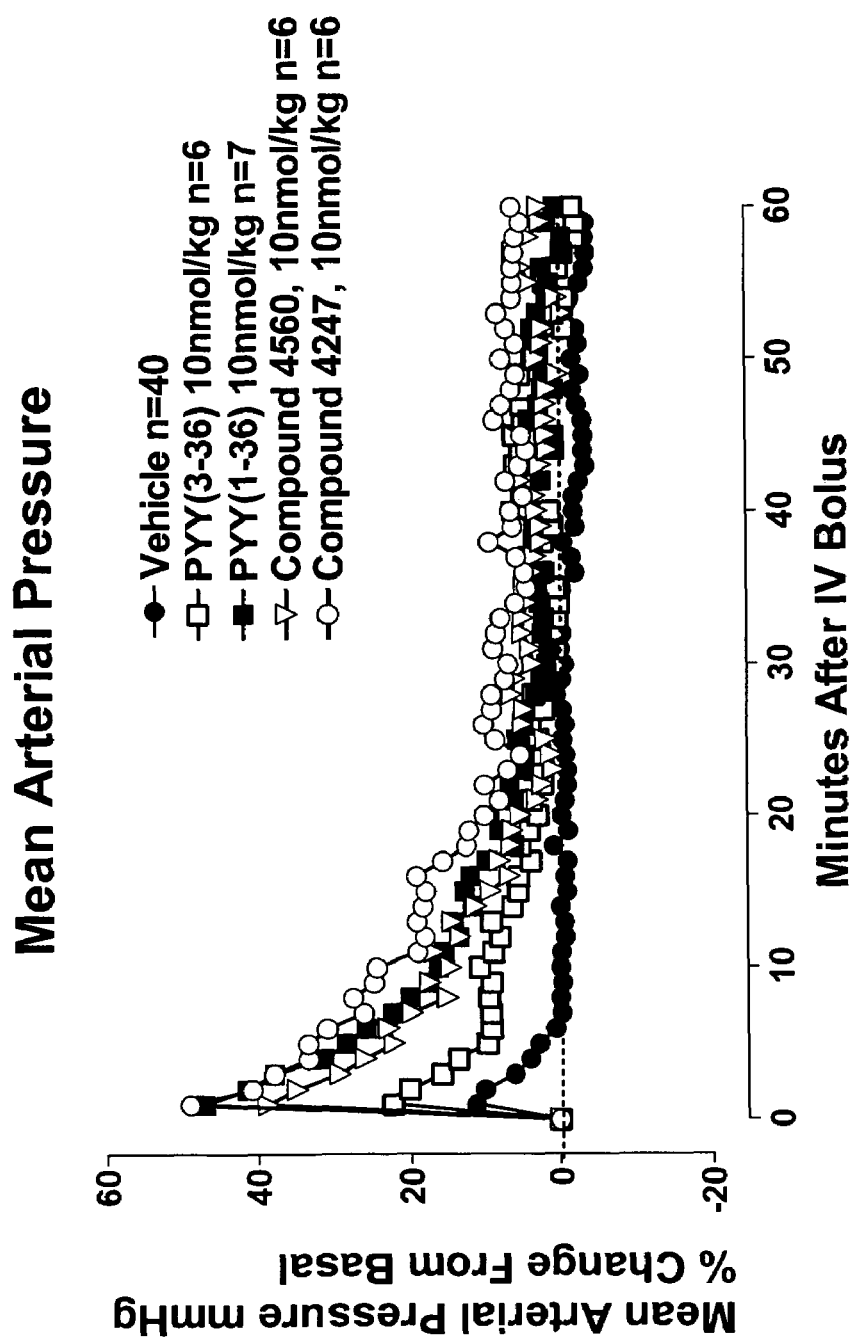
FIG. 9-D

Telemetry Studies (Rat):
Effect of PPF polypeptide Compound 4753 on Heart Rate
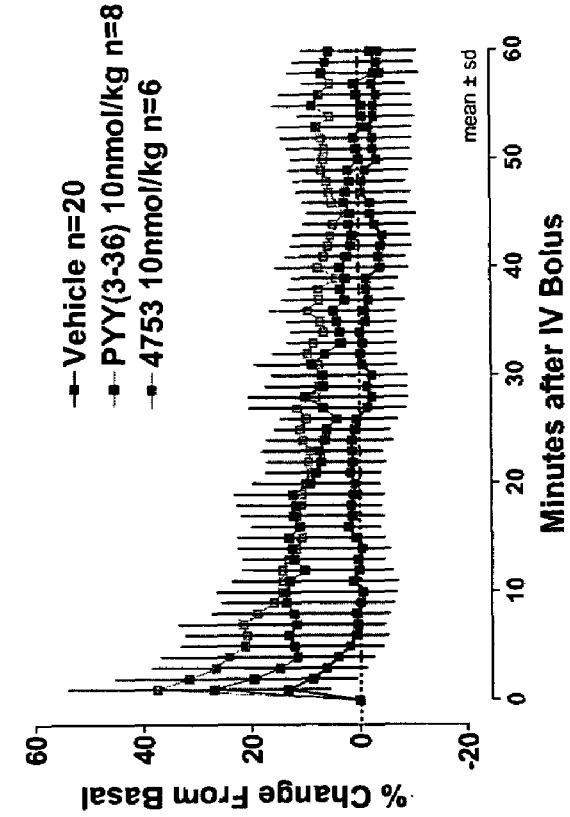
MAP
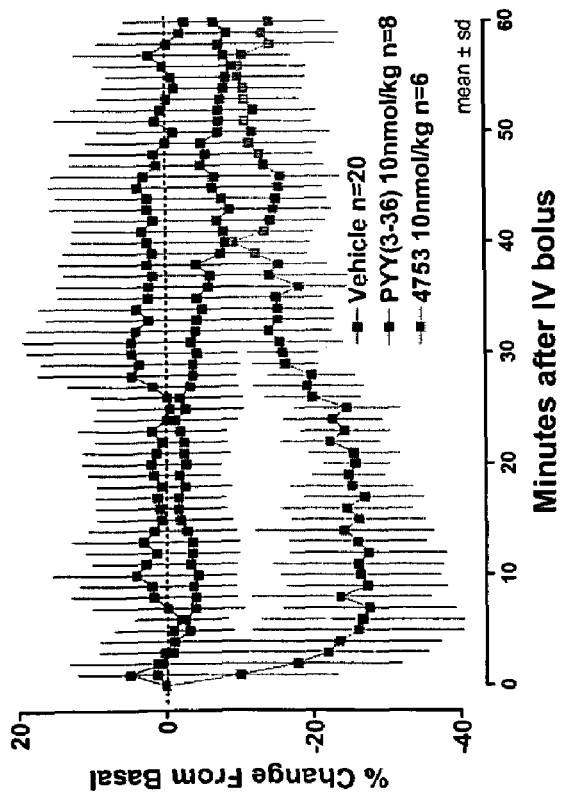
Heart Rate
FIG. 46

FIG. 50 Effect of Amylin & Compound 4917 on body composition

PANCREATIC POLYPEPTIDE FAMILY MOTIFS, POLYPEPTIDES AND METHODS COMPRISING THE SAME

RELATED APPLICATIONS

The present application claims priority to U.S. Provisional Application No. 60/543,406, filed Feb. 11, 2004; U.S. Provisional Application No. 60/543,407, filed Feb. 11, 2004; pending U.S. application Ser. No. 11/055,098, filed Feb. 11, 2005; PCT/US05/04351; and U.S. Provisional Application No. 60/635,897, filed Dec. 13, 2004, each of which is hereby incorporated by reference in its entirety.

INCORPORATION-BY-REFERENCE OF MATERIAL SUBMITTED ON COMPACT DISCS

The sequence listing in the present application is being submitted on two compact discs labeled "Sequence Listing-Copy 1" and "Sequence Listing-Copy 2"; each containing a file of 231 KB in size named "0406CIP seq list.txt" created on Dec. 12, 2005, the contents of which are hereby incorporated by reference.

BACKGROUND

A number of related hormones make up the pancreatic polypeptide family ("PPF"). Pancreatic polypeptide ("PP") was discovered as a contaminant of insulin extracts and was named by its organ of origin rather than functional importance (Kimmel et al., *Endocrinology* 83: 1323-30 (1968)). PP is a 36-amino acid peptide (SEQ ID NO: 1) containing distinctive structural motifs. A related peptide was subsequently discovered in extracts of intestine and named Peptide YY ("PYY") (SEQ ID NO: 2) because of the N- and C-terminal tyrosines (Tatemoto, *Proc. Natl. Acad. Sci. USA* 79: 2514-8 (1982)). A third related peptide was later found in extracts of brain and named Neuropeptide Y ("NPY") (SEQ ID NO: 4) (Tatemoto, *Proc. Natl. Acad. Sci. USA* 79: 5485-9 (1982); Tatemoto et al., *Nature* 296: 659-60 (1982)).

These three related peptides have been reported to exert various biological effects. Effects of PP include inhibition of pancreatic secretion and relaxation of the gallbladder. Centrally administered PP produces modest increases in feeding that may be mediated by receptors localized to the hypothalamus and brainstem (reviewed in Gehlert, *Proc. Soc. Exp. Biol. Med.* 218: 7-22 (1998)).

Release of PYY (SEQ ID NO: 2) occurs following a meal. An alternate molecular form of PYY is PYY(3-36) (SEQ ID NO: 3) (Eberlein et al., *Peptides* 10: 797-803 (1989); Grandt et al., *Regul. Pept.* 51: 151-9 (1994)). This fragment constitutes approximately 40% of total PYY-like immunoreactivity in human and canine intestinal extracts and about 36% of total plasma PYY immunoreactivity in a fasting state to slightly over 50% following a meal. It is apparently a dipeptidyl peptidase-IV (DPP4) cleavage product of PYY. PYY(3-36) is reportedly a selective ligand at the Y2 and Y5 receptors, which appear pharmacologically unique in preferring N-terminally truncated (i.e., C-terminal fragments of) NPY analogs. Peripheral administration of PYY reportedly reduces gastric acid secretion, gastric motility, exocrine pancreatic secretion (Yoshinaga et al., *Am. J. Physiol.* 263: G695-701 (1992); Guan et al., *Endocrinology* 128: 911-6 (1991); Pappas et al., *Gastroenterology* 91: 1386-9 (1986)), gallbladder contraction and intestinal motility (Savage et al., *Gut* 28: 166-70 (1987)). The effects of central injection of PYY on gastric emptying, gastric motility and gastric acid secretion, as seen after direct injection in or around the hindbrain/brainstem (Chen and Rogers, *Am. J. Physiol.* 269: R787-92 (1995); Chen et al., *Regul. Pept.* 61: 95-98 (1996); Yang and Tache, *Am. J. Physiol.* 268: G943-8 (1995); Chen et al., *Neurogastroenterol. Motil.* 9: 109-16 (1997)), may differ from those effects observed after peripheral injection. For example, centrally administered PYY had some effects opposite to those described herein for peripherally injected PYY(3-36) in that gastric acid secretion was stimulated, not inhibited. Gastric motility was suppressed only in conjunction with TRH stimulation, but not when administered alone, and was indeed stimulatory at higher doses through presumed interaction with PP receptors. PYY has been shown to stimulate food and water intake after central administration (Morley et al., *Brain Res.* 341: 200-3 (1985); Corp et al., *Am. J. Physiol.* 259: R317-23 (1990)).

Likewise, one of the earliest reported central effects of NPY (SEQ ID NO: 4) was to increase food intake, particularly in the hypothalamus (Stanley et al., *Peptides* 6: 1205-11 (1985)). PYY and PP are reported to mimic these effects, and PYY is more potent or as potent as NPY (Morley et al., *Brain Res.* 341: 200-3 (1985); Kanatani et al., *Endocrinology* 141: 1011-6 (2000); Nakajima et al., *J. Pharmacol. Exp. Ther.* 268: 1010-4 (1994)). Several groups found the magnitude of NPY-induced feeding to be higher than that induced by any pharmacological agent previously tested, and also extremely long-lasting. NPY-induced stimulation of feeding has been reproduced in a number of species. Among the three basic macronutrients (fat, protein, and carbohydrate), the intake of carbohydrates was preferentially stimulated. No tolerance was seen towards the orexigenic effect of NPY, and when administration of the peptide was repeated over 10 days, a marked increase in the rate of weight gain was observed. Following starvation, the concentration of NPY in the hypothalamic PVN increased with time, and returned rapidly to control levels following food ingestion.

Pharmacological studies and cloning efforts have revealed a number of seven transmembrane receptors for the PP family of peptides, and these receptors have been assigned the names Y1 through Y6 (and a putative PYY-preferring receptor Y7). Typical signaling responses of these receptors are similar to those of other $G_i/G_0$-coupled receptors, namely inhibition of adenylate cyclase. Even with fairly low sequence homology among receptors, it is apparent that there is a clustering of amino acid sequence similarity between Y1, Y4 and Y6 receptors, while Y2 and Y5 define other families. Other binding sites have been identified by the rank order of potency of various peptides. The NPY-preferring receptor, which has not been cloned, has been termed Y3, and there is evidence for the existence of PYY-preferring receptors (the putative Y7 receptor(s)) (reviewed in Michel et al., *Pharmacol. Rev.* 50:143-50 (1998); Gehlert, *Proc. Soc. Exp. Biol. Med.* 218: 7-22 (1998)).

The Y5 and Y1 receptors have been suggested as the primary mediators of the food intake response (Marsh et al., *Nat. Med.* 4: 718-21 (1998); Kanatani et al., *Endocrinology* 141: 1011-6 (2000)). The prevalent idea has been that endogenous NPY, via these receptors, increases feeding behavior. Proposed therapies for obesity have invariably been directed toward antagonism of NPY receptors, while therapies for treating anorexia have been directed toward agonists of this ligand family (see, e.g., U.S. Pat. Nos. 5,939,462; 6,013,622; and 4,891,357). In general, PYY and NPY are reported to be equipotent and equally effective in all Y1, Y5 (and Y2) receptor assays studied (Gehlert, *Proc. Soc. Exp. Biol. Med.* 218: 7-22 (1998)).

Pharmacologically, the Y2 receptor is distinguished from Y1 by exhibiting affinity for C-terminal fragments of neuropeptide Y. The Y2 receptor is most often differentiated by the affinity of neuropeptide Y(13-36), although the 3-36 fragment of neuropeptide Y and peptide YY provided improved affinity and selectivity (see Dumont et al., *Soc. for Neurosci. Abstracts* 19:726 (1993)). Signal transmission through both the Y1 and Y2 receptors are coupled to the inhibition of adenylate cyclase. Binding to the Y2 receptor was also found to reduce the intracellular levels of calcium in the synapse by selective inhibition of N-type calcium channels. In addition, the Y2 receptor, like the Y1 receptors, exhibits differential coupling to second messengers (see U.S. Pat. No. 6,355,478). Y2 receptors are found in a variety of brain regions, including the hippocampus, substantia nigra-lateralis, thalamus, hypothalamus, and brainstem. The human, murine, monkey and rat Y2 receptors have been cloned (e.g., see U.S. Pat. No. 6,420,532 and U.S. Pat. No. 6,355,478).

The main characteristic of putative Y3 receptors is that they recognize NPY, while PYY is at least an order of magnitude less potent. The Y3 receptor represents the only binding site/receptor that shows a preference for NPY.

There is an additional binding site/receptor which shows preference for PYYs, termed PYY-preferring receptor, which is referred to herein as the Y7 receptor(s). Different rank orders of binding to this receptor, or class of receptors, have been reported, suggesting that there may be more than one receptor in this class. In most cases it has been applied to describe a receptor where PYY was three to five times more potent than NPY. The International Union of Pharmacology recommendations for the nomenclature of NPY, PYY and PP receptors are that the term PYY-preferring receptor is not used unless a potency difference of at least twenty-fold between PYY and NPY is observed (Michel et al., *Pharmacol. Rev.* 50: 143-50 (1998)). However, for purposes of this disclosure, reference to the Y7 receptor or pharmacology of a PYY-preferring receptor means a receptor having any degree of preference for PYY over NPY.

Obesity and its associated disorders are common and very serious public health problems in the United States and throughout the world. It is estimated that about 64% of Americans are overweight or obese (roughly about 97 million adults) and it is generally believed that these numbers are increasing. People who are overweight or obese are considered those with a Body Mass Index (BMI) equal to or greater than 25. BMI is a mathematical formula commonly used to express the relationship of weight-to-height; a person's body weight in kilograms is divided by the square of his or her height in meters (i.e., $wt/(ht)^2$). In a human healthcare setting, individuals with a BMI of 25 to 29.9 are generally considered overweight, while individuals with a BMI of 30 or more are generally considered obese. Morbid obesity refers to a BMI of 40 or greater. According to the NIH Clinical Guidelines on the Identification, Evaluation, and Treatment of Overweight and Obesity in Adults, all adults (aged 18 years or older) who have a BMI of 25 or more are considered at risk for premature death and disability as a consequence of overweight and obesity. These health risks increase even more as the severity of an individual's obesity increases.

Being obese or overweight may substantially increase the risk of morbidity from hypertension; dyslipidemia; type 2 diabetes; coronary heart disease; stroke; gallbladder disease; osteoarthritis; sleep apnea and respiratory problems; and endometrial, breast, prostate, and colon cancers. Higher body weights are also associated with increases in all-cause mortality. Furthermore, being obese or overweight may cause a person to have a negative self-image about him or her self.

Upper body obesity is the strongest risk factor known for type 2 diabetes mellitus, and is a strong risk factor for cardiovascular disease. Obesity is a recognized risk factor for hypertension, atherosclerosis, congestive heart failure, stroke, gallbladder disease, osteoarthritis, sleep apnea, reproductive disorders such as polycystic ovarian syndrome, cancers of the breast, prostate, and colon, and increased incidence of complications, of general anesthesia (see, e.g., Kopelman, *Nature* 404: 635-43 (2000)). It reduces life-span and carries a serious risk of co-morbidities above, as well as disorders such as infections, varicose veins' acanthosis nigricans, eczema, exercise intolerance, insulin resistance, hypertension hypercholesterolemia, cholelithiasis, orthopedic injury, and thromboembolic disease (Rissanen et al., *Br. Med. J.* 301: 835-7 (1990)). Obesity is also a risk factor for the group of conditions called insulin resistance syndrome, or "Syndrome X." Recent estimate for the medical cost of obesity and associated disorders is $150 billion worldwide. The pathogenesis of obesity is believed to be multifactorial; generally, in obese or overweight subjects, when nutrient availability and energy expenditure equilibrate, an excess of adipose tissue results. Obesity is currently a poorly treatable, chronic, essentially intractable metabolic disorder. A therapeutic drug useful in weight reduction of obese persons could have a profound beneficial effect on their health.

For these reasons, there is an enormous interest in treating obesity. Existing therapies include standard diets and exercise, very low calorie diets, behavioral therapy, pharmacotherapy involving appetite suppressants, thermogenic drugs, food absorption inhibitors, mechanical devices such as jaw wiring, waist cords and balloons, and surgery, such as gastric bypass. Jung and Chong, *Clinical Endocrinology*, 35:11-20 (1991); Bray, *Am. J. Clin. Nutr.*, 55:538S-544S (1992).

In addition to the interest in treating obesity for physical health, the drive to look good and feel good about oneself has always been of interest and is a lucrative market. It has been reported by the American Society for Aesthetic Plastic Surgery that 6.9 million cosmetic procedures were performed in 2002. Liposuction was the most common surgical procedure. Moreover, the National Center for Health Statistics reported that, in 2002, about a third of all adult Americans engaged in regular leisure-time physical activity.

In general, while loss of fat is desired, loss of lean body mass (protein) is not. Lean body mass is highly active metabolically and physiologically. Lean body mass contains all the body protein. There is no real protein store as every protein molecule has a role in maintaining homeostasis. It is believed that loss of body protein is deleterious to the health of an individual. The majority of protein in the lean body mass is in the skeletal muscle mass. Lean body mass is 50-60% muscle mass by weight, the rest is bone and tendon. Protein makes up the critical cell structure in muscle, viscera, red cells and connective tissue. Enzymes, which direct metabolism, and antibodies, which maintain immune function, are also proteins. Moreover, a body with greater lean body mass to fat ratio may be more aesthetically pleasing to some individuals. Thus, it is desirable to prevent or minimize loss of lean body mass, even while reducing body fat.

Caloric restriction, regardless of its form, can cause catabolism of body protein and produce negative nitrogen balance. Protein-supplemented diets, therefore, have gained popularity as a means of lessening nitrogen loss during caloric restriction. Protein-sparing modified fasting has been reported to be effective in weight reduction in adolescents. Lee et al. *Clin. Pediatr.*, 31:234-236 (April 1992). However, these diets may produce only modest nitrogen sparing.

There remains a need to develop further PYY analog polypeptides. Accordingly, it is an object of the present invention to provide such PYY analog polypeptides and methods for producing and using them. A need exists for effective ways of promoting fat loss yet preserving lean body mass or minimizing its loss. Described herein are novel methods for modifying body composition.

All documents referred to herein are incorporated by reference into the present application as though fully set forth herein.

SUMMARY

The present invention relates generally to pancreatic polypeptide family ("PPF") polypeptides having at least 50%, at least 60%, at least 70%, at least 80%, at least 90%, at least 92%, at least 94% or at least 97% sequence identity to PYY(3-36) over the entire length of PYY(3-36), and also comprise at least two PPF motifs including at least the N-terminal polyproline PPF motif and the C-terminal tail PPF motif. Additional PPF motifs of the invention may correspond to any motif of any of the PP family polypeptides, including PP, PYY and NPY. In certain embodiments, the PPF polypeptides do not include unnatural amino acids. In other embodiments, the PPF polypeptides do not include known naturally occurring species variants.

In one aspect, the PPF polypeptides of the invention include PYY analog polypeptides. In yet another aspect of the invention, the PPF polypeptides of the invention include PPF chimeric polypeptides comprising a fragment of a PP, PYY or NPY polypeptide covalently linked to at least one additional fragment of a PP, PYY or NPY polypeptide, wherein each PP, PYY or NPY fragment includes a PPF motif. Such PPF analog polypeptides and PPF chimeric polypeptides of the invention will exhibit at least 50% sequence identity to a native PYY(3-36) over the entire length of the PYY(3-36). In certain embodiments, desirable PPF chimeric polypeptides include an N-terminal PP fragment in combination with a C-terminal PYY fragment. In other embodiments, PPF chimeric polypeptides include an N-terminal PP fragment in combination with a C-terminal NPY fragment. In other embodiments, PPF chimeric polypeptides include an N-terminal PYY fragment and a C-terminal PP or NPY fragment. In other embodiments, PPF chimeric polypeptides include an N-terminal NPY in combination with a C-terminal PYY or PP. In other embodiments, PPF chimeric polypeptides may not include an N-terminal PP fragment in combination with a C-terminal NPY fragment. In still other embodiments, PPF chimeric polypeptides may not include an N-terminal NPY fragment with a C-terminal PYY fragment.

In another aspect of the invention, methods for treating or preventing obesity are provided, wherein the method comprises administering a therapeutically or prophylactically effective amount of a PPF polypeptide of the invention to a subject in need thereof. In some embodiments, the subject is an obese or overweight subject. While "obesity" is generally defined as a body mass index over 30, for purposes of this disclosure, any subject, including those with a body mass index of less than 30, who needs or wishes to reduce body weight is included in the scope of "obese." Subjects who are insulin resistant, glucose intolerant, or have any form of diabetes mellitus (e.g., type 1, 2 or gestational diabetes) can benefit from this method.

In one general aspect, methods of the invention include the use of a PPF polypeptide to modify body composition, for example, reducing body fat, but not lean body mass. The change in body composition can be by, for example, weight (e.g., loss or gain by grams), by percent body fat and percent lean body mass or protein (used interchangeably), or by the ratio of body fat to lean tissue.

While it has been reported that PYY may be useful in regulating satiety (U.S. Pat. No. 6,558,708) or control of weight (U.S. patent application Ser. No. 10/016,969, WO2003026591 and WO2003057235), it has now surprisingly been discovered that PPF polypeptides may have a metabolic effect on the body and may be used to affect body composition, leading to the desirable loss of body fat, yet preserving lean body mass or minimizing its loss.

In certain embodiments, methods of the invention include reducing body fat or reducing or preventing body fat gain, while sparing, minimizing loss, or even increasing lean body mass. Other embodiments include controlling body weight and/or sculpting a body's appearance. The subjects to whom these methods may be of interest are those individuals who are overweight or obese, as well as those who are lean. For instance, subjects with lean body composition, e.g., body builders and other athletes, may benefit from the invention as well. It may be desirable for them to reduce or maintain their body weight, e.g., to stay in a certain weight class range, yet preserve or increase their lean body mass for greater strength, stamina, endurance and/or a more muscular appearance. Such methods may also be used on any animal for which a greater lean body mass to fat ratio is desired. Examples of such use include, but are not limited to, creating a superior show dog or creating a superior racehorse or workhorse.

In one general aspect, methods of the invention include the use of a PPF polypeptide to reduce the fat content in animals for consumption. Methods of the invention can include producing a leaner meat source. Compositions and methods of the invention can be used with livestock including, but not limited to, chicken, turkeys, cows, pigs, and sheep.

It is contemplated that methods of the invention can be used in combination with other forms of nutritional regimens and weight loss programs, such as those already described above, for example, those that include life-style changes that include monitoring food intake (quantity and quality) and exercising, as well as surgery. Nutritional regimens include those that are used to increase lean body mass such as those followed by body builders.

In another general aspect, PPF polypeptides reduce the respiratory quotient (RQ) in animals, which is indicative of improved fat utilization for energy at the tissue and cell level (increased fatty acid β-oxidation). Thus, PPF polypeptides may be therapeutically useful in conditions where improved fatty acid β-oxidation in non-adipose tissues is desirable with maintenance, minimization of loss, or an increase in lean body mass. Examples of such conditions include, but are not limited to, nonalcoholic steatohepatitis (NASH) (Grant et al. Nonalcoholic fatty liver disease, Ann Hepatol. 3(3):93-9 July-September 2004), in which patients display pathologically elevated liver fat content, and lipodystrophy, in which patients lack significant adipose stores, and hence display increased fat build-up in non-adipose tissues such as liver and skeletal muscle (Garg et al. Lipodystrophies: rare disorders causing metabolic syndrome, Endocrinol Metab Clin North Am. 33(2):305-31 June 2004).

In certain embodiments of the invention, a PPF polypeptide may be administered peripherally and not centrally, i.e, not through the central nervous system. In other embodiments, a therapeutically or prophylactically effective amount of a PPF polypeptide is administered in a single dose, multiple doses, or continuous administration.

In yet another aspect of the invention, compounds of the invention can be used for methods of reducing food intake, reducing nutrient availability, causing weight loss, affecting body composition, altering body energy content or energy expenditure (EE) and improving lipid profile (including reducing LDL cholesterol and/or triglyceride levels and/or changing HDL cholesterol levels). Thus, in certain embodiments, the methods of the invention are useful for treating or preventing conditions or disorders which can be alleviated by reducing nutrient availability in a subject in need thereof, comprising administering to said subject a therapeutically or prophylactically effective amount of a PPF polypeptide of the invention. Such conditions and disorders include, but are not limited to, hypertension, dyslipidemia, cardiovascular disease, eating disorders, insulin-resistance, obesity, diabetes mellitus of any kind, including Type I, Type II, and gestational diabetes. Compounds of the invention may also be useful in treating or preventing other conditions associated with obesity including stroke, cancer (e.g,. endometrial, breast, prostate, and colon cancer), gallbladder disease, sleep apnea, reduced fertility, and osteoarthritis, (see Lyznicki et al, *Am. Fam. Phys.* 63:2185, 2001).

Compounds of the invention may also be useful for potentiating, inducing, enhancing or restoring glucose responsivity in pancreatic islets or cells. These actions may also be used to treat or prevent conditions associated with metabolic disorders such as those described above and in U.S. patent application no. US20040228846.

In addition to the amelioration of hypertension in subjects in need thereof, compounds of the invention may be used to treat or prevent hypotension.

Compounds of the invention may also be useful in the treatment or prevention of any number of gastrointestinal disorders that are associated with excess intestinal electrolytes and water secretion as well as decreased absorption, e.g., infectious (e.g., viral or bacterial) diarrhea, inflammatory diarrhea, short bowel syndrome, or the diarrhea which typically occurs following surgical procedure, e.g., ileostomy (see e.g., Harrison's principles of Internal Medicine, McGraw Hill Inc., New York, 12th ed.). Examples of infectious diarrhea include, without limitation, acute viral diarrhea, acute bacterial diarrhea (e.g., *salmonella, campylobacter,* and *clostridium*) or diarrhea due to protozoal infections, or travellers' diarrhea (e.g., Norwalk virus or rotavirus). Examples of inflammatory diarrhea include, without limitation, malabsorption syndrome, tropical spue, chronic pancreatitis, Crohn's disease, diarrhea, and irritable bowel syndrome. It has also been discovered that the peptides of the invention can be used to treat or prevent an emergency or life-threatening situation involving a gastrointestinal disorder, e.g., after surgery or due to cholera. Furthermore, the compounds of the invention can be used to treat intestinal dysfunction in patients with Acquired Immune Deficiency Syndrome (AIDS), especially during cachexia. The compounds of the invention may also be useful for inhibiting small intestinal fluid and electrolyte secretion, and augmenting nutrient transport, as well as increasing cell proliferation in the gastrointestinal tract, regulating lipolysis in, e.g., adipose tissue and regulating blood flow in a mammal.

Compounds of the invention may also be useful for treating or preventing the above conditions by their gastrointestinal protective activity. Accordingly, compounds of the invention may be used to treat gastrointestinal or muscosal damage. Exemplary types of damage include, but are not limited to, inflammatory bowel disease, bowel atrophy, conditions characterized by loss of bowel mucosa or bowel mucosal function, and other conditions of the gastrointestinal tract, including those which may be brought about by exposure to cytotoxic agents, radiation, toxicity, infection and/or injury. Moreover, these compounds of the invention may be combined with analgesics, anti-inflammatory agents, growth hormone, heparin, or any other therapies that may be used to treat inflammatory bowel disease or other conditions listed above.

Moreover, compounds of the invention are useful in treating or preventing diseases and disorders that can be alleviated or ameliorated by their anti-secretory properties. Such anti-secretory properties include inhibition of gastric and/or pancreatic secretions and can be useful in the treatment or prevention of diseases and disorders including gastritis, pancreatitis, Barrett's esophagus, and Gastroesophageal Reflux Disease. These diseases may also be treated or prevented by the gastrointestinal protective functions of compounds of the invention.

Compounds of the invention may also be useful for reducing aluminum concentrations in the central nervous system of a subject to treat or prevent a disease or condition associated with abnormal aluminum concentrations (e.g., a patient afflicted with Alzheimer's disease or at risk for developing Alzheimer's disease, dialysis dementia, or increased aluminum levels due to occupational exposure).

The present invention also relates to pharmaceutical compositions comprising a therapeutically or prophylactically effective amount of at least one PPF polypeptide of the invention, or a pharmaceutically acceptable salt thereof, together with pharmaceutically acceptable diluents, preservatives, solubilizers, emulsifiers, adjuvants and/or carriers useful in the delivery of the PPF polypeptides.

These and other aspects of the invention will be more clearly understood with reference to the following embodiments and detailed description. The details of one or more embodiments of the invention are set forth in the accompanying drawings and the description below. Other features, objects, and advantages of the invention will be apparent from the description and drawings, and from the claims. All references cited herein are incorporated by reference.

BRIEF DESCRIPTION OF THE DRAWINGS

FIG. 8 demonstrates the activity of a PPF polypeptide of the invention in a food intake assay in the DIO mouse model, as compared to PYY(3-36).

FIGS. 9A-9D demonstrate the effect of PPF polypeptides of the invention on heart rate and blood pressure, as compared to PYY and PYY(3-36).

FIG. 46 depicts effects of administration of an exemplary PPF polypeptide on heart rate and mean arterial pressure (MAP) in rats.

DETAILED DESCRIPTION

Figure 1:
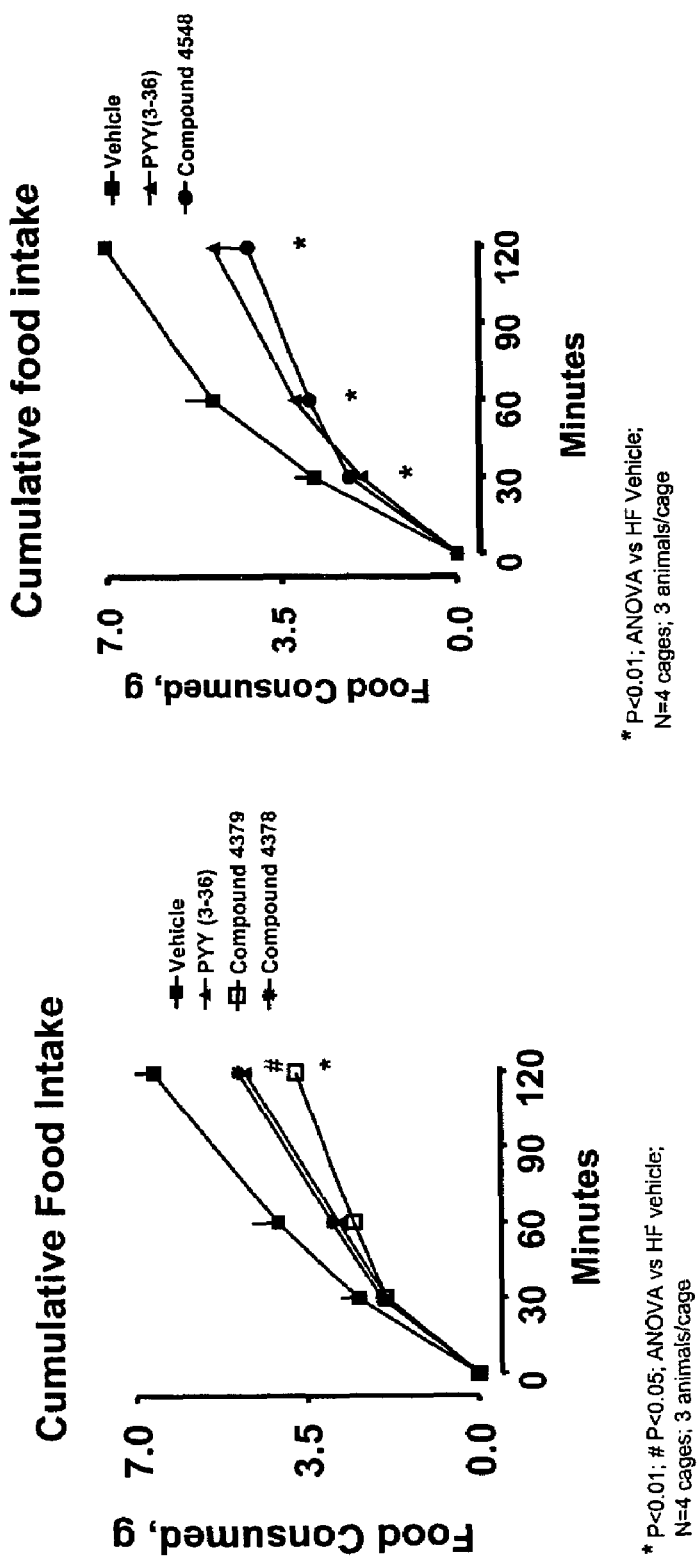
FIG. 1 demonstrates the activity of certain PPF polypeptides of the invention in a food intake assay.
Figure 2:
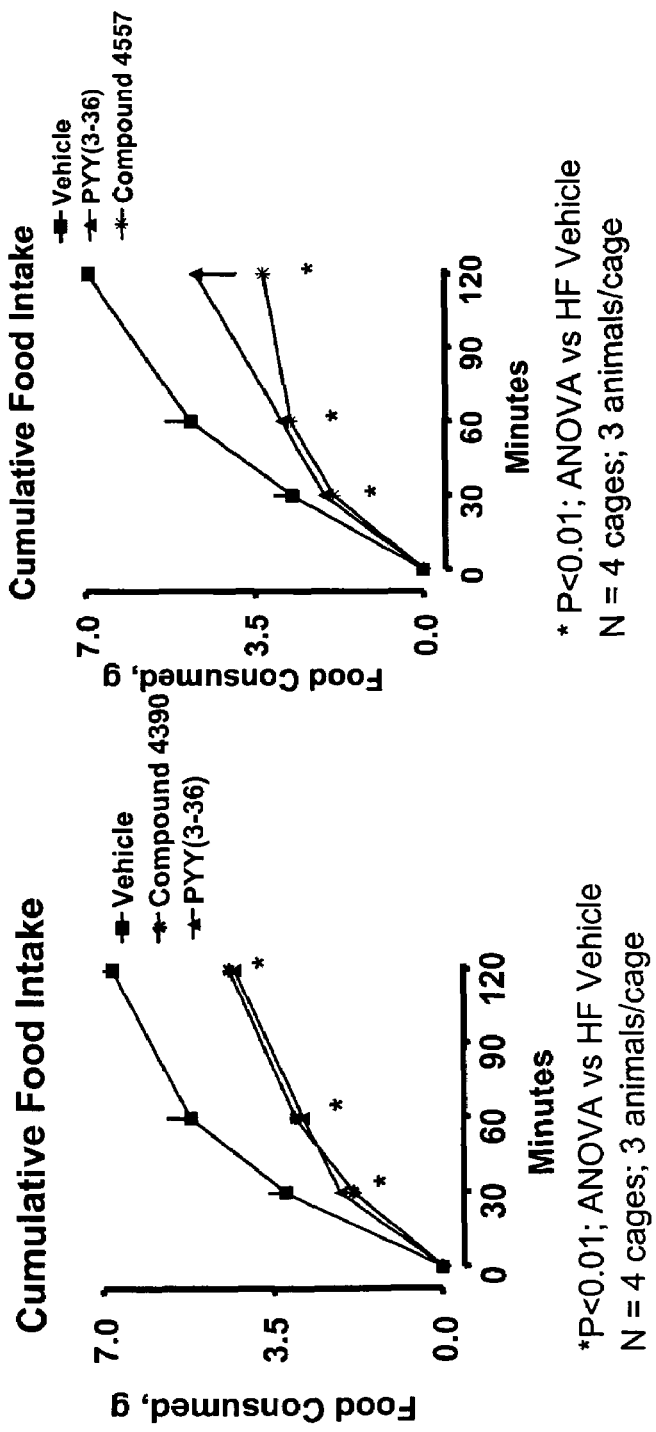
FIG. 2 demonstrates the activity of additional PPF polypeptides of the invention in a food intake assay.
Figure 3:
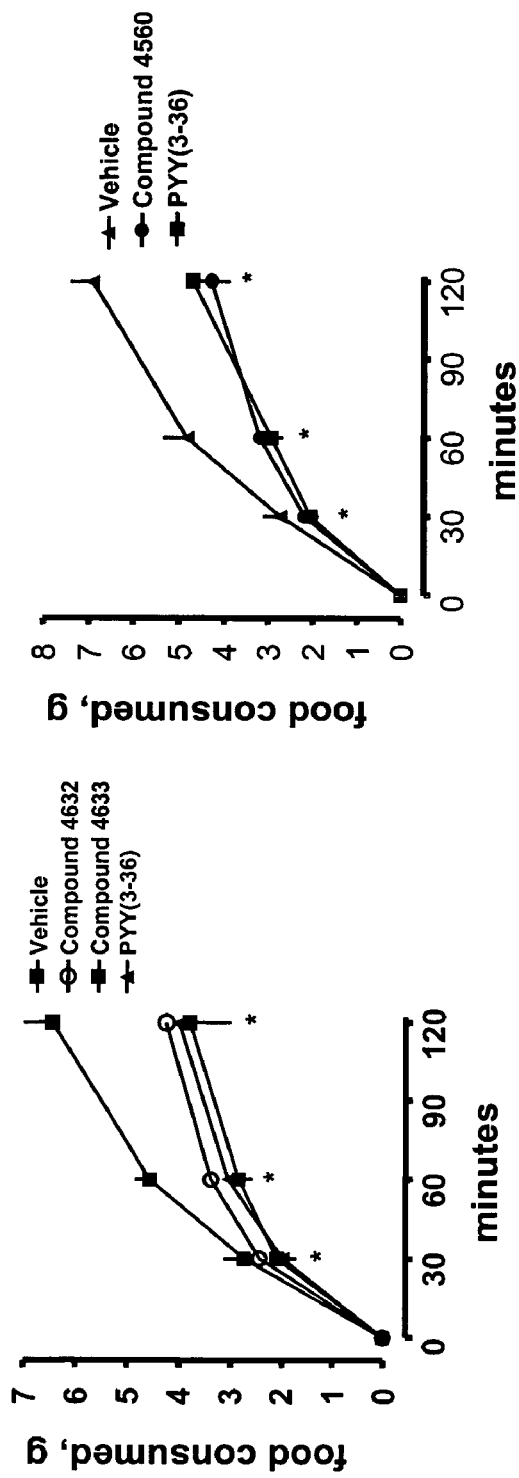
FIG. 3 demonstrates the activity of yet additional PPF polypeptides of the invention in a food intake assays.
Figure 4:
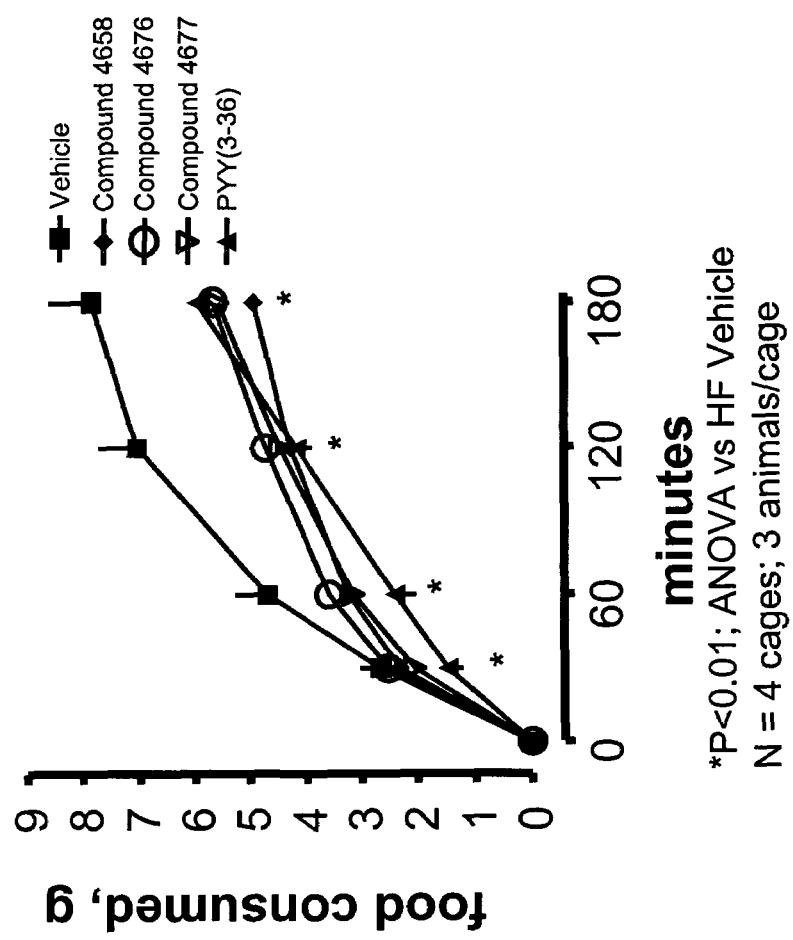
FIG. 4 demonstrates the activity of yet additional PPF polypeptides of the invention in a food intake assay.

The present invention relates generally to pancreatic polypeptide family ("PPF") polypeptides having at least 50%, at least 60%, at least 70%, at least 80%, at least 90%, at least 92%, at least 94% or at least 97% sequence identity to PYY(3-36) over the entire length of PYY(3-36). The PPF polypeptides may comprise not more than 10, not more than 5, not more than 3, not more than 2 or not more than 1 amino acid substitutions. The PPF polypeptides also comprise at least two PPF motifs including at least the N-terminal polyproline PPF motif and the C-terminal tail PPF motif. As used herein, "motif" refers to an amino acid sequence that is characteristic of a specific biochemical function or defines an independently folded domain. Additional PPF motifs of the invention may correspond to a motif of any of the PP family polypeptides, including PP, PYY and NPY, for example the type II β-turn region motif of PYY, or the α-helical motif at the C-terminal end of PYY. In certain embodiments, the PPF polypeptides of the invention may not include any unnatural amino acids.

The present invention also relates to PPF polypeptides useful in the treatment and prevention of metabolic conditions and disorders. In some embodiments, the PPF polypeptides of the invention may have comparable or higher potency in the treatment and/or prevention of metabolic conditions and disorders, as compared to native human PP, PYY, PYY(3-36) or NPY. In some embodiments, PPF polypeptides of the invention may exhibit less potency but may possess other desirable features such as improved ease of manufacture, stability, and/or ease of formulation, as compared to PP, PYY, PYY(3-36), or NPY.

In some embodiments, and without intending to be limited by theory, it is believed that the peripheral administration of the novel PPF polypeptides of the invention to a subject reduces nutrient availability, and thus is useful in the treatment and prevention of obesity and related metabolic conditions or disorders. As such, the present invention provides PPF polypeptide compositions and methods of using them to reduce nutrient availability in a subject in need thereof for treating and preventing metabolic conditions or disorders that may benefit from a reduction in nutrient availability. These methods may be useful in the treatment of, for example, obesity, diabetes, including but not limited to type 2 or non-insulin dependent diabetes, eating disorders, insulin-resistance syndrome, cardiovascular disease, or a combination of such conditions.

It has now been discovered that a PYY, PYY agonist or PPF polypeptide may have metabolic effects on the body and may be used to preferentially reduce or maintain body fat and spare or increase lean body mass.

The present invention is directed, in part, to affecting body composition by reducing body weight, maintaining body weight, or reducing body weight gain, while selectively reducing body fat or reducing or preventing body fat gain and maintaining or increasing lean body mass. In certain situations, however, e.g., body building, it may be desirable to increase body weight, for example, through selective nutrient intake (e.g., increasing the caloric or fat content), while reducing or maintaining percent body fat.

The methods of the invention contemplate the administration of an effective amount of a PYY, PYY agonist or PPF polypeptide to a subject to affect the desired results as described in the present application.

The administered PYY, PYY agonist or PPF polypeptide may be in the form of a peptide, a prodrug, or as pharmaceutical salts thereof. The term "prodrug" refers to a compound that is a drug precursor that, following administration, releases the drug in vivo via some chemical or physiological process, for example, proteolytic cleavage, or upon reaching an environment of a certain pH.

Methods of the invention can be used on any individual in need of such methods or individuals for whom practice of the methods is desired. These individuals may be any mammal including, but not limited to, humans, dogs, horses, cows, pigs, chickens, turkeys and other commercially valuable or companion animals.

The section headings are used herein for organizational purposes only, and are not to be construed as in any way limiting the subject matter described.

A. PPF Polypeptides of the Invention and PPF Motifs

As discussed above, the present invention relates, at least in part, to novel PPF polypeptides comprising at least two PPF motifs, wherein the at least two PPF motifs include at least the N-terminal polyproline PPF motif and the C-terminal tail PPF motif. The PPF polypeptides of the invention will also exhibit at least 50%, at least 60%, at least 70%, at least 80%, at least 90%, at least 92%, at least 94% or at least 97% sequence identity to a native PYY(3-36) over the entire length of the PYY(3-36). In some embodiments, the polypeptides of the present invention will retain, at least in part, a biological activity of native human PP, PYY or NPY, e.g., the polypeptides of the present invention will generally be PP, PYY and/or NPY agonists or antagonists. In some embodiments, the polypeptides of the present invention will exhibit biological activity in the treatment and prevention of metabolic conditions and disorders. Further, the PPF polypeptides of the invention may include internal linker compounds, may include chemical modifications at internal amino acid residues, or may be chemically modified at the N-terminal or C-terminal residue. In some embodiments, the polypeptides of the invention include only natural L amino acid residues and/or modified natural L amino acid residues. In some embodiments, the polypeptides of the invention do not include unnatural amino acid residues.

The PPF motifs of the invention may correspond to any motif of any of the native PP family polypeptides, including PP, PYY and NPY. A "PPF motif" is generally a structural component, primary, secondary, or tertiary, of a native PP family polypeptide that is critical to biological activity, i.e., biological activity is substantially decreased in the absence or disturbance of the motif. PPF motifs can include any of those known in the art, including, but not limited to, the N-terminal polyproline type II motif of a native PP family polypeptide, the type II β-turn motif of native PP family polypeptide, the α-helical motif at the C-terminal end of native PP family polypeptide, and the C-terminal tail motif of native PP family polypeptide. More particularly, in the N-terminal polyproline PPF motif, amino acids corresponding to residues 5 and 8 of a native PP family polypeptide are generally conserved as a proline. The type II β-turn motif will generally include amino acids corresponding to residues 12-14 of a native PP family polypeptide. The α-helical motif can generally extend from amino acids corresponding to approximately residue 14 of a native PP family polypeptide to any point up to and including the C-terminal end, so long as the α-helical motif includes a sufficient number of amino acid residues such that an α-helical turn is formed in solution. The α-helical motif can also include amino acid substitutions, insertions and deletions to the native PP family sequence, so long as the α-helical turn is still formed in solution. The C-terminal tail PPF motif generally includes amino acids corresponding to approximately the last 10 residues of a native PP family polypeptide. In some embodiments, the C-terminal tail motif includes the last 7, 6, or 5 residues of a native PP family polypeptide. In some embodiments, the C-terminal tail motif includes amino acid residues 32-35.

In one embodiment, the PPF polypeptides of the invention do not include any unnatural amino acid resides, and further with the provisio that the PPF polypeptides of the invention do not include any native PPF polypeptides (e.g., PP, NPY(1-36), NPY(3-36), PYY(1-36), PYY(3-36), NPY(2-36), NPY(4-36), PYY(2-36), PYY(4-36), PP(2-36), PP(3-36), or PP(4-36)). In some embodiments, the PPF polypeptides of the invention do not include: $Tyr^1hPP$, $Lys^4hPP$, $Asn^7hPP$, $Arg^{19}hPP$, $Tyr^{21}hPP$, $Glu^{21}hPP$, $Ala^{23}hPP$, $Gln^{23}hPP$, $Gln^{34}hPP$, $Phe^6Arg^{19}hPP$, $Phe^6Tyr^{21}hPP$, $Phe^6Glu^{21}hPP$, $Phe^6Ala^{23}hPP$, $Phe^6Gln^{23}hPP$, $Pro^{13}Ala^{14}hPP$, $Ile^{31}Gln^{34}PP$, $Arg^{19}Tyr^{20}Tyr^{21}Ser^{22}Ala^{23}hPP$, $Lys^4Arg^{19}Tyr^{20}Tyr^{21}Ser^{22}Ala^{23}hPP$, $Lys^4Arg^{19}Tyr^{20}Tyr^{21}Ser^{22}Ala^{23}hPP(2-36)$, $Ala^1NPY$, $Tyr^1NPY$, $Ala^2NPY$, $Leu^2NPY$, $Phe^2NPY$, $His^2NPY$, $Ala^3NPY$, $Ala^4NPY$, $Ala^6NPY$, $Tyr^7pNPY$, $Ala^7NPY$, $Ala^9NPY$, $Ala^{10}NPY$, $Ala^{11}NPY$, $Gly^{12}NPY$, $Ala^{13}NPY$, $Gly^{14}NPY$, $Ala^{15}NPY$, $Ala^{16}NPY$, $Ala^{17}NPY$, $Gly^{18}NPY$, $Ala^{19}NPY$, $Lys^{19}NPY$, $Ala^{20}NPY$, $Ala^{21}NPY$, $Ala^{22}NPY$, $Gly^{23}NPY$, $Ala^{24}NPY$, $Trp^{24}pNPY$, $Ala^{25}NPY$, $Lys^{25}NPY$, $Ala^{26}NPY$, $Ala^{27}NPY$, $Phe^{27}NPY$, $Ala^{28}NPY$, $Ala^{29}NPY$, $Gln^{29}NPY$, $Ala^{30}NPY$, $Phe^{30}NPY$, $Ala^{31}NPY$, $Trp^{31}pNPY$, $Ala^{32}NPY$, $Trp^{32}NPY$, $Ala^{33}NPY$, $Lys^{33}NPY$, $Ala^{34}NPY$, $Pro^{34}NPY$, $Leu^{34}NPY$, $Ala^{35}NPY$, $Lys^{35}NPY$, $Ala^{36}NPY$, $Phe^{36}NPY$, $His^{36}NPY$, $Glu^4Pro^{34}pNPY$, $Arg^6Pro^{34}pNPY$, $Phe^6Pro^{34}pNPY$, $Cys^6Pro^{34}pNPY$, $Asn^6Pro^{34}pNPY$, $Phe^7Pro^{34}pNPY$, $Arg^7Pro^{34}pNPY$, $Cys^7Pro^{34}pNPY$, $Asp^7Pro^{34}pNPY$, $Phe^8Pro^{34}pNPY$, $Arg^8Pro^{34}pNPY$, $Cys^8Pro^{34}pNPY$, $Asp^8Pro^{34}pNPY$, $Asn^8Pro^{34}pNPY$, $Pro^{11}Pro^{34}pNPY$, $Ser^{13}Pro^{14}pNPY$, $Trp^{24,31}pNPY$, $Ala^{31}Pro^{32}pNPY$, $Cys^{31}Pro\ pNPY$, $Leu^{31}Pro^{34}NPY$, $Phe^{32}Pro^{34}pNPY$, $Ala^{21,25}Pro^{34}pNPY$, $Pro^{11}Tyr^{13}Pro^{14}Pro^{34}pNPY$, Ahx(9-22)pNPY, Ahx(9-17)

pNPY, des-AA(10-20)-Cys$^{7,21}$Pro$^{34}$-pNPY, des-AA(10-17)-pNPY, des-AA(10-17)-Cys$^{2,27}$-pNPY, des-AA(10-17)-Ala$^{7,21}$-pNPY, des-AA(10-17)-Cys$^{7,21}$-pNPY, des-AA(10-17)-Glu$^{7}$Lys$^{21}$-pNPY, des-AA(10-17)Cys$^{7,21}$Pro$^{34}$pNPY, des-AA(10-17)Glu$^{7}$Lys$^{21}$Pro$^{34}$pNPY, des-AA(10-17) Cys$^{7,21}$Leu$^{31}$Pro$^{34}$pNPY, des-AA(11-17)Cys$^{7,21}$Pro$^{34}$pNPY, Pro$^{34}$PYY, His$^{34}$PYY, Lys$^{25}$hPYY(5-36), Arg$^{4}$hPYY(4-36), Gln$^{4}$hPYY(4-36), Asn$^{4}$hPYY(4-36), Lys$^{25}$hPYY(4-36), Leu$^{3}$hPYY(3-36), Val$^{3}$hPYY(3-36), Lys$^{25}$hPYY(3-36), Tyr$^{1,36}$pPYY, Pro$^{13}$Ala$^{14}$hPYY, Leu$^{31}$Pro$^{34}$PYY, FMS-PYY, FMS-PYY(3-36), Fmoc-PYY, Fmoc-PYY(3-36), FMS$_2$-PYY, FMS$_2$-PYY(3-36), Fmoc$_2$-PYY, Fmoc$_2$-PYY(3-36), hPP(1-7)-pNPY, hPP(1-17)-pNPY, hPP(19-23)-pNPY, hPP(19-23)-Pro$^{34}$pNPY, hPP(19-23)-His$^{34}$pNPY, rPP(19-23)-pNPY, rPP(19-23)-Pro$^{34}$pNPY, rPP(19-23)-His$^{34}$pNPY, hPP(1-7)-pNPY, hPP(1-17)-pNPY, hPP(1-17)-His$^{34}$pNPY, pNPY(1-7)-hPP, pNPY(1-7, 19-23)-hPP, cPP(1-7)-pNPY(19-23)-hPP, cPP(1-7)-NPY(19-23)-His$^{34}$hPP, hPP(1-17)-His$^{34}$pNPY, hPP(19-23)-pNPY, hPP(19-23)-Pro$^{34}$pNPY, hPP(19-23)-His$^{34}$pNPY, rPP(19-23)-pNPY, rPP(19-23)-Pro$^{34}$pNPY, rPP(19-23)-His$^{34}$pNPY, pNPY(1-7)-hPP, pNPY(19-23)-hPP, pNPY(19-23)-Gln$^{34}$hPP, pNPY(19-23)-His$^{34}$hPP, pNPY(19-23)-Phe$^{6}$Gln$^{34}$hPp, pNPY(19-23)-Phe$^{6}$His$^{34}$hPP, pNPY(1-7,19-23)-hPP, pNPY(1-7,19-23)-Gln$^{34}$hPP, cPP(20-23)-Pro$^{34}$-pNPY, cPP(21-23)-Pro$^{34}$-pNPY, cPP(22-23)-Pro$^{34}$-pNPY, cPP(1-7)-Pro$^{34}$-pNPY, cPP(20-23)-Pro$^{34}$-pNPY, cPP(1-7,20-23)-Pro$^{34}$-pNPY, cPP(1-7)-pNPY(19-23)-hPP, cPP(1-7)-pNPY(19-23)-His$^{34}$hPP, or cPP(1-7)-gPP(19-23)-hPP.

In another embodiment, such PPF polypeptides of the invention also do not include: Thr$^{27}$hPYY(3-36), Ile$^{30}$hPYY(3-36), Ser$^{32}$hPYY(3-36), Lys$^{33}$hPYY(3-36), Asn$^{34}$hPYY(3-36), Lys$^{35}$hPYY(3-36), Thr$^{36}$hPYY(3-36), Lys$^{25}$Thr$^{27}$hPYY(3-36), Lys$^{25}$Ile$^{30}$hPYY(3-36), Lys$^{25}$Ser$^{32}$hPYY(3-36), Lys$^{25}$Lys$^{33}$hPYY(3-36), Lys$^{25}$Asn$^{24}$hPYY(3-36), Lys$^{25}$Lys$^{35}$hPYY(3-36), Lys$^{25}$Thr$^{36}$hPYY(3-36), Thr$^{27}$Ile$^{28}$hPYY(3-36), Thr$^{27}$Val$^{28}$hPYY(3-36), Thr$^{27}$Gln$^{29}$hPYY(3-36), Thr$^{27}$Ile$^{30}$hPYY(3-36), Thr$^{27}$Val$^{30}$hPYY(3-36), Thr$^{27}$Ile$^{31}$hPYY(3-36), Thr$^{27}$Leu$^{34}$hPYY(3-36), Thr$^{27}$Ser$^{32}$hPYY(3-36), Thr$^{27}$Lys$^{33}$hPYY(3-36), Thr$^{27}$Asn$^{34}$hPYY(3-36), Thr$^{27}$Lys$^{35}$hPYY(3-36), Thr$^{27}$Thr$^{36}$hPYY(3-36), Thr$^{27}$Phe$^{36}$hPYY(3-36), Phe$^{27}$Ile$^{30}$hPYY(3-36), Phe$^{27}$Ser$^{32}$hPYY(3-36), Phe$^{27}$Lys$^{33}$hPYY(3-36), Phe$^{27}$Asn$^{34}$hPYY(3-36), Phe$^{27}$Lys$^{35}$hPYY(3-36), Phe$^{27}$Thr$^{36}$hPYY(3-36), Gln$^{29}$Ile$^{30}$hPYY(3-36), Gln$^{29}$Ser$^{32}$hPYY(3-36), Gln$^{29}$Leu$^{33}$hPYY(3-36), Gln$^{29}$Asn$^{34}$hPYY(3-36), Gln$^{29}$Leu$^{35}$hPYY(3-36), Gln$^{29}$Thr$^{36}$hPYY(3-36), Ile$^{30}$Ile$^{31}$hPYY(3-36), Ile$^{30}$Leu$^{31}$hPYY(3-36), Ile$^{30}$Ser$^{32}$hPYY(3-36), Ile$^{30}$Lys$^{33}$hPYY(3-36), Ile$^{30}$Asn$^{34}$hPYY(3-36), Ile$^{30}$Lys$^{35}$hPYY(3-36), Ile$^{30}$Thr$^{36}$hPYY(3-36), Ile$^{30}$Phe$^{36}$hPYY(3-36), Val$^{30}$Ser$^{32}$hPYY(3-36), Val$^{30}$Lys$^{33}$hPYY(3-36), Val$^{30}$Asn$^{34}$hPYY(3-36), Val$^{30}$Lys$^{35}$hPYY(3-36), Val$^{30}$Thr$^{36}$hPYY(3-36), Ile$^{31}$Ser$^{32}$hPYY(3-36), Ile$^{31}$Lys$^{33}$hPYY(3-36), Ile$^{31}$Asn$^{34}$hPYY(3-36), Ile$^{30}$Lys$^{35}$hPYY(3-36), Ile$^{31}$Thr$^{36}$hPYY(3-36), Ile$^{31}$Phe$^{36}$hPYY(3-36), Leu$^{31}$Ser$^{32}$hPYY(3-36), Leu$^{31}$Lys$^{33}$hPYY(3-36), Leu$^{31}$Asn$^{34}$hPYY(3-36), Leu$^{31}$Lys$^{35}$hPYY(3-36), Leu$^{31}$Thr$^{36}$hPYY(3-36), Ser$^{32}$Lys$^{33}$hPYY(3-36), Ser$^{32}$Asn$^{34}$hPYY(3-36), Ser$^{32}$Lys$^{35}$hPYY(3-36), Ser$^{32}$Lys$^{35}$hPYY(3-36), Ser$^{32}$Phe$^{36}$hPYY(3-36), Lys$^{33}$Asn$^{34}$hPYY(3-36), Lys$^{33}$Lys$^{35}$hPYY(3-36), Lys$^{33}$Thr$^{36}$hPYY(3-36), Lys$^{33}$Phe$^{36}$hPYY(3-36), Asn$^{34}$Lys$^{35}$hPYY(3-36), Asn$^{34}$Phe$^{36}$hPYY(3-36), Lys$^{35}$Thr$^{36}$hPYY(3-36), Lys$^{35}$Phe$^{36}$hPYY(3-36), Thr$^{27}$hPYY(4-36), Phe$^{27}$hPYY(4-36), Ile$^{28}$hPYY(4-36), Val$^{28}$hPYY(4-36), Gln$^{29}$hPYY(4-36), Ile$^{30}$hPYY(4-36), Val$^{30}$hPYY(4-36), Ile$^{31}$hPYY(4-36), Leu$^{31}$hPYY(4-36), Ser$^{32}$hPYY(4-36), Lys$^{33}$hPYY(4-36), Asn$^{34}$hPYY(4-36), Lys$^{35}$hPYY(4-36), Thr$^{36}$hPYY(4-36), Phe$^{36}$hPYY(4-36), Lys$^{25}$Thr$^{27}$hPYY(4-36), Lys$^{25}$Phe$^{27}$hPYY(4-36), Lys$^{25}$Ile$^{28}$hPYY(4-36), Lys$^{25}$Val$^{28}$hPYY(4-36), Lys$^{25}$Gln$^{29}$hPYY(4-36), Lys$^{25}$Ile$^{30}$hPYY(4-36), Lys$^{25}$Val$^{30}$hPYY(4-36), Lys$^{25}$Ile$^{31}$hPYY(4-36), Lys$^{25}$Leu$^{31}$hPYY(4-36), Lys$^{25}$Ser$^{32}$hPYY(4-36), Lys$^{25}$Lys$^{33}$hPYY(4-36), Lys$^{25}$Asn$^{24}$hPYY(4-36), Lys$^{25}$Lys$^{35}$hPYY(4-36), Lys$^{25}$Thr$^{36}$PYY(4-36), Lys$^{25}$Phe$^{36}$hPYY(4-36), Thr$^{27}$Ile$^{28}$hPYY(4-36), Thr$^{27}$Val$^{28}$hPYY(4-36), Thr$^{27}$Gln$^{29}$hPYY(4-36), Thr$^{27}$Ile$^{30}$hPYY(4-36), Thr$^{27}$Val$^{30}$hPYY(4-36), Thr$^{27}$Ile$^{31}$hPYY(4-36), Thr$^{27}$Leu$^{31}$hPYY(4-36), Thr$^{27}$Ser$^{32}$hPYY(4-36), Thr$^{27}$Lys$^{33}$hPYY(4-36), Thr$^{27}$Asn$^{34}$hPYY(4-36), Thr$^{27}$Lys$^{35}$hPYY(4-36), Thr$^{27}$Thr$^{36}$hPYY(4-36), Thr$^{27}$Phe$^{36}$hPYY(4-36), Phe$^{27}$Ile$^{28}$hPYY(4-36), Phe$^{27}$Val$^{28}$hPYY(4-36), Phe$^{27}$Gln$^{29}$hPYY(4-36), Phe$^{27}$Ile$^{30}$hPYY(4-36), Phe$^{27}$Val$^{30}$hPYY(4-36), Phe$^{27}$Ile$^{31}$hPYY(4-36), Phe$^{27}$Leu$^{31}$hPYY(4-36), Phe$^{27}$Ser$^{32}$hPYY(4-36), Phe$^{27}$Lys$^{33}$PYY(4-36), Phe$^{27}$Asn$^{34}$hPYY(4-36), Phe$^{27}$Lys$^{35}$hPYY(4-36), Phe$^{27}$Thr$^{36}$hPYY(4-36), Phe$^{27}$Phe$^{36}$hPYY(4-36), Gln$^{29}$Ile$^{30}$hPYY(4-36), Gln$^{29}$Val$^{30}$hPYY(4-36), Gln$^{29}$Ile$^{31}$hPYY(4-36), Gln$^{29}$Leu$^{31}$hPYY(4-36), Gln$^{29}$Ser$^{32}$hPYY(4-36), Gln$^{29}$Leu$^{33}$hPYY(4-36), Gln$^{29}$Asn$^{34}$hPYY(4-36), Gln$^{29}$Leu$^{35}$hPYY(4-36), Gln$^{29}$Thr$^{36}$hPYY(4-36), Gln$^{29}$Phe$^{36}$hPYY(4-36), Ile$^{30}$Ile$^{31}$hPYY(4-36), Ile$^{30}$Leu$^{31}$hPYY(4-36), Ile$^{30}$Ser$^{32}$hPYY(4-36), Ile$^{30}$Lys$^{33}$hPYY(4-36), Ile$^{30}$Asn$^{34}$hPYY(4-36), Ile$^{30}$Lys$^{35}$hPYY(4-36), Ile$^{30}$Thr$^{36}$hPYY(4-36), Ile$^{30}$Phe$^{36}$hPYY(4-36), Val$^{30}$Ile$^{31}$hPYY(4-36), Val$^{30}$Leu$^{31}$hPYY(4-36), Val$^{30}$Ser$^{32}$hPYY(4-36), Val$^{30}$Lys$^{33}$hPYY(4-36), Val$^{30}$Asn$^{34}$hPYY(4-36), Val$^{30}$Lys$^{35}$hPYY(4-36), Val$^{30}$Thr$^{36}$hPYY(4-36), Val$^{30}$Phe$^{36}$hPYY(4-36), Ile$^{31}$Ser$^{32}$hPYY(4-36), Ile$^{31}$Lys$^{33}$hPYY(4-36), Ile$^{31}$Asn$^{34}$hPYY(4-36), Ile$^{31}$Lys$^{35}$hPYY(4-36), Ile$^{31}$Thr$^{36}$hPYY(4-36), Leu$^{3}$Phe$^{36}$hPYY(4-36), Leu$^{31}$Phe$^{36}$hPYY(4-36), Leu$^{31}$Ser$^{32}$hPYY(4-36), Val$^{31}$Lys$^{33}$hPYY(4-36), Leu$^{31}$Asn$^{34}$hPYY(4-36), Leu$^{31}$Lys$^{35}$hPYY(4-36), Leu$^{31}$Thr$^{36}$hPYY(4-36), Leu$^{31}$Phe$^{36}$hPYY(4-36), Ser$^{32}$Lys$^{33}$hPYY(4-36), Ser$^{32}$Asn$^{34}$hPYY(4-36), Ser$^{32}$Lys$^{35}$hPYY(4-36), Ser$^{32}$Thr$^{36}$hPYY(4-36), Ser$^{32}$Phe$^{36}$hPYY(4-36), Lys$^{33}$Asn$^{34}$hPYY(4-36), Lys$^{33}$Lys$^{35}$hPYY(4-36), Lys$^{33}$Thr$^{36}$hPYY(4-36), Lys$^{33}$Phe$^{36}$hPYY(4-36), Asn$^{34}$Lys$^{35}$hPYY(4-36), Asn$^{34}$Phe$^{36}$hPYY(4-36), Lys$^{35}$Thr$^{36}$hPYY(4-36), Lys$^{35}$Phe$^{36}$hPYY(4-36), Thr$^{27}$hPYY(5-36), Phe$^{27}$hPYY(5-36), Ile$^{28}$hPYY(5-36), Val$^{28}$hPYY(5-36), Gln$^{29}$hPYY(5-36), Ile$^{30}$hPYY(5-36), Val$^{30}$hPYY(5-36), Ile$^{31}$hPYY(5-36), Leu$^{31}$hPYY(5-36), Ser$^{32}$hPYY(5-36), Lys$^{33}$hPYY(5-36), Asn$^{34}$hPYY(5-36), Lys$^{35}$hPYY(5-36), Thr$^{36}$hPYY(5-36), Phe$^{36}$hPYY(5-36), Lys$^{25}$Thr$^{27}$hPYY(5-36), Lys$^{25}$Phe$^{27}$hPYY(5-36), Lys$^{25}$Ile$^{28}$hPYY(5-36), Lys$^{25}$Val$^{28}$hPYY(5-36), Lys$^{25}$Gln$^{29}$hPYY(5-36), Lys$^{25}$Ile$^{30}$hPYY(5-36), Lys$^{25}$Val$^{30}$hPYY(5-36), Lys$^{25}$Ile$^{31}$hPYY(5-36), Lys$^{25}$Leu$^{31}$hPYY(5-36), Lys$^{25}$Ser$^{32}$hPYY(5-36), Lys$^{25}$Lys$^{33}$hPYY(5-36), Lys$^{25}$Asn$^{24}$hPYY(5-36), Lys$^{25}$Lys$^{35}$hPYY(5-36), Lys$^{25}$Thr$^{36}$hPYY(5-36), Lys$^{25}$Phe$^{36}$hPYY(5-36), Thr$^{27}$Ile$^{28}$hPYY(5-36), Thr$^{27}$Val$^{28}$hPYY(5-36), Thr$^{27}$Gin$^{29}$hPYY(5-36), Thr$^{27}$Ile$^{30}$hPYY(5-36), Thr$^{27}$Val$^{30}$hPYY(5-36), Thr²⁷Ile³¹hPYY(5-36), Thr²⁷Leu³¹hPYY(5-36), Thr²⁷Ser³²hPYY(5-36), Thr²⁷Lys³⁶hPYY(5-36), Thr²⁷Asn³⁴hPYY(5-36), Thr²⁷Lys³⁵hPYY(5-36), Thr²⁷Thr³⁶hPYY(5-36), Thr²⁷Phe³⁶hPYY(5-36), Phe²⁷Ile²⁸hPYY(5-36), Phe²⁷Val²⁸hPYY(5-36), Phe²⁷Gln²⁹hPYY(5-36), Phe²⁷Ile³⁰hPYY(5-36), Phe²⁷Val³⁰hPYY(5-36), Phe²⁷Ile³¹hPYY(5-36), Phe²⁷Leu³⁶hPYY(5-36), Phe²⁷Ser³²hPYY(5-36), Phe²⁷Lys³³hPYY(5-36), Phe²⁷Asn³⁴hPYY(5-36), Phe²⁷Lys³⁵hPYY(5-36), Phe²⁷Thr³⁶hPYY(5-36), Phe²⁷Phe³⁶hPYY(5-36), Gln²⁹Ile³⁰hPYY(5-36), Gln²⁹Val³⁰hPYY(5-36), Gln²⁹Ile³¹hPYY(5-36), Gln²⁹Leu³¹hPYY(5-36), Gln²⁹Ser³²hPYY(5-36) Gln²⁹Leu³³hPYY(5-36), Gln²⁹Asn³⁴hPYY(5-36), Gln²⁹Leu³⁵hPYY(5-36), Gln²⁹Thr³⁶hPYY(5-36), Gln²⁹Phe³⁶hPYY(5-36), Ile³⁰Ile³¹hPYY(5-36), Ile³⁰Leu³¹hPYY(5-36), Ile³⁰Ser³²hPYY(5-36), Ile³⁰Lys³³hPYY(5-36), Ile³⁰Asn³⁴hPYY(5-36), Ile³⁰Lys³⁵hPYY(5-36), Ile³⁰Thr³⁶hPYY(5-36), Ile³⁰Phe³⁶hPYY(5-36), Val³⁰Ile³¹hPYY(5-36), Val³⁰Leu³⁵hPYY(5-36), Val³⁰Ser³²hPYY(5-36), Val³⁰Lys³³hPYY(5-36), Val³⁰Asn³⁴hPYY(5-36), Val³⁰Lys³⁵hPYY(5-36), Val³⁰Thr³⁶hPYY(5-36), Val³⁰Phe³⁶hPYY(5-36), Ile³¹Ser³²hPYY(5-36), Ile³⁰Lys³³hPYY(5-36), Ile³¹Asn³⁴hPYY(5-36), Ile³⁰Lys³⁵hPYY(5-36), Ile³⁰Thr³⁶hPYY(5-36), Leu³¹Phe³⁶hPYY(5-36), Leu³¹Phe³⁶hPYY(5-36), Leu³¹Ser³²hPYY(5-36), Val³¹Lys³³hPYY(5-36), Leu³¹Asn³⁴hPYY(5-36), Leu³¹Lys³⁵hPYY(5-36), Leu³¹Thr³⁶hPYY(5-36), Leu³¹Phe³⁶hPYY(5-36), Ser³²Lys³³hPYY(5-36), Ser³²Asn³⁴hPYY(5-36), Ser³²Lys³⁵hPYY(5-36), Ser³²Thr³⁶hPYY(5-36), Ser³²Phe³⁶hPYY(5-36), Lys³³Asn³⁴hPYY(5-36), Lys³³Lys³⁵hPYY(5-36), Lys³³Thr³⁶hPYY(5-36), Lys³³Phe³⁶hPYY(5-36), Asn³⁴Lys³⁵hPYY(5-36), Asn³⁴Phe³⁶hPYY(5-36), Lys³⁵Thr³⁶hPYY(5-36), or Lys³⁵Phe³⁶hPYY(5-36).

In another embodiment, the PPF polypeptides of the invention do not include any unnatural amino acid residues, and comprise a C-terminal tail motif of hPYY. The C-terminal tail motif may comprise amino acid residues 32-35 of hPYY, e.g., Thr, Arg, Gln, Arg (SEQ ID NO: 351). In such an embodiment, the PPF polypeptides of the invention do not include any native PPF polypeptides (e.g., NPY(1-36), NPY(3-36), PYY(1-36), PYY(3-36)), NPY(2-36), PYY(4-36), PYY(5-36)), (2-36)NPY, (2-36)PYY, Gln³⁴hPP, Ile³¹Gln³⁴PP, Ala¹NPY, Tyr¹NPY, Ala²NPY, Leu²NPY, Phe²NPY, His²NPY, Ala³NPY, Ala⁴NPY, Ala⁶NPY, Tyr⁷pNPY, Ala⁷NPY, Ala⁹NPY, Ala¹⁰NPY, Ala¹¹NPY, Gly¹²NPY, Ala¹³NPY, Gly¹⁴NPY, Ala¹⁵NPY, Ala¹⁶NPY, Ala¹⁷NPY, Gly¹⁸NPY Ala¹⁹NPY, Lys¹⁹NPY, Ala²⁰NPY, Ala²¹NPY, Ala²²NPY, Gly²³NPY, Ala²⁴NPY, Trp²⁴pNPY, Ala²⁵NPY, Lys²⁵NPY, Ala²⁶NPY, Ala²⁷NPY, Phe²⁷NPY, Ala²⁸NPY, Ala²⁹NPY, Gln²⁹NPY, Ala³⁰NPY, Phe³⁰NPY, Ala³¹NPY, Trp³¹pNPY, Ala³⁶NPY, Phe³⁶NPY, His³⁶NPY, Ahx(9-22)pNPY, Ahx(9-17)pNPY, des-AA(10-17)-pNPY, des-AA(10-17)-Cys²,²⁷-pNPY des-AA(10-17)-Ala⁷,²¹-pNPY, des-AA(10-17)-Cys⁷,²¹-pNPY, des-AA(10-17)-Glu⁷Lys²¹-pNPY, Lys²⁵hPYY(5-36), Arg⁴hPYY(4-36), Gln⁴hPYY(4-36), Asn⁴hPYY(4-36), Lys²⁵hPYY(4-36), Leu³hPYY(4-36), Val³hPYY(3-36), Lys²⁵hPYY(3-36), Tyr¹,³⁶pPYY, Pro¹³Ala¹⁴hPYY, FMS-PYY, FMS-PYY(3-36), Fmoc-PYY, Fmoc-PYY(3-36), FMS₂-PYY, FMS₂-PYY(3-36), Fmoc₂-PYY, Fmoc₂-PYY(3-36), hPP(1-7)-pNPY, hPP(1-17)-pNPY, hPP(19-23)-pNPY, rPP(19-23)-pNPY, hPP(1-7)-pNPY, hPP(1-17)-pNPY, hPP(19-23)-pNPY, rPP(19-23)-pNPY, pNPY(19-23)-Gln³⁴hPP, pNPY(19-23)-Phe⁶Gln³⁴hPP, or pNPY(11-7,19-23)-Gln³⁴hPP.

In another aspect, such PPF polypeptides of the invention comprising a C-terminal tail motif of hPYY also do not include: Thr²⁷hPYY(3-36), Ile³⁰hPYY(3-36), Thr³⁶hPYY(3-36), Lys²⁵Thr²⁷hPYY(3-36), Lys²⁵Ile³⁰hPYY(3-36), Lys²⁵Asn²⁴hPYY(3-36), Lys²⁵Thr³⁶hPYY(3-36), Thr³⁷Ile²⁸hPYY(3-36), Thr²⁷Val²⁸hPYY(3L36), Thr²⁷Gln²⁹hPYY(3-36), Thr²⁷Ile³⁰hPYY(3-36), Thr²⁷Val³⁰hPYY(3-36), Thr²⁷Ile³¹hPYY(3-36), Thr²⁷Leu³¹hPYY(3-36), Thr²⁷Thr³⁶hPYY(3-36), Thr²⁷Phe³⁶hPYY(3-36), Phe²⁷Ile³⁰hPYY(3-36), Phe²⁷Thr³⁶hPYY(3-36), Gln²⁹Ile³⁰hPYY(3-36), Gln²⁹Thr³⁶hPYY(3-36), Ile³⁰Ile³¹hPYY(3-36), Ile³⁰Leu³¹hPYY(3-36), Ile³⁰Thr³⁶hPYY(3-36), Ile³⁰Phe³⁶hPYY(3-36), Val³⁰Thr³⁶hPYY(3-36), Ile³¹Thr³⁶hPYY(3-36), Ile³¹Phe³⁶hPYY(3-36), Leu³¹Thr³⁶hPYY(3-36), Thr²⁷hPYY(4-36), Phe²⁷hPYY(4-36), Ile²⁸hPYY(4-36), Val²⁸hPYY(4-36), Gln²⁹hPYY(4-36), Ile³⁰hPYY(4-36), Val³⁰hPYY(4-36), Ile³¹hPYY(4-36), Leu³¹hPYY(4-36), Thr³⁶hPYY(4-36), Phe³⁶hPYY(4-36), Lys²⁵Thr²⁷hPYY(4-36), Lys²⁵Phe²⁷hPYY(4-36), Lys²⁵Ile²⁸hPYY(4-36), Lys²⁵Val²⁸hPYY(4-36), Lys²⁵Gln²⁹hPYY(4-36), Lys²⁵Ile³⁰hPYY(4-36), Lys²⁵Val³⁰hPYY(4-36), Lys²⁵Ile³¹hPYY(4-36), Lys²⁵Leu³¹hPYY(4-36), Lys²⁵Thr³⁶PYY(4-36), Lys²⁵Phe³⁶hPYY(4-36), Thr²⁷Ile²⁸hPYY(4-36), Thr²⁷Val²⁸hPYY(4-36), Thr²⁷Gln²⁹hPYY(4-36), Thr²⁷Ile³⁰hPYY(4-36), Thr²⁷Val³⁰hPYY(4-36), Thr²⁷Ile³¹hPYY(4-36), Thr²⁷Leu³¹hPYY(4-36), Thr²⁷Thr³⁶hPYY(4-36), Thr²⁷Phe³⁶hPYY(4-36), Phe²⁷Ile²⁸hPYY(4-36), Phe²⁷Val²⁸hPYY(4-36), Phe²⁷Gln²⁹hPYY(4-36), Phe²⁷Ile³⁰hPYY(4-36), Phe²⁷Val³⁰hPYY(4-36), Phe²⁷Ile³¹hPYY(4-36), Phe²⁷Leu³¹hPYY(4-36), Phe²⁷Thr³⁶hPYY(4-36), Phe²⁷Phe³⁶hPYY(4-36), Gln²⁹Ile³⁰hPYY(4-36), Gln²⁹Val³⁰hPYY(4-36), Gln²⁹Ile³¹hPYY(4-36), Gln²⁹Leu³¹hPYY(4-36), Gln²⁹Thr³⁶hPYY(4-36), Gln²⁹Phe³⁶hPYY(4-36), Ile³⁰Ile³¹hPYY(4-36), Ile³⁰Leu³¹hPYY(4-36), Ile³⁰Thr³⁶hPYY(4-36), Ile³⁰Phe³⁶hPYY(4-36), Val³⁰Ile³¹hPYY(4-36), Val³⁰Leu³¹hPYY(4-36), Val³⁰Thr³⁶hPYY(4-36), Val³⁰Phe³⁶hPYY(4-36), Ile³¹Thr³⁶hPYY(4-36), Leu³¹Phe³⁶hPYY(4-36), Leu³¹Phe³⁶hPYY(4-36), Leu³¹Thr³⁶hPYY(4-36), Leu³¹Phe³⁶hPYY(4-36), Thr²⁷hPYY(5-36), Phe²⁷hPYY(5-36), Ile²⁸hPYY(5-36), Val²⁸hPYY(5-36), Gln²⁹hPYY(5-36), Ile³⁰hPYY(5-36), Val³⁰hPYY(5-36), Ile³¹hPYY(5-36), Leu³¹hPYY(5-36), Thr³⁶hPYY(5-36), Phe³⁶hPYY(5-36), Lys²⁵Thr²⁷hPYY(5-36), Lys²⁵Phe²⁷hPYY(5-36), Lys²⁵Ile²⁸hPYY(5-36), Lys²⁵Val²⁸hPYY(5-36), Lys²⁵Gln²⁹hPYY(5-36), Lys²⁵Ile³⁰hPYY(5-36), Lys²⁵Val³⁰hPYY(5-36), Lys²⁵Ile³¹hPYY(5-36), Lys²⁵Leu³¹hPYY(5-36), Lys²⁵Thr³⁶hPYY(5-36), Lys²⁵Phe³⁶hPYY(5-36), Thr²⁷Ile²⁸hPYY(5-36), Thr²⁷Val²⁸hPYY(5-36), Thr²⁷Gln²⁹hPYY(5-36), Thr²⁷Ile³⁰hPYY(5-36), Thr²⁷Val³⁰hPYY(5-36), Thr²⁷Ile³¹hPYY(5-36), Thr²⁷Leu³¹hPYY(5-36), Thr²⁷Thr³⁶hPYY(5-36), Thr²⁷Phe³⁶hPYY(5-36), Phe²⁷Ile²⁸hPYY(5-36), Phe²⁷Val²⁸hPYY(5-36), Phe²⁷Gln²⁹hPYY(5-36), Phe²⁷Val³⁰hPYY(5-36), Phe²⁷Ile³⁰hPYY(5-36), Phe²⁷Ile³¹hPYY(5-36), Phe²⁷Leu³¹hPYY(5-36), Phe²⁷Thr³⁶hPYY(5-36), Phe²⁷Phe³⁶hPYY(5-36), Gln²⁹Ile³⁰hPYY(5-36), Gln²⁹Val³¹hPYY(5-36), Gln²⁹Ile³¹hPYY(5-36), Gln²⁹Leu³⁴hPYY(5-36), Gln²⁹Thr³⁶hPYY(5-36), Gln²⁹Phe³⁶hPYY(5-36), Ile$^{30}$Ile$^{31}$hPYY(5-36), Ile$^{30}$Leu$^{36}$hPYY(5-36),
Ile$^{30}$Thr$^{36}$hPYY(5-36), Ile$^{30}$Phe$^{36}$hPYY(5-36)
Val$^{30}$Ile$^{31}$hPYY(5-36), Val$^{30}$Leu$^{31}$hPYY(5-36),
Val$^{30}$Thr$^{36}$hPYY(5-36), Val$^{30}$Phe$^{36}$hPYY(5-36),
Ile$^{31}$Thr$^{36}$hPYY(5-36), Leu$^{31}$Phe$^{36}$hPYY(5-36),
Leu$^{31}$Phe$^{36}$hPYY(5-36), Leu$^{31}$Thr$^{36}$hPYY(5-36),
Leu$^{31}$Phe$^{36}$hPYY(5-36).

In yet another emobodiment, the PPF polypeptides of the invention do not include those PPF-related polypeptides disclosed in WO 03/026591 and WO 03/057235, which are herein incorporated by reference in their entirety.

In another embodiment, the polypeptides of the invention are at least 34 amino acids in length. In other embodiments, the PPF polypeptides may be at least 21, 22, 23, 24, 25, 26, 27, 28, 29, 30, 31, 32, or 33 amino acids in length. Further, in one embodiment, the polypeptides of the invention include only natural L amino acid residues and/or modified natural L amino acid residues. Alternatively, in another embodiment, the polypeptides of the invention do not include unnatural amino acid residues.

In yet another embodiment, PPF polypeptides of the invention may exhibit at least 60%, 65%, 70%, 80%, or 90% sequence identity to a native PYY(3-36) over the entire length of the PYY(3-36). Such PPF polypeptides of the invention may also exhibit at least 50%, at least 60%, at least 70%, at least 80%, at least 90%, at least 92%, at least 94% or at least 97% sequence identity to a native PP. In yet another embodiment, such PPF polypeptides of the invention may exhibit at least 50%, at least 60%, at least 70%, at least 80%, at least 90%, at least 92%, at least 94% or at least 97% sequence identity to a native NPY.

More specifically, in one aspect, the present invention relates to novel PPF polypeptides comprising at least two PPF motifs, wherein the at least two PPF motifs include at least the N-terminal polyproline PPF motif and the C-terminal tail PPF motif, and the PPF polypeptide does not include any unnatural amino acid residues. Such PPF polypeptides of the invention will exhibit at least 50% sequence identity to a native PYY(3-36) over the entire length of the PYY(3-36). In some embodiments, such PPF polypeptides have at least 34 amino acid residues. In some embodiments, such PPF polypeptides of the invention may exhibit at least 60%, at least 70%, at least 80%, at least 90%, at least 92%, at least 94% or at least 97% sequence identity to a native PYY(3-36) over the entire length of the PYY(3-36). Such PPF polypeptides of the invention may also exhibit at least 50%, at least 60%, at least, 70%, at least 80%, at least 90%, at least 92%, at least 94% or at least 97% sequence identity to a native PP. In some embodiments, the PPF polypeptides may comprise not more than 10, not more than 5, not more than 3, not more than 2 or not more than 1 amino acid substitutions. In yet another embodiment, such PPF polypeptides of the invention may exhibit at least 50%, at least 60%, at least 70%, at least 80%, at least 90%, at least 92%, at least 94% or at least 97% sequence identity to a native NPY.

In another aspect, the PPF polypeptides of the invention include PYY analog polypeptides. In yet another aspect of the invention, the PPF polypeptides of the invention include PPF chimeric polypeptides comprising a fragment of a PP, PYY or NPY polypeptide covalently linked to at least one additional fragment of a PP, PYY or NPY polypeptide, wherein each PP, PYY or NPY fragment includes a PPF motif. Such PPF analog polypeptides and PPF chimeric polypeptides of the invention will exhibit at least 50% sequence identity to a native PYY(3-36) over the entire length of the PYY(3-36). In some embodiments, such PPF polypeptides of the invention may exhibit at least 60%, at least 70%, at least 80%, at least 90%, at least 92%, at least 94% or at least 97% sequence identity to a native PYY(3-36) over the entire length of the PYY(3-36). PPF polypeptides of the invention may also exhibit at least 50%, at least 60%, at least 70%, at least 80%, at least 90%, at least 92%, at least 94% or at least 97% sequence identity to a native PP. In yet another embodiment, PPF polypeptides of the invention may exhibit at least 50%, at least 60%, at least 70%, at least 80%, at least 90%, at least 92%, at least 94% or at least 97% sequence identity to a native NPY. In certain embodiments, desirable PPF polypeptides may not include N-terminal PP fragments in combination with C-terminal NPY fragments.

PPF polypeptides useful in the invention may have a PPF activity greater than or less than the native compounds for a particular activity. Thus, for example, PYY agonists may have 3, 5, 10, 50, 100, 500, 1000 times or more activity than native PYY. Furthermore, while it is desirable to use a PYY agonist having similar or greater activity than native PYY, one of ordinary skill in the art would understand that agonists having less activity than native PYY would also be useful in the present invention. Such agonists, for example, may have anywhere from 2, 5, 10, 15, or 20 times less activity than native PYY, but possess other desirable characteristics, e.g., solubility, bioavailability, ease in manufacturing or formulation, or fewer side effects. In some embodiments, a PPF polypeptide useful in the invention may be a PYY antagonist.

Examples of PYY agonists, more particularly PYY analog agonists or agonist analogs (analogs and derivatives of PYY), are described in U.S. Pat. No. 5,574,010, WO04/089279, WO 04/066966, WO 03/057235, WO 03/026591, WO 98/20885, WO 94/22467, the contents of which are incorporated by reference in their entirety. Other PYY analog agonists are described in Balasubramaniam et al., Pept Res 1(1):32-5, 1998, Balasubramaniam et al., Peptides 14: 1011-1016, 1993, Boublik et al., J. Med. Chem 32: 597-601, 1989, Liu et al., J. Gastrointest Surg 5(2):147-52, 2001, Gehlert et al., Proc Soc Exp Biol Med, 218:7-22, 1998, Sheikh et al., Am J. Physiol. 261:G701-15, 1991, Potter et al., Eur J Pharmacol 267(3): 253-362, 1994, Lebon et al., J. Med. Chem 38:1150-57, 1995, Fournier et al., Mol Pharmacol 45(1):93-101, 1994, Kirby et al., J. Med Chem 38:4579-86, 1995, Beck et al., FEBS Letters 244(1): 119-122, 1989, Rist et al., Eur J Biochemistry 247: 1019-1028, 1997, Soll et al., Eur J Biochem 268 (10): 2828-37, 2001, Cabrele et al., J Pept Sci 6(3): 97-122, 2000, Balasubramaniam et al., J Med Chem 43: 3420-3427, 2000, Kirby et al., J Med Chem 36:3802-08, 1993, Grundemar et al., Regulatory Peptides 62:131-136, 1996, Feinstein et al. J Med Chem 35:2836-2843, 1992, Cox et al. Regulatory Peptides 75-76: 3-8, 1998, Cabrele et al., Peptides 22: 365-378, 2001, Keire et al. Biochemistry 39: 9935-9942, 2000, Keire et al. Am. J. Physiol Gastrointest Liver Physiol 279: G126-G131, 2000, and incorporated herein by reference.

PYY, NPY, and PP constitute a family of C-terminally amidated peptides involved in the regulation of gastrointestinal function, blood pressure, and feeding behavior. Without intending to be limited by theory, the ability of these peptides to selectively bind and activate Y receptor subtypes is believed to depend strongly on a stable solution structure, including the so-called "PP-fold". Table I (below) shows PP family ligand potencies at the known receptors and the rank order of potencies of various ligands.

TABLE 1

Summary of receptor pharmacology for the PP family of receptors

| RECEPTORS | PHARMACOLOGY | REFERENCE |
|---|---|---|
| Food Intake Inhibition (peripheral) | PYY(3-36) ≧ PYY >> NPY, NPY(3-36), PP, Ac-PYY(22-36) | |
| Gastric Emptying | PYY(3-36) ≧ PYY >> NPY, NPY(3-36), PP, Ac-PYY(22-36) | |
| Food Intake Stimulation (central) | PYY ≧ PYY(3-36) = NPY = NPY(3-36) > PP | Iyengar et al., J. Pharmacol. Exp. Ther. 289: 1031-40, 1999 |
| Y1 | NPY = PYY > NPY(3-36) = PYY(3-36) = PP | Iyengar et al., J. Pharmacol. Exp. Ther. 289: 1031-40, 1999; Gehlert, Proc. Soc. Exp. Biol. Med. 218: 7-22, 1998; Michel et al., Pharmacol. Rev. 50: 143-50, 1998; U.S. Pat. No. 5,968,819 |
| Y2 | NPY = PYY = PYY(3-36) = NPY(3-36) >> PP | Iyengar et al., J. Pharmacol. Exp. Ther. 289: 1031-40, 1999; Gehlert, Proc. Soc. Exp. Biol. Med. 218: 7-22, 1998; Michel et al., Pharmacol. Rev. 50: 143-50, 1998; U.S. Pat. No. 5,968,819 |
| Y3 | NPY > PP > PYY | Gehlert, Proc. Soc. Exp. Biol. Med. 218: 7-22, 1998; Michel et al., Pharmacol. Rev. 50: 143-50, 1998. |
| Y4 | PP > PYY > NPY > PYY(3-36) = NPY(3-36) | Iyengar et al., J. Pharmacol. Exp. Ther. 289: 1031-40, 1999; Gehlert, Proc. Soc. Exp. Biol. Med. 218: 7-22, 1998; Michel et al., Pharmacol. Rev. 50: 143-50, 1998; U.S. Pat. No. 5,968,819 |
| Y5 | NPY = PYY ≧ PP ≧ PYY(3-36) = NPY(3-36) | Iyengar et al., J. Pharmacol. Exp. Ther. 289: 1031-40, 1999; Gehlert, Proc. Soc. Exp. Biol. Med. 218: 7-22, 1998; Michel et al., Pharmacol. Rev. 50: 143-50, 1998; U.S. Pat. No. 5,968,819 |
| Y6 | NPY = PYY ≧ NPY(3-36) > PP | Iyengar et al., J. Pharmacol. Exp. Ther. 289: 1031-40, 1999; Gehlert, Proc. Soc. Exp. Biol. Med. 218: 7-22, 1998; Michel et al., Pharmacol. Rev. 50: 143-50, 1998; U.S. Pat. No. 5,968,819 |
| (Y7) | PYY > NPY >> PYY(3-36) = PP | Yang et al., Br. J. Pharmacol. 123: 1549-54, 1998 |
| (Y7) | PYY(3-36) ≧ PYY > NPY >> PP | Haynes et al., Br. J. Pharmacol. 122: 1530-6, 1997 |
| (Y7) | PYY >> NPY = PYY(3-36) = PP | Kawakubo et al., Brain Res. 854: 30-4, 2000 |

Research has suggested that the differences in Y receptor binding affinities are correlated with secondary and tertiary structural differences. See, e.g., Keire et al., *Biochemistry* 2000, 39, 9935-9942. Native porcine PYY has been characterized as including two C-terminal helical segments from residues 17 to 22 and 25 to 33 separated by a kink at residues 23, 24, and 25, a turn centered around residues 12-14, and the N-terminus folded near residues 30 and 31. Further, full-length porcine PYY has been characterized as including the PP fold, stabilized by hydrophobic interactions among residues in the N- and C-termini. See id.

By "PP" is meant a pancreatic peptide polypeptide obtained or derived from any species. Thus, the term "PP" includes both the human full length, 36 amino acid peptide as set forth in SEQ ID NO: 1, and species variations of PP, including, e.g., murine, hamster, chicken, bovine, rat, and dog PP. In this sense, "PP," "wild-type PP," and "native PP," i.e., unmodified PP, are used interchangeably.

By "NPY" is meant a neuropeptide Y polypeptide obtained or derived from any species. Thus, the term "NPY" includes both the human full length, 36 amino acid peptide as set forth in SEQ ID NO: 4, and species variations of NPY, including, e.g., murine, hamster, chicken, bovine, rat, and dog NPY. In this sense, "NPY," "wild-type NPY," and "native NPY", i.e., unmodified NPY, are used interchangeably.

By "PYY" is meant a peptide YY polypeptide obtained or derived from any species. Thus, the term "PYY" includes both the human full length, 36 amino acid peptide as set forth in SEQ ID NO: 2, and species variations of PYY, including e.g., murine, hamster, chicken, bovine, rat, and dog PYY. In this sense, "PYY" and "wild-type PYY" and "native PYY," i.e., unmodified PYY, are used interchangeably. In the context of the present invention, all modifications discussed with reference to the PYY analog polypeptides of the present invention are based on the 36 amino acid sequence of native human PYY (SEQ ID NO: 2).

By "PP agonist", "PYY agonist", or "NPY agonist" is meant a compound which elicits a biological activity of native human PP, PYY, or NPY, respectively. In some embodiments, the terms refer to a compound which elicits a biological effect in the reduction of nutrient availability similar to that of native human PP, PYY, or NPY, for example a compound (1) having activity in food intake, gastric emptying, pancreatic secretion, or weight loss assays similar to native human PP, PYY, or NPY, and/or (2) which binds specifically in a Y receptor assay or in a competitive binding assay with labeled PP, PYY, PYY(3-36), or NPY from certain tissues having an abundance of Y receptors, including, e.g., area postrema. In some embodiments, the agonist is not PP, PYY, PYY(3-36), and/or NPY. In some embodiments, the agonists will bind in such assays with an affinity of greater than 1 µM. In some embodiments, the agonists will bind in such assays with an affinity of greater than 1-5 nM. Such agonists may comprise a polypeptide having a PPF motif, an active fragment of PP, PYY, or NPY, or a small chemical molecule.

PYY, PYY(3-36) or agonists thereof may be modified at the N-terminal end, C-terminal end and/or along its length to modify other characteristics as available in the art. Insertions, extensions, or substitutions as described above may be with other natural amino acids, synthetic amino acids, peptidomimetics, or other chemical compounds. The analog polypeptides of the invention may be derivatized by chemical alterations such as amidation, glycosylation, acylation, sulfation, phosphorylation, acetylation, and cyclization. Such chemical alterations may be obtained through chemical or biochemical methodologies, as well as through in-vivo processes, or any combination thereof. Derivatives of the analog polypeptides of the invention may also include conjugation to one or more polymers or small molecule substituents. One type of polymer conjugation is linkage or attachment of polyethylene glycol ("PEG") polymers, polyamino acids (e.g., poly-his, poly-arg, poly-lys, etc.) and/or fatty acid chains of various lengths to the N- or C-terminus or amino acid residue side chains of a polypeptide analog. Small molecule substituents include short alkyls and constrained alkyls (e.g., branched, cyclic, fused, adamantyl), and aromatic groups.

"Reduced nutrient availability" is meant to include any means by which the body reduces the nutrients available to the body to store as fat. Reducing nutrient availability may be by means that include, but are not limited to, reducing appetite, increasing satiety, affecting food choice/taste aversion, increasing metabolism, and/or decreasing or inhibiting food absorption. Exemplary mechanisms that may be affected include delayed gastric emptying or decreased absorption of food in the intestines.

"Increased nutrient availability" is meant to include any means by which the body increases the nutrients available to the body to store as fat. Increasing nutrient availability may be by means that include, but are not limited to, increasing appetite, decreasing satiety, affecting food choice, decreasing taste aversion, decreasing metabolism, and/or increasing food absorption. Exemplary mechanisms that may be affected include decreasing gastric hypomotility or increasing absorption of food in the intestines.

With regard to the methods to reduce nutrient availability, as used herein, a "subject in need thereof" includes subjects who are overweight or obese or morbidly obese, or desirous of losing weight. In addition, subjects who are insulin resistant, glucose intolerant, or have any form of diabetes mellitus (e.g., type 1, 2 or gestational diabetes) can benefit from these methods to reduce nutrient availability.

With regard to the methods to increase nutrient availability, as used herein, a "subject in need thereof" includes subjects who are underweight or desirous of gaining weight.

A "subject" is meant to include any animal, including humans, primates, and other mammals including rats, mice, pets such as cats, dogs, livestock such as horses, cattle, pigs, sheep and goats, as well as chickens, turkeys and any other commercially valuable or companion animal for which body weight or altering body composition may be an issue.

As used herein, the term "dieting" is meant to include any means by which a subject has a reduced caloric intake relative to his or her caloric intake before beginning dieting. Examples of dieting may include, but are not limited to, reducing the total amount of food consumed overall, reducing consumption of any one or more of protein, carbohydrate or fat components of the diet, or reducing the proportion of fat relative to the proportion of carbohydrates and/or protein in the diet.

By "metabolic rate" is meant the amount of energy liberated/expended per unit of time. Metabolism per unit time can be estimated by food consumption, energy released as heat, or oxygen used in metabolic processes. It is generally desirable to have a higher metabolic rate when one wants to lose weight. For example, a person with a high metabolic rate may be able to expend more energy (e.g., the body burns more calories) to perform an activity than a person with a low metabolic rate for that activity.

As used herein, "lean mass" or "lean body mass" refers to muscle and bone. Lean body mass does not necessarily indicate fat free mass. Lean body mass contains a small percentage of fat (roughly 3%) within the central nervous system (brain and spinal cord), marrow of bones, and internal organs. Lean body mass is measured in terms of density. Methods of measuring fat mass and lean mass include, but are not limited to, underwater weighing, air displacement plethysmograph, x-ray, DEXA scans, magnetic resonance imaging (MRI), computed tomography (CT) scans, adiabatic bomb calorimetry. In some embodimesnt, body composition is measured pre- and post treatment using a rodent NMR machine (EchoMRI-700™). Animals are placed in a restraining tube and placed in the NMR for 2 minutes, and the amount of fat and lean mass, in grams, is quantified. In some embodiments, body composition (lean mass, fat mass) for each animal is analyzed using a Dual Energy X-ray Absorptiometry (DEXA) instrument per manufacturer's instructions (Lunar Piximus, GE Imaging System). In some embodiments, fat mass and lean mass is measured using underwater weighing. In some embodiments, body composition is measured using MRI. In some embodiments, body composition is measured using a CT scan. In some embodiments, body composition is measured using adiabatic bomb calorimetry. In some embodiments, body composition is measured using an x-ray. In some embodiments, body composition is measured using an air displacement plethysmograph. In some embodiments, at the time of termination of animal subjects, the retroperitoneal and mesenteric fat pads, markers of visceral adiposity, are dissected out and weighed.

By "fat distribution" is meant the location of fat deposits in the body. Such locations of fat deposition include, for example, subcutaneous, visceral and ectopic fat depots.

By "subcutaneous fat" is meant the deposit of lipids just below the skin's surface. The amount of subcutaneous fat in a subject can be measured using any method available for the measurement of subcutaneous fat. Methods of measuring subcutaneous fat are known in the art, for example, those described in U.S. Pat. No. 6,530,886, the entirety of which is incorporated herein by reference.

By "visceral fat" is meant the deposit of fat as intra-abdominal adipose tissue. Visceral fat surrounds vital organs and can be metabolized by the liver to produce blood cholesterol. Visceral fat has been associated with increased risks of conditions such as polycystic ovary syndrome, metabolic syndrome and cardiovascular diseases.

By "ectopic fat storage" is meant lipid deposits within and around tissues and organs that constitute the lean body mass (e.g., skeletal muscle, heart, liver, pancreas, kidneys, blood vessels). Generally, ectopic fat storage is an accumulation of lipids outside classical adipose tissue depots in the body.

As used herein, and as well-understood in the art, "treatment" is an approach for obtaining beneficial or desired results, including clinical results. "Treating" or "palliating" a disease, disorder, or condition means that the extent and/or undesirable clinical manifestations of a condition, disorder, or a disease state are lessened and/or time course of the progression is slowed or lengthened, as compared to not treating the disorder. For example, in treating obesity, a decrease in body weight, e.g., at least a 5% decrease in body weight, is an example of a desirable treatment result. Beneficial or desired clinical results include, but are not limited to, alleviation or amelioration of one or more symptoms, diminishment of extent of disease, stabilized (i.e., not worsening) state of disease, delay or slowing of disease progression, amelioration or palliation of the disease state, and remission (whether partial or total), whether detectable or undetectable.

"Treatment" can also mean prolonging survival as compared to expected survival if not receiving treatment. Further, treating does not necessarily occur by administration of one dose, but often occurs upon administration of a series of doses. Thus, a therapeutically effective amount, an amount sufficient to palliate, or an amount sufficient to treat a disease, disorder, or condition may be administered in one or more administrations.

As used herein, the term "therapeutically effective amount" means the amount of the PPF polypeptide in the composition that will elicit the biological or medical response in a tissue, system, subject, or human that is being sought by the subject, researcher, veterinarian, medical doctor or other clinician, which includes alleviation of the symptoms of the disorder being treated. The novel methods of treatment of this invention are for disorders known to those skilled in the art.

As used herein, the term "prophylactically effective amount" means the amount of the active compounds in the composition that will elicit the biological or medical response in a tissue, system, subject, or human that is being sought by the subject, researcher, veterinarian, medical doctor or other clinician, to prevent the onset of obesity or an obesity-related disorder, condition or disease in subjects as risk for obesity or the obesity-related disorder, condition or disease.

As used herein, the singular form "a", "an", and "the" includes plural references unless otherwise indicated or clear from context. For example, as will be apparent from context, "a" PYY agonist can include one or more PYY agonists.

By "amino acid" and "amino acid residue" is meant natural amino acids, unnatural amino acids, and modified amino acid. Unless stated to the contrary, any reference to an amino acid, generally or specifically by name, includes reference to both the D and the L stereoisomers if their structure allow such stereoisomeric forms. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), Lysine (Lys), methionine (Met), phenylalanine (Phe), proline (Pro), serine (Ser), threonine (Thr), tryptophan (Trp), tyrosine (Tyr) and valine (Val). Unnatural amino acids include, but are not limited to homolysine, homoarginine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid, thioproline, sarcosine and citrulline. Additional unnatural amino acids include modified amino acid residues which are chemically blocked, reversibly or irreversibly, or chemically modified on their N-terminal amino group or their side chain groups, as for example, N-methylated D and L amino acids or residues wherein the side chain functional groups are chemically modified to another functional group. For example, modified amino acids include methionine sulfoxide; methionine sulfone; aspartic acid-(beta-methyl ester), a modified amino acid of aspartic acid; N-ethylglycine, a modified amino acid of glycine; or alanine carboxamide, a modified amino acid of alanine. Additional residues, that can be incorporated are described in Sandberg et al., *J. Med. Chem.* 41: 2481-91, 1998.

By "Ahx" is meant 6-amino hexanoic acid.

Certain human sequences of peptides in the PPF are as follows (in conventional one-letter amino acid code):

```
PP:         APLEPVYPGD NATPEQMAQY AADLRRYINM LTRPRY (SEQ ID NO:1)

PYY:        YPIKPEAPGE DASPEELNRY YASLRHYLNL VTRQRY (SEQ ID NO:2)

PYY(3-36):    IKPEAPGE DASPEELNRY YASLRHYLNL VTRQRY (SEQ ID NO:3)

NPY:        YPSKPDNPGE DAPAEDMARY YSALRHYINL ITRQRY (SEQ ID NO:4)
```

Species homologs of human PYY include those amino acid sequences of SEQ ID NOs. 7-29.

As mentioned above, these peptides are C-terminally amidated when expressed physiologically, but need not be for the purposes of the instant invention. In other words, the C-terminus of these peptides, as well as the PPF polypeptides of the present invention, may have a free —OH or —NH$_2$ group. These peptides may also have other post-translational modifications. One skilled in the art will appreciate that the PPF polypeptides of the present invention may also be constructed with an N-terminal methionine residue.

PPF polypeptides of the invention include the PPF polypeptides of the Formula (I) (SEQ ID NO: 30):

$Xaa_1$ $Xaa_2$ $Xaa_3$ $Xaa_4$ Pro $Xaa_6$ $Xaa_7$ Pro $Xaa_9$ $Xaa_{10}$
$Xaa_{11}$ $Xaa_{12}$ $Xaa_{13}$ $Xaa_{14}$ $Xaa_{15}$ $Xaa_{16}$ $Xaa_{17}$ $Xaa_{18}$
$Xaa_{19}$ Tyr $Xaa_{21}$ $Xaa_{22}$ $Xaa_{23}$ Leu $Xaa_{25}$ $Xaa_{26}$ $Xaa_{27}$
$Xaa_{28}$ $Xaa_{29}$ $Xaa_{30}$ $Xaa_{31}$ Thr Arg Gln Arg $Xaa_{36}$ wherein:
$Xaa_1$ is Tyr, Ala, Phe, Trp, or absent;
$Xaa_2$ is Pro, Gly, d-Ala, homoPro, hydroxyPro, or absent;
$Xaa_3$ is Ile, Ala, NorVal, Val, Leu, Pro, Ser, Thr or absent;
$Xaa_4$ is Lys, Ala, Gly, Arg, d-Ala, homoLys, homo-Arg, Glu, Asp, or absent;
$Xaa_6$ is Glu, Ala, Val, Asp, Asn, or Gln;
$Xaa_7$ is Ala, Asn, His, Ser, or Tyr;
$Xaa_9$ is Gly, Ala Ser, sarcosine, Pro, or Aib;
$Xaa_{10}$ is Glu, Ala, Asp, Asn, Gln, Pro, Aib, or Gly;
$Xaa_{11}$ is Asp, Ala, Glu, Asn, Gln, Pro, Aib, or Gly;
$Xaa_{12}$ is Ala or d-Ala;
$Xaa_{13}$ is Ser, Ala, Thr, Pro, or homoSer;
$Xaa_{14}$ is Pro, Ala, homo-Pro, hydroxyPro, Aib, or Gly;
$Xaa_{15}$ is Glu, Ala, Asp, Asn, Gln, Pro, Aib, or Gly;
$Xaa_{16}$ is Glu, Ala, Asp, Asn, or Gln;
$Xaa_{17}$ is Leu, Ala, Met, Trp, Ile, Val, or NorVal;
$Xaa_{18}$ is Asn, Asp, Ala, Glu, Gln, Ser, or Thr;
$Xaa_{19}$ is Arg, Tyr, Lys, Ala, Gln, or N(Me)Ala;
$Xaa_{21}$ is Tyr, Ala, Met, Phe, or Leu;
$Xaa_{22}$ is Ala, Ser, Thr, or d-Ala;
$Xaa_{23}$ is Ser, Ala, Asp, Thr, or homoSer;
$Xaa_{25}$ is Arg, homoArg, Lys, homoLys, Orn, or Cit;
$Xaa_{26}$ is His, Ala, Arg, homoArg, homoLys, Orn, or Cit;
$Xaa_{27}$ is Tyr or Phe;

Xaa$_{28}$ is Leu, Ile, Val, or Ala;
Xaa$_{29}$ is Asn or Gln;
Xaa$_{30}$ is Leu, Ala, NorVal, Val, Ile, or Met;
Xaa$_{31}$ is Ala, Val, Ile, or Leu; and
Xaa$_{36}$ is Tyr, N(Me)Tyr, His, Trp, or Phe;

with the proviso that said PPF polypeptide is not a native PPF polypeptide, NPY(2-36), NPY(4-36), PYY(2-36), PYY (4-36), PP(2-36), PP(4-36), Ala$^1$NPY, Ala$^3$NPY, Ala$^4$NPY, Ala$^6$NPY, Ala$^7$NPY, Tyr$^7$pNPY, Ala$^9$NPY, Ala$^{10}$NPY, Ala$^{11}$NPY, Ala$^{13}$NPY, Gly$^{14}$NPY, Ala$^{15}$NPY, Ala$^{16}$NPY, Ala$^{17}$NPY, Ala$^{19}$NPY, Lys$^{19}$NPY, Ala$^{21}$NPY, Ala$^{22}$NPY, Lys$^{25}$NPY, Ala$^{26}$NPY, Phe$^{27}$NPY, Ala$^{28}$NPY, Gln$^{29}$NPY, Ala$^{30}$NPY, Ala$^{31}$NPY, Phe$^{36}$NPY, His$^{36}$NPY, Leu$^3$hPYY(3-36), Val$^3$hPYY(3-36), Lys$^{25}$hPYY(3-36), Pro$^{13}$Ala$^{14}$hPYY, hPP(1-7)-pNPY, hPP(1-17)-pNPY, Tyr$^1$NPY, Ala$^7$NPY or hPP(19-23)-pNPY.

In another embodiment, the PPF polypeptides of Formula I also do not include: Phe$^{27}$hPYY(3-36), Ile$^{28}$hPYY(3-36), Val$^{28}$hPYY(3-36), Gln$^{29}$hPYY(3-36), Val$^{30}$hPYY(3-36), Ile$^{31}$hPYY(3-36), Leu$^{31}$hPYY(3-36), Phe$^{36}$hPYY(3-36), Lys$^{25}$Phe$^{27}$hPYY(3-36), Lys$^{25}$Ile$^{28}$hPYY(3-36), Lys$^{25}$Val$^{28}$hPYY(3-36), Lys$^{25}$Gln$^{29}$hPYY(3-36), Lys$^{25}$Val$^{30}$hPYY(3-36), Lys$^{25}$Ile$^{31}$hPYY(3-36), Lys$^{25}$Leu$^{31}$hPYY(3-36), Lys$^{25}$Phe$^{36}$hPYY(3-36), Phe$^{27}$Ile$^{28}$hPYY(3-36), Phe$^{27}$Val$^{28}$hPYY(3-36), Phe$^{27}$Gln$^{29}$hPYY(3-36), Phe$^{27}$Val$^{30}$hPYY(3-36), Phe$^{27}$Ile$^{31}$hPYY(3-36), Phe$^{27}$Leu$^{31}$hPYY(3-36), Phe$^{27}$Phe$^{36}$hPYY(3-36), Gln$^{29}$Val$^{30}$hPYY(3-36), Gln$^{29}$Ile$^{31}$hPYY(3-36), Gln$^{29}$Leu$^{31}$hPYY(3-36), Gln$^{29}$Phe$^{36}$hPYY(3-36), Val$^{30}$Ile$^{31}$hPYY(3-36), Val$^{30}$Leu$^{31}$hPYY(3-36), Val$^{30}$Phe$^{36}$hPYY(3-36), or Leu$^{31}$Phe$^{36}$hPYY(3-36).

As will be recognized by one of skill in the art, the polypeptides of Formula I may be in the free acid form, or may be C-terminally amidated.

1. PYY Analog Polypeptides of the Present Invention

The PYY analog polypeptides of the present invention will generally include at least two PPF motifs including the N-terminal polyproline PPF motif and the C-terminal tail PPF motif, and will generally retain, at least in part, a biological activity of native human PYY, e.g., the PYY analog polypeptides of the present invention will generally be PYY agonists. Moreover, the PYY analog polypeptide will have at least 50%, at least 60%, at least 70%, at least 80%, at least 90%, at least 92%, at least 94% or at least 97% sequence identity to PYY(3-36). In some embodiments, the PYY analog polypeptides of the present invention will exhibit PYY activity in the treatment and prevention of metabolic conditions and disorders.

In one embodiment, the PYY analog polypeptides of the invention do not include any unnatural amino acid resides, and further with the proviso that the PYY analog polypeptides of the invention do not include any native PYY polypeptides or 1-4 N-terminal deletions thereof (e.g., PYY(1-36), PYY(2-36), PYY(3-36)), PYY(4-36)). In some embodiments, the PYY analog polypeptides of the invention do not include: Pro$^{34}$PYY, His$^{34}$PYY Lys$^{25}$hPYY(5-36), Arg$^4$hPYY(4-36), Gln$^4$hPYY(4-36), Asn$^4$hPYY(4-36), Lys$^{25}$hPYY(4-36), Leu$^3$hPYY(3-36), Val$^3$hPYY(3-36), Lys$^{25}$hPYY(3-36), Tyr$^{1,36}$pPYY, Pro$^{13}$Ala$^{14}$hPYY, Leu$^{31}$Pro$^{34}$PYY, FMS-PYY, FMS-PYY(3-36), Fmoc-PYY, Fmoc-PYY(3-36), FMS$_2$-PYY, FMS$_2$-PYY(3-36), Fmoc$_2$-PYY, or Fmoc$_2$-PYY(3-36).

In another embodiment, such PYY analog polypeptides of the invention also do not include: Thr$^{27}$hPYY(3-36), Ile$^{30}$hPYY(3-36), Ser$^{32}$hPYY(3-36), Lys$^{33}$hPYY(3-36), Asn$^{34}$hPYY(3-36), Lys$^{35}$hPYY(3-36), Thr$^{36}$hPYY(3-36), Lys$^{25}$Thr$^{27}$hPYY(3-36), Lys$^{25}$Ser$^{32}$hPYY(3-36), Lys$^{25}$Asn$^{24}$hPYY(3-36), Lys$^{25}$Thr$^{36}$hPYY(3-36), Thr$^{27}$Val$^{28}$hPYY(3-36), Thr$^{27}$Ile$^{30}$hPYY(3-36), Thr$^{27}$Ile$^{31}$hPYY(3-36), Thr$^{27}$Ser$^{32}$hPYY(3-36), Thr$^{27}$Asn$^{34}$hPYY(3-36), Thr$^{27}$Thr$^{36}$hPYY(3-36), Phe$^{27}$Ile$^{31}$hPYY(3-36), Phe$^{27}$Lys$^{33}$hPYY(3-36), Phe$^{27}$Lys$^{35}$hPYY(3-36), Gln$^{29}$Ile$^{30}$hPYY(3-36), Gln$^{29}$Leu$^{33}$hPYY(3-36), Gln$^{29}$Leu$^{35}$hPYY(3-36), Ile$^{30}$Ile$^{31}$IhPYY(3-36), Ile$^{30}$Ser$^{32}$hPYY(3-36), Ile$^{30}$Asn$^{34}$hPYY(3-36), Ile$^{30}$Thr$^{36}$hPYY(3-36), Val$^{30}$Ser$^{32}$hPYY(3-36), Val$^{30}$Asn$^{34}$hPYY(3-36), Val$^{30}$Thr$^{36}$hPYY(3-36), Ile$^{31}$Lys$^{33}$hPYY(3-36), Ile$^{31}$Lys$^{35}$hPYY(3-36), Ile$^{31}$Phe$^{36}$hPYY(3-36), Leu$^{31}$Lys$^{33}$hPYY(3-36), Leu$^{31}$Lys$^{35}$hPYY(3-36), Ser$^{32}$Lys$^{33}$hPYY(3-36). Ser$^{32}$Lys$^{35}$hPYY(3-36), Ser$^{32}$Phe$^{36}$hPYY(3-36), Lys$^{33}$Lys$^{35}$hPYY(3-36), Lys$^{33}$Phe$^{36}$hPYY(3-36), Asn$^{34}$Phe$^{36}$hPYY(3-36), Lys$^{35}$Phe$^{36}$hPYY(3-36), Lys$^{25}$Ile$^{30}$hPYY(3-36), Lys$^{25}$Lys$^{33}$hPYY(3-36), Lys$^{25}$Lys$^{35}$hPYY(3-36), Thr$^{27}$Ile$^{28}$hPYY(3-36), Thr$^{27}$Gln$^{29}$hPYY(3-36), Thr$^{27}$Val$^{30}$hPYY(3-36), Thr$^{27}$Leu$^{31}$hPYY(3-36), Thr$^{27}$Lys$^{33}$hPYY(3-36), Thr$^{27}$Lys$^{35}$hPYY(3-36), Thr$^{27}$Phe$^{36}$hPYY(3-36), Phe$^{27}$Ser$^{32}$hPYY(3-36), Phe$^{27}$Asn$^{34}$hPYY(3-36), Phe$^{27}$Thr$^{36}$hPYY(3-36), Gln$^{29}$Ser$^{32}$hPYY(3-36), Gln$^{29}$Asn$^{34}$hPYY(3-36), Gln$^{29}$Thr$^{36}$hPYY(3-36), Ile$^{30}$Leu$^{31}$hPYY(3-36), Ile$^{30}$Lys$^{33}$hPYY(3-36), Ile$^{30}$Lys$^{35}$hPYY(3-36), Ile$^{30}$Phe$^{36}$hPYY(3-36), Val$^{30}$Lys$^{33}$hPYY(3-36), Val$^{30}$Lys$^{35}$hPYY(3-36), Ile$^{31}$Ser$^{32}$hPYY(3-36), Ile$^{31}$Asn$^{34}$hPYY(3-36), Ile$^{31}$Thr$^{36}$hPYY(3-36), Leu$^{31}$Ser$^{32}$hPYY(3-36), Leu$^{31}$Asn$^{34}$hPYY(3-36), Leu$^{31}$Thr$^{36}$hPYY(3-36), Ser$^{32}$Asn$^{34}$hPYY(3-36), Ser$^{32}$Thr$^{36}$hPYY(3-36), Lys$^{33}$Asn$^{34}$hPYY(3-36), Lys$^{33}$Thr$^{36}$hPYY(3-36), Asn$^{34}$Lys$^{35}$hPYY(3-36), Lys$^{35}$Thr$^{36}$hPYY(3-36), Thr$^{27}$hPYY(4-36), Phe$^{27}$hPYY(4-36), Ile$^{28}$hPYY(4-36), Val$^{28}$hPYY(4-36), Gln$^{29}$hPYY(4-36), Ile$^{30}$hPYY(4-36), Val$^{30}$hPYY(4-36), Ile$^{31}$hPYY(4-36), Leu$^{31}$hPYY(4-36), Ser$^{32}$hPYY(4-36), Lys$^{33}$hPYY(4-36), Asn$^{34}$hPYY(4-36), Lys$^{35}$hPYY(4-36), Thr$^{36}$hPYY(4-36), Phe$^{36}$hPYY(4-36), Lys$^{25}$Thr$^{27}$hPYY(4-36), Lys$^{25}$Phe$^{27}$hPYY(4-36), Lys$^{25}$Ile$^{28}$hPYY(4-36), Lys$^{25}$Val$^{28}$hPYY(4-36), Lys$^{25}$Gln$^{29}$hPYY(4-36), Lys$^{25}$Ile$^{30}$hPYY(4-36), Lys$^{25}$Val$^{30}$hPYY(4-36), Lys$^{25}$Ile$^{31}$hPYY(4-36), Lys$^{25}$Leu 31hPYY(4-36), Lys$^{25}$Ser$^{32}$hPYY(4-36), Lys$^{25}$Lys$^{33}$hPYY(4-36), Lys$^{25}$Asn$^{24}$hPYY(4-36), Lys$^{25}$Lys$^{35}$hPYY(4-36), Lys$^{25}$Thr$^{36}$hPYY(4-36), Lys$^{25}$Phe$^{36}$hPYY(4-36), Thr$^{27}$Ile$^{28}$hPYY(4-36), Thr$^{27}$Val$^{28}$hPYY(4-36), Thr$^{27}$Gln$^{29}$hPYY(4-36), Thr$^{27}$Ile$^{30}$hPYY(4-36), Thr$^{27}$Val$^{30}$hPYY(4-36), Thr$^{27}$Ile$^{31}$hPYY(4-36), Thr$^{27}$Leu$^{31}$hPYY(4-36), Thr$^{27}$Ser$^{32}$hPYY(4-36), Thr$^{27}$Lys$^{33}$hPYY(4-36), Thr$^{27}$Asn$^{34}$hPYY(4-36), Thr$^{27}$Lys$^{35}$hPYY(4-36), Thr$^{27}$Thr$^{36}$hPYY(4-36), Thr$^{27}$Phe$^{36}$hPYY(4-36), Phe$^{27}$Ile$^{28}$hPYY(4-36), Phe$^{27}$Val$^{28}$hPYY(4-36), Phe$^{27}$Gln$^{29}$hPYY(4-36), Phe$^{27}$Ile$^{30}$hPYY(4-36), Phe$^{27}$Val hPYY(4-36), Phe$^{27}$Ile$^{31}$hPYY(4-36), Phe$^{27}$Leu$^{31}$hPYY(4-36), Phe$^{27}$Ser$^{32}$hPYY(4-36), Phe$^{27}$Lys$^{31}$hPYY(4-36), Phe$^{27}$Asn$^{34}$hPYY(4-36), Phe$^{27}$Lys$^{35}$hPYY(4-36), Phe$^{27}$Thr$^{36}$hPYY(4-36), Phe$^{27}$Phe$^{36}$hPYY(4-36), Gln$^{29}$Ile$^{35}$hPYY(4-36), Gln$^{29}$Val$^{30}$hPYY(4-36), Gln$^{29}$Ile$^{31}$hPYY(4-36), Gln$^{29}$Leu$^{31}$hPYY(4-36), Gln$^{29}$Ser$^{32}$hPYY(4-36), Gln$^{29}$Leu$^{33}$hPYY(4-36), Gln$^{29}$Asn$^{34}$hPYY(4-36), Gln$^{29}$Leu$^{35}$hPYY(4-36), Gln$^{29}$Thr$^{36}$hPYY(4-36), Gln$^{29}$Phe$^{36}$hPYY(4-36), Ile$^{30}$Ile$^{31}$hPYY(4-36), Ile$^{30}$Leu$^{31}$hPYY(4-36), Ile$^{30}$Ser$^{32}$hPYY(4-36), Ile$^{30}$Lys$^{33}$hPYY(4-36), Ile³⁰Asn³⁴hPYY(4-36), Ile³⁰Lys³⁵hPYY(4-36), Lys³³Lys³⁵hPYY(5-36), Lys³³Thr³⁶hPYY(5-36), Ile³⁰Thr³⁶hPYY(4-36), Ile³⁰Phe³⁶hPYY(4-36), Lys³³Phe³⁶hPYY(5-36), Asn³⁴Lys³⁵hPYY(5-36), Val³⁰Ile³¹hPYY(4-36), Val³⁰Leu³¹hPYY(4-36), Asn³⁴Phe³⁶hPYY(5-36), Lys³⁵Thr³⁶hPYY(5-36), or Val³⁰Ser³²hPYY(4-36), Val³⁰Lys³³hPYY(4-36), Lys³⁵Phe³⁶hPYY(5-36).

Val³⁰Asn³⁴hPYY(4-36), Val³⁰Lys³⁵hPYY(4-36), In some embodiments, the PYY analog polypeptides of the Val³⁰Thr³⁶hPYY(4-36), Val³⁰Phe³⁶hPYY(4-36), invention do not include any unnatural amino acid residues, Ile³¹Ser³²hPYY(4-36), Ile³¹Lys³³hPYY(4-36), and comprise a C-terminal tail motif of hPYY. The C-terminal Ile³¹Asn³⁴hPYY(4-36), Ile³¹Lys³⁵hPYY(4-36), motif may comprise amino acid residues 32-35 of hPYY, e.g., Ile³¹Thr³⁶hPYY(4-36), Leu³¹Phe³⁶hPYY(4-36), Thr, Arg, Gln, Arg (SEQ ID NO: 351). In such an embodi-Leu³¹Phe³⁶hPYY(4-36), Leu³¹Ser³²hPYY(4-36), ment, the PYY analog polypeptides of the invention do not Val³¹Lys³³hPYY(4-36), Leu³¹Asn³⁴hPYY(4-36), include any native PYY polypeptides or 1-4 N-terminal dele-Leu³¹Lys³⁵hPYY(4-36), Leu³¹Thr³⁶hPYY(4-36), tions thereof (e.g., PYY(1-36), PYY(2-36), PYY(3-36) and, Leu³¹Phe³⁶hPYY(4-36), Ser³²Lys³³hPYY(4-36), PYY(4-36)). In some embodiments, such PYY analogs do Ser³²Asn³⁴hPYY(4-36), Ser³²Lys³⁵hPYY(4-36), not include: Lys²⁵hPYY(5-36), Arg⁴hPYY(4-36), Ser³²Thr³⁶hPYY(4-36), Ser³²Phe³⁶hPYY(4-36), Gln⁴hPYY(4-36), Asn⁴hPYY(4-36), Lys²⁵hPYY(4-36), Lys³³Asn³⁴hPYY(4-36), Lys³³Lys³⁵hPYY(4-36), Leu³hPYY(3-36), Val³hPYY(3-36), Lys²⁵hPYY(3-36), Lys³³Thr³⁶hPYY(4-36), Lys³³Phe³⁶hPYY(4-36), Tyr¹,³⁶pPYY, Pro¹³Ala¹⁴hPYY, FMS-PYY, FMS-PYY(3-Asn³⁴Lys³⁵hPYY(4-36), Asn³⁴Phe³⁶hPYY(4-36), 36), Fmoc-PYY, Fmoc-PYY(3-36), FMS₂-PYY, FMS₂-PYY Lys³⁵Thr³⁶hPYY(4-36), Lys³⁵Phe³⁶hPYY(4-36), (3-36), Fmoc₂-PYY, or Fmoc₂-PYY(3-36).

Thr²⁷hPYY(5-36), Phe²⁷hPYY(5-36), Ile²⁸hPYY(5-36), In another aspect, such PYY analog polypeptides of the Val²⁸hPYY(5-36), Gln²⁹hPYY(5-36), Ile³⁰hPYY(5-36), invention comprising a C-terminal tail motif of hPYY also do Val³⁰hPYY(5-36), Ile³¹hPYY(5-36), Leu³¹hPYY(5-36), not include: Thr²⁷hPYY(3-36), Ile³⁰hPYY(3-36), Ser³²hPYY(5-36), Lys³³hPYY(5-36), Asn³⁴hPYY(5-36), Thr³⁶hPYY(3-36), Lys²⁵Thr²⁷hPYY(3-36), Lys³⁵hPYY(5-36), Thr³⁶hPYY(5-36), Phe³⁶hPYY(5-36), Lys²⁵Ile³⁰hPYY(3-36), Lys²⁵Asn²⁴hPYY(3-36), Lys²⁵Thr²⁷hPYY(5-36), Lys²⁵Phe²⁷hPYY(5-36), Lys²⁵Thr³⁶hPYY(3-36), Thr²⁷Ile²⁸hPYY(3-36), Lys²⁵Ile²⁸hPYY(5-36), Lys²⁵Val²⁸hPYY(5-36), Thr²⁷Val²⁸hPYY(3-36), Thr²⁷Gln²⁹hPYY(3-36), Lys²⁵Gln²⁹hPYY(5-36), Lys²⁵Ile³³hPYY(5-36), Thr²⁷Ile³⁰hPYY(3-36), Thr²⁷Val³⁰hPYY(3-36), Lys²⁵Val³⁰hPYY(5-36), Lys²⁵Ile³hPYY(5-36), Thr²⁷Ile³⁶hPYY(3-36), Thr²⁷Leu³¹hPYY(3-36), Lys²⁵Leu³¹hPYY(5-36), Lys²⁵Ser³²hPYY(5-36), Thr²⁷Thr³⁶hPYY(3-36), Thr²⁷Phe³⁶hPYY(3-36), Lys²⁵Lys³³hPYY(5-36), Lys²⁵Asn²⁴hPYY(5-36), Phe²⁷Ile³⁰hPYY(3-36), Phe²⁷Thr³hPYY(3-36), Lys²⁵Lys³⁵hPYY(5-36), Lys²⁵Thr³⁶hPYY(5-36), Gln²⁹Ile³⁰hPYY(3-36), Gln²⁹Thr³⁶hPYY(3-36), Lys²⁵Phe³⁶hPYY(5-36), Thr²⁷Ile²⁸hPYY(5-36), Ile³⁰Ile³¹hPYY(3-36), Ile³⁰Leu³¹hPYY(3-36), Thr²⁷Val²⁸hPYY(5-36), Thr²⁷Gln²⁹hPYY(5-36), Ile³⁰Thr³⁶hPYY(3-36), Ile³⁰Phe³⁶hPYY(3-36), Thr²⁷Ile³⁰hPYY(5-36), Thr²⁷Val³²hPYY(5-36), Val³⁰Thr³⁶hPYY(3-36), Ile³¹Thr³⁶hPYY(3-36), Thr²⁷Ile³¹hPYY(5-36), Thr²⁷Leu³¹hPYY(5-36), Ile³⁰Phe³⁶hPYY(3-36), Leu³¹Thr³⁶hPYY(3-36), Thr²⁷Ser³²hPYY(5-36), Thr²⁷Lys³³hPYY(5-36), Thr²⁷hPYY(4-36), Phe²⁷hPYY(4-36), Ile²⁸hPYY(4-36), Thr²⁷Asn³⁴hPYY(5-36), Thr²⁷Lys³⁵hPYY(5-36), Val²⁸hPYY(4-36), Gln²⁹hPYY(4-36), Ile³⁰hPYY(4-36), Thr²⁷Thr³⁶hPYY(5-36), Thr²⁷Phe³⁶hPYY(5-36), Val³⁰hPYY(4-36), Ile³¹hPYY(4-36), Leu³¹hPYY(4-36), Phe²⁷Ile²⁸hPYY(5-36), Phe²⁷Val²⁸hPYY(5-36), Thr³⁶hPYY(4-36), Phe³⁶hPYY(4-36), Lys²⁵Thr²⁷hPYY(4-Phe²⁷Gln²⁹hPYY(5-36), Phe²⁷Ile³⁰hPYY(5-36), 36), Lys²⁵Phe²⁷hPYY(4-36), Lys²⁵Ile²⁸hPYY(4-36), Phe²⁷Val³⁰hPYY(5-36), Phe²⁷Ile³¹hPYY(5-36), Lys²⁵Val²⁸hPYY(4-36), Lys²⁵Gln²⁹hPYY(4-36), Phe²⁷Leu³¹hPYY(5-36), Phe²⁷Ser³²hPYY(5-36), Lys²⁵Ile³⁰hPYY(4-36), Lys²⁵Val³⁰hPYY(4-36), Phe²⁷Lys³³hPYY(5-36), Phe²⁷Asn³⁴hPYY(5-36), Lys²⁵Ile³¹hPYY(4-36), Lys²⁵Leu³¹hPYY(4-36), Phe²⁷Lys³⁵hPYY(5-36), Phe²⁷Thr³⁶hPYY(5-36), Lys²⁵Thr³⁶hPYY(4-36), Lys²⁵Phe³⁶hPYY(4-36), Phe²⁷Phe³⁶hPYY(5-36), Gln²⁹Ile³⁰hPYY(5-36), Thr²⁷Ile²⁸hPYY(4-36), Thr²⁷Val²⁸hPYY(4-36), Gln²⁹Val³⁰hPYY(5-36), Gln²⁹Ile³¹hPYY(5-36), Thr²⁷Gln²⁹hPYY(4-36), Thr²⁷Ile³⁰hPYY(4-36), Gln²⁹Leu³¹hPYY(5-36), Gln²⁹Ser³²,hPYY(5-36), Thr²⁷Val³⁰hPYY(4-36), Thr²⁷Ile³¹hPYY(4-36), Gln²⁹Leu³³hPYY(5-36), Gln²⁹Asn³⁴hPYY(5-36), Thr²⁷Leu³¹hPYY(4-36), Thr²⁷Thr³⁶hPYY(4-36), Gln²⁹Leu³⁵hPYY(5-36), Gln²⁹Thr³⁶hPYY(5-36), Thr²⁷Phe³⁶hPYY(4-36), Phe²⁷Ile²⁸hPYY(4-36), Gln²⁹Phe³⁶hPYY(5-36), Ile³⁰Ile³¹hPYY(5-36), Phe²⁷Val²⁸hPYY(4-36), Phe²⁷Gln²⁹hPYY(4-36), Ile³⁰Leu³¹hPYY(5-36), Ile³⁰Ser³²hPYY(5-36), Phe²⁷Ile³⁰hPYY(4-36), Phe²⁷Val³⁰hPYY(4-36), Ile³⁰Lys³³hPYY(5-36), Ile³⁰Asn³⁴hPYY(5-36), Phe²⁷Ile³¹hPYY(4-36), Phe²⁷Leu³¹hPYY(4-36), Ile³⁰Lys³⁵hPYY(5-36), Ile³⁰Thr³⁶hPYY(5-36), Phe²⁷Thr³⁶hPYY(4-36), Phe²⁷Phe³⁶PYY(4-36), Ile³⁰Phe³⁶hPYY(5-36), Val³⁰Ile³¹hPYY(5-36), Gln²⁹Ile³⁰hPYY(4-36), Gln²⁹Val³⁰hPYY(4-36), Val³⁰Leu³¹hPYY(5-36), Val³⁰Ser³²hPYY(5-36), Gln²⁹Ile³¹hPYY(4-36), Gln²⁹Leu³¹hPYY(4-36), Val³⁰Lys³³hPYY(5-36), Val³⁰Asn³⁴hPYY(5-36), Gln²⁹Thr³⁶hPYY(4-36), Gln²⁹Phe³⁶hPYY(4-36), Val³⁰Lys³⁵hPYY(5-36), Val³⁰Thr³⁶hPYY(5-36), Ile³⁰Ile³¹hPYY(4-36), Ile³⁰Leu³¹hPYY(4-36), Val³⁰Phe³⁶hPYY(5-36), Ile³¹Ser³²hPYY(5-36), Ile³⁰Thr³⁶hPYY(4-36), Ile³⁰Phe³⁶hPYY(4-36), Ile³¹Asn³⁴hPYY(5-36), Val³⁰Ile³¹hPYY(4-36), Val³⁰Leu³¹hPYY(4-36), Ile³¹Thr³⁶hPYY(5-36), Val³⁰Thr³⁶hPYY(4-36), Val³⁰Phe³⁶hPYY(4-36), Leu³Phe³⁶hPYY(5-36), Ile³¹Thr³⁶hPYY(4-36), Leu³¹Phe³⁶hPYY(4-36), Leu³¹Ser³²hPYY(5-36), Val³¹Lys³³hPYY(5-36), Leu³¹Thr³% hPYY(4-36), Leu³¹Asn³⁴hPYY(5-36), Leu³¹Lys³⁵hPYY(5-36), Leu³¹Phe³⁶hPYY(4-36), Thr²⁷hPYY(5-36), Phe²⁷hPYY(5-Leu³¹Thr³⁶hPYY(5-36), Leu³¹Phe³⁶hPYY(5-36), 36), Ile²⁸hPYY(5-36), Val²⁸hPYY(5-36), Gln²⁹hPYY(5-36), Ser³²Lys³³hPYY(5-36), Ser³²Asn³⁴hPYY(5-36), Ile³⁰hPYY(5-36), Val³⁰hPYY(5-36), Ile³⁰hPYY(5-36), Ser³²Lys³⁵hPYY(5-36), Ser³²Thr³⁶hPYY(5-36), Leu³¹hPYY(5-36), Thr³⁶hPYY(5-36), Phe³⁶hPYY(5-36), Ser³²Phe³⁶hPYY(5-36), Lys³³Asn³⁴hPYY(5-36), Lys²⁵Thr²⁷hPYY(5-36), Lys²⁵Phe²⁷hPYY(5-36), Lys²⁵Ile²⁸hPYY(5-36), Lys²⁵Val²⁸hPYY(5-36),
Lys²⁵Gln²⁹hPYY(5-36), Lys²⁵Ile³³hPYY(5-36),
Lys²⁵Val³⁰hPYY(5-36), Lys²⁵Ile³¹hPYY(5-36),
Lys²⁵Leu³¹hPYY(5-36), Lys²⁵Thr³⁶hPYY(5-36),
Lys²⁵Phe³⁶hPYY(5-36), Thr²⁷Ile²⁸hPYY(5-36),
Thr²⁷Val²⁸hPYY(5-36), Thr²⁷Gln²⁹hPYY(5-36),
Thr²⁷Ile³⁰hPYY(5-36), Thr²⁷Val³⁰hPYY(5-36),
Thr²⁷Ile³¹hPYY(5-36), Thr²⁷Leu³¹hPYY(5-36),
Thr²⁷Thr³⁶hPYY(5-36), Thr²⁷Phe³⁶hPYY(5-36),
Phe²⁷Ile²⁸hPYY(5-36), Phe²⁷Val²⁸hPYY(5-36),
Phe²⁷Gln²⁹hPYY(5-36), Phe²⁷Ile³⁰hPYY(5-36),
Phe²⁷Val³⁰hPYY(5-36), Phe²⁷Ile³¹hPYY(5-36),
Phe²⁷Leu³¹hPYY(5-36), Phe²⁷Thr³⁶hPYY(5-36),
Phe²⁷Phe³⁶hPYY(5-36), Gln²⁹Ile³⁰hPYY(5-36),
Gln²⁹Val³⁰hPYY(5-36), Gln²⁹Ile³¹hPYY(5-36),
Gln²⁹Leu³¹hPYY(5-36), Gln²⁹Thr³⁶hPYY(5-36),
Gln²⁹Phe³⁶hPYY(5-36), Ile³⁰Ile³¹hPYY(5-36),
Ile³⁰Leu³¹hPYY(5-36), Ile³⁰Thr³⁶hPYY(5-36),
Ile³⁰Phe³⁶hPYY(5-36), Val³⁰Ile³¹hPYY(5-36),
Val³⁰Leu³¹hPYY(5-36), Vl³⁰Thr³⁶hPYY(5-36),
Val³⁰Phe³⁶hPYY(5-36), Ile³Thr³⁶hPYY(5-36),
Leu³¹Phe³⁶hPYY(5-36), Leu³¹Phe³⁶hPYY(5-36),
Leu³¹Thr³⁶hPYY(5-36), or Leu³¹Phe³⁶hPYY(5-36).

In some embodiments, the PYY analog polypeptides of the invention are at least 34 amino acids in length. In some embodiments, the PYY analog polypeptides of the invention include only natural L amino acid residues and/or modified natural L amino acid residues. In some embodiments, the PYY analog polypeptides of the invention do not include unnatural amino acid residues.

More particularly, in one aspect, the present invention relates to PYY analog polypeptides including one or more amino acid sequence modifications. Such modifications include substitutions, insertions, and/or deletions, alone or in combination. In some embodiments, the PYY analog polypeptides of the invention include one or more modifications of a "non-essential" amino acid residue. In the context of the invention, a "non-essential" amino acid residue is a residue that can be altered, i.e., deleted or substituted, in the native human PYY amino acid sequence without abolishing or substantially reducing the PYY agonist activity of the PYY analog polypeptide. In some embodiments, the PYY analog polypeptides of the invention retain at least about 25%, or from about 30%, about 40%, about 50%, about 60%, about 70%, about 80%, about 90%, about 95%, about 98%, or about 99% percent of the biological activity of native human PYY with regard to the reduction of nutrient availability. In another embodiment, the PYY analog polypeptides of the invention exhibit improved PYY agonist activity. In some embodiments, the PYY analog polypeptides of the invention exhibits at least about 110%, about 125%, about 130%, about 140%, about 150%, about 200%, or more of the biological activity of native human PYY with regard to the reduction of nutrient availability.

PYY analog polypeptides are those having a potency in one of the assays described herein (including food intake, gastric emptying, pancreatic secretion, body composition or weight reduction assays) which is equal to or greater than the potency of NPY, PYY, or PYY(3-36) in that same assay. In some embodiments, PYY analog polypeptides of the invention may exhibit improved ease of manufacture, stability, and/or ease of formulation, as compared to PP, NPY, PYY, or PYY(3-36).

a. Substitutions

In one embodiment, the PYY analog polypeptides of the invention may have one or more substitutions in the amino acid sequence of native human PYY (SEQ ID NO: 2), alone or in combination with one or more insertions or deletions. In some embodiments, the substitution does not abolish or substantially reduce the PYY agonist activity of the PYY analog polypeptide. In one aspect, the present invention relates to PYY analog polypeptides that have a single substitution, or consecutive or non-consecutive substitution of more than one amino acid residues in the amino acid sequence of native human PYY (SEQ ID NO: 2). In some embodiments, the PYY analog polypeptides of the invention include one, two, three, four, five, six, seven, eight, nine, or ten amino acid substitutions.

In some embodiments, the amino acid residues of native human PYY (SEQ ID NO: 2) at the helical C-terminus region of PYY (e.g., residues 20, 24, 25, 27 and 29), the tail end residues (32-36), and/or the N-terminus prolines at position 5 and 8 are not substituted. In some embodiments, amino acid residues are not substituted at positions 32 through 36 of native human PYY (SEQ ID NO: 2). In another embodiment, amino acid residues of native human PYY (SEQ ID NO: 2) are not substituted at one or more amino acid sequence positions selected from: 5, 7, 8, 20, 24, 25, 27, 29, 32, 33, 34, 35, 36, and any combination thereof.

Substitutions may include conserved amino acid substitutions. A "conservative amino acid substitution" is one in which the amino acid residue is replaced with an amino acid residue having a similar side chain, or physicochemical characteristics (e.g., electrostatic, hydrogen bonding, isosteric, hydrophobic features). Families of amino acid residues having similar side chains are known in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, methionine, cysteine), nonpolar side chains (e.g., alanine, valine, leucine, isoleucine, proline, phenylalanine, tryptophan), β-branched side chains (e.g., threonine, valine, isoleucine) and aromatic side chains (e.g., tyrosine, phenylalanine, tryptophan, histidine).

In another embodiment, the PYY analog polypeptides of the invention may include substitutions of one or more unnatural and/or non-amino acids, e.g., amino acid mimetics, into the sequence of PYY (SEQ ID NO: 2). In some embodiments, the non-amino acids inserted into the sequence of PYY (SEQ ID NO: 2) may be β-turn mimetics or linker molecules, such as —NH—X—CO—, wherein X=(CH₂)ₙ (where n can be 2-20) or —NH—CH₂CH₂(—O—CH₂CH₂—O—)ₘ—CH₂—CO— (where m=1-5). Linker molecules can include aminocaproyl ("Aca"), β-alanyl, and 8-amino-3,6-dioxaoctanoyl. β-turn mimetics are available commercially (BioQuadrant Inc, Quebec, Canada) and have been described in literature (Hanessian et al., Tetrahedron 12789-854 (1997); Gu et al., Tetrahedron Letters 44: 5863-6 (2003); Bourguet et al., Bioorganic & Medicinal Chemistry Letters 13: 1561-4 (2003); Grieco et al., Tetrahedron Letters 43: 6297-9 (2002); Souers et al., Tetrahedron 57: 7431-48 (2001); Tsai et al., Bioorganic & Medicinal Chemistry 7: 29-38 (1999); Virgilio et al., Tetrahedron 53: 6635-44 (1997)). β-turn mimetics can include mimic A and mimic B illustrated below.

mimic A          mimic B

PYY analog polypeptides comprising amino acid sequence β-turn mimetic substitutions include native human PYY (SEQ ID NO: 2), wherein amino acids at positions x and x+1 are substituted with β-turn mimetics selected from the group consisting of mimic A and mimic B, wherein x is selected from the amino acids at amino acid positions 8 to 14 of native human PYY. Altenatively, known dipeptide turn inducers may be susbtituted, for example, Ala-Aib and Ala-Pro dipeptides.

Other PYY analog polypeptides comprising amino acid sequence substitutions include the PYY analog polypeptides of the Formula (II) (SEQ ID NO: 88):

```
Xaa1 Xaa2 Xaa3 Xaa4 Pro Xaa6 Xaa7 Pro Xaa9 Xaa10
Xaa11 Xaa12 Xaa13 Xaa14 Xaa15 Xaa16 Xaa17 Xaa18
Xaa19 Tyr Xaa21 Xaa22 Xaa23 Leu Arg Xaa26 Tyr
Xaa28 Asn Xaa30 Xaa31 Thr Arg Gln Arg Xaa36
``` wherein:
Xaa$_1$ is Tyr, Ala, Phe, Trp, or absent;
Xaa$_2$ is Pro, Gly, d-Ala, homoPro, hydroxy-Pro, or absent;
Xaa$_3$ is Ile, Ala, NorVal, Val, Leu, Pro, Ser or Thr;
Xaa$_4$ is Lys, Ala, Gly, Arg, d-Ala, homoLys, homoArg, Glu, or Asp;
Xaa$_6$ is Glu, Ala, Val, Asp, Asn, or Gln;
Xaa$_7$ is Ala, Asn, His, Ser, or Tyr;
Xaa$_9$ is Gly, Ala Ser, sarcosine, Pro, or Aib;
Xaa$_{10}$ is Glu, Ala, Asp, Asn, Gln, Pro, Aib, or Gly;
Xaa$_{11}$ is Asp, Ala, Glu, Asn, Gln, Pro, Aib, or Gly;
Xaa$_{12}$ is Ala or d-Ala;
Xaa$_{13}$ is Ser, Ala, Thr, or homoSer;
Xaa$_{14}$ is Pro, Ala, homo-Pro, hydroxy-Pro, Aib, or Gly;
Xaa$_{15}$ is Glu, Ala, Asp, Asn, Gln, Pro, Aib, or Gly;
Xaa$_{16}$ is Glu, Ala, Asp, Asn, or Gln;
Xaa$_{17}$ is Leu, Ala, Met, Trp, Ile, Val, or NorVal;
Xaa$_{18}$ is Asn, Asp, Ala, Glu, Gln, Ser or Thr;
Xaa$_{19}$ is Arg, Tyr, Lys, Ala, Gln, or N(Me)Ala;
Xaa$_{21}$ is Tyr, Ala, Met, Phe, or Leu;
Xaa$_{22}$ is Ala, Ser, Thr, or d-Ala;
Xaa$_{23}$ is Ser, Ala, Thr, or homoSer;
Xaa$_{26}$ is His or Ala;
Xaa$_{28}$ is Leu, Ile, Val, or Ala;
Xaa$_{30}$ is Leu, Ala, NorVal, Val, Ile, or Met;
Xaa$_{31}$ is Ala, Val, Ile, or Leu; and
Xaa$_{36}$ is Tyr, N(Me)Tyr, His, Trp, or Phe;
with the proviso that said polypeptide is not a native PPF polypeptide, PYY(2-36), PP(2-36), Ala$^{13}$NPY, Leu$^3$hPYY(3-36), Val$^3$hPYY(3-36), hPP(1-7)-pNPY, or hPP(1-17)-pNPY.

In another embodiment, the PYY analog polypeptides of Formula II also do not include: Ile$^{28}$hPYY(3-36), Val$^{28}$hPYY(3-36), Val$^{30}$hPYY(3-36), Ile$^{31}$IhPYY(3-36), Leu$^{31}$hPYY(3-36), Phe$^{36}$hPYY(3-36), Val$^{30}$Ile$^{31}$hPYY(3-36), Val$^{30}$Leu$^{31}$hPYY(3-36), Val$^{30}$Phe$^{36}$hPYY(3-36), or Leu$^{31}$Phe$^{36}$hPYY(3-36).

As will be recognized by one of skill in the art, the polypeptides of Formula II may be in the free acid form, or may be C-terminally amidated.

Other PYY analog polypeptides comprising amino acid sequence substitutions include the PYY analog polypeptides of the Formula (III) (SEQ ID NO: 348):

```
Xaa1 Xaa2 Xaa3 Xaa4 Pro Xaa6 Xaa7 Pro Xaa9 Xaa10
Xaa11 Xaa12 Xaa13 Xaa14 Xaa15 Xaa16 Xaa17 Xaa18
Xaa19 Tyr Xaa21 Xaa22 Xaa23 Leu Arg Xaa26 Tyr
Xaa28 Asn Xaa30 Xaa31 Thr Arg Gln Arg Xaa36
``` wherein:
Xaa$_1$ is Tyr, Phe, Trp, or absent;
Xaa$_2$ is Pro, Gly, d-Ala, homoPro, hydroxy-Pro, or absent;
Xaa$_3$ is Ile, Ala, NorVal, Val, Leu, Pro, Ser or Thr;
Xaa$_4$ is Lys, Ala, Gly, Arg, d-Ala, homoLys, homoArg, Glu, or Asp;
Xaa$_6$ is Glu, Ala, Val, Asp, Asn, or Gln;
Xaa$_7$ is Ala, Asn, His, Ser, or Tyr;
Xaa$_9$ is Gly, Ala Ser, sarcosine, Pro, or Aib;
Xaa$_{10}$ is Glu, Ala, Asp, Asn, Gln, Pro, Aib, or Gly;
Xaa$_{11}$ is Asp, Ala, Glu, Asn, Gln, Pro, Aib, or Gly;
Xaa$_{12}$ is Ala or d-Ala;
Xaa$_{13}$ is Ser, Ala, Thr, Pro, or homoSer;
Xaa$_{14}$ is Pro, Ala, homo-Pro, hydroxyPro, Aib, or Gly;
Xaa$_{15}$ is Glu, Ala, Asp, Asn, Gln, Pro, Aib, or Gly;
Xaa$_{16}$ is Glu, Ala, Asp, Asn, or Gln;
Xaa$_{17}$ is Leu, Ala, Met, Trp, Ile, Val, or NorVal;
Xaa$_{18}$ is Asn, Asp, Ala, Glu, Gln, Ser or Thr;
Xaa$_{19}$ is Arg, Tyr, Lys, Ala, Gln, or N(Me)Ala;
Xaa$_{21}$ is Tyr, Ala, Met, Phe, or Leu;
Xaa$_{22}$ is Ala, Ser, Thr, or d-Ala;
Xaa$_{23}$ is Ser, Ala, Thr, or homoSer;
Xaa$_{26}$ is His or Ala;
Xaa$_{28}$ is Leu, Ile, Val, or Ala;
Xaa$_{30}$ is Leu, Ala, NorVal, Val, Ile, or Met;
Xaa$_{31}$ is Ala, Val, Ile, or Leu; and
Xaa$_{36}$ is Tyr, N(Me)Tyr, His, Trp, or Phe;
with the proviso that said polypeptide is not a native PPF polypeptide, NPY(2-36), PYY(2-36), PP(2-36), Ala$^3$NPY, Ala$^4$NPY, Ala$^6$NPY, Ala$^7$NPY, Tyr$^7$pNPY, Ala$^9$NPY, Ala$^{10}$NPY, Ala$^{11}$NPY, Ala$^{13}$NPY, Gly$^{14}$NPY, Ala$^{15}$NPY, Ala$^{16}$NPY, Ala$^{17}$NPY, Ala$^{19}$NPY, Lys$^{19}$NPY, Ala$^{21}$NPY, Ala$^{22}$NPY, Lys$^{25}$NPY, Ala$^{26}$NPY, Phe$^{27}$NPY, Ala$^{28}$NPY, Gln$^{29}$NPY, Ala$^{30}$NPY, Ala$^{31}$NPY, Phe$^{36}$NPY, His$^{36}$NPY, Leu$^3$hPYY(3-36), Val$^3$hPYY(3-36), Lys$^{25}$hPYY(3-36), Pro$^{13}$Ala$^{14}$hPYY(3-36), Tyr$^1$NPY, Ala$^7$NPY, or hPP(19-23)-pNPY.

In another embodiment, the PYY analog polypeptides of Formula III also do not include: Ile$^{28}$hPYY(3-36), Val$^{28}$hPYY(3-36), Val$^{30}$hPYY(3-36), Ile$^{31}$hPYY(3-36), Leu$^{31}$hPYY(3-36), Phe$^{36}$hPYY(3-36), Val$^{30}$Ile$^{31}$hPYY(3-36), Val$^{30}$Leu$^{31}$hPYY(3-36), Val$^{30}$Phe$^{36}$PYY(3-36), or Leu$^{31}$Phe$^{36}$hPYY(3-36).

As will be recognized by one of skill in the art, the polypeptides of Formula III may be in the free acid form, or may be C-terminally amidated.

Other PYY analog polypeptides comprising amino acid sequence substitutions include the PYY analog polypeptides of the Formula (IV) (SEQ ID NO: 349):

```
Xaa1 Xaa2 Xaa3 Xaa4 Pro Xaa6 Xaa7 Pro Xaa9 Xaa10
Xaa11 Xaa12 Xaa13 Xaa14 Xaa15 Xaa16 Xaa17 Xaa18
Xaa19 Tyr Xaa21 Xaa22 Xaa23 Leu Arg Xaa26 Tyr
Xaa28 Asn Xaa30 Xaa31 Thr Arg Gln Arg Xaa36
``` wherein:
Xaa$_1$ is Tyr, Phe, Trp, or absent;
Xaa$_2$ is Pro, Gly, d-Ala, homoPro, hydroxy-Pro, or absent;
Xaa$_3$ is Ile, Ala, NorVal, Val, Leu, Pro, Ser or Thr;
Xaa$_4$ is Lys, Ala, Gly, Arg, d-Ala, homoLys, homoArg, Glu, or Asp;
Xaa$_6$ is Glu, Ala, Val, Asp, Asn, or Gln;
Xaa$_7$ is Ala, Asn, His, Ser, or Tyr;
Xaa$_9$ is Gly, Ala Ser, sarcosine, Pro, or Aib;
Xaa$_{10}$ is Glu, Ala, Asp, Asn, Gln, Pro, Aib, or Gly;
Xaa$_{11}$ is Asp, Ala, Glu, Asn, Gln, Pro, Aib, or Gly;
Xaa$_{12}$ is Ala or d-Ala;

Xaa$_{13}$ is Ser, Ala, Thr, or homoSer;
Xaa$_{14}$ is Pro, Ala, homo-Pro, hydroxyPro, Aib, or Gly;
Xaa$_{15}$ is Glu, Ala, Asp, Asn, Gln, Pro, Aib, or Gly;
Xaa$_{16}$ is Glu, Ala, Asp, Asn, or Gln;
Xaa$_{17}$ is Leu, Ala, Met, Trp, Ile, Val, or NorVal;
Xaa$_{18}$ is Asn, Asp, Ala, Glu, Gln, Ser or Thr;
Xaa$_{19}$ is Arg, Tyr, Lys, Ala, Gln, or N(Me)Ala;
Xaa$_{21}$ is Tyr, Ala, Met, Phe, or Leu;
Xaa$_{22}$ is Ala, Ser, Thr, or d-Ala;
Xaa$_{23}$ is Ser, Ala, Thr, or homoSer;
Xaa$_{26}$ is His or Ala;
Xaa$_{28}$ is Leu, Ile, Val, or Ala;
Xaa$_{30}$ is Leu, Ala, NorVal, Val, Ile, or Met;
Xaa$_{31}$ is Ala, Val, Ile, or Leu; and
Xaa$_{36}$ is Tyr, N(Me)Tyr, His, Trp, or Phe;
with the proviso that said polypeptide is not a native PPF polypeptide, PYY(2-36), Ala$^{13}$NPY, Leu$^3$hPYY(3-36), or Val$^3$hPYY(3-36).

In another embodiment, the PYY analog polypeptides of Formula IV also do not include: Ile$^{28}$hPYY(3-36), Val$^{28}$hPYY(3-36), Val$^{30}$hPYY(3-36), Ile$^{31}$hPYY(3-36), Leu$^{31}$hPYY(3-36), Phe$^{36}$hPYY(3-36), Val$^{30}$Ile$^{31}$hPYY(3-36), Val$^{30}$Leu$^{31}$hPYY(3-36), Val$^{30}$Phe$^{36}$hPYY(3-36), or Leu$^{31}$Phe$^{36}$hPYY(3-36).

As will be recognized by one of skill in the art, the polypeptides of Formula IV may be in the free acid form, or may be C-terminally amidated.

Other PYY analog polypeptides comprising amino acid sequence linker substitutions include PYY(1-4)Aminocaproyl(14-36) (IUPAC [Aca$^{5-13}$]PYY) (Aminocaproyl is abbreviated as "Aca"), PYY(1-4)Aca(15-36), PYY(1-4)Aca(16-36), PYY(1-4)Aca(22-36) (IUPAC [Aca$^{5-21}$]PYY), and PYY(1-4)Aca(25-36) (IUPAC [Aca$^{5-24}$]PYY) (SEQ ID NOS: 180-184).

b. Deletions and Truncations

In another embodiment, the PYY analog polypeptides of the invention may have one or more amino acid residues deleted from the amino acid sequence of native human PYY (SEQ ID NO: 2), alone or in combination with one or more insertions or substitutions. In one aspect, the PYY analog polypeptides of the invention may have one or more amino acid residues deleted from the N-terminus or C-terminus of native human PYY (SEQ ID NO: 2), with the proviso that the polypeptide is not SEQ ID NO: 3. In another embodiment, the PYY analog polypeptides of the invention may have one or more amino acid residues deleted at amino acid positions 2 through 35 of native human PYY (SEQ ID NO: 2). Such deletions may include more than one consecutive or non-consecutive deletions at amino acid positions 2 through 35 of native human PYY (SEQ ID NO: 2). In some embodiments, the amino acid residues at positions 24 through 36 of native human PYY (SEQ ID NO: 2) are not deleted.

In another embodiment, the PPF polypeptides of the invention described in Formulas I to VII may include N or C-terminal truncations, or internal deletions at amino acid positions 2 to 35 of Formula I, II, III, IV, V, VI or VII, so long as at least one biological activity of a native PPF polypeptide is retained. In some embodiments, the amino acid residues at positions 5 through 8 and 24 through 36 are not deleted. In some embodiments, the amino acid residues at positions 5 through 8 and 32 through 35 are not deleted.

c. Insertions

In another embodiment, the PYY analog polypeptides of the invention may have one or more amino acid residues inserted into the amino acid sequence of native human PYY (SEQ ID NO: 2), alone or in combination with one or more deletions and/or substitutions. In one aspect, the present invention relates to PYY analog polypeptides that have a single insertion, or consecutive or non-consecutive insertions of more than one amino acid residues into the amino acid sequence of native human PYY (SEQ ID NO: 2). In some embodiments, amino acid residues are not inserted at positions 24 through 36 of native human PYY (SEQ ID NO: 2).

In another embodiment, the PYY analog polypeptides of the invention may include insertions of one or more unnatural amino acids and/or non-amino acids into the sequence of PYY (SEQ ID NO: 2). In some embodiments, the unnatural amino acids inserted into the sequence of PYY (SEQ ID NO: 2) may be β-turn mimetics or linker molecules. Linker molecules include aminocaproyl ("Aca"), β-alanyl, and 8-amino-3,6-dioxaoctanoyl. β-turn mimetics include mimic A and mimic B illustrated below, also Ala-Aib and Ala-Pro dipeptides.

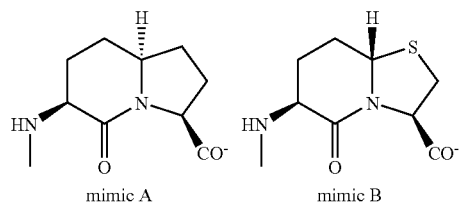

mimic A          mimic B

In another embodiment, PYY analog polypeptides of the invention may include insertions of polyamino acid sequences (e.g., poly-his, poly-arg, poly-lys, poly-ala, etc.) at either terminus of the polypeptide, known as "extensions" or "tails."

PYY analog polypeptides comprising amino acid sequence insertions include alanine substitutions at each amino acid position along the length of native human PYY. Such PYY analog polypeptides include PYY (+Axa), wherein x is selected from 1' to 36 (SEQ ID NOS: 54-87).

d. Derivatives

The present invention also relates to derivatives of the PYY analog polypeptides of the invention. Such derivatives include PYY analog polypeptides conjugated to one or more water soluble polymer molecules, such as polyethylene glycol ("PEG") or fatty acid chains of various lengths (e.g., stearyl, palmitoyl, octanoyl), by the addition of polyamino acids, such as poly-his, poly-arg, poly-lys, and poly-ala, or by addition of small molecule substituents include short alkyls and constrained alkyls (e.g., branched, cyclic, fused, adamantyl), and aromatic groups. In some embodiments, the water soluble polymer molecules will have a molecular weight ranging from about 500 to about 20,000 Daltons.

Such polymer-conjugations may occur singularly at the N- or C-terminus or at the side chains of amino acid residues within the sequence of the PYY analog polypeptides. Alternatively, there may be multiple sites of derivatization along the PYY analog polypeptide. Substitution of one or more amino acids with lysine, aspartic acid, glutamic acid, or cysteine may provide additional sites for derivatization. See, e.g., U.S. Pat. Nos. 5,824,784 and 5,824,778. In some embodiments, the PYY analog polypeptides may be conjugated to one, two, or three polymer molecules.

In some embodiments, the water soluble polymer molecules are linked to an amino, carboxyl, or thiol group, and may be linked by N or C termini, or at the side chains of lysine, aspartic acid, glutamic acid, or cysteine. Alternatively, the water soluble polymer molecules may be linked with diamine and dicarboxylic groups. In some embodiments, the PYY analog polypeptides of the invention are conjugated to one, two, or three PEG molecules through an epsilon amino group on a lysine amino acid.

PYY analog polypeptide derivatives of the invention also include PYY analog polypeptides with chemical alterations to one or more amino acid residues. Such chemical alterations include amidation, glycosylation, acylation, sulfation, phosphorylation, acetylation, and cyclization. The chemical alterations may occur singularly at the N- or C-terminus or at the side chains of amino acid residues within the sequence of the PYY analog polypeptides. In one embodiment, the C-terminus of these peptides may have a free —OH or —NH$_2$ group. In another embodiment, the N-terminal end may be capped with an isobutyloxycarbonyl group, an isopropyloxycarbonyl group, an n-butyloxycarbonyl group, an ethoxycarbonyl group, an isocaproyl group ("isocap"), an octanyl group, an octyl glycine group (denoted as "G(Oct)" or "octylGly"), an 8-aminooctanic acid group, a dansyl, and/or a Fmoc group. In some embodiments, cyclization can be through the formation of disulfide bridges, see, e.g., SEQ ID NO. 171. Alternatively, there may be multiple sites of chemical alteration along the PYY analog polypeptide.

In some embodiments, PYY analog polypeptide derivatives may include PYY analog polypeptides with chemical alterations to one or more amino acid residues. These chemical alterations may occur singularly at the N- or C-terminus or at the side chains of amino acid residues within the sequence of the PYY analog polypeptides. In exemplary embodiments, PYY analog polypeptides are chemically altered to include a Bolton-Hunter group. Bolton-Hunter reagents are known in the art ("Radioimmunoassay and related methods," A. E. Bolton and W. M. Hunter, Chapter 26 of *Handbook of Experimental Immunology*, Volume I, Immunochemistry, edited by D. M. Weir, Blackwell Scientific Publications, 1986), and may be used to introduce tyrosine-like moieties with a neutral linkage, through amino-terminal α-amino groups or ε-amino groups of lysine. In some embodiments, the N-terminal end of a PYY analog polypeptide is modified with a Bolton-Hunter group. In some embodiments, an internal lysine residue is modified with a Bolton-Hunter group. In some embodiments, there may be multiple sites of Bolton-Hunter modification along the PYY analog polypeptide. Bolton-Hunter reagents used for polypeptide modification are commercially available, and may include, but are not limited to, water-soluble Bolton-Hunter reagent, Sulfosuccinimidyl-3-[4-hydrophenyl]propionate (Pierce Biotechnology, Inc., Rockford, Ill.) and Bolton-Hunter reagent-2, N-Succinimidyl 3-(4-hydroxy-3-iodophenyl) Priopionate (Wako Pure Chemical Industries, Ltd., Japan, catalog # 199-09341). An exemplary Bolton-Hunter group conjugated through an amide linkage to a PYY analog polypeptide is illustrated below, wherein the dashed line passes through the amide bond:

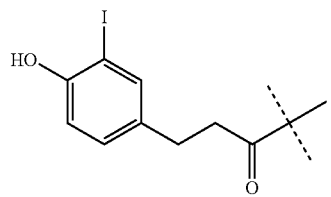

PYY analog polypeptides may be iodinated (such as radiolabeled with $^{125}$I) before or after Bolton-Hunter modification. $^{125}$I-Bolton-Hunter labeled PYY or PYY analogs may also be purchased from Amersham Corporation (Arlington Heights, Ill.). Bolton-Hunter derivatives are abbreviated as "BH-modified" in Table 4. (SEQ ID NOS: 475-480).

e. Analogs and Derivatives

In some embodiments, the PYY analog polypeptide include combinations of the above-described modifications, i.e., deletion, insertion, and substitution.

By way of example, PYY analog polypeptides may include N-terminal deletions in combination with one or more amino acid substitutions. For instance, PYY analog polypeptides include PYY (3-36) with the one or more of the following amino acid substitutions: Ala$^3$, Leu$^3$, Pro$^3$, Ala$^4$, Gly$^4$, d-Ala$^4$, homoLys$^4$, Glu$^4$, Ala$^5$, Ala$^6$, Val$^6$, d-Ala$^7$, Tyr$^7$, His$^7$, Ala$^8$, Ala$^9$, Ala$^{10}$, Ala$^{11}$, d-Ala$^{12}$, Ala$^{13}$, homoSer$^{13}$, Ala$^{14}$, Ala$^{15}$, Gln$^{15}$, Ala$^{16}$, Ala$^{17}$, Met$^{17}$, Ala$^{18}$, Ser$^{18}$, nor-Val$^{13}$, Ala$^{19}$, N-Me-Ala$^{19}$, Lys$^{19}$, homoArg$^{19}$, Ala$^{20}$, Ala$^{21}$, d-Ala$^{22}$, Ala$^{23}$, Ala$^{24}$, Ala$^{25}$, Lys$^{25}$, homoArg$^{25}$, Ala$^{26}$, Ala$^{27}$, Ala$^{28}$, Ala$^{29}$, Ala$^{30}$, Ala$^{31}$, Ala$^{32}$, Ala$^{33}$, Lys$^{33}$, Ala$^{34}$, Ala$^{35}$, Ala$^{36}$, His$^{36}$, Trp$^{36}$, N-Me-Tyr$^{36}$, and Phe$^{36}$. In some embodiments, the PYY analog polypeptide includes one, two, or three amino acid substitutions. Certain PYY analog polypeptides comprise deletions in combination with amino acid insertions. (see, e.g., SEQ ID NOS: 89-174)

PYY analog polypeptides include the polypeptides of the Formula (V) (SEQ ID NO: 350):

```
Xaa3 Xaa4 Pro Xaa6 Xaa7 Pro Xaa9 Xaa10 Xaa11 Xaa12
Xaa13 Xaa14 Xaa15 Xaa16 Xaa17 Xaa18 Xaa19 Tyr
Xaa21 Xaa22 Xaa23 Leu Arg Xaa26 Tyr Xaa28 Asn
Xaa30 Xaa31 Thr Arg Gln Arg Xaa36
``` wherein:
Xaa$_3$ is Ile, Ala, Pro, Ser, Thr, or NorVal;
Xaa$_4$ is Lys, Ala, Gly, Glu, Asp, d-Ala, homoLys, or homoArg;
Xaa$_6$ is Glu, Ala, Val, Asp, Asn, or Gln;
Xaa$_7$ is Ala, Asn, His, Ser, or Tyr;
Xaa$_9$ is Gly, Ala, Ser, sarcosine, Pro, or Aib;
Xaa$_{10}$ is Glu, Ala, Asp, Asn, Gln, Pro, Aib, or Gly;
Xaa$_{11}$ is Asp, Ala, Glu, Asn, Gln, Pro, Aib, or Gly;
Xaa$_{12}$ is Ala or d-Ala;
Xaa$_{13}$ is Ser, Ala, Thr, or homoSer;
Xaa$_{14}$ is Pro, Ala, homoPro, hydroxyPro, Aib, or Gly;
Xaa$_{15}$ is Glu, Ala, Asp, Asn, Gln, Pro, Aib, or Gly;
Xaa$_{16}$ is Glu, Ala, Asp, Asn, or Gln;
Xaa$_{17}$ is Leu, Ala, Met, Trp, Ile, Val, or NorVal;
Xaa$_{18}$ is Asn, Asp, Ala, Glu, Gln, Ser or Thr;
Xaa$_{19}$ is Arg, Tyr, Lys, Ala, Gln, or N(Me)Ala;
Xaa$_{21}$ is Tyr, Ala, Met, Phe, or Leu;
Xaa$_{22}$ is Ala, Ser, Thr, or d-Ala;
Xaa$_{23}$ is Ser, Ala, Thr, or homoSer;
Xaa$_{26}$ is His or Ala;
Xaa$_{28}$ is Leu or Ala;
Xaa$_{30}$ is Leu, Ala, NorVal, or Ile;
Xaa$_{31}$ is Ala or Val; and
Xaa$_{36}$ is Tyr, N(Me)Tyr, His, or Trp;

with the proviso that said polypeptide is not a native PPF polypeptide.

As will be recognized by one of skill in the art, the polypeptides of Formula V may be in the free acid form, or may be C-terminally amidated.

Also included within the scope of the invention are PYY analog polypeptides of Formulas II to VII, wherein the indicated amino acid residue is chemical modified or derivitized (e.g., through fatty acid derivitization, PEGylation, amidation, glycolization, etc.). Also contemplated within the scope of the invention are D-amino acid residues of the indicated amino acids.

In some embodiments, PYY analog polypeptides include the polypeptides of Formulas II to VII with internal deletions, particularly in areas not corresponding to the C-terminal tail PPF motif, as described herein.

PYY analog polypeptides comprising substitutions of unnatural amino acids include PYY(3-36), wherein amino acids at positions x and x+1 are substituted with β-turn mimetics selected from the group consisting of mimic A and mimic B, wherein x is selected from positions 8 to 14 (see, e.g., SEQ ID NOS: 211-217 and 231-237).

Derivatives of the PYY analog polypeptides of the invention can include polymer-conjugated PYY analog polypeptides, wherein the PYY analog polypeptide includes any of the above-described insertions, deletions, substitutions, or combinations thereof, and the polymer molecule is conjugated at a lysine residue. Other derivatives of PYY analog polypeptides include PYY, PYY(3-36) or PYY(4-36) with the following substitutions and alterations: [Lys$^4$-fatty acid chain]PYY(3-36); [Lys$^4$-fatty acid chain]PYY(4-36); [Ala$^2$Lys$^{19}$-fatty acid chain]PYY(3-36); [Ile$^3$-fatty acid chain]PYY(3-36); [Ser$^{13}$-OAc] PYY(3-36) (OAc is O-Acylation with fatty acids or acetyl groups); [Ser$^{23}$-OAc]PYY(3-36); [Ile$^2$-Octanoyl chain]PYY(3-36); [Lys$^{19}$-Octanoyl chain]PYY(3-36); and [Lys$^{19}$-Stearyl chain]PYY(3-36). (see e.g., SEQ ID NOS: 185-208).

Further examples of the PYY analog polypeptides of the present invention are provided in the Sequence Listing and discussed in the Examples section below.

2. PPF Chimeric Polypeptides

In yet another aspect of the invention, the PPF polypeptides of the invention include PPF chimeric polypeptides comprising a fragment of a PP, PYY or NPY polypeptide covalently linked to at least one additional fragment of a second PP, PYY or NPY polypeptide, wherein each PP, PYY or NPY fragment includes a PPF motif. Alternatively, the PPF chimeric polypeptides of the invention may comprise a fragment of a PP family polypeptide linked to one, two, three, or four polypeptides segments, wherein at least one of the linked polypeptide segments is a fragment of a second PP family polypeptide. In certain embodiments, PPF polypeptides do not include an N-terminal PP fragment with a C-terminal NPY fragment. PPF chimeric polypeptides of the invention will exhibit at least 50% sequence identity to a native PYY (3-36) over the entire length of the PYY(3-36). In some embodiments, such PPF chimeric polypeptides of the invention may exhibit at least 60%, at least 70%, at least 80%, at least 90%, at least 92%, at least 94% or at least 97% sequence identity to a native PYY(3-36) over the entire length of the PYY(3-36). Such PPF chimeric polypeptides of the invention may also exhibit at least 50%, at least 60%, at least 70%, at least 80%, at least 90%, at least 92%, at least 94% or at least 97% sequence identity to a native PP. In yet another embodiment, such PPF chimeric polypeptides of the invention may exhibit at least 50%, at least 60%, at least 70%, at least 80%, at least 90%, at least 92%, at least 94% or at least 97% sequence identity to a native NPY. In some embodiments, the PPF chimeric polypeptides of the invention include at least the N-terminal polyproline PPF motif and the C-terminal tail PPF motif.

Again, the PPF polypeptides of the present invention will generally retain, at least in part, a biological activity of native human PP, PYY, or NPY. In some embodiments, the PPF chimeric polypeptides of the present invention will exhibit biological activity in the treatment and prevention of metabolic conditions and disorders.

The polypeptide fragments may be covalently linked together in any manner known in the art, including but not limited to direct amide bonds or chemical linker groups. Chemical linker groups may include peptide mimetics which induce or stabilize polypeptide conformation. PPF chimeric polypeptides of the invention include PYY-PP, PYY-NPY, PP-PYY, PP-NPY, NPY-PP, or NPY-PYY chimeras.

The PPF chimeric polypeptides of the invention may be at least 21, 22, 23, 24, 25, 26, 27, 28, 29, 30, 31, 32, 33, or 34 amino acids in length. In some embodiments, the PYY analog polypeptides of the invention include only natural L amino acid residues and/or modified natural L amino acid residues. In some embodiments, the PYY analog polypeptides of the invention do not include unnatural amino acid residues.

In some embodiments, the PPF chimeric polypeptides of the invention do not include: hPP(1-7)-pNPY, hPP(1-17)-pNPY, hPP(19-23)-pNPY, hPP(19-23)-Pro$^{34}$pNPY, hPP(19-23)-His$^{34}$pNPY, rPP(19-23)-pNPY, rPP(19-23)-Pro$^{34}$pNPY, rPP(19-23)-His$^{34}$pNPY, hPP(1-17)-His$^{34}$pNPY, pNPY(1-7)-hPP, pNPY(1-7, 19-23)-hPP, cPP(1-7)-pNPY(19-23)-hPP, cPP(1-7)-NPY(19-23)-His$^{34}$hPP, hPP(1-17)-His$^{34}$pNPY, hPP(19-23)-pNPY, hPP(19-23)-Pro$^{34}$pNPY, pNPY(1-7)-hPP, pNPY(19-23)-hPP, pNPY(19-23)-Gln$^{34}$hPP, pNPY(19-23)-His$^{34}$hPP, pNPY(19-23)-Phe$^6$Gln$^{34}$hPp, pNPY(19-23)-Phe$^6$His$^{34}$hPP, pNPY(1-7,19-23)-hPP, pNPY(1-7,19-23)-Gln$^{34}$hPP, cPP(20-23)-Pro$^{34}$-pNPY, cPP(21-23)-Pro$^{34}$-pNPY, cPP(22-23)-Pro$^{34}$-pNPY, cPP(1-7)-Pro$^{34}$-pNPY, cPP (20-23)-Pro$^{34}$-pNPY, cPP(1-7,20-23)-Pro$^{34}$-pNPY, cPP(1-7)-pNPY(19-23)-hPP, cPP(1-7)-pNPY(19-23)-His$^{34}$hPP, cPP(1-7)-gPP(19-23)-hPP, cPP(1-7)-pNPY(19-23)-Ala$^{31}$Aib$^{32}$Gln$^{34}$-hPP, cPP(1-7)-pNPY(19-23)-Ala$^{31}$Aib$^{32}$His$^{34}$-hPp hPP(1-7)-Ala$^{31}$Aib$^{32}$-pNPY, hPP(1-17)-Ala$^{31}$Aib$^{32}$-pNPY, pNPY(1-7)-Ala$^{31}$Aib$^{32}$Gln$^{34}$-hPp, or pNPY(1-7, 19-23)-Ala$^{31}$Aib$^{32}$Gln$^{34}$-hPP.

In some embodiments, the PPF chimeric polypeptides of the invention may comprise fragments of PP family analog polypeptides. For instance, the PPF chimeric polypeptides may comprise PPF analog polypeptides described herein, as well as PP analog polypeptides, and NPY analog polypeptides.

PYY analog polypeptide are those having a potency in one of the assays described herein (including food intake, gastric emptying, pancreatic secretion, body composition or weight reduction assays) which is equal to or greater than the potency of NPY, PYY, or PYY(3-36) in that same assay. In some embodiments, PYY analog polypeptides of the invention may exhibit improved ease of manufacture, stability, and/or ease of formulation, as compared to PP, NPY, PYY, or PYY(3-36).

In some embodiments, the PPF chimeric polypeptides of the invention retain at least about 25%, or from about 30%, about 40%, about 50%, about 60%, about 70%, about 80%, about 90%, about 95%, about 98%, or about 99% percent of the biological activity of native human PYY with regard to the reduction of nutrient availability, the reduction of food intake, the effect of body weight gain, and/or the treatment and prevention of metabolic conditions and disorders. In another embodiment, the PPF chimeric polypeptides of the invention exhibit improved PYY agonist activity. In some embodiments, the PPF chimeric polypeptides of the invention exhibits at least about 110%, about 125%, about 130%, about 140%, about 150%, about 200%, or more of the biological activity of native human PYY with regard to the reduction of nutrient availability the reduction of food intake, the effect of body weight gain, and/or the treatment and prevention of metabolic conditions and disorders.

More particularly, in one aspect, the PPF chimeric polypeptides comprise a fragment of PP linked to a fragment of PYY. In one embodiment, the PPF chimeric polypeptides of the invention comprise an N-terminal fragment of PP or a PP analog polypeptide linked at its C-terminal end to a C-terminal fragment of PYY or a PYY analog polypeptide. In another embodiment, the PPF chimeric polypeptides of the invention comprise an N-terminal fragment of PYY, PYY(3-36), or a PYY analog polypeptide linked at its C-terminal end to a C-terminal fragment of PP or a PP analog polypeptide.

In some embodiments, the PPF chimeric polypeptides comprise a fragment of PYY linked to a fragment of NPY. In one embodiment, the PPF chimeric polypeptides of the invention comprise an N-terminal fragment of PYY, PYY(3-36), or a PYY analog polypeptide linked at its C-terminal end to a C-terminal fragment of NPY or a NPY analog polypeptide. In another embodiment, the PPF chimeric polypeptides of the invention comprise an N-terminal fragment of NPY or a NPY analog polypeptide linked at its C-terminal end to a C-terminal fragment of PYY or a PYY analog polypeptide.

In some embodiments, the PPF chimeric polypeptides comprise a fragment of PP linked to a fragment of NPY. In one embodiment, the PPF chimeric polypeptides of the invention comprise an N-terminal fragment of PP or a PP analog polypeptide linked at its C-terminal end to a C-terminal fragment of NPY or a NPY analog polypeptide. In another embodiment, the PPF chimeric polypeptides of the invention comprise an N-terminal fragment of NPY or a NPY analog polypeptide linked at its C-terminal end to a C-terminal fragment of PP or a PP analog polypeptide.

In some embodiments, a fragment of PP, a PP analog polypeptide, PYY, PYY(3-36), a PYY analog polypeptide, NPY, or an NPY analog polypeptide is a fragment comprising anywhere from 4 to 20 amino acid residues of the PP, PP analog polypeptide, PYY, PYY(3-36), PYY analog polypeptide, NPY, or NPY analog polypeptide. In some embodiments, the length of fragment is selected so as to obtain a final PPF chimeric polypeptide of at least 34 amino acids in length.

The PPF chimeric polypeptides of the present invention may also comprise further modifications including, but are not limited to, substitution, deletion, and insertion to the amino acid sequence of such PPF chimeric polypeptides and any combination thereof. In some embodiments, the PPF chimeric polypeptides of the invention include one or more modifications of a "non-essential" amino acid residue. In the context of the invention, a "non-essential" amino acid residue is a residue that can be altered, i.e., deleted or substituted, in the native human amino acid sequence of the fragment, e.g., the PP family polypeptide fragment, without abolishing or substantially reducing the PYY agonist activity of the PPF chimeric polypeptide.

The present invention also relates to derivatives of the PPF chimeric polypeptides. Such derivatives include PPF chimeric polypeptides conjugated to one or more water soluble polymer molecules, such as polyethylene glycol ("PEG") or fatty acid chains of various lengths (e.g., stearyl, palmitoyl, octanoyl, oleoyl etc.), or by the addition of polyamino acids, such as poly-his, poly-arg, poly-lys, and poly-ala. Modifications to the PPF chimeric polypeptides can also include small molecule substituents, such as short alkyls and constrained alkyls (e.g., branched, cyclic, fused, adamantyl), and aromatic groups. In some embodiments, the water soluble polymer molecules will have a molecular weight ranging from about 500 to about 20,000 Daltons.

Such polymer-conjugations and small molecule substituent modifications may occur singularly at the N- or C-terminus or at the side chains of amino acid residues within the sequence of the PPF chimeric polypeptides. Alternatively, there may be multiple sites of derivatization along the PPF chimeric polypeptide. Substitution of one or more amino acids with lysine, aspartic acid, glutamic acid, or cysteine may provide additional sites for derivatization. See, e.g., U.S. Pat. Nos. 5,824,784 and 5,824,778. In some embodiments, the PPF chimeric polypeptides may be conjugated to one, two, or three polymer molecules.

In some embodiments, the water soluble polymer molecules are lined to an amino, carboxyl, or thiol group, and may be linked by N or C terminus, or at the side chains of lysine, aspartic acid, glutamic acid, or cysteine. Alternatively, the water soluble polymer molecules may be linked with diamine and dicarboxylic groups. In some embodiments, the PPF chimeric polypeptides of the invention are conjugated to one, two, or three PEG molecules through an epsilon amino group on a lysine amino acid.

PPF chimeric polypeptide derivatives of the invention also include PPF chimeric polypeptides with chemical alterations to one or more amino acid residues. Such chemical alterations include amidation, glycosylation, acylation, sulfation, phosphorylation, acetylation, and cyclization. The chemical alterations may occur singularly at the N- or C-terminus or at the side chains of amino acid residues within the sequence of the PPF chimeric polypeptides. In one embodiment, the C-terminus of these peptides may have a free —OH or —NH$_2$ group. In another embodiment, the N-terminal end may be capped with an isobutyloxycarbonyl group, an isopropyloxycarbonyl group, an n-butyloxycarbonyl group, an ethoxycarbonyl group, an isocaproyl group (isocap), an octanyl group, an octyl glycine group (G(Oct)), or an 8-aminooctanic acid group. In some embodiments, cyclization can be through the formation of disulfide bridges. Alternatively, there may be multiple sites of chemical alteration along the PYY analog polypeptide.

In some embodiments, the PPF chimeric polypeptides include those having an amino acid sequence of SEQ ID NOs. 238-347.

Examples of the PPF chimeric polypeptides of the present invention are provided in the Sequence Listing and further discussed in the Examples section below.

Other PPF polypeptides include polypeptides of the Formula (VI) (SEQ ID NO: 481):

```
Xaa₁ Xaa₂ Xaa₃ Xaa₄ Pro Glu Xaa₇ Pro Xaa₉ Glu Asp
Xaa₁₂ Xaa₁₃ Xaa₁₄ Glu Xaa₁₆ Xaa₁₇ Xaa₁₈ Xaa₁₉ Tyr
Xaa₂₁ Xaa₂₂ Xaa₂₃ Leu Xaa₂₅ Xaa₂₆ Tyr Xaa₂₈ Asn
Xaa₃₀ Xaa₃₁ Thr Arg Gln Xaa₃₅ Xaa₃₆
``` wherein:
  $Xaa_1$ is Tyr or absent;
  $Xaa_2$ is Ile, Pro, or absent;
  $Xaa_3$ is Ile, BH-modified Lys, Lys, Val, or Pro;
  $Xaa_4$ is Lys, BH-modified Lys, Ala, Ser, or Arg;
  $Xaa_7$ is Ala, Gly, or His;
  $Xaa_9$ is Gly or Ala;
  $Xaa_{12}$ is Ala or Pro;
  $Xaa_{13}$ is Ser or Pro;
  $Xaa_{14}$ is Pro, Ala, or Ser;
  $Xaa_{16}$ is Glu or Asp;
  $Xaa_{17}$ is Leu or Ile;
  $Xaa_{18}$ is Asn or Ala;
  $Xaa_{19}$ is Arg, Lys, BH-modified Lys, Gln, or N(Me)Ala;
  $Xaa_{21}$ is Tyr, Ala, Phe, Lys or BH-modified Lys;
  $Xaa_{22}$ is Ala or Ser;
  $Xaa_{23}$ is Ser, Ala, or Asp;

Xaa$_{25}$ is Arg, Lys or BH-modified Lys;
Xaa$_{26}$ is His, Ala, or Arg;
Xaa$_{28}$ is Leu or Ile;
Xaa$_{30}$ is Leu or Met;
Xaa$_{31}$ is Val, Ile, or Leu;
Xaa$_{35}$ is Lys, BH-modified Lys, or Arg; and
Xaa$_{36}$ is Tyr, Trp, or Phe;
with the proviso that said PPF polypeptide is not a native PPF polypeptide, PYY(2-36), Val$^3$hPYY(3-36), Lys$^{25}$hPYY(3-36), Lys$^{25}$Ile$^{28}$hPYY(3-36), Lys$^{25}$Ile$^{31}$hPYY(3-36), Lys$^{25}$Leu$^{31}$hPYY(3-36), Lys$^{25}$Phe$^{36}$hPYY(3-36), Ile$^{28}$hPYY(3-36), Ile$^{31}$hPYY(3-36), Leu$^{31}$hPYY(3-36), Phe$^{36}$hPYY(3-36), Leu$^{31}$Phe$^{36}$hPYY(3-36), or Pro$^{13}$Ala$^{14}$HPYY.

As will be recognized by one of skill in the art, the polypeptides of Formula VI may be in the free acid form, or may be C-terminally amidated.

In some embodiments, the PPF polypeptide may comprise an N-terminal fragment consisting essentially of the first 17 amino acid residues of native human PYY (SEQ ID NO: 2) linked to a C-terminal fragment consisting essentially of amino acid residues 18-36 of native human NPY (SEQ ID NO: 4), wherein one or more amino acid residues at the N-terminus of the PYY fragment may be deleted or absent, and wherein one, two, three, four, five, six, seven, eight, nine or ten amino acid substitutions may be made in each of the PYY and NPY fragments. In some embodiments, an N-terminal fragment consisting essentially of the first 17 amino acids of the PPF polypeptide may exhibit at least 50%, at least 60%, at least 70%, at least 80%, at least 90%, at least 92%, at least 94% or at least 97% sequence identity to the first 17 amino acids of a native PYY. In some embodiments, a C-terminal fragment of the PPF polypeptide consisting essentially of amino acid residues 18-36 may exhibit at least 50%, at least 60%, at least 70%, at least 80%, at least 90%, at least 92%, at least 94% or at least 97% sequence identity to amino acids 18-36 of a native NPY. In some embodiments, amino acids in the N-terminal fragment of PYY (e.g., prolines at position 5 and 8, glutamates at positions 6, 10 and 15, or aspartate at position II), and/or amino acids in the C-terminal fragment of NPY (e.g., tyrosines at positions 20 and 27, leucine at position 24, asparagine at position 29, threonine at position 32, arginine at position 33, or glutamine at position 34) are not substituted. In some embodiments, the PPF polypeptides include those having an amino acid sequence of SEQ ID Nos. 266, 267, 274, 282, 320, and 436 to 480. In some embodiments, the PPF polypeptides further comprise an N-terminal cap. Examples of these PPF polypeptides include SEQ ID NOs: 282, 320, 437, 441, 444, 445-447, 452, 454-459, 461-464, 466, 468-470 and 472-480.

Other PPF polypeptides include polypeptides of the Formula (VII) (SEQ ID NO: 482):

```
Xaa1  Xaa2  Pro  Xaa4  Pro  Xaa6  His  Pro  Xaa9  Xaa10
Xaa11 Xaa12 Xaa13 Xaa14 Xaa15 Xaa16 Xaa17 Ala
Xaa19 Tyr  Xaa21 Xaa22 Xaa23 Leu  Xaa25 Xaa26 Xaa27
Xaa28 Xaa29 Xaa30 Xaa31 Thr  Arg  Gln  Arg  Tyr
``` wherein:
Xaa$_1$ is Tyr or absent;
Xaa$_2$ is Ile, Pro, or absent;
Xaa$_4$ is Lys, BH-modified Lys, Ala, Ser, or Arg;
Xaa$_6$ is Glu, Gln, Ala, Asn, Asp, or Val;
Xaa$_9$ is Gly or Ala;
Xaa$_{10}$ is Glu, Ala, Asp, Asn, Gln, Gly, Pro, or Aib;
Xaa$_{11}$ is Glu, Ala, Asp, Asn, Gln, Gly, Pro, or Aib;
Xaa$_{12}$ is Ala or Pro;
Xaa$_{13}$ is Ser or Pro;
Xaa$_{14}$ is Pro, Ala, or Ser;
Xaa$_{15}$ is Glu, Ala, Asp, Asn, Gln, Gly, Pro, or Aib;
Xaa$_{16}$ is Glu or Asp;
Xaa$_{17}$ is Leu or Ile;
Xaa$_{19}$ is Arg, Lys, BH-modified Lys, Gln, or N(Me)Ala;
Xaa$_{21}$ is Tyr, Ala, Phe, Lys, or BH-modified Lys;
Xaa$_{22}$ is Ala or Ser;
Xaa$_{23}$ is Ser, Ala, or Asp;
Xaa$_{25}$ is Arg, Lys or BH-modified Lys;
Xaa$_{26}$ is His, Ala, or Arg;
Xaa$_{27}$ is Tyr, or Phe;
Xaa$_{28}$ is Leu or Ile;
Xaa$_{29}$ is Asn, or Gln;
Xaa$_{30}$ is Leu or Met; and
Xaa$_{31}$ is Val, Ile, or Leu.

As will be recognized by one of skill in the art, the polypeptides of Formula VII may be in the free acid form, or may be C-terminally amidated.

In some embodiments, the PPF polypeptide may comprise an N-terminal fragment consisting essentially of the first 17 amino acid residues of native human PYY (SEQ ID NO: 2) linked to a C-terminal fragment consisting essentially of amino acid residues 18-36 of native human NPY (SEQ ID NO: 4), wherein one or more amino acid residues at the N-terminus of the PYY fragment may be deleted or absent, and wherein one, two, three, four, five, six, seven, eight, nine or ten amino acid substitutions may be made in each of the PYY and NPY fragments. In some embodiments, an N-terminal fragment consisting essentially of the first 17 amino acids of the PPF polypeptide may exhibit at least 50%, at least 60%, at least 70%, at least 80%, at least 90%, at least 92%, at least 94% or at least 97% sequence identity to the first 17 amino acids of a native PYY. In some embodiments, a C-terminal fragment of the PPF polypeptide consisting essentially of amino acid residues 18-36 may exhibit at least 50%, at least 60%, at least 70%, at least 80%, at least 90%, at least 92%, at least 94% or at least 97% sequence identity to amino acids 18-36 of a native NPY. In some embodiments, amino acids in the N-terminal fragment of PYY (e.g., prolines at positions 3, 5 and 8, or histidine 7), and/or amino acids in the C-terminal fragment of NPY (e.g., alanine at position 18, tyrosines at positions 20 and 36, leucine at position 24, threonine at position 32, arginine at position 33, glutamine at position 34, or arginine at position 35) are not substituted. In some embodiments, the PPF polypeptides include those having an amino acid sequence of SEQ ID Nos. 266, 437, 438, 439, 442, 462, 469, 470, 471 and 472. In some embodiments, the PPF polypeptides further comprise an N-terminal cap. Examples of these PPF polypeptides include SEQ ID NOs: 437, 462, 469, 470 and 472.

Examples of the PPF polypeptides of the present invention are provided in the Sequence Listing and further discussed in the Examples section below.

B. Use of PPF Polypeptides in the Treatment or Prevention of Metabolic Conditions or Disorders It has been generally accepted that endogenous NPY (reviewed in Schwartz et al., Nature 404: 661-71 (2000)) and PYY (Morley et al., Brain Res. 341: 200-3 (1985)), via their receptors, increase feeding behavior. Methods directed at therapies for obesity have invariably attempted to antagonize Y receptors, while claims for treating anorexia have been directed at agonists of this ligand family. However, as described and claimed in the commonly-owned pending U.S. Patent Application No. 20020141985, it has been surprisingly discovered that peripheral administration of PYY analog polypeptides has a potent effect to reduce nutrient availability (see also Batterham et al., Nature 418: 650-4, 2002; WO 03/026591; and WO 03/057235), rather than increase it as suggested by reports in the patent and scientific literature (see, e.g., U.S. Pat. Nos. 5,912,227 and 6,315,203 which disclose the use of PYY receptor agonists to increase weight gain). The spectrum of actions of inhibition of food intake, slowing of gastric emptying, inhibition of gastric acid secretion, and inhibition of pancreatic enzyme secretion, are useful to exert clinical benefit in metabolic diseases such as type 1, type 2, or gestational diabetes mellitus, obesity and other manifestations of insulin-resistance syndrome (Syndrome X), and in any other use for reducing nutrient availability.

As such, in another aspect of the invention, methods for treating or preventing obesity are provided, wherein the method comprises administering a therapeutically or prophylactically effective amount of a PPF polypeptide to a subject in need thereof. In some embodiments, the subject is an obese or overweight subject. While "obesity" is generally defined as a body mass index over 30, for purposes of this disclosure, any subject, including those with a body mass index of less than 30, who needs or wishes to reduce body weight is included in the scope of "obese." Subjects who are insulin resistant, glucose intolerant, or have any form of diabetes mellitus (e.g., type 1, 2 or gestational diabetes) can benefit from this method.

In other aspects of the invention, methods of reducing food intake, reducing nutrient availability, causing weight loss, affecting body composition, and altering body energy content or increasing energy expenditure, treating diabetes mellitus, and improving lipid profile (including reducing LDL cholesterol and/or triglyceride levels and/or changing HDL cholesterol levels) are provided, wherein the methods comprise administering to a subject an effective amount of a PPF polypeptide of the invention. In some embodiments, the methods of the invention are used to treat or prevent conditions or disorders which can be alleviated by reducing nutrient availability in a subject in need thereof, comprising administering to said subject a therapeutically or prophylactically effective amount of a PPF polypeptide of the invention. Such conditions and disorders include, but are not limited to, hypertension, dyslipidemia, cardiovascular disease, eating disorders, insulin-resistance, obesity, and diabetes mellitus of any kind.

Without intending to be limited by theory, it is believed that the effects of peripherally-administered PPF polypeptides of the present invention in the reduction of food intake, in the delay of gastric emptying, in the reduction of nutrient availability, and in the causation of weight loss are determined by interactions with one or more unique receptor classes in, or similar to, those in the PP family. More particularly, it appears that a receptor or receptors similar to the PYY-preferring (or Y7) receptors are involved.

Additional assays useful to the invention include those that can determine the effect of PPF compounds on body composition. An exemplary assay can be one that involves utilization of a diet-induced obese (DIO) mouse model for metabolic disease. Prior to the treatment period, male C57BL/6J mice can be fed a high-fat diet (#D12331, 58% of calories from fat; Research Diets, Inc.) for 6 weeks beginning at 4 weeks of age. During the study, the mice can continue to eat their high-fat diet. Water can be provided ad libitum throughout the study. One group of similarly-aged non-obese mice can be fed a low-fat diet (#D12329, 11% of calories from fat) for purposes of comparing metabolic parameters to DIO groups.

DIO mice can be implanted with subcutaneous (SC) intrascapular osmotic pumps to deliver either vehicle (50% dimethylsulfoxide [DMSO] in water) n=20 or a compound of the invention n=12. The pumps of the latter group can be set to deliver any amount, e.g., 1000 µg/kg/d of a compound of the invention for 7 days.

Body weights and food intake can be measured over regular intervals throughout the study periods. Respiratory quotient (RQ, defined as $CO_2$ production÷$O_2$ consumption) and metabolic rate can be determined using whole-animal indirect calorimetry (Oxymax, Columbus Instruments, Columbus, Ohio). The mice can be euthanized by isoflurane overdose, and an index of adiposity (bilateral epididymal fat pad weight) measured. Moreover, prior to determination of epididymal weight, body, composition (lean mass, fat mass) for each mouse can be analyzed using a Dual Energy X-ray Absorptiometry (DEXA) instrument per manufacturer's instructions (Lunar Piximus, GE Imaging System). In some embodiments, PPF polypeptides of the invention are those having a potency in one of the assays described herein (including the food intake, gastric emptying, pancreatic secretion, weight reduction or body composition assays) which is greater than the potency of PP, NPY, PYY, or PYY(3-36) in that same assay.

In addition to the amelioration of hypertension in subjects in need thereof as a result of reduced food intake, weight loss, or treating obesity, compounds of the invention may be used to treat hypotension as described in Example 4.

Compounds of the invention may also be useful for potentiating, inducing, enhancing or restoring glucose responsivity in pancreatic islets or cells. These actions may be useful for treating or preventing conditions associated with metabolic disorders such as those described above and in U.S. patent application no. US20040228846. Assays for determining such activity are known in the art. For example, in published U.S. patent application no. US20040228846 (incorporated by reference in its entirety), assays are described for islet isolation and culture as well as determining fetal islet maturation. In the examples of patent application US20040228846, intestine-derived hormone peptides including pancreatic polypeptide (PP), neuropeptide Y (NPY), neuropeptide K (NPK), PYY, secretin, glucagon-like peptide-1 (GLP-1) and bombesin were purchased from Sigma. Collagenase type XI was obtained from Sigma. RPMI 1640 culture medium and fetal bovine serum were obtained from Gibco. A radioimmunoassay kit containing anti-insulin antibody ($[^{125}I]$-RIA kit) was purchased from Linco, St Louis.

Post-partem rat islets were obtained from P-02 year old rats. Adult rat islets were obtained from 6-8 week old rats. Fetal rat islets were obtained as follows. Pregnant female rats were sacrificed on pregnancy day e21. Fetuses were removed from the uterus. 10-14 pancreata were dissected from each litter and washed twice in Hanks buffer. The pancreata were pooled, suspended in 6 ml 1 mg/ml collagenase (Type XI, Sigma) and incubated at 37° C. for 8-10 minutes with constant shaking. The digestion was stopped by adding 10 volumes of ice-cold Hanks buffer followed by three washes with Hanks buffer. The islets were then purified by Ficoll gradient and cultured in 10% fetal bovine serum (FBS)/RPMI medium with or without addition of 1 µM IBMX. At the end of five days, 20 islets were hand picked into each tube and assayed for static insulin release. Generally, islets were first washed with KRP buffer and then incubated with 1 ml of KRP buffer containing 3 mM (low) glucose for 30 minutes at 37° C. with constant shaking. After collecting the supernatant, the islets were then incubated with 17 mM (high) glucose for one hour at 37° C. The insulin released from low or high glucose stimulation were assayed by radioimmunoassay (RIA) using the [$^{125}$I]I-RIA kit. E21 fetal islets were cultured for 5 days in the presence of 200 ng/ml PYY, PP, CCK, NPK, NPY, Secretin, GLP-1 or Bombesin.

An exemplary in vivo assay is also provided using the Zucker Diabetic Fatty (ZDF) male rat, an inbred (>F30 Generations) rat model that spontaneously expresses diabetes in all fa/fa males fed a standard rodent diet Purina 5008. In ZDF fa-fa males, hyperglycemia begins to develop at about seven weeks of age and glucose levels (fed) typically reach 500 mg/DL by 10 to 11 weeks of age. Insulin levels (fed) are high during the development of diabetes. However, by 19 weeks of age insulin drops to about the level of lean control litter mates. Plasma triglyceride and cholesterol levels of obese rats are normally higher than those of leans. In the assay, three groups of 7-week old ZDF rats, with 6 rats per group, received the infusion treatment by ALZA pump for 14 days: 1) vehicle control, 2) and 3), PYY with two different doses, 100 pmol/kg/hr and 500 pmol/kg/hr respectively. Four measurements were taken before the infusion and after the infusion at day 7 and day 14: 1) plasma glucose level, 2) plasma insulin level, and 3) plasma triglycerides (TG) level, as well as oral glucose tolerance (OGTT) test. Accordingly, these assays can be used with compounds of the invention to test for desired activity.

Other uses contemplated for the PPF polypeptides include methods for reducing aluminum (Al) concentrations in the central nervous system (see U.S. Pat. No. 6,734,166, incorporated by reference in its entirety) for treating, preventing, or delay the onset of Alzheimer's disease. Assays for determining effects on Al are known in the art and can be found in U.S. Pat. No. 6,734,166 using diploid and Ts mice. These mice were individually housed in Nalgeneg brand metabolism or polypropylene cages and given three days to adjust to the cages before experimentation. Mice had free access to food (LabDiet® NIH Rat and Moust/Auto 6F5K52, St. Louis, Mo.) and water during the experiment except for the 16 hours prior to euthanasia when no food was provided. Mice were given daily subcutaneous injections of either active compound or saline. Mice were sacrificed at the end of day 13 for one experiment and day 3 for another, and samples were collected. Mice brain samples were weighted in clean teflon liners and prepared for analysis by microwave digestion in low trace element grade nitric acid. Sample were then analyzed for Al content using Inductively Coupled Plasma Mass Spectrometry (Nuttall et al., Annals of Clinical and Laboratory Science 25, 3, 264-271 (1995)). All tissue handling during analysis took place in a clean room environment utilizing HEPA air filtration systems to minimize background contamination.

The compounds of the invention exhibit a broad range of biological activities, some related to their antisecretory and antimotility properties. The compounds may suppress gastrointestinal secretions by direct interaction with epithelial cells or, perhaps, by inhibiting secretion of hormones or neurotransmitters which stimulate intestinal secretion. Antisecretory properties include inhibition of gastric and/or pancreatic secretions and can be useful in the treatment or prevention of diseases and disorders including gastritis, pancreatitis, Barrett's esophagus, and Gastroesophageal Reflux Disease.

Compounds of the invention are useful in the treatment of any number of gastrointestinal disorders (see e.g., Harrison's Principles of Internal Medicine, McGraw-Hill Inco, New York, 12th Ed.) that are associated with excess intestinal electrolyte and water secretion as well as decreased absorption, e.g., infectious diarrhea, inflammatory diarrhea, short bowel syndrome, or the diarrhea which typically occurs following surgical procedures, e.g., ileostomy. Examples of infectious diarrhea include, without limitation, acute viral diarrhea, acute bacterial diarrhea (e.g., *salmonella, campylobacter*, and *clostridium* or due to protozoal infections), or traveller's diarrhea (e.g., Norwalk virus or rotavirus). Examples of inflammatory diarrhea include, without limitation, malabsorption syndrome, tropical sprue, chronic pancreatitis, Crohn's disease, diarrhea, and irritable bowel syndrome. It has also been discovered that the peptides of the invention can be used to treat an emergency or life-threatening situation involving a gastrointestinal disorder, e.g., after surgery or due to cholera.

Compounds of the invention may also be useful for treating or preventing intestinal damage as opposed to merely treating the symptoms associated with the intestinal damage (for example, diarrhea). Such damage to the intestine may be, or a result of, ulcerative colitis, inflammatory bowel disease, bowel atrophy, loss bowel mucosa, and/or loss of bowel mucosal function (see WO 03/105763, incorporated herein by reference in its entirety). A simple and reproducible rat model of chronic colonic inflammation has been previously described by Morris G P, et al., "Hapten-induced model of chronic inflammation and ulceration in the rat colon." Gastroenterology. 1989; 96:795-803. It exhibits a relatively long duration of inflammation and ulceration, affording an opportunity to study the pathophysiology of colonic inflammatory disease in a specifically controlled fashion, and to evaluate new treatments potentially applicable to inflammatory bowel disease in humans.

Assays for such activity, as described in WO 03/105763, include 11 week old male HSD rats, ranging 250-300 grams housed in a 12:12 light:dark cycle, and allowed ad libitum access to a standard rodent diet (Teklad LM 485, Madison, Wis.) and water. The animals were fasted for 24 hours before the experiment. Rats were anesthetized with 3% isofluorane and placed on a regulated heating pad set at 37° C. A gavage needle was inserted rectally into the colon 7 cm. The hapten trinitrobenzenesulfonic acid (TNBS) dissolved in 50% ethanol (v/v) was delivered into the lumen of the colon through the gavage needle at a dose of 30 mg/kg, in a total volume of 0 0.4-0.6 mL, as described in Mazelin, et al., "Protective role of vagal afferents in experimentally-induced colitis in rats." Juton Nerv Syst. 1998;73:38 45. Control groups received saline solution (NaCl 0.9%) intracolonically.

Four days after induction of colitis, the colon was resected from anesthetized rats, which were then euthanized by decapitation. Weights of excised colon and spleen were measured, and the colons photographed for scoring of gross morphologic damage. Inflammation was defined as regions of hyperemia and bowel wall thickening.

Compounds of the invention may also be used to treat or prevent pancreatic tumors (e.g., inhibit the proliferation of pancreatic tumors). Methods of the invention include reducing the proliferation of tumor cells. The types of benign pancreatic tumor cells which may be treated in accordance with the present invention include serous cyst adenomas, microcystic tumors, and solid-cystic tumors. The method is also effective in reducing the proliferation of malignant pancreatic tumor cells such as carcinomas arising from the ducts, acini, or islets of the pancreas. U.S. Pat. No. 5,574,010 (incorporated by reference in its entirety) provides exemplary assays for testing anti-proliferative properties. For example, the '010 patent provides that PANC-1 and MiaPaCa-2 are two human pancreatic adenocarcinoma cancer cell lines which are available commercially from suppliers such as American Type Culture Collection, ATCC (Rockville, Md.). The two tumor cells were grown in RPMI-1640 culture media supplemented with 10% fetal bovine serum, 29.2 mg/L of glutamine, 25 μg gentamicin, 5 ml penicillin, streptomycin, and ftingizone solution (JRH Biosciences, Lenexa, Kans.) at 37 degrees Celcius in a NAPCO water jacketed 5% $CO_2$ incubator. All cell lines were detached with 0.25% trypsin (Clonetics, San Diego, Calif.) once to twice a week when a confluent monolayer of tumor cells was achieved. Cells were pelleted for 7 minutes at 500 g in a refrigerated centrifuge at 4 degrees Celcius, and resuspended in trypsin free fortified RPMI 1640 culture media. Viable cells were counted on a hemocytometer slide with trypan blue.

Ten thousand, 20,000, 40,000 and 80,000 cells of each type were added to 96 well microculture plates (Costar, Cambridge, Mass.) in a total volume of 200 ul of culture media per well. Cells were allowed to adhere for 24 hours prior to addition of the PYY or test peptide. Fresh culture media was exchanged prior to addition of peptides. In vitro incubation of pancreatic tumor cells with either PYY or test compound was continued for 6 hours and 36 hours in length. PYY was added to cells at doses of 250 pmol, 25 pmol, and 2.5 pmol per well (N=14). Test compound was added to cells cultures at doses of 400 pmol, 40 pmol, and 4 pmol per well. Control wells received 2 ul of 0.9% saline to mimic the volume and physical disturbance upon adhered tumor cells. Each 96 well plate contained 18 control wells to allow for comparison within each plate during experimentation. Ninety-six (96) well plates were repeated 6 times with varying concentrations of PYY and test compound in both the PANC-1 and MiaPaCa-2 cells.

At the end of the incubation period, 3-(4,5-dimethylthiazolyl-2-yl)-2,5-diphenyltetrazolium Bromide, MTT tetrazolium bromide (Sigma, St. Louis, Mo.) was added to fresh culture media at 0.5 mg/ml. Culture media was exchanged and tumor cells were incubated for 4 hours with MTT tetrazolium bromide at 37 degrees Celcius. At the end of incubation, culture media was aspirated. Formazon crystal precipitates were dissolved in 200 ul of dimethyl sulfoxide (Sigrna, St. Louis, Mo.). Quantitation of solubilized formazon was performed by obtaining absorption readings at 500 nm wavelength on an ELISA reader (Molecular Devices, Menlo Park, Calif.). The MTT assay measures mitochondrial NADH dependent dehydrogenase activity, and it has been among the most sensitive and reliable method to quantitative in vitro chemotherapy responses of tumor cells. (Alley, M. C., Scudiero, D. A., Monk, A., Hursey, M. L., Dzerwinski, M. J., Fine, D. L., Abbott, B. J., Mayo, J. G., Shoemaker, R. H. and Boyd, M. R., Feasibility of drug screening with panels of human tumor cell lines using a microculture tetrazolium assay Cancer Res., 48:589-601, 1988; Carmichael, J., DeGraff, W. G., Gazdar, A. F., Minna, J. D. and Mitchell, J. B., Evaluation of a tetrazolium-based semiautomated colorimetric assay: Assessment of chemosensitivity testing. Cancer Res., 47:936-942, 1987; McHale, A. P., McHale, L., Use of a tetrazolium based colorimetric assay in assessing photoradiation therapy in vitro. Cancer Lett., 41:315-321, 1988; and Saxton, R. E., Huang, M. Z., Plante D., Fetterman, H. F., Lufkin, R. B., Soudant, J., Castro, D. J., Laser and daunomycin chemophototherapy of human carcinoma cells. J. Clin. Laser Med. and Surg., 10(5):331-336, 1992.) Analysis of absorption readings at 550 nm were analyzed by grouping wells of the same test conditions and verifying differences occurring between control and the various peptide concentration treatments by one-way ANOVA.

An exemplary in vivo assay is also provided. The human pancreatic ductal adenocarcinoma Mia Paca-2 was examined for in vivo growth inhibition by peptide YY and test compound. Seventy thousand to 100,000 human Mia PaCa-2 cells were orthotopically transplanted into 48 male athymic mice. After one week, the animals were treated with either PYY or test compound at 200 pmol/kg/hr via mini-osmotic pumps for four weeks. The paired cultures received saline. At sacrifice, both tumor size and mass were measured. Control mice had significant human cancer growth within the pancreas as evidenced by histologic sections. At 9 weeks, ninety percent (90%) of control mice had substantial metastatic disease. Tumor mass was decreased by 60.5% in test treated mice and 27% in PYY treated mice.

PPF polypeptides may be administered alone or in combination with pharmaceutically acceptable carriers or excipients, in either single or multiple doses. These pharmaceutical compounds may be formulated with pharmaceutically acceptable carriers or diluents as well as any other known adjuvants and excipients in accordance with conventional techniques such as those disclosed in Remington's Pharmaceutical Sciences by E. W. Martin. See also Wang, Y. J. and Hanson, M. A. "Parenteral Formulations of Proteins and Peptides: Stability and Stabilizers," Journal of Parenteral Science and Technology, Technical Report No. 10, Supp. 42:2S (1988), incorporated by reference.

The PPF polypeptides may be provided in dosage unit form. For example, therapeutically effective amounts of the PPF polypeptide for affecting body composition will vary with many factors including the age and weight of the patient, the patient's physical condition, their use in combination with other treatments, the ultimate goal that is to be achieved, such as overall weight loss and/or maintaining or increasing lean body mass, as well as other factors. However, typical doses may contain from a lower limit of about 0.05 μg, about 0.1 μg, about 1 μg, about 5 μg, about 10 μg, about 50 μg, about 75 kg or about 100 μg, to an upper limit of about 50 μg, about 100 μg, about 500 μg, about 1 mg, about 5 mg, about 10 mg, about 15 mg, about 50 mg, about 100 mg or about 150 mg of the pharmaceutical compound per day. Also contemplated are other dose ranges such as 0.1 μg to 1 mg of the compound per dose, or at about 0.001 μg/kg to about 500 μg/kg per dose. In some embodiments, the PPF polypeptide of the invention is administered peripherally at a dose of about 0.5 μg to about 5 mg per day in single or divided doses or controlled continual release, or at about 0.01 μg/kg to about 500 μg/kg per dose, or at about 0.05 μg/kg to about 250 μg/kg. In some embodiments, the PPF polypeptide is administered at a dose below about 50 μg/kg. Dosages in these ranges will vary with the potency of each analog or derivative, of course, and may be readily determined by one of skill in the art.

The doses per day may be delivered in discrete unit doses, provided continuously in a 24 hour period or any portion of that the 24 hours. The number of doses per day may be from 1 to about 4 per day, although it could be more. Continuous delivery can be in the form of a continuous infusion. Other contemplated exemplary doses and infusion rates include from 0.005 nmol/kg to about 20 nmol/kg per discrete dose or from about 0.01/pmol/kg/min to about 10 pmol/kg/min in a continuous infusion. These doses and infusions can be delivered by any known conventional or future-developed peripheral method, e.g., intravenous (i.v.), intradermal, intramuscular, intramammary, intraperitoneal, intrathecal, retrobulbar, intrapulmonary (e.g., term release); subcutaneous administration (s.c.), by oral, sublingual, nasal, anal, vaginal, or transdermal delivery, or by surgical implantation at a particular site. Exemplary total dose/delivery of the pharmaceutical composition given i.v. may be about 1 μg to about 8 mg per day, whereas total dose/delivery of the pharmaceutical composition given s.c. may be about 6 μg to about 16 mg per day.

In one general aspect, methods of the invention may include the use of other body weight or body fat regulating compounds in combination with a PPF polypeptide. In the methods of the present invention, a PYY, PYY agonist or PPF polypeptide of the invention may be administered separately or together with one or more other compounds and compositions that exhibit a long term or short-term action to reduce nutrient availability, food intake, body weight, body weight gain or to alter body composition, for example. Such compounds include, but are not limited to, other compounds and compositions that comprise an amylin, amylin agonist or amylin analog agonist, salmon calcitonin, a cholecystokinin (CCK) or CCK agonist, a leptin (OB protein) or leptin agonist, an exendin or exendin analog agonist, a glucagon-like peptide-1 (GLP-1), GLP-1 agonist or GLP-1 analog agonist, CCK, CCK agonists, calcitonin, calcitonin agonists, small molecule cannabinoid CB1 receptor antagonists, rimonabant, 11 beta-hydroxysteroid dehydrogenase-1 inhibitors, sibutramine, phentermine and other drugs marketed for the treatment of obesity, such as appetite control. These compounds may be administered in combination, simultaneously or sequentially. Suitable amylin agonists include, for example, [$^{25,28,29}$Pro-] human amylin (also known as "pramlintide," and described in U.S. Pat. Nos. 5,686,511 and 5,998,367) and salmon calcitonin. In some embodiments, the CCK used is CCK octopeptide (CCK-8). Leptin is discussed in, for example, (Pelleymounter et al., Science 269: 540-3 (1995); Halaas et al., Science 269: 543-6 (1995); Campfield et al., Science 269: 546-9 (1995)). Suitable exendins include exendin-3 and exendin-4, and exendin agonist compounds include, for example, those described in PCT Publications WO 99/07404, WO 99/25727, and WO 99/25728.

C. Polypeptide Production and Purification

The PPF polypeptides described herein may be prepared using standard recombinant techniques or chemical peptide synthesis techniques known in the art, e.g., using an automated or semi-automated peptide synthesizer, or both.

The PPF polypeptides of the invention can be synthesized in solution or on a solid support in accordance with conventional techniques. Various automatic synthesizers are commercially available and can be used in accordance with known protocols. See, e.g., Stewart and Young, Solid Phase Peptide Synthesis, 2d. ed., Pierce Chemical Co. (1984); Tam et al., J. Am. Chem. Soc. 105: 6442 (1983); Merrifield, Science 232: 341-7 (1986); and Barany and Merrifield, The Peptides, Gross and Meienhofer, eds., Academic Press, New York, 1-284 (1979). Solid phase peptide synthesis may be carried out with an automatic peptide synthesizer (e.g., Model 430A, Applied Biosystems Inc., Foster City, Calif.) using the NMP/HOBt (Option 1) system and tBoc or Fmoc chemistry (see, Applied Biosystems User's Manual for the ABI 430A Peptide Synthesizer, Version 1.3B Jul. 1, 1988, section 6, pp. 49-70, Applied Biosystems, Inc., Foster City, Calif.) with capping. Peptides may also be assembled using an Advanced ChemTech Synthesizer (Model MPS 350, Louisville, Ky.). Peptides may be purified by RP-HPLC (preparative and analytical) using, e.g., a Waters Delta Prep 3000 system and a C4, C8, or C18 preparative column (10µ, 2.2×25 cm; Vydac, Hesperia, Calif.). The active protein can be readily synthesized and then screened in screening assays designed to identify reactive peptides.

The PPF polypeptides of the present invention may alternatively be produced by recombinant techniques well known in the art. See, e.g., Sambrook et al., Molecular Cloning: A Laboratory Manual, 2d ed., Cold Spring Harbor (1989). These PYY analog polypeptides produced by recombinant technologies may be expressed from a polynucleotide. One skilled in the art will appreciate that the polynucleotides, including DNA and RNA, that encode such encoded PYY analog polypeptides may be obtained from the wild-type PYY cDNA, taking into consideration the degeneracy of codon usage. These polynucleotide sequences may incorporate codons facilitating transcription and translation of mRNA in microbial hosts. Such manufacturing sequences may readily be constructed according to the methods well known in the art. See, e.g., WO 83/04053. The polynucleotides above may also optionally encode an N-terminal methionyl residue. Non-peptide compounds useful in the present invention may be prepared by art-known methods. For example, phosphate-containing amino acids and peptides containing such amino acids may be prepared using methods known in the art. See, e.g., Bartlett and Landen, Bioorg. Chem. 14: 356-77 (1986).

A variety of expression vector/host systems may be utilized to contain and express a PPF polypeptide coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems. Mammalian cells that are useful in recombinant protein productions include but are not limited to VERO cells, HeLa cells, Chinese hamster ovary (CHO) cell lines, COS cells (such as COS-7), WI 38, BHK, HepG2, 3T3, RIN, MDCK, A549, PC12, K562 and 293 cells. Exemplary protocols for the recombinant expression of the protein are described herein below.

As such, polynucleotide sequences provided by the invention are useful in generating new and useful viral and plasmid DNA vectors, new and useful transformed and transfected procaryotic and eucaryotic host cells (including bacterial, yeast, and mammalian cells grown in culture), and new and useful methods for cultured growth of such host cells capable of expression of the present PPF polypeptides. The polynucleotide sequences encoding PPF polypeptides herein may be useful for gene therapy in instances where underproduction of PP, PYY, or NPY would be alleviated, or the need for increased levels of such would be met.

The present invention also provides for processes for recombinant DNA production of the present PPF polypeptides. Provided is a process for producing the PPF polypeptides from a host cell containing nucleic acids encoding such PPF polypeptides comprising: (a) culturing said host cell containing polynucleotides encoding such PPF polypeptides under conditions facilitating the expression of such DNA molecule; and (b) obtaining such PPF polypeptides.

Host cells may be prokaryotic or eukaryotic and include bacteria, mammalian cells (such as Chinese Hamster Ovary (CHO) cells, monkey cells, baby hamster kidney cells, cancer cells or other cells), yeast cells, and insect cells.

Mammalian host systems for the expression of the recombinant protein also are well known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Post-translational processing, which cleaves a "prepro" form of the protein, may also be important for correct insertion, folding and/or function. Different host cells, such as CHO, HeLa, MDCK, 293, WI38, and the like, have specific cellular machinery and characteristic mechanisms for such post-translational activities, and may be chosen to ensure the correct modification and processing of the introduced foreign protein.

Alternatively, a yeast system may be employed to generate the PPF polypeptides of the present invention. The coding region of the PPF polypeptide cDNA is amplified by PCR. A DNA encoding the yeast pre-pro-alpha leader sequence is amplified from yeast genomic DNA in a PCR reaction using one primer containing nucleotides 1-20 of the alpha mating factor gene and another primer complementary to nucleotides 255-235 of this gene (Kudjan and Herskowitz, Cell, 30: 933-43 (1982)). The pre-pro-alpha leader coding sequence and PPF polypeptide coding sequence fragments are ligated into a plasmid containing the yeast alcohol dehydrogenase (ADH2) promoter, such that the promoter directs expression of a fusion protein consisting of the pre-pro-alpha factor fused to the mature PPF polypeptide. As taught by Rose and Broach, Meth. Enz. 185: 234-79, Goeddel ed., Academic Press, Inc., San Diego, Calif. (1990), the vector further includes an ADH2 transcription terminator downstream of the cloning site, the yeast "2-micron" replication origin, the yeast leu-2d gene, the yeast REP1 and REP2 genes, the E. coli β-lactamase gene, and an E. coli origin of replication. The β-lactamase and leu-2d genes provide for selection in bacteria and yeast, respectively. The leu-2d gene also facilitates increased copy number of the plasmid in yeast to induce higher levels of expression. The REP1 and REP2 genes encode proteins involved in regulation of the plasmid copy number.

The DNA construct described in the preceding paragraph is transformed into yeast cells using a known method, e.g., lithium acetate treatment (Steams et al., Meth. Enz. 185: 280-97 (1990)). The ADH2 promoter is induced upon exhaustion of glucose in the growth media (Price et al., Gene 55: 287 (1987)). The pre-pro-alpha sequence effects secretion of the fusion protein from the cells. Concomitantly, the yeast KEX2 protein cleaves the pre-pro sequence from the mature PYY analog polypeptides (Bitter et al., Proc. Natl. Acad. Sci. USA 81: 5330-4 (1984)).

PPF polypeptides of the invention may also be recombinantly expressed in yeast using a commercially available expression system, e.g., the Pichia Expression System (Invitrogen, San Diego, Calif.), following the manufacturer's instructions. This system also relies on the pre-pro-alpha sequence to direct secretion, but transcription of the insert is driven by the alcohol oxidase (AOX1) promoter upon induction by methanol. The secreted PPF polypeptide is purified from the yeast growth medium by, e.g., the methods used to purify PPF polypeptide from bacterial and mammalian cell supernatants.

Alternatively, the cDNA encoding PYY analog polypeptides may be cloned into the baculovirus expression vector pVL1393 (PharMingen, San Diego, Calif.). This PPF polypeptides-containing vector is then used according to the manufacturer's directions (PharMingen) to infect Spodoptera frugiperda cells in sF9 protein-free media and to produce recombinant protein. The protein is purified and concentrated from the media using a heparin-Sepharose column (Pharmacia, Piscataway, N.J.) and sequential molecular sizing columns (Amicon, Beverly, Mass.), and resuspended in PBS. SDS-PAGE analysis shows a single band and confirms the size of the protein, and Edman sequencing on a Proton 2090 Peptide Sequencer confirms its N-terminal sequence.

For example, the DNA sequence encoding the predicted mature PYY analog polypeptide may be cloned into a plasmid containing a desired promoter and, optionally, a leader sequence (see, e.g., Better et al., Science 240: 1041-3 (1988)). The sequence of this construct may be confirmed by automated sequencing. The plasmid is then transformed into E. coli, strain MC1061, using standard procedures employing CaCl2 incubation and heat shock treatment of the bacteria (Sambrook et al., supra). The transformed bacteria are grown in LB medium supplemented with carbenicillin, and production of the expressed protein is induced by growth in a suitable medium. If present, the leader sequence will affect secretion of the mature PYY analog polypeptide and be cleaved during secretion. The secreted recombinant protein is purified from the bacterial culture media by the method described herein below.

Alternatively, the PPF polypeptides of the invention may be expressed in an insect system. Insect systems for protein expression are well known to those of skill in the art. In one such system, Autographa californica nuclear polyhedrosis virus (AcNPV) is used as a vector to express foreign genes in Spodoptera frugiperda cells or in Trichoplusia larvae. The PPF polypeptide coding sequence is cloned into a nonessential region of the virus, such as the polyhedrin gene, and placed under control of the polyhedrin promoter. Successful insertion of PYY analog polypeptide will render the polyhedrin gene inactive and produce recombinant virus lacking coat protein coat. The recombinant viruses are then used to infect S. frugiperda cells or Trichoplusia larvae in which PYY analog polypeptide is expressed (Smith et al., J. Virol. 46: 584 (1983); Engelhard et al., Proc. Natl. Acad. Sci. USA 91: 3224-7 (1994)).

In another example, the DNA sequence encoding the PPF polypeptide may be amplified by PCR and cloned into an appropriate vector, for example, pGEX-3X (Pharmacia, Piscataway, N.J.). The pGEX vector is designed to produce a fusion protein comprising glutathione-S-transferase (GST), encoded by the vector, and a protein encoded by a DNA fragment inserted into the vector's cloning site. The primers for the PCR may be generated to include, for example, an appropriate cleavage site. The recombinant fusion protein may then be cleaved from the GST portion of the fusion protein. The pGEX-3x/PYY analog polypeptide construct is transformed into E. coli XL-1 Blue cells (Stratagene, La Jolla, Calif.), and individual transformants are isolated and grown at 37° C. in LB medium (supplemented with carbenicillin) to an optical density at wavelength 600 nm of 0.4, followed by further incubation for 4 hours in the presence of 0.5 mM Isopropyl β-D-Thiogalactopyranoside (Sigma Chemical Co., St. Louis, Mo.). Plasmid DNA from individual transformants is purified and partially sequenced using an automated sequencer to confirm the presence of the desired PPF polypeptide-encoding gene insert in the proper orientation.

The fusion protein, expected to be produced as an insoluble inclusion body in the bacteria, may be purified as follows. Cells are harvested by centrifugation; washed in 0.15 M NaCl, 10 mM Tris, pH 8, 1 mM EDTA; and treated with 0.1 mg/mL lysozyme (Sigma Chemical Co.) for 15 min. at room temperature. The lysate is cleared by sonication, and cell debris is pelleted by centrifugation for 10 min. at 12,000×g. The fusion protein-containing pellet is resuspended in 50 mM Tris, pH 8, and 10 mM EDTA, layered over 50% glycerol, and centrifuged for 30 min. at 6000×g. The pellet is resuspended in standard phosphate buffered saline solution (PBS) free of $Mg^{++}$ and $Ca^{++}$. The fusion protein is further purified by fractionating the resuspended pellet in a denaturing SDS polyacrylamide gel (Sambrook et al., supra). The gel is soaked in 0.4 M KCl to visualize the protein, which is excised and electroeluted in gel-running buffer lacking SDS. If the GST/PYY analog polypeptide fusion protein is produced in bacteria as a soluble protein, it may be purified using the GST Purification Module (Pharmacia Biotech).

The fusion protein may be subjected to digestion to cleave the GST from the mature PYY analog polypeptide. The digestion reaction (20-40 μg fusion protein, 20-30 units human thrombin (4000 U/mg (Sigma) in 0.5 mL PBS) is incubated 16-48 hrs. at room temperature and loaded on a denaturing SDS-PAGE gel to fractionate the reaction products. The gel is soaked in 0.4 M KCl to visualize the protein bands. The identity of the protein band corresponding to the expected molecular weight of the PYY analog polypeptide may be confirmed by partial amino acid sequence analysis using an automated sequencer (Applied Biosystems Model 473A, Foster City, Calif.).

In one method of recombinant expression of the PPF polypeptides of the present invention, HEK 293 cells may be co-transfected with plasmids containing the PYY analog polypeptide cDNA in the pCMV vector (5' CMV promoter, 3' HGH poly A sequence) and pSV2neo (containing the neo resistance gene) by the calcium phosphate method. In some embodiments, the vectors should be linearized with ScaI prior to transfection. Similarly, an alternative construct using a similar pCMV vector with the neo gene incorporated can be used. Stable cell lines are selected from single cell clones by limiting dilution in growth media containing 0.5 mg/mL G418 (neomycin-like antibiotic) for 10-14 days. Cell lines are screened for PYY analog polypeptide expression by ELISA or Western blot, and high-expressing cell lines are expanded for large scale growth.

In some embodiments, the transformed cells are used for long-term, high-yield protein production and stable expression may be desirable. Once such cells are transformed with vectors that contain selectable markers along with the desired expression cassette, the cells may be allowed to grow for 1-2 days in an enriched media before they are switched to selective media. The selectable marker is designed to confer resistance to selection, and its presence allows growth and recovery of cells that successfully express the introduced sequences. Resistant clumps of stably transformed cells can be proliferated using tissue culture techniques appropriate to the cell.

A number of selection systems may be used to recover the cells that have been transformed for recombinant protein production. Such selection systems include, but are not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr, that confers resistance to methotrexate; gpt, that confers resistance to mycophenolic acid; neo, that confers resistance to the aminoglycoside, G418; also, that confers resistance to chlorsulfuron; and hygro, that confers resistance to hygromycin. Additional selectable genes that may be useful include trpB, which allows cells to utilize indole in place of tryptophan, or hisD, which allows cells to utilize histinol in place of histidine. Markers that give a visual indication for identification of transformants include anthocyanins, β-glucuronidase and its substrate, GUS, and luciferase and its substrate, luciferin.

Many of the PPF polypeptides of the present invention may be produced using a combination of both automated peptide synthesis and recombinant techniques. For example, a PPF polypeptide of the present invention may contain a combination of modifications including deletion, substitution, and insertion by PEGylation. Such a PPF polypeptide may be produced in stages. In the first stage, an intermediate PPF polypeptide containing the modifications of deletion, substitution, insertion, and any combination thereof, may be produced by recombinant techniques as described. Then after an optional purification step as described below, the intermediate PPF polypeptide is PEGylated through chemical modification with an appropriate PEGylating reagent (e.g., from NeKtar Therapeutics, San Carlos, Calif.) to yield the desired PPF polypeptide. One skilled in the art will appreciate that the above-described procedure may be generalized to apply to a PPF polypeptide containing a combination of modifications selected from deletion, substitution, insertion, derivation, and other means of modification well known in the art and contemplated by the present invention.

It may be desirable to purify the PPF polypeptides generated by the present invention. Peptide purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography, polyacrylamide gel electrophoresis, and isoelectric focusing. A particularly efficient method of purifying peptides is reverse phase HPLC, followed by characterization of purified product by liquid chromatography/mass spectrometry (LC/MS) and Matrix-Assisted Laser Desorption Ionization (MALDI) mass spectrometry. Additional confirmation of purity is obtained by determining amino acid analysis.

Certain aspects of the present invention concern the purification, and in particular embodiments, the substantial purification, of an encoded protein or peptide. The term "purified peptide" as used herein, is intended to refer to a composition, isolatable from other components, wherein the peptide is purified to any degree relative to its naturally obtainable state. A purified peptide therefore also refers to a peptide, free from the environment in which it may naturally occur.

Generally, "purified" will refer to a peptide composition that has been subjected to fractionation to remove various other components, and which composition substantially retains its expressed biological activity. Where the term "substantially purified" is used, this designation will refer to a composition in which the peptide forms the major component of the composition, such as constituting about 50%, about 60%, about 70%, about 80%, about 90%, about 95% or more of the peptides in the composition.

Various techniques suitable for use in peptide purification will be well known to those of skill in the art. These include, for example, precipitation with ammonium sulphate, PEG, antibodies, and the like; heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the peptides always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed, utilizing an HPLC apparatus, will generally result in a greater "-fold" purification than the same technique utilizing a low pressure chromatography system. Methods exhibiting a lower degree of relative purification may have advantages in total recovery of protein product, or in maintaining the activity of an expressed protein.

One may optionally purify and isolate such PPF polypeptides from other components obtained in the process. Methods for purifying a polypeptide can be found in U.S. Pat. No. 5,849,883. These documents describe specific exemplary methods for the isolation and purification of G-CSF compositions that may be useful in isolating and purifying the PPF polypeptides of the present invention. Given the disclosure of these patents, it is evident that one of skill in the art would be well aware of numerous purification techniques that may be used to purify PPF polypeptides from a given source.

Also it is contemplated that a combination of anion exchange and immunoaffinity chromatography may be employed to produce purified PPF polypeptide compositions of the present invention.

D. Pharmaceutical Compositions

The present invention also relates to pharmaceutical compositions comprising a therapeutically or prophylactically effective amount of at least one PPF polypeptide of the invention, or a pharmaceutically acceptable salt thereof, together with pharmaceutically acceptable diluents, preservatives, solubilizers, emulsifiers, adjuvants and/or carriers useful in the delivery of the PPF polypeptides. Such compositions may include diluents of various buffer content (e.g., acetate, citrate, glutamate, tartrate, phosphate, TRIS), pH and ionic strength; additives such as surfactants and solubilizing agents (e.g., sorbitan monooleate, lecithin, Pluronics, Tween 20 & 80, Polysorbate 20 & 80, propylene glycol, ethanol, PEG-40, sodium dodecyl sulfate), anti-oxidants (e.g., monothioglyercol, ascorbic acid, acetylcysteine, sulfurous acid salts (bisulfise and metabisulfite), preservatives (e.g., phenol, meta-cresol, benzyl alcohol, parabens (methyl, propyl, butyl), benzalkonium chloride, chlorobutanol, thimersol, phenylmercuric salts, (acetate, borate, nitrate), and tonicity/bulking agents (glycerine, sodium chloride, mannitol, sucrose, trehalose, dextrose); incorporation of the material into particulate preparations of polymeric compounds, such as polylactic acid, polyglycolic acid, etc., or in association with liposomes. Such compositions will influence the physical state, stability, rate of in vivo release, and rate of in vivo clearance of the present PPF polypeptides. See, e.g., Remington's Pharmaceutical Sciences 1435-712, 18th ed., Mack Publishing Co., Easton, Pa. (1990).

In general, the present PPF polypeptides will be useful in the same way that PP, PYY, or NPY is useful in view of their pharmacological properties. One exemplary use is to peripherally administer such PPF polypeptides for the treatment or prevention of metabolic conditions and disorders. In particular, the compounds of the invention possess activity as agents to reduce nutrient availability, reduce of food intake, and effect weight loss.

The present PPF polypeptides may be formulated for peripheral administration, including formulation for injection, oral administration, nasal administration, pulmonary administration, topical administration, or other types of administration as one skilled in the art will recognize. More particularly, administration of the pharmaceutical compositions according to the present invention may be via any common route so long as the target tissue is available via that route. In some embodiments, the pharmaceutical compositions may be introduced into the subject by any conventional peripheral method, e.g., by intravenous, intradermal, intramuscular, intramammary, intraperitoneal, intrathecal, retrobulbar, intrapulmonary (e.g., term release); by oral, sublingual, nasal, anal, vaginal, or transdermal delivery, or by surgical implantation at a particular site. The treatment may consist of a single dose or a plurality of doses over a period of time. Controlled continual release of the compositions of the present invention is also contemplated.

The formulation may be composed in various forms, e.g., solid, liquid, semisolid or liquid. The formulation may be liquid or may be solid, such as lyophilized, for reconstitution. The term "solid," as used herein, is meant to encompass all normal uses of this term including, for example, powders and lyophilized formulations. Aqueous compositions of the present invention comprise an effective amount of the PPF polypeptide, dissolved or dispersed in a pharmaceutically acceptable carrier or aqueous medium. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in therapeutic compositions is contemplated. Supplementary active ingredients also can be incorporated into the compositions. In some cases, it will be convenient to provide a PPF polypeptide and another food-intake-reducing, plasma glucose-lowering or plasma lipid-altering agent, such as an amylin, an amylin agonist analog, a CCK or CCK agonist, or a leptin or leptin agonist, or an exendin or exendin agonist analog, and small molecule cannabinoid CB1 receptor antagonists, rimonabant, beta-hydroxysteroid dehydrogenase-1 inhibitors, sibutramine, phentermine and other drugs marketed for treatment of obesity in a single composition or solution for administration together. In other cases, it may be more advantageous to administer the additional agent separately from said PPF polypeptide.

The PPF polypeptide of the invention may be prepared for administration as solutions of free base, or pharmacologically acceptable salts in water suitably mixed with surface active agents (e.g., sorbitan monooleate, polyoxyethylene sorbitain monolaurate (Tween 20), polyoxyethylene sorbitan monooleate (Tween 80), lecithin, polyoxyethylene-polyoxypropylene copolymers (Pluronics), hydroxypropylcellulose) or complexation agents (e.g., hydroxypropyl-b-cyclodextrin, sulfobutyether-b-cyclodextrin (Captisol), polyvinylpyrrolidone). Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like. Such products are readily prepared by procedures well known to those skilled in the art. Dispersions also can be prepared in glycerol, liquid polyethylene glycols, and mixtures thereof and in oils.

A preservative is, in the common pharmaceutical sense, a substance that prevents or inhibits microbial growth and may be added to a formulation for this purpose to avoid consequent spoilage of the formulation by microorganisms. While the amount of the preservative is not great, it may nevertheless affect the overall stability of the peptide. Generally, under ordinary conditions of storage and use, these preparations contain a preservative to prevent the growth of microorganisms. While the preservative for use in the pharmaceutical compositions can range from 0.005 to 1.0% (w/v), in some embodiments, the range for each preservative, alone or in combination with others, is: benzyl alcohol (0.1-1.0%), or m-cresol (0.1-0.6%), or phenol (0.1-0.8%) or combination of methyl (0.05-0.25%) and ethyl or propyl or butyl (0.005%-0.03%) parabens. The parabens are lower alkyl esters of para-hydroxybenzoic acid.

Surfactants can cause denaturation of protein, both of hydrophobic disruption and by salt bridge separation. Relatively low concentrations of surfactant may exert a potent denaturing activity, because of the strong interactions between surfactant moieties and the reactive sites on proteins. However, judicious use of this interaction can stabilize proteins against interfacial or surface denaturation. Surfactants which could further stabilize the peptide may optionally be present in the range of about 0.001 to 0.3% (w/v) of the total formulation and include polysorbate 80 (i.e., polyoxyethylene(20) sorbitan monooleate), CHAPS® (i.e., 3-[(3-cholamidopropyl) dimethylammonio] 1-propanesulfonate), Brij® (e.g., Brij 35, which is (polyoxyethylene (23) lauryl ether), poloxamer, or another non-ionic surfactant.

The stability of a peptide formulation of the present invention is enhanced by maintaining the pH of the formulation in the range of about 3.0 to about 7.0 when in liquid form. In some embodiments, the PPF polypeptide is suspended in an aqueous carrier, for example, in an buffer solution at a pH of about 3.0 to about 8.0, about 3.5 to about 7.4, about 3.5 to about 6.0, about 3.5 to about 5.0, about 3.7 to about 4.7, about 3.7 to about 4.3 or about 3.8 to about 4.2. In some embodiments, parenteral formulations are isotonic or substantially isotonic. In some embodiments, the vehicle for parenteral products is water. Water of suitable quality for parenteral administration can be prepared either by distillation or by reverse osmosis. Water may be used as the aqueous vehicle for injection for use in the pharmaceutical formulations. Useful buffers include sodium acetate/acetic acid, sodium lactate/lactic acid, ascorbic acid, sodium citrate-citric acid, sodium bicarbonate/carbonic acid, sodium succinate/succinic acid, Histidine, Sodium benzoate/benzoic acid, and sodium phosphates, and Tris(hydroxymethyl)aminomehane. A form of repository or "depot" slow release preparation may be used so that therapeutically effective amounts of the preparation are delivered into the bloodstream over many hours or days following transdermal injection or delivery.

In some embodiments, the pharmaceutical compositions of the present invention are formulated so as to be suitable for parenteral administration, e.g., via injection or infusion. In some embodiments, liquid formulations are intended for parenteral administration. Suitable routes of administration include intramuscular, intravenous, subcutaneous, intradermal, mucosal, intraarticular, intrathecal, bronchial and the like. These routes include, but are not limited to, oral, nasal, sublingual, pulmonary and buccal routes that may include administration of the PPF polypeptide in liquid, semi-solid or solid form. Administration via some routes require substantially more PPF polypeptide to obtain the desired biological effects due to decreased bioavailability compared to parenteral delivery. In addition, parenteral controlled release delivery can be achieved by forming polymeric microcapsules, matrices, solutions, implants and devices and administering them parenterally or by surgical means. Examples of controlled release formulations are described in U.S. Pat. Nos. 6,368,630, 6,379,704, and 5,766,627, which are incorporated herein by reference. These dosage forms may have a lower bioavailability due to entrapment of some of the peptide in the polymer matrix or device. See e.g., U.S. Pat. Nos. 6,379,704, 6,379,703, and 6,296,842. In some embodiments, pharmaceutical compositions suitable for injectable use include sterile aqueous solutions or dispersions and sterile powders for the extemporaneous preparation of sterile injectable solutions or dispersions. In some embodiments, the form should be sterile and should be fluid to the extent that is easily syringable. It is also desirable for the PPF polypeptide of the invention to be stable under the conditions of manufacture and storage and must be preserved against the contaminating action of microorganisms, such as bacteria and fungi. The carrier can be a solvent or dispersion medium containing, for example, water, ethanol, polyol (e.g., sorbitol, glycerol, propylene glycol, and liquid polyethylene glycol, and the like), dimethylacetamide, cremorphor EL, suitable mixtures thereof, and oils (e.g., soybean, sesame, castor, cottonseed, ethyl oleate, isopropyl myristate, glycofurol, corn). The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, meta-cresol, benzyl alcohol, parabens (methyl, propyl, butyl), chlorobutanol, phenol, phenylmercuric salts (acetate, borate, nitrate), sorbic acid, thimerosal, and the like. In some embodiments, tonicity agents (for example, sugars, sodium chloride) may be included. Prolonged absorption of the injectable compositions can be brought about by the use in the compositions of agents delaying absorption (for example, aluminum monostearate and gelatin).

In some embodiments, for example non-parenteral formulations, sterilization may not be required. However, if sterilization is desired or necessary, any suitable sterilization process can be used in developing the peptide pharmaceutical formulation of the present invention. Typical sterilization processes include filtration, steam (moist heat), dry heat, gases (e.g., ethylene oxide, formaldehyde, chlorine dioxide, propylene oxide, beta-propiolacctone, ozone, chloropicrin, peracetic acid methyl bromide and the like), exposure to a radiation source, and aseptic handling. Filtration is the preferred method of sterilization for liquid formulations of the present invention. The sterile filtration involves filtration through 0.45 µm and 0.22 µm (1 or 2) which may be connected in series. After filtration, the solution is filled into appropriate vials or containers. Sterile injectable solutions may be prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle that contains the basic dispersion medium and the required other ingredients from those enumerated above. In the case of sterile powders for the preparation of sterile injectable solutions, exemplary methods of preparation are vacuum-drying and freeze-drying techniques that yield a powder of the active ingredient plus any additional desired ingredient from a previously sterile-filtered solution thereof.

In general, the PPF compounds may be formulated into a stable, safe pharmaceutical composition for administration to a patient. Pharmaceutical formulations contemplated for use in the methods of the invention may comprise from about 0.01 to about 20% (w/v), or from about 0.05 to about 10%, of the PPF compound. The PPF compounds may be in an acetate, phosphate, citrate or glutamate buffer (for example, at a final formulation concentration of from about 1-5 to about 60 mM) allowing a pH of the final composition of about 3.0 to about 7.0 containing carbohydrate or polyhydric alcohol as tonicity modifier and, optionally, approximately 0.005 to 5.0% (w/v) of a preservative selected from the group consisting of m-cresol, benzyl alcohol, methyl, ethyl, propyl and butyl parabens and phenol. Such a preservative is generally included if the formulated peptide is to be included in a multiple use product.

Optionally, a stabilizer may be included in the present formulation. If included, however, a stabilizer useful in the practice of the present invention is a carbohydrate or a polyhydric alcohol. A suitable stabilizer useful in the practice of the present invention is approximately 1.0 to 10% (w/v) of a carbohydrate or polyhydric alcohol. The polyhydric alcohols and carbohydrates share the same feature in their backbones, i.e., —CHOH—CHOH—, which is responsible for stabilizing the proteins. The polyhydric alcohols include such compounds as sorbitol, mannitol, glycerol, and polyethylene glycols (PEGs). These compounds are straight-chain molecules. The carbohydrates, such as mannose, ribose, sucrose, fructose, trehalose, maltose, inositol, and lactose, on the other hand, are cyclic molecules that may contain a keto or aldehyde group. These two classes of compounds have been demonstrated to be effective in stabilizing protein against denaturation caused by elevated temperature and by freeze-thaw or freeze-drying processes. Suitable carbohydrates include: galactose, arabinose, lactose or any other carbohydrate which does not have an adverse affect on a diabetic patient (if this is a desirable property), i.e., the carbohydrate is not metabolized to form unacceptably large concentrations of glucose in the blood.

In some embodiments, if a stabilizer is included, the PPF polypeptide is stabilized with a polyhydric alcohol such as sorbitol, mannitol, inositol, glycerol, xylitol, and polypropylene/ethylene glycol copolymer, as well as various polyethylene glycols (PEG) of molecular weight 200, 400, 1450, 3350, 4000, 6000, and 8000). Another useful feature of the lyophilized formulations of the present invention is the maintenance of the tonicity of the lyophilized formulations described herein with the same formulation component that serves to maintain their stability. In some embodiments, mannitol is the polyhydric alcohol used for this purpose.

Containers may also be considered to be a part of the formulation of an injection, for there is no container that is totally inert, or does not in some way affect the liquid it contains, particularly if the liquid is aqueous. Therefore, the selection of a container for a particular injection must be based on a consideration of the composition of the container, as well as of the solution, and the treatment to which it will be subjected. If necessary, adsorption of the peptide to the glass surface of the vial can also be minimized, by use of borosilicate glass, for example, Wheaton Type I borosilicate glass #33 (Wheaton Type I-33) or its equivalent (Wheaton Glass Co.). Other vendors of similar borosilicate glass vials and cartridges acceptable for manufacture include Kimbel Glass Co., West Co., Buinder Glas GMBH and Form a Vitrum. The biological and chemical properties of the PPF polypeptide may be stabilized by formulation and lyophilization in a Wheaton Type I-33 borosilicate serum vial to a final concentration of 0.1 mg/ml and 10 mg/ml of the PPF polypeptide in the presence of 5% mannitol, and 0.02% Tween 80. In order to permit introduction of a needle from a hypodermic syringe into a multiple-dose vial and provide for resealing as soon as the needle is withdrawn, the open end of each vial may be sealed with a rubber stopper closure held in place by an aluminum band. Stoppers for glass vials, such as, West 4416/50, 4416/50 (Teflon faced) and 4406/40, Abbott 5139 or any equivalent stopper can be used as the closure for pharmaceutical for injection. These stoppers are compatible with the peptide as well as the other components of the formulation. The inventors have also discovered that these stoppers pass the stopper integrity test when tested using patient use patterns, e.g., the stopper can withstand at least about 100 injections. In some embodiments, the peptide can be lyophilized in to vials, syringes or cartridges for subsequent reconstitution. Liquid formulations of the present invention can be filled into one or two chambered cartridges, or one or two chamber syringes.

In some embodiments, the manufacturing process for liquid formulations involves compounding, sterile filtration and filling steps. In some embodiments, the compounding procedure involves dissolution of ingredients in a specific order (preservative followed by stabilizer/tonicity agents, buffers and peptide) or dissolving at the same time.

The United States Pharmacopeia (USP) states that antimicrobial agents in bacteriostatic or fungistatic concentrations must be added to preparations contained in multiple dose containers. They must be present in adequate concentration at the time of use to prevent the multiplication of microorganisms inadvertently introduced into the preparation while withdrawing a portion of the contents with a hypodermic needle and syringe, or using other invasive means for delivery, such as pen injectors. Antimicrobial agents should be evaluated to ensure compatibility with all other components of the formula, and their activity should be evaluated in the total formula to ensure that a particular agent that is effective in one formulation is not ineffective in another. It is not uncommon to find that a particular antimicrobial agent will be effective in one formulation but not effective in another formulation.

In a particular embodiment of the present invention, a pharmaceutical formulation of the present invention may contain a range of concentrations of PPF compounds, e.g., between about 0.01% to about 98% w/w, or between about 1 to about 98% w/w, or between 80% and 90% w/w, or between about 0.01% to about 50% w/w, or between about 10% to about 25% w/w. A sufficient amount of water for injection may be used to obtain the desired concentration of solution. The pharmaceutical formulations described herein may be lyophilized. An exemplary formulation can be 1 mg/mL PPF compound in 10 mM sodium acetate buffer solution, pH 4.2, containing 9.3% sucrose as an osmolality modifier.

Tonicifying agents such as sodium chloride, as well as other known excipients, may be present, if desired. If such excipients are present, it may be preferable to maintain the overall tonicity of the PPF polypeptide. An excipient may be included in the presently described formulations at various concentrations. For example, an excipient may be included in the concentration range from about 0.02% to about 20% w/w, between about 0.02% and 0.5% w/w, about 0.02% to about 10% w/w, or about 1% to about 20% w/w. In addition, similar to the present formulations themselves, an excipient may be included in solid (including powdered), liquid, semi-solid or gel form.

It is possible that other ingredients may be present in the formulations. Such additional ingredients may include, e.g., wetting agents, emulsifiers, oils, antioxidants, bulking agents, tonicity modifiers, chelating agents, metal ions, oleaginous vehicles, proteins (e.g., human serum albumin, gelatin or proteins) and a zwitterion (e.g., an amino acid such as betaine, taurine, arginine, glycine, lysine and histidine). Additionally, polymer solutions, or mixtures with polymers provide the opportunity for controlled release of the peptide. Such additional ingredients, of course, should not adversely affect the overall stability of the formulation of the present invention.

Generally, a therapeutically or prophylactically effective amount of the present PPF polypeptides will be determined by the age, weight, and condition or severity of the diseases or metabolic conditions or disorders of the recipient. See, e.g., Remington's Pharmaceutical Sciences 697-773. See also Wang and Hanson, Parenteral Formulations of Proteins and Peptides: Stability and Stabilizers, Journal of Parenteral Science and Technology, Technical Report No. 10, Supp. 42:2S (1988). Typically, a dosage of between about 0.001 µg/kg body weight/day to about 1000 µg/kg body weight/day, may be used, but more or less, as a skilled practitioner will recognize, may be used. Dosing may be one, two, three, four or more times daily, or less frequently, such as once a week, once a month, or once a quarter, depending on the formulation, and may be in conjunction with other compositions as described herein. It should be noted that the present invention is not limited to the dosages recited herein.

Appropriate dosages may be ascertained through the use of established assays for determining level of metabolic conditions or disorders in conjunction with relevant dose-response data. The final dosage regimen will be determined by the attending physician, considering factors that modify the action of drugs, e.g., the drug's specific activity, severity of the damage and the responsiveness of the patient, the age, condition, body weight, sex and diet of the patient, the severity of any infection, time of administration and other clinical factors. As studies are conducted, further information will emerge regarding appropriate dosage levels and duration of treatment for specific diseases and conditions.

In some embodiments, an effective dose will typically be in the range of about 0.5 µg to about 5 mg/day, about 10 µg to about 2 mg/day, about 100 µg to about 1 mg/day, or about 5 µg to about 500 µg/day, administered in a single or divided doses of two, three, four or more administration. Accordingly, exemplary doses can be derived from the total amount of drug to be given a day and the number doses administered a day. Exemplary doses can range from about 0.125 µg/dose (0.5 µg given four times a day) to about 5 mg/dose (5 mg given once a day). Other dosages can be between about 0.01 to about 250 µg/kg/dose. The exact dose to be administered may be determined by one of skill in the art and is dependent upon the potency of the particular compound, as well as upon the age, weight and condition of the individual. Administration should begin whenever the suppression of nutrient availability, food intake, weight, blood glucose or plasma lipid lowering is desired, for example, at the first sign of symptoms or shortly after diagnosis of obesity, diabetes mellitus, or insulin-resistance syndrome. Administration may be by any route, e.g., injection, subcutaneous or intramuscular, oral, nasal, transdermal, etc. Dosages for certain routes, for example oral administration, may be increased to account for decreased bioavailablity, for example, by about 5-100 fold.

In some embodiments, where the pharmaceutical formulation is to be administered parenterally, the composition is formulation so as to deliver a dose of PPF polypeptide ranging from 0.1 µg/kg to 100 mg/kg body weight/day. In some embodiments, the doses range from 1 µg/kg to about 50 mg/kg body weight/day. Exemplary daily amounts may be in the range of a lower limit of 2, 5, 10, 20, 40, 60 or 80 to an upper limit of 80 100, 150, 200, or 250. Parenteral administration may be carried out with an initial bolus followed by continuous infusion to maintain therapeutic circulating levels of drug product. Those of ordinary skill in the art will readily optimize effective dosages and administration regimens as determined by good medical practice and the clinical condition of the individual patient.

The frequency of dosing will depend on the pharmacokinetic parameters of the agents and the routes of administration. The optimal pharmaceutical formulation will be determined by one of skill in the art depending on the route of administration and the desired dosage. See, e.g., Remington's Pharmaceutical Sciences, supra, pages 1435-1712. Such formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein, as well as the pharmacokinetic data observed in animals or human clinical trials.

It will be appreciated that the pharmaceutical compositions and treatment methods of the invention may be useful in fields of human medicine and veterinary medicine. Thus the subject to be treated may be a mammal. In some embodiments, the mammal is a human or other animal. For veterinary purposes, subjects include for example, farm animals including cows, sheep, pigs, horses and goats, companion animals such as dogs and cats, exotic and/or zoo animals, laboratory animals including mice, rats, rabbits, guinea pigs and hamsters; and poultry such as chickens, turkeys, ducks and geese.

In addition, the present invention contemplates a kit comprising a PPF polypeptide of the invention, components suitable for preparing said PPF polypeptide of the invention for pharmaceutical application, and instructions for using said PPF polypeptide and components for pharmaceutical application.

To assist in understanding the present invention, the following Examples are included. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

The present invention is described in more detail with reference to the following non-limiting examples, which are offered to more fully illustrate the invention, but are not to be construed as limiting the scope thereof. The examples illustrate the preparation of the present PPF polypeptides, and the testing of these PPF polypeptides of the invention in vitro and/or in vivo. Those of skill in the art will understand that the techniques described in these examples constitute best modes of practice and represent techniques described by the inventors to function well in the practice of the invention. However, it should be appreciated that those of skill in the art should, in light of the present disclosure, understand that many changes can be made in the specific methods that are disclosed and still obtain a like or similar result without departing from the spirit and scope of the invention.

Example 1

Preparation of PPF Polypeptides

Peptides of the invention may be assembled on a Symphony peptide synthesizer (Protein Technologies, Inc.) using Rink amide resin (Novabiochem) with a loading of 0.43-0.49 mmol/g at 0.050-0.100 mmol. Fmoc amino acid (5.0 eq, 0.250-0.500 mmol) residues are dissolved at a concentration of 0.10 M in 1-methyl-2-pyrrolidinone (NMP). Other reagents ((O-Benzotriazole-N,N,N',N'-tetramthyl-uronium-hexafluoro-phosphate (HBTU), 1-hydroxybenzotriazole hydrate (HOBt) and N,N-Diisopropylethylamine (DIEA)) are prepared as 0.55 M dimethylformamide solutions. The Fmoc protected amino acids are then coupled to the resin-bound amino acid using, HBTU (2.0 eq, 0.100-0.200 mmol), 1-hydroxybenzotriazole hydrate (1.8 eq, 0.090-0.18 mmol), N,N-diisopropylethylamine (2.4 eq, 0.120-0.240 mmol) for 2 hours. Following the last amino acid coupling, the peptide is deprotected using 20% (v/v) piperidine in dimethylformamide (DMF) for 1 hour. Once peptide sequence is complete, the Symphony peptide synthesizer is programmed to cleave the peptide from the resin. Trifluoroacetic acid (TFA) cleavage of the peptide from resin is carried out using 93% TFA, 3% phenol, 3% water and 1% triisopropylsilane for 1 hour. The cleaved peptide is precipitated using tert-butyl methyl ether, pelleted by centrifugation and lyophilized. The pellet is re-dissolved in water (10-15 mL), filtered and purified via reverse phase HPLC using a C18 column and an acetonitrile/water gradient containing 0.1% TFA. The resulting peptides are purified to homogeneity by reverse phase HPLC and the purity is confirmed by LC/MS.

A general procedure for N-capping the peptides of the invention with fatty acids and Acyl functionalities (e.g., octanoic and stearic acids, and isocaproyl and isobutyloxy-carbonyl modifications) is as follows: peptide on Rink amide resin (0.1 mmol) is suspended in NMP (5 mL). In a separate vial, HBTU (0.3 mmol), HOBt (0.3 mmol) is dissolved in DMF (5 mL) followed by the addition of DIEA (0.6 mmol). This solution is added to the resin and this suspension is shaken for 2 hours. The solvent is filtered and washed thoroughly with NMP (5 mL×4) and $CH_2Cl_2$ (20 mL), dried and is subjected to TFA cleavage for 1 hr. The yield of the desired peptide is about 40 mg after cleavage and purification. N-Carbamate derivatives (isobutyloxy, isopropyloxy, n-butyloxy, ethoxy) were obtained by coupling the corresponding carbonyl chlorides and peptides on Rink amide resin using DIEA, DMAP and dry CH2Cl2.

A general procedure for incorporating fatty acids on the epsilon amino group of a lysine is as follows: the modifications are carried out in solution on a free epsilon-amino group of a lysine of a purified peptide in the presence of the fatty acid and activating agent (HBTU/HOBt) in DMF. The resulting derivatives are purified by reverse phase HPLC and the purity is confirmed by LC/MS.

PEG modification may be carried out in solution on a free epsilon-amino group of lysine or a terminal amino group of a purified peptide using commercially available activated PEG esters. The resulting PEGylated derivatives are purified to homogeneity by reverse phase HPLC and the purity is confirmed by LC/MS and MALDI-MS.

Intramolecular disulphide bond formation may be performed on free cysteines using iodine/acetic acid as oxidizing agent.

The PPF polypeptides of the invention may be tested in a variety of biological assays in vitro, including Y-receptor binding assays using binding assay methodologies generally known to those skilled in the art, or in vivo, using food intake, body weight, and body composition assays using methodologies generally known to those skilled in the art. Exemplary assays include those described below.

Assays for signaling by $G_i/G_0$-coupled receptors: Without intending to be limited by theory, G-protein coupled receptor (GPCR) signaling mediated by heterotrimeric G-proteins can be categorized into signaling classes based upon an alpha-subunit composition. $G_s$, $G_q$ and $G_i/G_0$ proteins mediate intracellular signaling through activation of signaling pathways leading to distinct physiological endpoints. Activation of $G_s$ and $G_i/G_0$-coupled receptors leads to stimulation or inhibition of adenylate cyclase, respectively, while activation of $G_q$-coupled receptors results in stimulation of phospholipase C (PLC) and an increase in intracellular calcium concentration. Measuring a reduction in cAMP resulting from activation of $G_i/G_0$-coupled receptors can be technically difficult, whereas measuring a $G_q$-coupled increase in intracellular calcium is relatively easier. Thus, assays have been developed for assessing the activity of $G_i/G_0$-coupled receptors using cells co-transfected with promiscuous G-alpha subunits to redirect $G_i/G_0$ signaling through PLC and employing reporter genes or calcium sensitive fluorophores are known in the art. These assays may be used to assess the ability of PPF polypeptides to act as agonists or antagonists at Y-receptors. See, for example, Stables, et al., (1997) Anal. Biochem. 252 (1):115-26.

NPY Y1 receptor binding assay: Membranes are prepared from confluent cultures of SK-N-MC cells that endogenously expresses the neuropeptide Y1 receptors. Membranes are incubated with 60 pM [$^{125}$I]-human Peptide YY (2200 Ci/mmol, PerkinElmer Life Sciences), and with unlabeled PPF polypeptide for 60 minutes at ambient temperature in a 96 well polystyrene plate. The well contents are then harvested onto a 96 well glass fiber plate using a Perkin Elmer plate harvestor. Dried glass fiber plates are combined with scintillant and counted on a Perkin Elmer scintillation counter.

NPY Y2 receptor binding assay: Membranes are prepared from confluent cultures of SK-N-BE cells that endogenously expresses the neuropeptide Y2 receptors. Membranes are incubated with 30 pM [$^{125}$I]-human Peptide YY (2200 Ci/mmol, PerkinElmer Life Sciences), and with unlabeled PPF polypeptide for 60 minutes at ambient temperature in a 96 well polystyrene plate. The well contents are then harvested onto a 96 well glass fiber plate using a Perkin Elmer plate harvestor. Dried glass fiber plates are combined with scintillant and counted on a Perkin Elmer scintillation counter.

NPY Y4 receptor binding assay: CHO-K1 cells are transiently transfected with cDNA encoding neuropeptide Y4 gene, and then forty-eight hours later membranes are prepared from confluent cell cultures. Membranes are incubated with 18 pM [$^{125}$I]-human Pancreatic Polypeptide (2200 Ci/mmol, PerkinElmer Life Sciences), and with unlabeled PPF polypeptide for 60 minutes at ambient temperature in a 96 well polystyrene plate. The well contents are then harvested onto a 96 well glass fiber plate using a Perkin Elmer plate harvestor. Dried glass fiber plates are combined with scintillant and counted on a Perkin Elmer scintillation counter.

NPY Y5 receptor binding assay: CHO-K1 cells are transiently transfected with cDNA encoding neuropeptide Y5 gene, and then forty-eight hours later membranes are prepared from confluent cell cultures. Membranes are incubated with 44 pM [$^{125}$I]-human Peptide YY (2200 Ci/mmol, PerkinElmer Life Sciences), and with unlabeled PPF polypeptide for 60 minutes at ambient temperature in a 96 well polystyrene plate. The well contents are then harvested onto a 96 well glass fiber plate using a Perkin Elmer plate harvestor. Dried glass fiber plates are combined with scintillant and counted on a Perkin Elmer scintillation counter.

Table 2 demonstrates certain PPF polypeptides of the invention and their activity in various Y-receptor binding assays such as those described above.

TABLE 2

| SEQ ID NO: | Y1RBA (nM) | Y2RBA (nM) | Y4 RBA (nM) | Y5RBA (nM) |
|---|---|---|---|---|
| 1 | 10 | 1000 | 0.034 | 1.6 |
| 2 | 0.2 | 0.058 | 4.5 | 0.31 |
| 3 | 6.2 | 0.041 | 54 | 0.85 |
| 4 | 0.48 | 0.24 | 39 | 0.43 |
| 5 | >1000 | 229 | >1000 | 0.59 |
| 6 | 0.42 | 0.19 | 0.84 | 0.19 |
| 7 | 1000 | 21 | 1000 | 1000 |
| 8 | 1000 | 12 | 1000 | 1000 |
| 9 | 0.61 | 0.085 | 51 | 0.47 |
| 10 | 1.3 | 0.023 | 107 | 0.49 |
| 11 | 2.6 | 0.059 | 96 | 0.41 |
| 12 | 1.7 | 0.14 | 16 | 0.31 |
| 13 | 3.2 | 0.42 | 169 | 0.54 |
| 14 | 1000 | 1.6 | 1000 | 6.8 |
| 15 | 1.6 | 0.026 | 52 | 0.33 |
| 16 | 4.1 | 0.048 | 29 | 0.15 |
| 17 | 11 | 0.037 | 104 | 0.36 |
| 18 | 0.32 | 0.031 | 19 | 0.32 |
| 19 | 5.4 | 0.036 | 117 | 0.73 |
| 20 | 2.9 | 0.04 | 93 | 0.42 |
| 21 | 24 | 0.31 | 182 | 3.3 |
| 22 | 12 | 0.1 | 75 | 7.4 |
| 23 | 13 | 0.2 | 54 | 3.2 |
| 26 | 4.4 | 0.04 | 120 | 0.42 |
| 27 | 7 | 0.18 | 104 | 1.3 |
| 28 | 0.55 | 0.032 | 9.2 | 0.23 |
| 29 | 14 | 0.46 | 178 | 0.95 |
| 50 | 0.86 | 0.15 | 14 | 0.6 |
| 51 | 0.68 | 0.14 | 7.7 | 0.56 |
| 52 | 2.7 | 0.19 | 21 | 0.93 |
| 53 | 2.2 | 0.084 | 7.4 | 0.64 |
| 89 | 4.7 | 0.11 | 38 | 0.99 |
| 90 | 15 | 0.46 | 50 | 7.3 |
| 91 | 9.2 | 0.35 | 99 | 1.9 |
| 92 | 9.8 | 0.36 | 107 | 5 |
| 93 | 8.6 | 0.28 | 99 | 5.6 |
| 94 | 1.8 | 0.048 | 27 | 0.54 |
| 95 | 8.2 | 0.67 | 101 | 7.3 |
| 96 | 7.4 | 0.29 | 56 | 6.6 |
| 97 | 8.6 | 0.19 | 54 | 2.9 |
| 98 | 4.4 | 0.099 | 49 | 2.1 |
| 99 | 3.5 | 0.065 | 43 | 0.99 |
| 100 | 5.9 | 0.28 | 70 | 4 |
| 101 | 8.6 | 0.18 | 65 | 3.4 |
| 102 | 7.8 | 0.09 | 58 | 1.8 |
| 103 | 1.8 | 0.038 | 22 | 0.66 |
| 104 | 4.6 | 0.053 | 27 | 0.89 |
| 105 | 4.4 | 0.3 | 68 | 3.3 |
| 106 | 5.4 | 0.081 | 37 | 0.92 |
| 107 | 11 | 0.27 | 70 | 5.1 |
| 108 | 8.8 | 0.12 | 51 | 2.1 |
| 109 | 9.5 | 0.73 | 74 | 34 |
| 110 | 20 | 0.81 | 97 | 8.7 |
| 111 | 17 | 0.41 | 71 | 10 |
| 112 | 5.6 | 0.33 | 76 | 6.3 |
| 113 | 6.8 | 0.1 | 37 | 1.2 |
| 114 | 71 | 0.25 | 119 | 14 |
| 115 | 34 | 6.2 | 193 | 55 |
| 116 | 8.9 | 0.23 | 40 | 10 |
| 117 | 7.3 | 0.21 | 74 | 5.8 |
| 118 | 88 | 0.97 | 180 | 31 |
| 119 | 158 | 1.1 | 92 | 47 |
| 120 | 17 | 1.5 | 44 | 27 |
| 121 | 14 | 0.19 | 51 | 14 |
| 122 | 36 | 0.4 | 68 | 2.4 |
| 123 | 45 | 9.2 | 66 | 1.7 |
| 124 | >1000 | 86 | >1000 | 56 |
| 125 | 28 | 9.1 | 129 | 8.4 |
| 126 | 24 | 34 | 88 | 2.4 |
| 127 | >1000 | >1000 | >1000 | >1000 |
| 128 | >1000 | 113 | >1000 | >1000 |
| 130 | 4.5 | 0.25 | 46 | 5.2 |
| 131 | 6.8 | 0.28 | 80 | 2.9 |
| 132 | 17 | 0.56 | 113 | 7 |
| 133 | 1000 | 8.3 | 1000 | 138 |
| 135 | 293 | 43 | 1000 | 1000 |
| 136 | 88 | 0.081 | 863 | 1.8 |
| 138 | 7.9 | 0.43 | 165 | 5 |
| 139 | 301 | 20 | 1000 | 354 |
| 140 | 1000 | 380 | 1000 | 1000 |
| 142 | 6.2 | 0.12 | 61 | 1.2 |
| 143 | 3.8 | 0.19 | 56 | 2.3 |
| 144 | 4.5 | 0.39 | 52 | 4.6 |
| 145 | 5.4 | 0.12 | 47.5 | 1.5 |
| 146 | 8.7 | 0.19 | 73 | 2.3 |
| 147 | 5.1 | 0.092 | 48 | 1.7 |
| 148 | 5 | 0.1 | 50 | 1.8 |
| 150 | 276 | 11 | 1000 | 118 |
| 151 | 7.6 | 0.25 | 115 | 2.1 |
| 152 | 3.7 | 0.24 | 3.9 | 0.82 |
| 153 | 8.4 | 0.28 | 135 | 2.9 |
| 155 | 7.6 | 0.24 | 108 | 2.3 |
| 156 | 7.3 | 0.35 | 147 | 3.3 |
| 157 | 5.8 | 0.11 | 63 | 1.6 |
| 158 | 6.1 | 0.11 | 66 | 2.1 |
| 160 | 6.3 | 0.56 | 71 | 2.9 |
| 162 | 11 | 0.47 | 86 | 2.8 |
| 165 | 4.8 | 0.072 | 59 | 1.3 |
| 171 | 33 | 0.53 | 97 | 10 |
| 172 | 22 | 3.3 | 59 | 9.1 |
| 173 | 14 | 0.99 | 52 | 7.8 |
| 174 | 11 | 0.35 | 64 | 80 |
| 175 | 20 | 0.72 | >1000 | >1000 |
| 176 | 7.6 | 0.84 | 120 | 8.5 |
| 177 | 5.8 | 0.34 | 46 | 11 |
| 178 | 7.7 | 0.29 | 38 | 17 |
| 179 | 30 | 5.4 | 33 | 208 |
| 180 | 4.3 | 0.11 | 49 | 3.9 |
| 181 | 6.3 | 0.41 | 46 | 2.4 |
| 182 | 4.4 | 0.21 | 65 | 5.8 |
| 183 | 4.7 | 0.071 | 60 | 9.2 |
| 184 | 26 | 0.14 | 54 | 42 |
| 185 | 3 | 0.13 | 38 | 3.8 |
| 186 | 0.85 | 0.11 | 29 | 2.8 |
| 187 | 1000 | 62 | 1000 | 128 |
| 188 | 1000 | 102 | 1000 | 968 |
| 189 | 1000 | 57 | 1000 | 202 |
| 190 | 1000 | 24 | 1000 | 578 |
| 193 | 308 | 78 | 331 | 180 |
| 194 | 32 | 1.5 | 89 | 15 |
| 195 | 15 | 1.7 | 146 | 5.7 |
| 196 | 1000 | 612 | 1000 | 1000 |
| 197 | 1000 | 46 | 611 | 1000 |
| 198 | 10 | 0.7 | 88 | 9.9 |
| 199 | 38 | 4.1 | 143 | 58 |
| 200 | 106 | 7 | 426 | 74 |
| 201 | 27 | 2.2 | 99 | 29 |
| 202 | 36 | 148 | 23 | 80 |
| 203 | 33 | 4.4 | 108 | 78 |
| 204 | 47 | 1.1 | 223 | 37 |
| 205 | 44 | 1.5 | 172 | 18 |
| 206 | 66 | 15 | 204 | 45 |
| 207 | 180 | 0.69 | 1000 | 114 |
| 208 | 228 | 93 | 407 | 568 |

TABLE 2-continued

| SEQ ID NO: | Y1RBA (nM) | Y2RBA (nM) | Y4 RBA (nM) | Y5RBA (nM) |
|---|---|---|---|---|
| 211 | 3.7 | 0.24 | 50 | 5.4 |
| 212 | 2.9 | 0.046 | 59 | 0.8 |
| 225 | 6.7 | 0.15 | 79 | 1.8 |
| 226 | 3 | 0.059 | 35 | 0.57 |
| 227 | 1 | 0.032 | 38 | 0.11 |
| 228 | 4.1 | 0.1 | 61 | 1.1 |
| 229 | 8.2 | 0.23 | 57 | 2.7 |
| 230 | 3.4 | 0.1 | 45 | 1.2 |
| 231 | 5.6 | 0.37 | 55 | 9.4 |
| 235 | 8.7 | 0.65 | 77 | 12 |
| 236 | 6.5 | 0.24 | 62 | 4.6 |
| 237 | 2.1 | 0.11 | 35 | 2.8 |
| 239 | 0.18 | 0.092 | 18 | 0.27 |
| 240 | 2.4 | 0.059 | 89 | 0.58 |
| 241 | 4 | 0.15 | 61 | 0.88 |
| 242 | 2.7 | 0.13 | 71 | 1 |
| 243 | 18 | 0.74 | 124 | 7.2 |
| 244 | 11 | 1.5 | 88 | 7.5 |
| 245 | 0.19 | 0.077 | 16 | 0.35 |
| 246 | 3.9 | 0.11 | 119 | 0.7 |
| 247 | 0.38 | 0.12 | 25 | 0.76 |
| 248 | 0.48 | 0.12 | 24 | 0.44 |
| 249 | 0.36 | 0.11 | 21 | 0.34 |
| 250 | 2.2 | 0.075 | 73 | 0.51 |
| 251 | 0.42 | 0.12 | 28 | 0.52 |
| 252 | 2.1 | 0.074 | 52 | 0.64 |
| 253 | 1.3 | 0.041 | 34 | 0.29 |
| 254 | 2.3 | 0.051 | 85 | 0.56 |
| 255 | 5.7 | 0.26 | 208 | 2 |
| 256 | 1.7 | 0.039 | 395 | 0.48 |
| 258 | 0.39 | 0.12 | 22 | 0.89 |
| 260 | 0.42 | 0.16 | 22 | 0.74 |
| 261 | 2.9 | 0.11 | 71 | 1 |
| 262 | 1.7 | 0.087 | 61 | 0.91 |
| 263 | 3.2 | 0.1 | 141 | 1.2 |
| 264 | 1.8 | 0.22 | 98 | 0.48 |
| 265 | 7.3 | 1.1 | 272 | 11 |
| 266 | 2 | 0.13 | 193 | 1.7 |
| 267 | 0.25 | 0.1 | 9.5 | 0.32 |
| 268 | 0.31 | 0.14 | 21 | 0.57 |
| 269 | 3.8 | 0.084 | 77 | 0.74 |
| 270 | 3.3 | 0.13 | 97 | 1.4 |
| 271 | 0.51 | 0.094 | 4.2 | 0.25 |
| 272 | 0.26 | 0.1 | 12 | 0.27 |
| 273 | 0.32 | 0.18 | 21 | 0.89 |
| 274 | 4.9 | 0.42 | 181 | 1.5 |
| 275 | 0.59 | 0.099 | 81 | 1.5 |
| 276 | 0.68 | 0.3 | 8.3 | 1.3 |
| 277 | 3.4 | 0.16 | 150 | 2.5 |
| 278 | 3.6 | 0.078 | 138 | 1.4 |
| 279 | 6.4 | 1.2 | 200 | 12 |
| 280 | 2.1 | 0.38 | 108 | 1.6 |
| 281 | 2.8 | 0.1 | 117 | 0.67 |
| 282 | 0.55 | 0.04 | 18 | 0.15 |
| 283 | 30 | 3.4 | 87 | 10.6 |
| 284 | 1.1 | 0.071 | 47 | 0.56 |
| 285 | 0.67 | 0.18 | 16 | 0.54 |
| 286 | 0.65 | 0.11 | 0.75 | 0.3 |
| 287 | 5.2 | 0.16 | 10 | 1.2 |
| 288 | 1.8 | 0.35 | 11 | 1.1 |
| 289 | | | 48 | 0.83 |
| 290 | | | 187 | 0.51 |
| 291 | 186 | 201 | 9.5 | 0.71 |
| 292 | 1.4 | 0.17 | 0.77 | 0.32 |
| 293 | 0.82 | 0.18 | 0.87 | 0.48 |
| 294 | 0.94 | 0.17 | 0.98 | 0.51 |
| 295 | 1 | 0.18 | 1 | 0.63 |
| 296 | 2.7 | 0.76 | 2.9 | 2.1 |
| 297 | 3.6 | 0.32 | 4 | 1.8 |
| 298 | 5.5 | 1.2 | 3.4 | 3.9 |
| 299 | 11 | 3.2 | 16 | 7.5 |
| 300 | 83 | 16 | 311 | 78 |
| 301 | 26 | 3.7 | 70 | 28 |
| 302 | 5.1 | 0.68 | 93 | 2.9 |
| 303 | 6 | 0.5 | 7.1 | 3.3 |
| 304 | 0.51 | 0.14 | 0.48 | 0.28 |
| 306 | 0.6 | 0.16 | 1.2 | 0.27 |
| 307 | 0.53 | 0.13 | 0.73 | 0.47 |
| 308 | 1 | 0.56 | 2.1 | 1.4 |
| 309 | 3.3 | 78 | 5.6 | 1.5 |
| 310 | 29 | 454 | 27 | 5.1 |
| 311 | 16 | 0.49 | 51 | 1.8 |
| 312 | 70 | 0.42 | 91 | 3.4 |
| 313 | 9.2 | 0.57 | 151 | 2.6 |
| 314 | 8.2 | 0.67 | 202 | 2.5 |
| 315 | 9.2 | 2.1 | 467 | 5.6 |
| 316 | 7.1 | 0.63 | 52 | 1.1 |
| 317 | 4.3 | 0.097 | 16 | 0.69 |
| 318 | 100 | 1.3 | 84 | 1.9 |
| 319 | 35 | 1.04 | 77 | 1.2 |
| 320 | 77 | 3.1 | 243 | 13 |
| 321 | 12 | 3.7 | 57 | 5.6 |
| 332 | 13 | 0.54 | 38 | 1 |
| 333 | 4.8 | 0.54 | 37 | 0.87 |
| 334 | 21 | 0.45 | 101 | 2.4 |
| 335 | 34 | 0.72 | 109 | 3.6 |
| 338 | 8.1 | 0.68 | 46 | 1.1 |
| 341 | 1.8 | 0.15 | 11 | 0.3 |
| 342 | 15 | 0.62 | 84 | 1.4 |
| 343 | 12 | 0.38 | 69 | 1.3 |
| 347 | 35 | 18 | 740 | 51 |
| 436 | 4 | 0.07 | 36 | 1.4 |
| 437 | 5.1 | 0.45 | 371 | 2.1 |
| 438 | 1.5 | 0.079 | 167 | 1.2 |
| 439 | 0.93 | 0.05 | 176 | 0.47 |
| 440 | 1.6 | 0.1 | 100 | 1.2 |
| 441 | 4.8 | 0.65 | 224 | 7 |
| 442 | 1.6 | 0.11 | 214 | 1.3 |
| 443 | 474 | 113 | 914 | 592 |
| 444 | 6.6 | 0.36 | 97 | 3.8 |
| 445 | 9.1 | 0.56 | 269 | 6.3 |
| 446 | 13 | 1 | 141 | 6.6 |
| 447 | 8.3 | 0.5 | 206 | 25 |
| 448 | 6.6 | 0.1 | 61 | 1.1 |
| 449 | 3.6 | 0.068 | 78 | 3.1 |
| 450 | 1000 | 0.51 | 1000 | 11 |
| 451 | 7.8 | 0.89 | 71 | 18 |
| 452 | 7 | 0.34 | 62 | 3 |
| 453 | 0.7 | 0.084 | 17 | 0.82 |
| 454 | 4.4 | 0.27 | 278 | 6.1 |
| 455 | 4.5 | 0.81 | 146 | 5.3 |
| 456 | 8.5 | 1.1 | 246 | 10 |
| 458 | 10 | 0.47 | 593 | 3.6 |
| 459 | 79 | 0.48 | 100 | 6.2 |
| 460 | 1.4 | 0.08 | 115 | 0.59 |
| 461 | 6.5 | 0.59 | 303 | 3.3 |
| 462 | 8.2 | 0.91 | 356 | 10 |
| 463 | 23 | 4 | 361 | 19 |
| 467 | 2.7 | 0.17 | 158 | 1.5 |
| 468 | 5.7 | 0.74 | 283 | 5.6 |
| 469 | 3.4 | 0.48 | 508 | 5.1 |
| 470 | 6.8 | 0.78 | 585 | 12 |
| 471 | 2.6 | 0.18 | 178 | 3.1 |
| 472 | 11 | 1.5 | 368 | 20 |
| 473 | 7.3 | 0.95 | 212 | 5.4 |
| 474 | 0.68 | 0.3 | 8.3 | 1.3 |
| 475 | 26 | 6.7 | 358 | 21 |
| 476 | 27 | 7.4 | 53 | 15 |
| 477 | 265 | 4.4 | 164 | 18 |
| 478 | 1000 | 31 | 273 | 17 |
| 479 | 1.8 | 0.357 | 74 | 3.5 |
| 480 | 7.7 | 2.2 | 211 | 18 |

Example 2

PPF Polypeptides Suppress Food Intake in Food Intake Assay

Female NIH/Swiss mice (8-24 weeks old) are group housed with a 12:12 hour light:dark cycle with lights on at 0600. Water and a standard pelleted mouse chow diet are available ad libitum, except as noted. Animals are fasted starting at approximately 1500 hrs, one day prior to experiment. The morning of the experiment, animals are divided into experimental groups. In a typical study, n=4 cages with 3 mice/cage.

At time=0 min, all animals are given an intraperitoneal injection of vehicle or compound in an amount ranging from about 10 nmol/kg to 100 nmol/kg, and immediately given a pre-weighed amount (10-15 g) of the standard chow. Food is removed and weighed at 30, 60, and 120 min to determine the amount of food consumed (Morley, Flood et al., Am. J. Physiol. 267: R178-R184, 1994). Food intake is calculated by subtracting the weight of the food remaining at the 30, 60, 120, 180 and/or 240 minute time points, for example, from the weight of the food provided initially at time=0. Significant treatment effects were identified by ANOVA ($p<0.05$). Where a significant difference exists, test means are compared to the control mean using Dunnett's test (Prism v. 2.01, GraphPad Software Inc., San Diego, Calif.)

Figure 40:
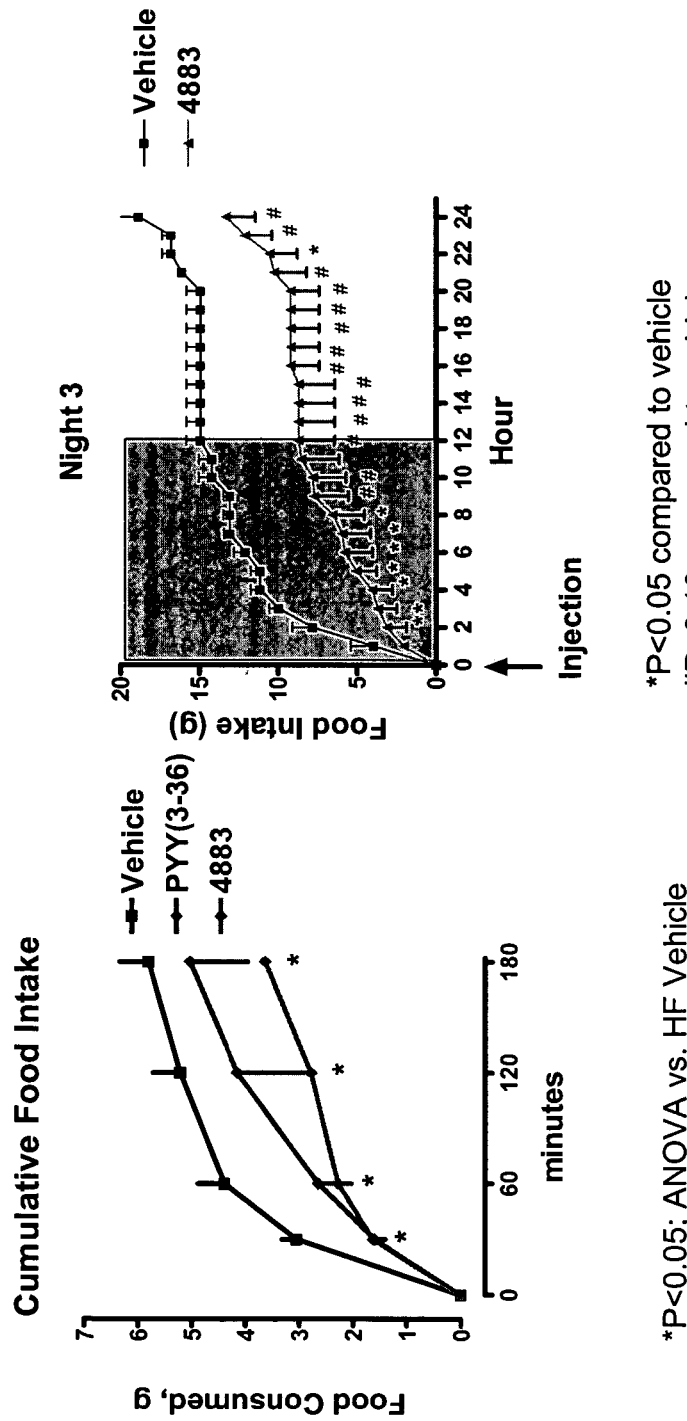
FIG. 40 demonstrates exemplary effects of acute administration of a PPF polypeptide in food intake assays in mouse and rat models, as compared to PYY(3-36).

FIGS. 1-4 show the ability of several PPF polypeptides of the invention to reduce cumulative food intake in the food intake assay described above. Furthermore, FIG. 40 shows that acute administration of PPF polypeptide compound 4883 was found to be more effective than PYY(3-36) in reducing food intake in the NIH/Swiss mouse and HSD rat models.

Example 3

PPF Polypeptides Decrease Body Weight Gain in High Fat Fed (Diet-induced-obesity, or DIO) C57BL/6 Mice and High Fat-fed HSD Rats Mice: Male C57BL/6 mice (4 weeks old at start of study) are fed high fat (HF, 58% of dietary kcal as fat) or low fat (LF, 11% of dietary kcal as fat) chow. After 4 weeks on chow, each mouse is implanted with an osmotic pump (Alzet # 2002) that subcutaneously delivers a predetermined dose of PPF polypeptide continuously for two weeks. Body weight and food intake are measured weekly (Surwit et al., Metabolism—Clinical and Experimental, 44: 645-51, 1995). Effects of the test compound are expressed as the mean +/−sd of % body weight change (i.e., % change from starting weight) of at least 14 mice per treatment group ($p<0.05$ ANOVA, Dunnett's test, Prism v. 2.01, GraphPad Software Inc., San Diego, Calif.).

Rats: The night before treatment, male Sprague-Dawley® rats (average weight=415) consuming a high fat diet (45% kCal from fat) were assigned to two treatment groups based on equal 24 hr food intake. On test night, each animal received a single IP injection of Vehicle (10% DMSO) or Compound (1 mg/kg) just prior to lights off (1800 h), and were then placed individually into a DietPro automated feeding cage. Each cage contains a food hopper resting on a scale connected to a computer, and a water bottle. Hourly food intake (in grams) is recorded for the following 24 hours. Animals received injections for six consecutive nights. Body weights were recorded nightly.

Figure 5:
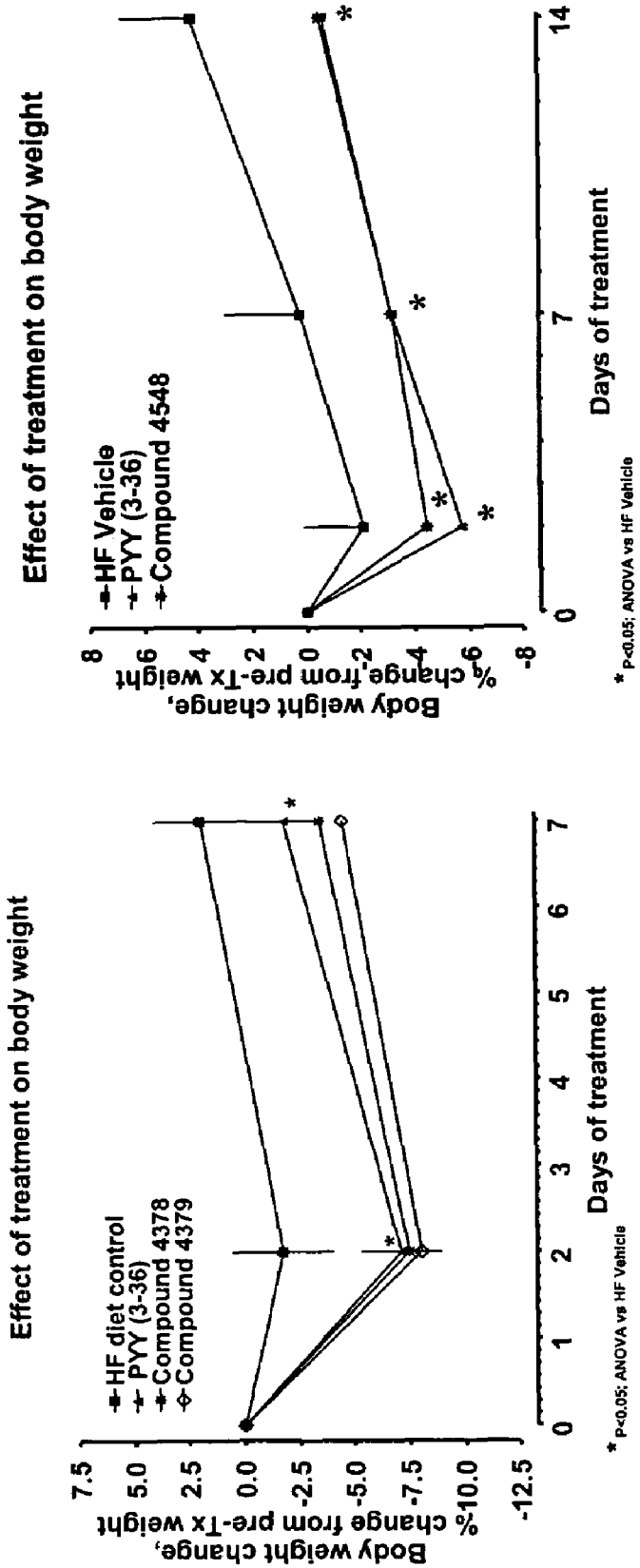
FIG. 5 demonstrates the activity of certain PPF polypeptides of the invention in the diet-induced obese (DIO) mouse model.
Figure 6:
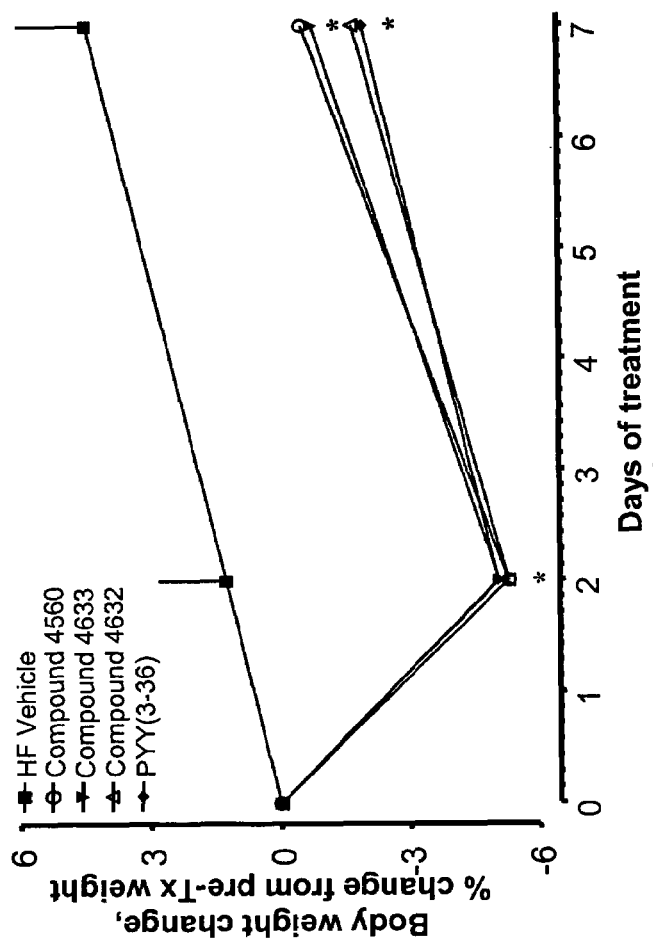
FIG. 6 demonstrates the activity of additional PPF polypeptides of the invention in the DIO mouse model.
Figure 7:
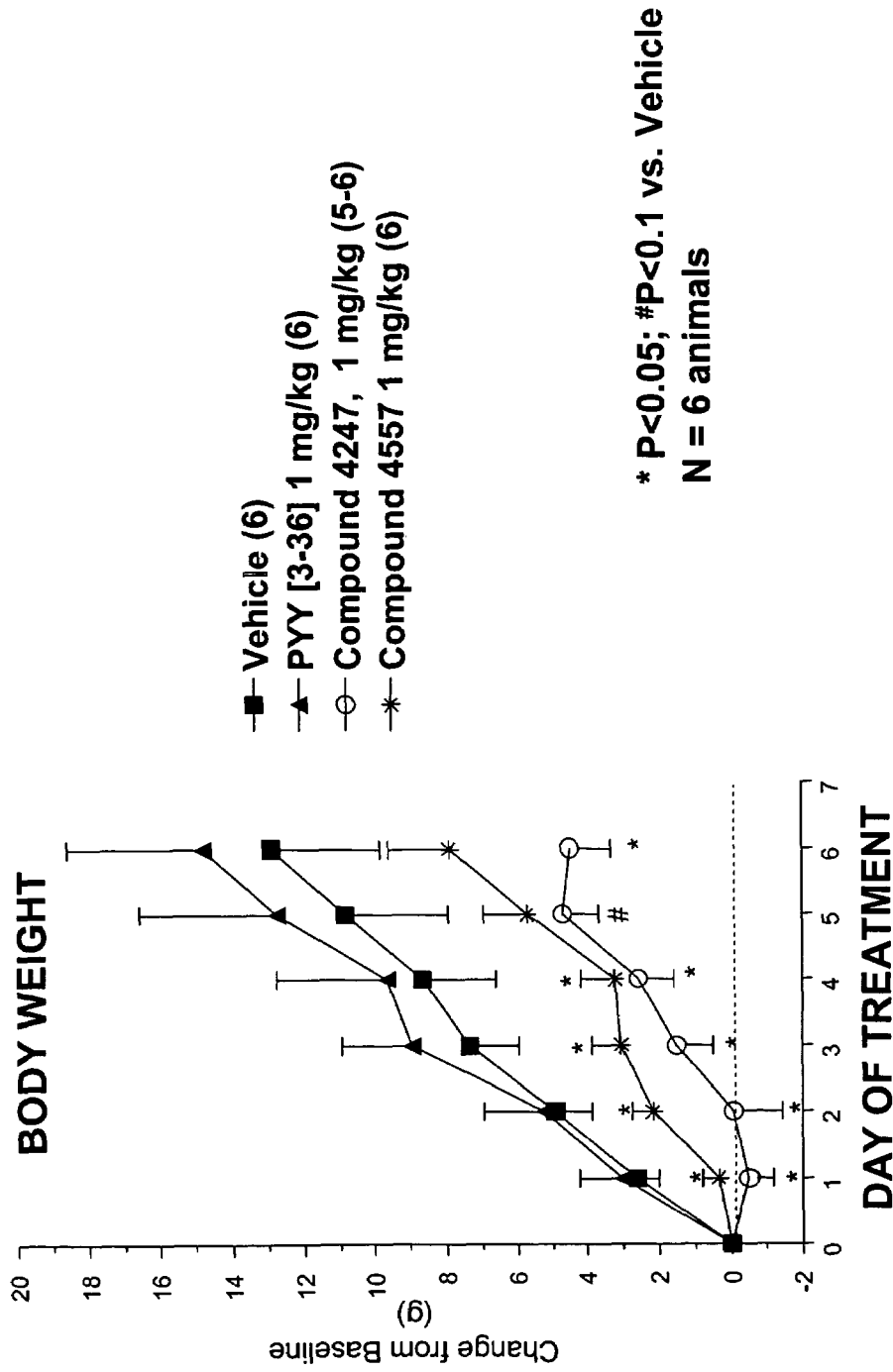
FIG. 7 shows weight gain in rats.
Figure 42:
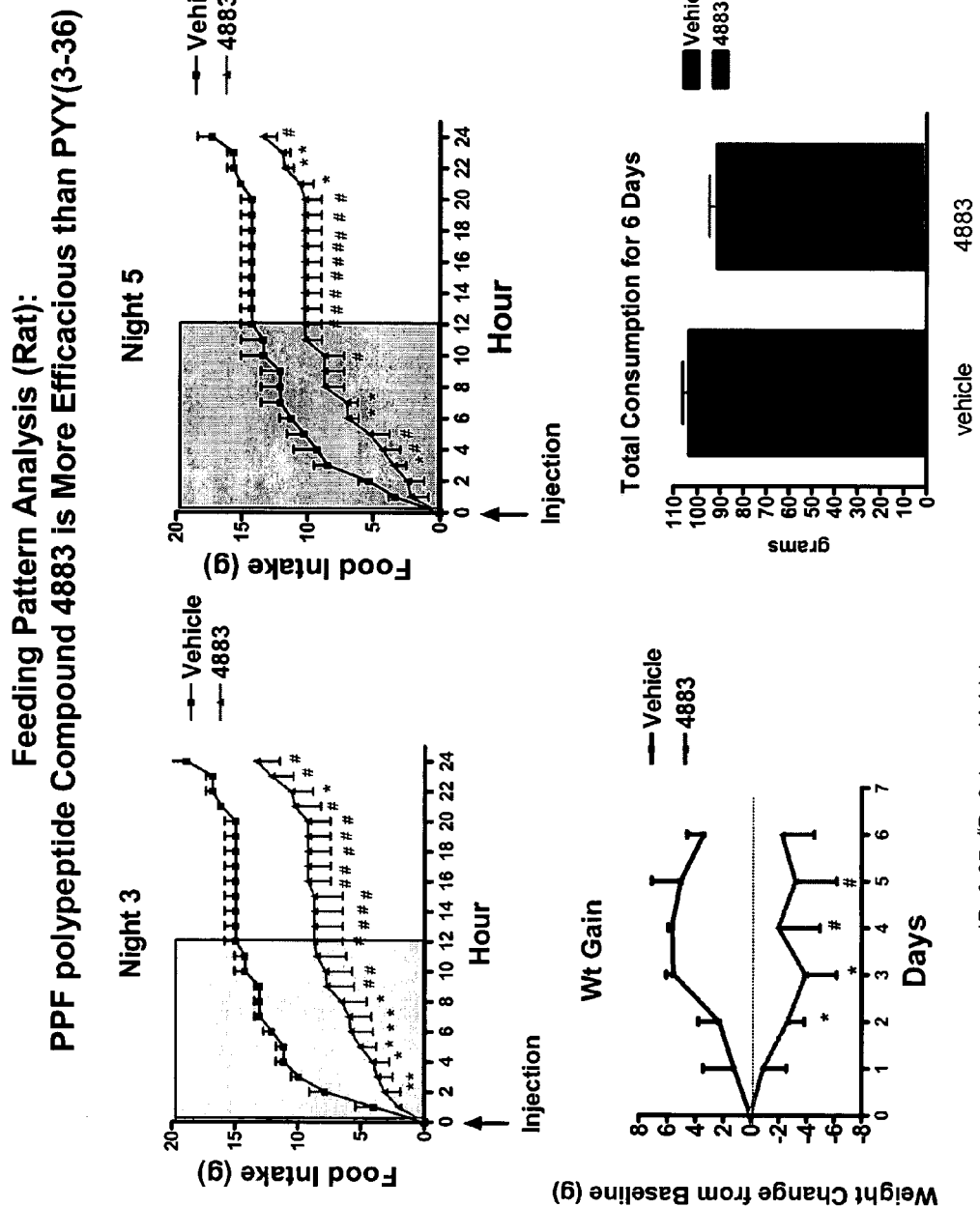
FIG. 42 depicts effects of administration of an exemplary PPF polypeptide on feeding pattern in a rat model.

FIGS. 5-6 demonstrate the ability of several PPF polypeptides of the invention to decrease body weight gain in the DIO mouse assay described above. FIG. 7 demonstrates that once daily injections resulted in a significant reduction in body weight gain on several nights ($P<0.05$) in high fat-fed rats. For example, FIG. 8 demonstrates that a PPF polypeptide of the invention exhibits greater efficacy than PYY(3-36) in both the food intake assay and the DIO mouse assay. For example, FIG. 42 demonstrates the effects of another PPF polypeptide of the invention on feeding pattern, and shows that PPF polypeptide compound 4883 reduces food intake on nights 3 and 5, significantly reduces weight over seven days, and reduces total food consumption for six days.

Example 4

PPF Polypeptides Reduce Blood Pressure

Male Harlan Sprague Dawley (HSD) rats housed at 22.8±0.8° C. in a 12:12 hour light:dark cycle were used to study the effects of PPF Polypeptides on the circulatory system through the use of telemetry. The experiments were performed during the light cycle. Telemetry allows for real-time hemodynamic readings including arterial blood pressure, heart rate and arterial dP/dt, via an implanted radio transmitter in conscious, non-anesthetized, unrestrained rats. In the present Example, rats were injected with either vehicle, 10 nmol/kg PYY, 10 nmol/kg PYY(3-36) or 10 nmol/kg of several PPF polypeptides by remote intravenous dosing. Remote intravenous dosing was achieved through in-dwelling vascular access ports (Access Technologies (Skokie, Ill.). The port is secured to the underlying muscle just below the skin between the scapulae. The catheter resides in the jugular vein. Data were collected for up to 60 minutes following injection.

As shown in FIGS. 9A-B, the effect of compound 4676 to increase mean arterial pressure (MAP) are similar to those of PYY(3-36). FIGS. 9C-D show that while the effects of compound 4247 to increase mean arterial pressure and decrease heart rate are similar to those of PYY(1-36), those effects are blunted with compound 4560.

Figure 47:
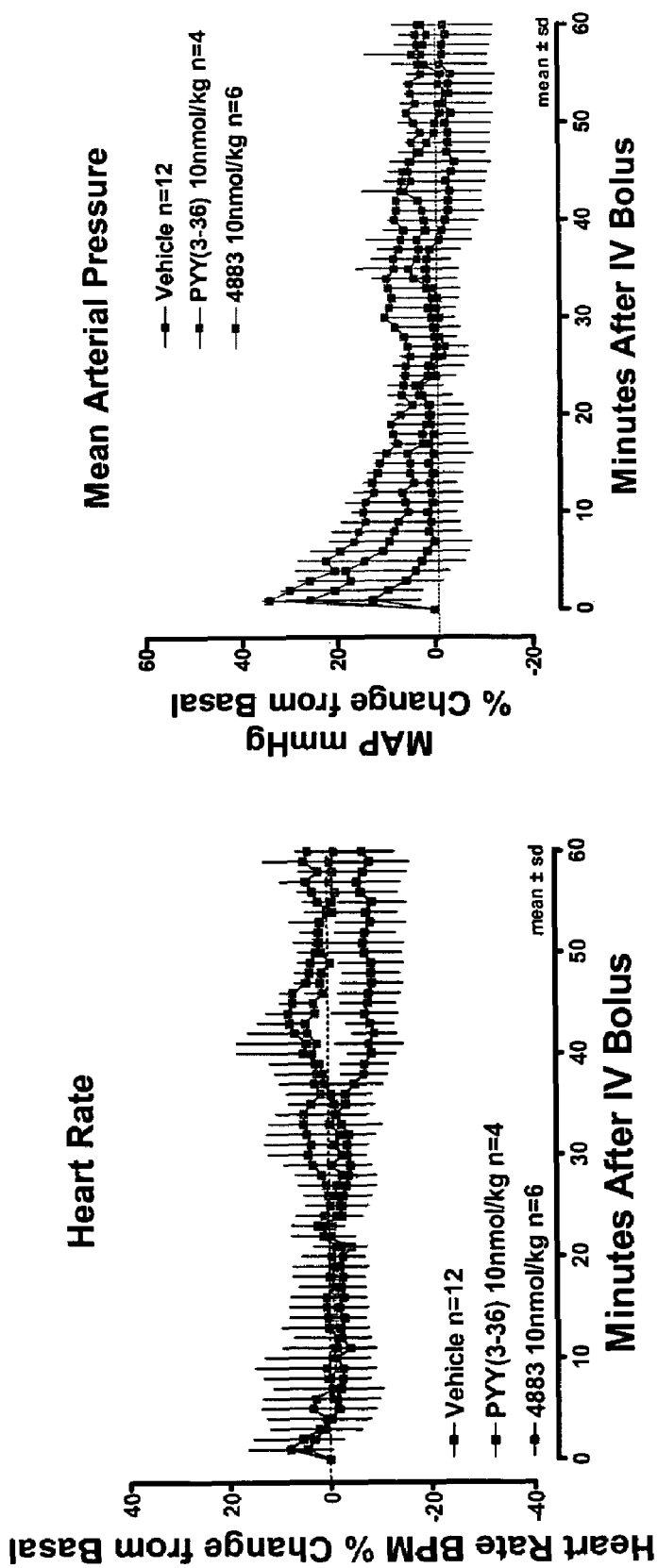
FIG. 47 depicts effects of administration of an exemplary PPF polypeptide on heart rate and mean arterial pressure (MAP) in rats.

FIG. 46 demonstrates that PPF polypeptide compound 4753 also decreases heart rate as compared to PYY(3-36), while its effect on MAP is comparable to that of PYY(3-36). FIG. 47 demonstrates that the effects of PPF polypeptide compound 4883 on heart rate and MAP are comparable to those of PYY(3-36).

Example 5

Antisecretory Effects of PYY and PYY Agonists

Gastric Acid Secretion

Male Harlan Sprague Dawley rats were housed at 22.8±0.8° C. in a 12:12 hour light:dark cycle. The experiments were performed during the light cycle. Animals, fed rat chow (Teklad LM 485, Madison, Wis.), were fasted for approximately 20 hours before experimentation. They were given free access to water until the start of the experiment.

The rats (age 11-16 weeks, body mass 291-365 g) were surgically fitted with gastric fistulae custom made by David Osborne, Department of Biology, UCLA. Overnight fasted rats were weighed and their gastric fistulae were uncapped and attached to flexible Tygon tubing (⅜×1/16) into which was fitted a piece of PE205 tubing that would extend into the stomach. Saline was injected through the narrower PE205 tubing and the effluent collected from the Tygon tubing. To ensure proper flow through the fistulae and an empty stomach, the stomach was flushed several times with ~5 ml of room temperature saline solution until flow was easy and the effluent was clean. Gastric acid secretion was measured at 10 min intervals by injecting 5 mL of saline (pH 7.0) followed by 3 ml of air and collecting the effluent. Three ml of each gastric aspirate were titrated to 7.0 with 0.01 N sodium hydroxide using a pH meter (Beckman model number PHI34 Fullerton, Calif.). The amount of base required for each titration, corrected to the total volume collected, was used to calculate the moles of acid in each sample.

After a baseline sample was collected, and the recovered volume recorded, the animal was given a subcutaneous injection of 125 µg/kg pentagastrin (Sigma, lot#40K0616) and then 10 min. gastric sampling was continued for a further 2 hours. Forty minutes after pentagastrin injection, when a stable plateau of gastric acid secretion was typically observed, the rats were given a subcutaneous injection of (PYY(3-36)) at a dose per animal of 1, 3, 10, 100 µg or saline, (3.45,10.34,34.5, 344.8 µg/kg, respectively, in a rat weighing 290 grams) (n=3, 2, 4, 4, 6 respectively).

Figure 10:
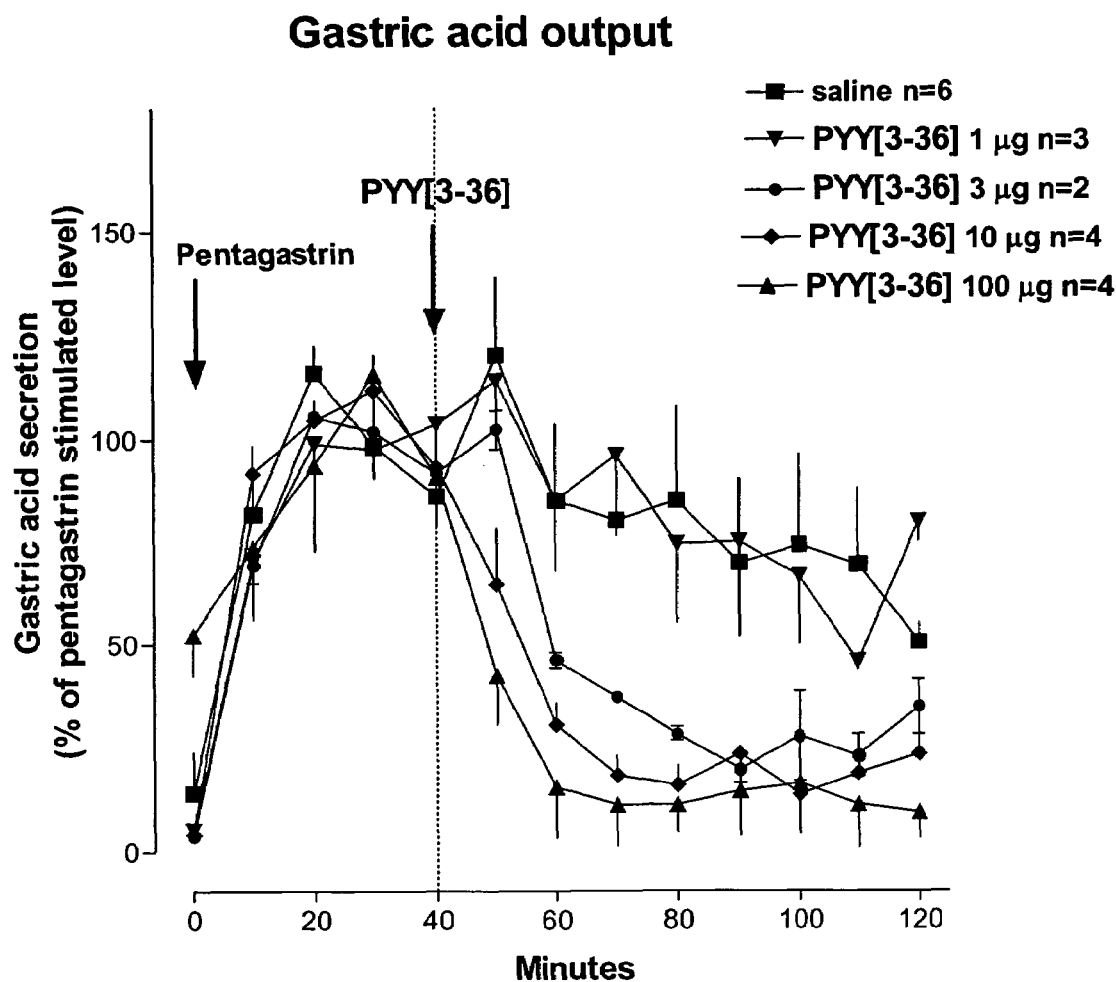
FIG. 10 demonstrates the activity of PPF polypeptides of the invention on gastric acid secretion.
Figure 11:
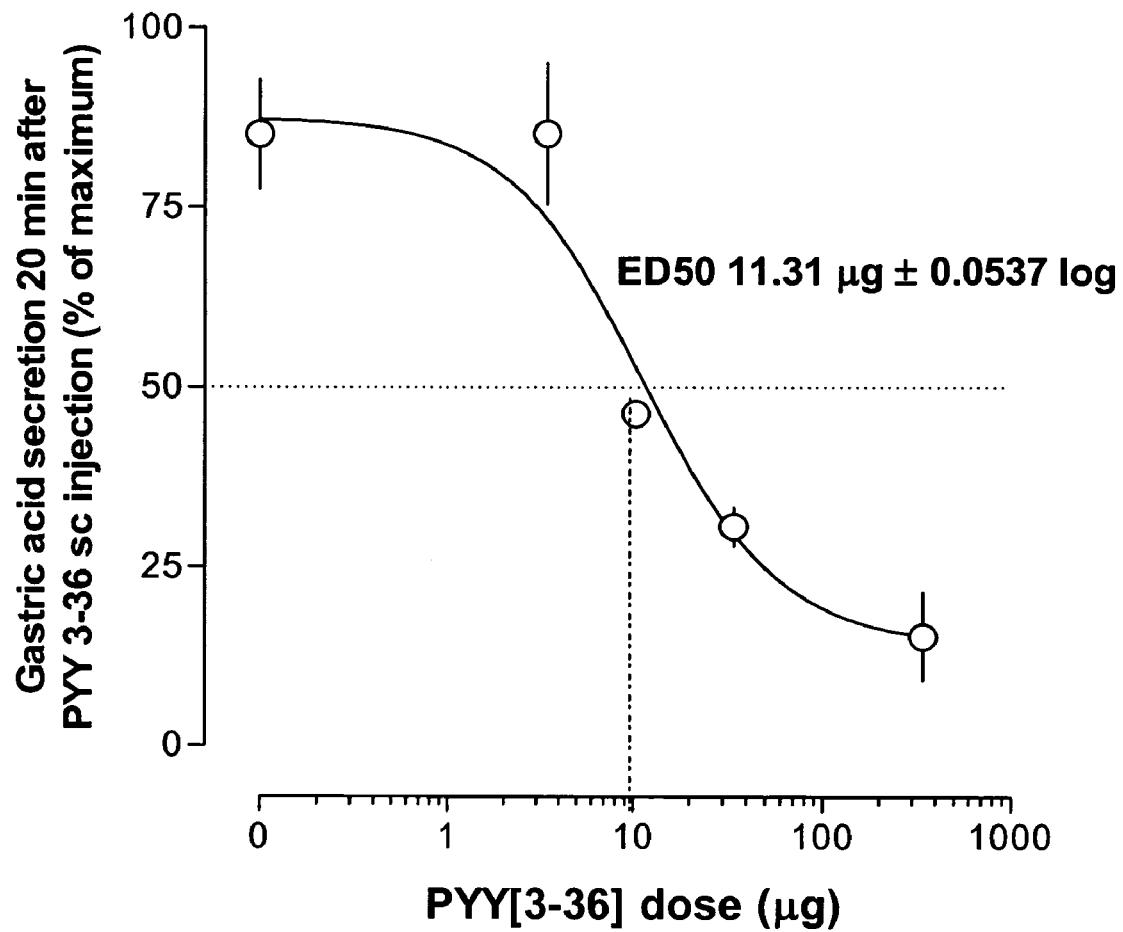
FIG. 11 demonstrates the activity of PPF polypeptides of the invention on gastric acid secretion.
Figure 12:
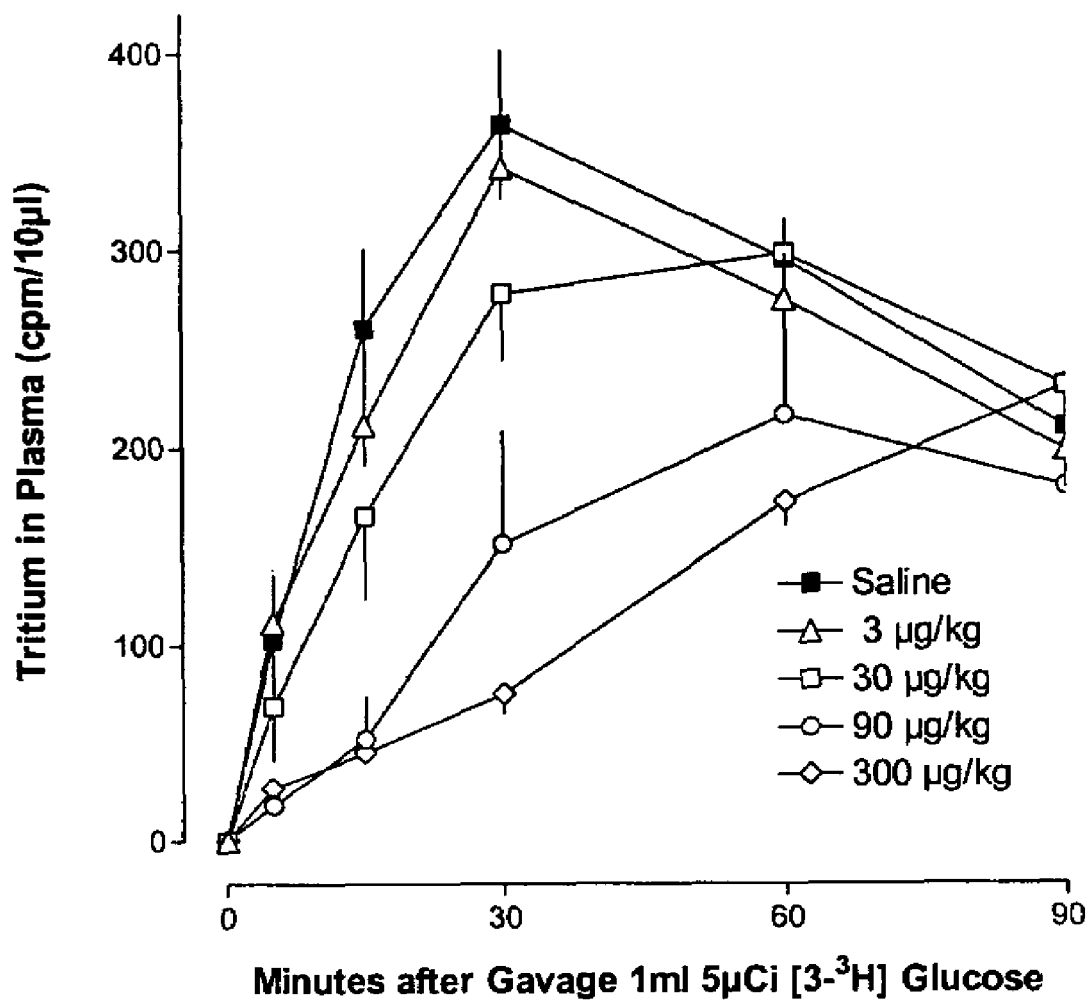
FIGS. 12-17 demonstrate the activity of PPF polypeptides of the invention on gastric emptying.
Figure 13:
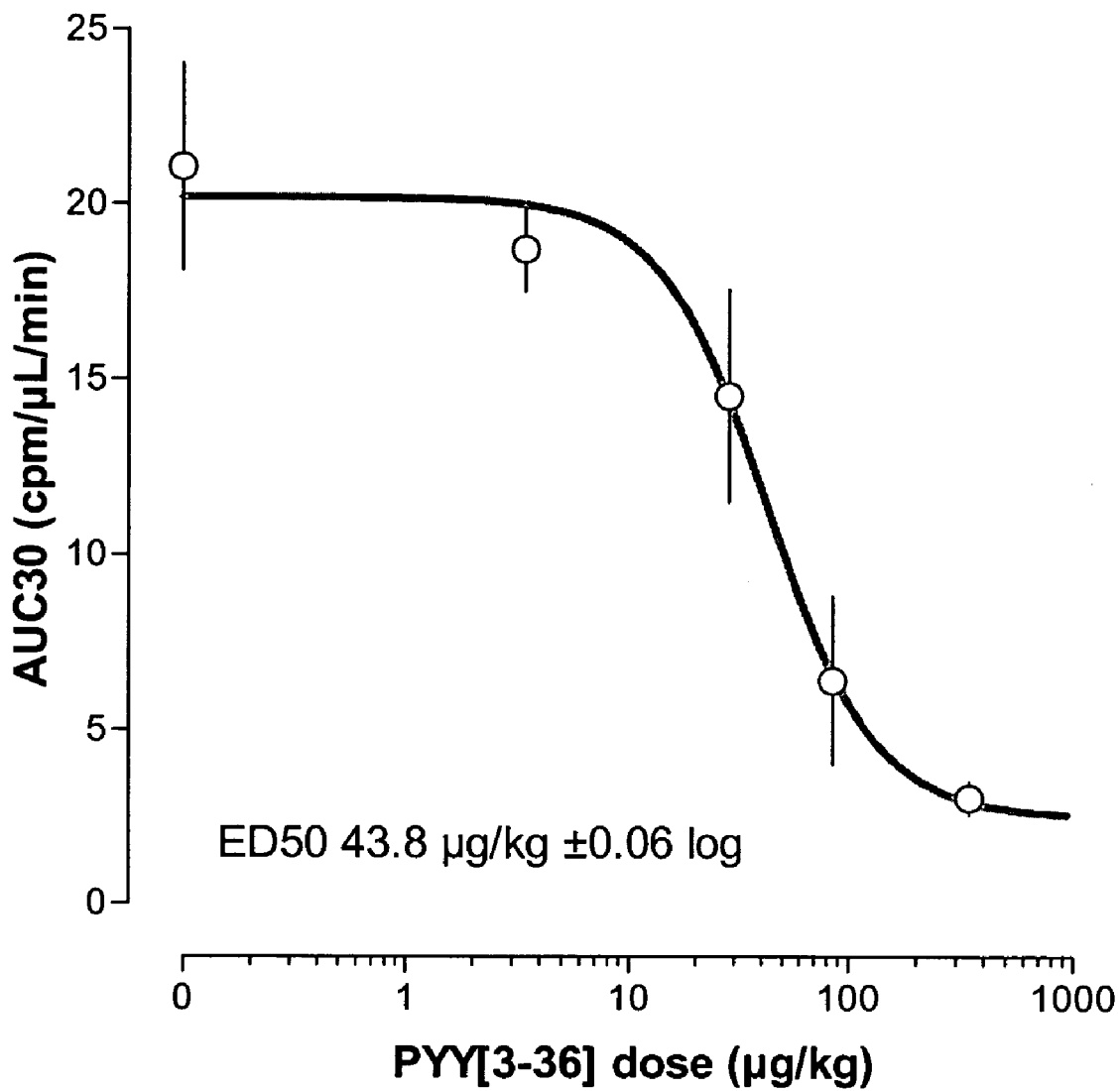
Figure 14:
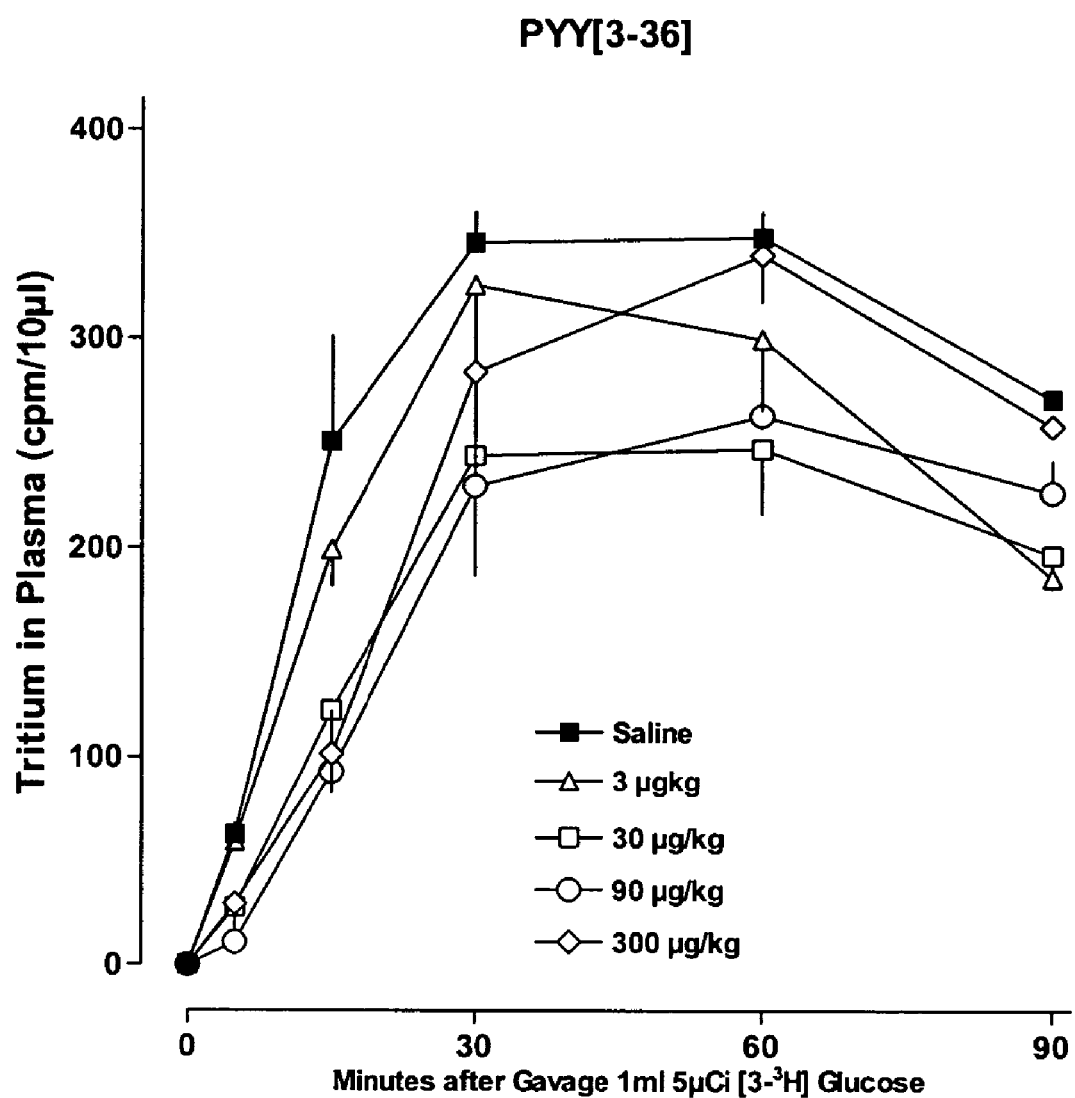
Figure 15:
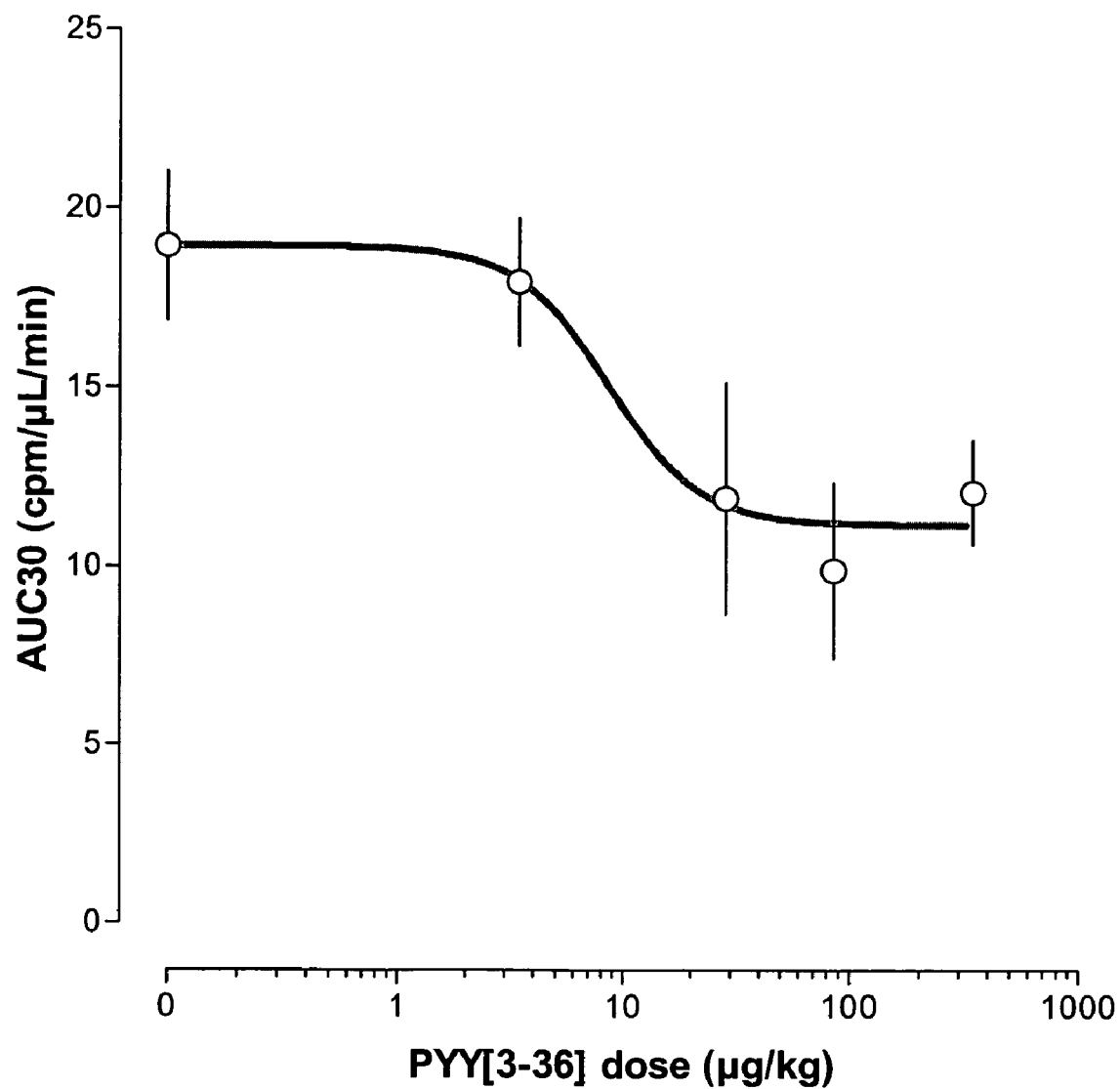
Figure 16:
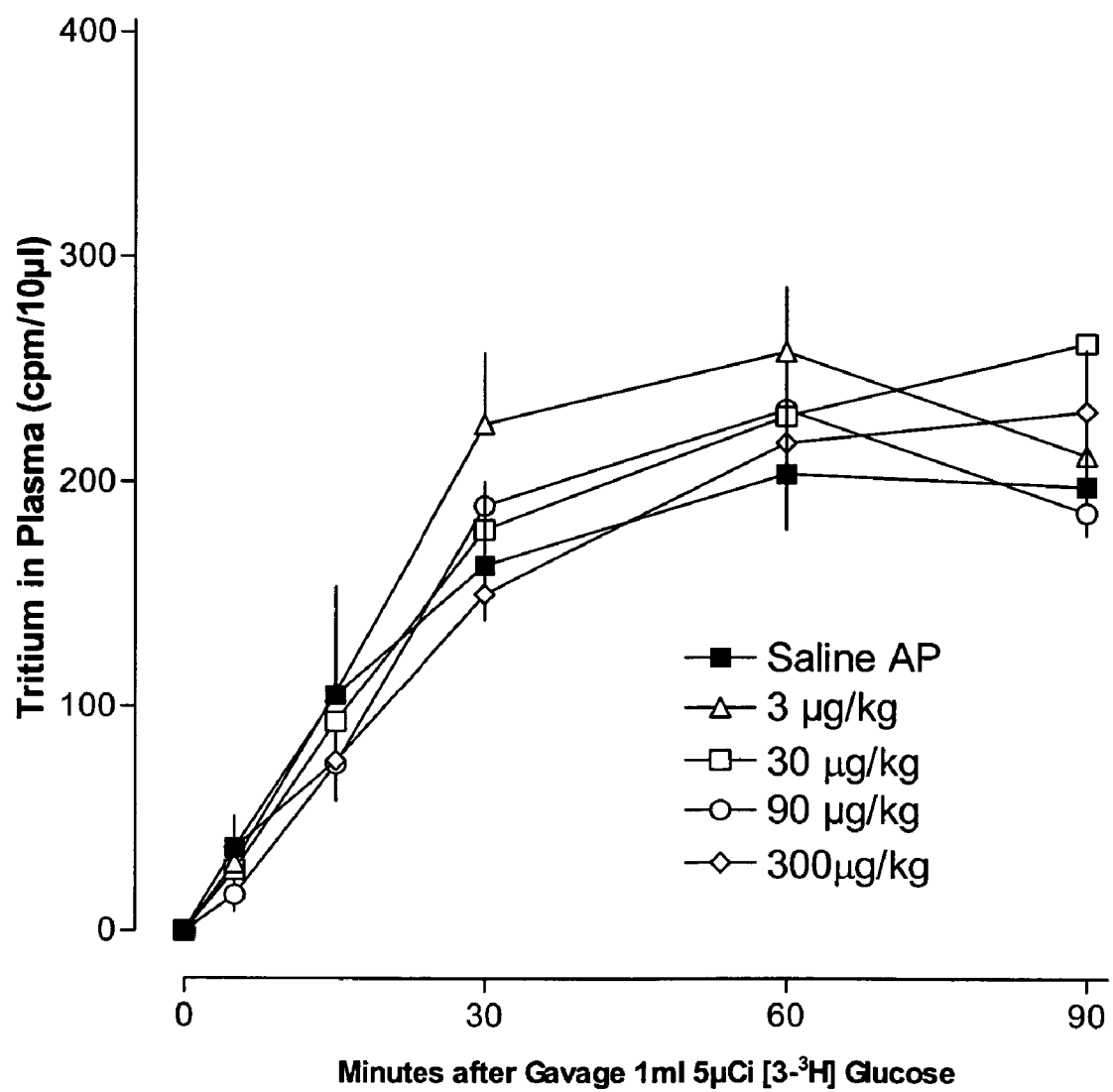
Figure 17:
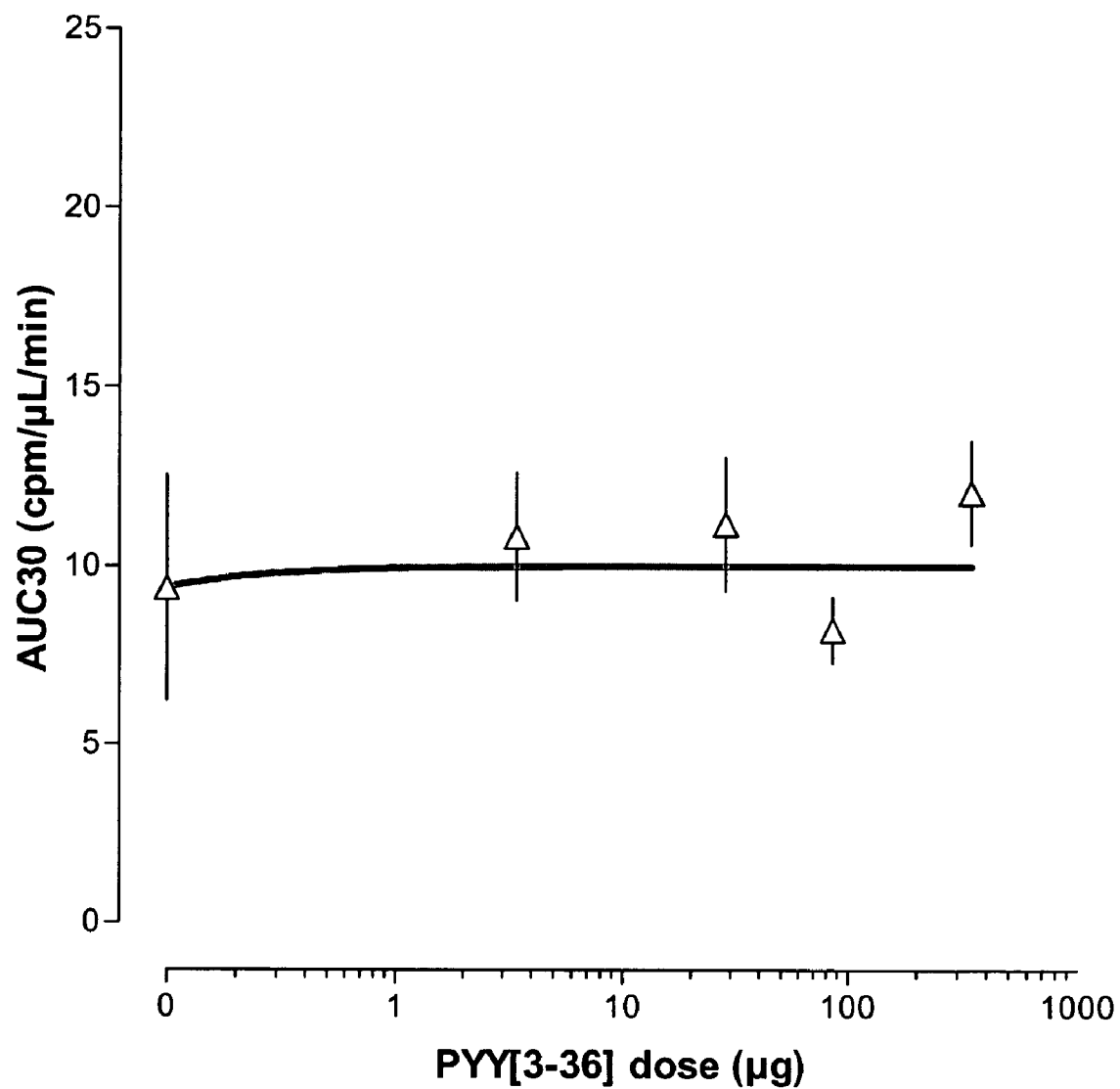

As shown in FIG. 10, gastric acid output was expressed as % of pentagastrin-stimulated secretion, calculated as the average of time points 20, 30, and 40 minutes after injection of pentagastrin. In response to pentagastrin, gastric acid secretion increased 6.8-fold from a basal rate of 9.3±5.8 µmol/10 min to 62.8±3.8 µmol/10 min 40 min after injection (grand means: $P<0.01$). PYY(3-36) injected 40 min after pentagastrin dose-dependently and significantly inhibited gastric acid production. With doses of 10 µg (34.5 µg/kg) and 100 µg (344.8 µg/kg), PYY(3-36), acid secretion was reduced by 74.7±7.2% and 84.7±9.7%, respectively ($P<0.05$ and $P<0.01$; t-test, 20 minutes after PYY(3-36) injection) (see t=60 min in FIGS. 11-17). The dose response for PYY(3-36) inhibition of pentagastrin-stimulated acid secretion is shown in FIG. 11. The $ED_{50}$ for the antacid effect of PYY(3-36) was 11.31 µg/kg±0.054 log units.

Gastric Emptying

To determine the effects of PYY [3-36] on gastric emptying, conscious, non-fasted male Harlan Sprague Dawley rats were randomly divided into three overall treatment groups: 1) for animals designated "APx," vacuum-aspiration lesions were made to the area postrema; 2) for the animals designated "Sham," to control for effects of the surgery, sham-operations were performed in which the cranial region region was surgically opened, but no lesion was made to the brain and 3) unoperated control animals, designated "Control," were not subjected to surgery. For each of the three overall treatment groups, animals were then divided into dosage groups, in which they were administered either saline only, or bolus doses of 3, 30, 90, or 300 µg/kg PYY(3-36) dissolved in saline. Experiments were performed at least two weeks post surgery (weight 426±8 g) and again three weeks later (weight 544±9 g). All rats were housed at 22.7° C. in a 12:12 h light:dark cycle (experiments performed during light cycle) and were fed and watered ad libitum (diet LM-485 Teklad, Madison, Wis., USA).

PYY(3-36) dissolved in saline was administered as a 0.1 ml subcutaneous bolus 5 min before gavage of 5 µCi D-[3-$^3$H]-glucose (lot #3165036 Dupont, Wilmington, Del., USA) in 1 ml water. The vehicle or different doses of PYY was given subcutaneouly after animals had been given an oral liquid meal.

There were 15 Treatment Groups:

| (1) Control saline | n = 4 |
| (2) Control 3 µg/kg | n = 3 |
| (3) Control 30 µg/kg | n = 4 |
| (4) Control 90 µg/kg | n = 5 |
| (5) Control 300 µg/kg | n = 5 |
| (6) Sham saline | n = 5 |
| (7) Sham 3 µg/kg | n = 2 |

-continued

| (8) Sham 30 µg/kg | n = 4 |
| (9) Sham 90 µg/kg | n = 3 |
| (10) Sham 300 µg/kg | n = 5 |
| (11) APx saline | n = 5 |
| (12) APx 3 µg/kg | n = 3 |
| (13) APx 30 µg/kg | n = 3 |
| (14) APx 90 µg/kg | n = 3 |
| (15) APx 300 µg/kg | n = 5 |

Blood was collected from anesthetized tails of the rats at −15, 0, 5, 15, 30, 60 and 90 min after gavage for measurements and the plasma separated to measure the plasma glucose-derived tritium (CPM per 10 µl counted in β-counter). The appearance of tritium in plasma has previously been shown to reflect gastric emptying. The integrated tritium appearance in plasma was calculated using the trapezoidal method as the increment above the levels before the tritium gavage (the area-under-the-curve (AUC) for 30 minutes).

In unoperated control rats, PYY(3-36) dose-dependently inhibited label appearance, (10.5±1.5, 7.26±1.52 and 3.20±1.21 cpm/µL.min for 30 µg/kg, 90 µg/kg, 300 µg/kg PYY(3-36), respectively; $P<0.0001$ ANOVA; see FIGS. 12 and 13). In sham-operated rats, 30 µg/kg (n=4) and 90 µg PYY(3-36) injections (n=3) also delayed appearance of label compared to saline-injected controls (n=5) in dose dependent manner (11.89±3.23, 9.88±2.45, 18.94±3.23 cpm/mL/min, respectively; $P<0.05$ ANOVA; see FIGS. 14 and 15). Maximal effect of PYY in sham-operated animals was less compared to intact unoperated control rats with $ED_{50}$ also lower than in unoperated control animals (decreases from 43.77 to 10.20 µg/kg PYY [3-36]. In APx rats, gastric emptying was slowed compared to that in sham-operated or unoperated control rats (9.38±3.25 cpm/µL/min; $P<0.05$, 0.05, see FIGS. 16 and 17), but was not altered by administration of PYY(3-36). Regression analysis confirmed absence of dose dependency.

Results showed that PYY(3-36) potently regulates the rate of gastric emptying in normal Sprague Dawley rats. A dose-dependent inhibition of gastric emptying was observed following the injection of PYY(3-36) (30, 90 and 300 µg/kg). AP-lesioned animals had a tendency to delay gastric emptying compared to unoperated control and sham-operated rats (n.s.). PYY(3-36) administration had no additional effect on gastric emptying rate in the AP-lesioned animals.

Figure 45:
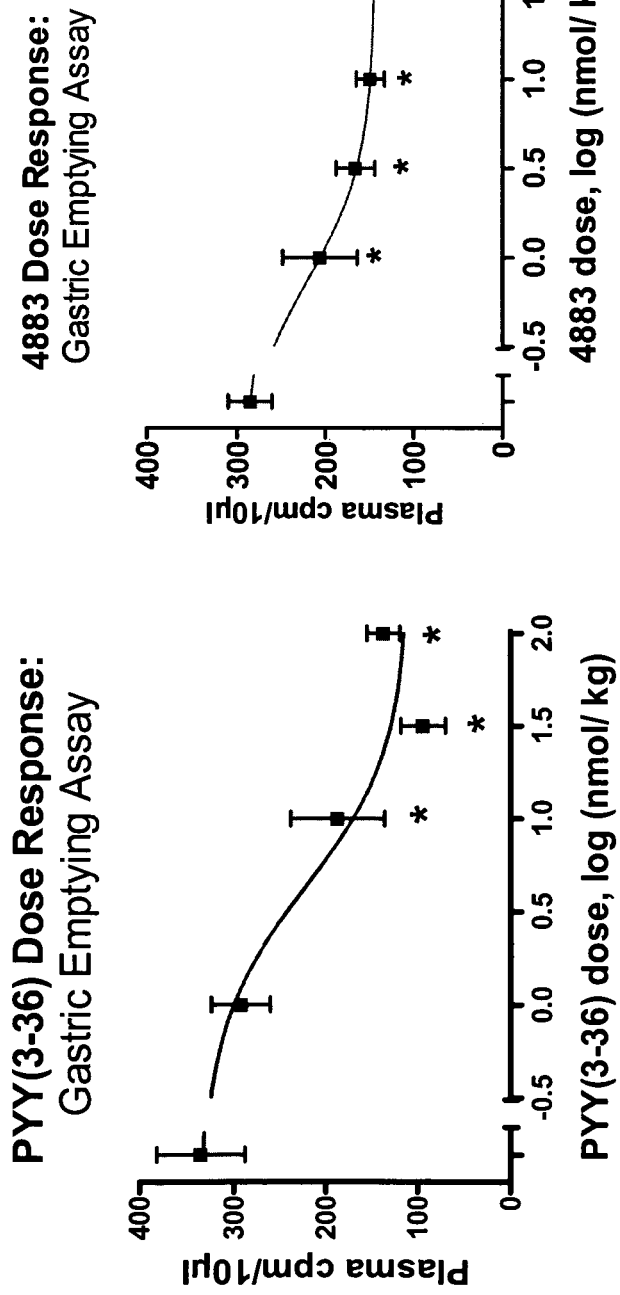
FIG. 45 depicts effects of administration of an exemplary PPF polypeptide on gastric emptying, as compared to PYY(3-36), in rats.

FIG. 45 demonstrates that administration of PPF polypeptide compound 4883 is more potent than PYY(3-36) in inhibiting gastric emptying.

Gallbladder Emptying

In the processes of normal digestion, gastric emptying rates and gallbladder emptying rates may be coordinated. Circulating PYY has been reported to suppress the cephalic phase of postprandial gallbladder emptying, but not meal stimulated maximum emptying. It was also hypothesized that the effect of PYY on gallbladder emptying is mediated by vagal-dependent rather than cholecystokinin-dependent pathways (Hoentjen, F, et al., *Scand. J. Gastroenterol.* 2001 36(10):1086-91). To determine the effect of PYY [3-36] on gallbladder emptying, eight week old, male NIH Swiss mice were housed at 22.8±0.8° in a 12:12 light:dark cycle, and allowed ad libitum access to a standard rodent diet (Teklad LM 7012, Madison, Wis.) and water. The mice were food deprived for 3 hours prior to experimentation. At t=0, PYY(3-36), CCK-8 or saline was injected subcutaneously in conscious mice. Thirty min later, mice were euthanized by cervical dislocation, a midline laparotomy was performed and the gallbladder was excised and weighed.

Treatment Groups:
Group A: saline 100 μl subcutaneously at t=0, n=14.
Group B: PYY(3-36) 1 μg/kg subcutaneously at t=0, n=6.
Group C: PYY(3-36) 10 μg/kg subcutaneously at t=0, n=10.
Group D: PYY(3-36) 100 μg/kg subcutaneously at t=0, n=8.
Group E: CCK-8 1 μg/kg subcutaneously at t=0, n=3.
Group F: CCK-8 10 μg/kg subcutaneously at t=0, n=3.
Group G: PYY(3-36) 10 μg/kg+CCK-8 1 μg/kg subcutaneously at t=0, n=4.
Group H: PYY(3-36) 10 μg/kg+CCK-8 10 μg/kg subcutaneously at t=0, n=4.

Figure 18:
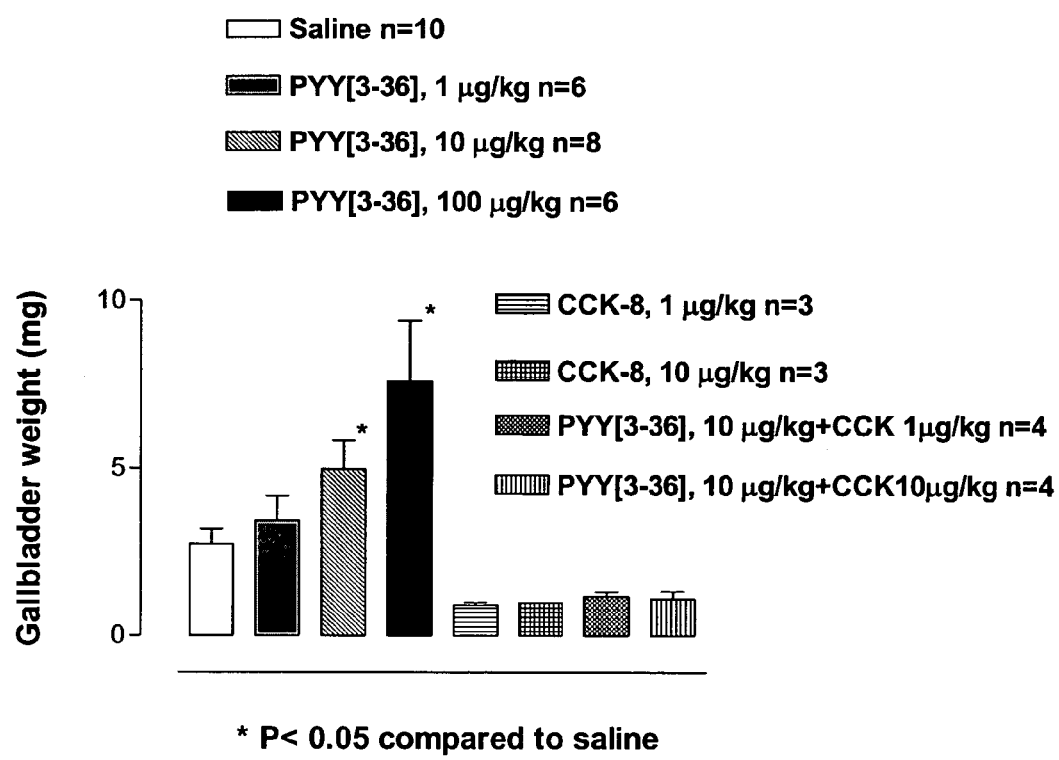
FIG. 18 demonstrates the activity of PPF polypeptides of the invention on gallbladder emptying.
Figure 19:
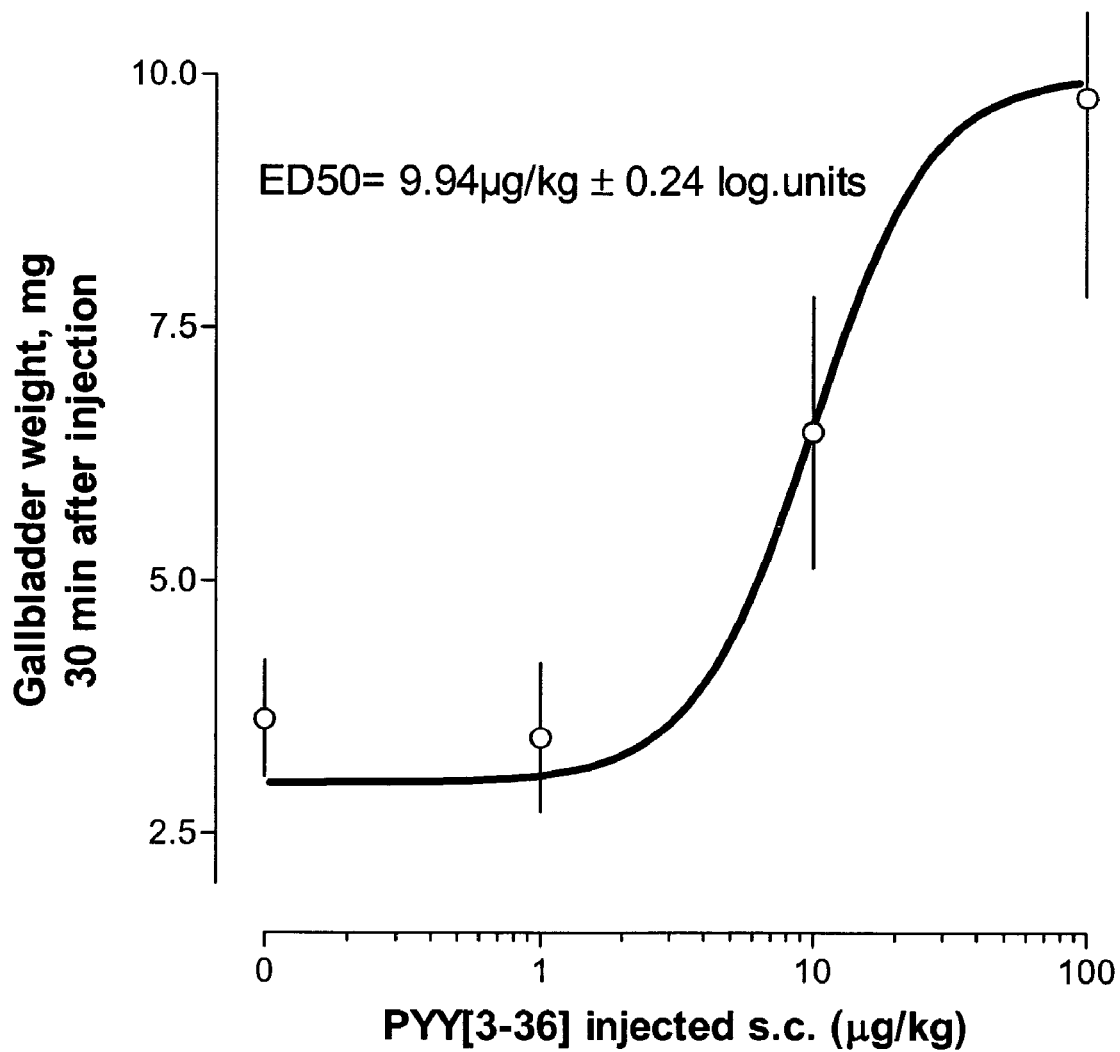
FIG. 19 demonstrates the activity of PPF polypeptides of the invention on gallbladder emptying.

The results are shown in FIGS. 18 and 19. PYY(3-36) dose dependently inhibited basal gallbladder emptying with an $ED_{50}$ of 9.94 μg/kg±0.24 log units. The highest dose (Group D) increased gallbladder weight by 168% over that observed in saline injected controls (Group A) (P<0.005). PYY(3-36) did not affect CCK-8 stimulated gallbladder emptying. The data indicate that PYY(3-36) inhibits gallbladder emptying via CCK-independent pathways. Gallbladder emptying in response to exogenous CCK was not affected by PYY(3-36). A similar result was obtained with PYY[1-36] in conscious dogs; a 400 ng/kg bolus+800 pmol/kg/h infusion did not inhibit CCK-8-stimulated gallbladder contraction.

It is possible that the effects of PYY(3-36) on gallbladder emptying are mediated by vagal-cholinergic pathways. This idea is supported by findings that specific peptide YY (PYY) binding sites have recently been autoradiographically identified in the area postrema, nucleus of the solitary tract, and dorsal motor nucleus regions (collectively referred to as the dorsal vagal complex (DVC)) in rats. These medullary brain stem regions are responsible for vagovagal reflex control of gastrointestinal functions, including motility and secretion. PYY(3-36) inhibits other digestive functions that are mediated by vagal-cholinergic mechanisms, such as gastric emptying.

Example 6

Gastroprotective Effects of PYY and PYY Agonists

Male Harlan Sprague Dawley rats were housed at 22.8±0.8° in a 12:12 light:dark cycle, and allowed ad libitum access to a standard rodent diet (Teklad LM 485, Madison, Wis.) and water. The rats, 200-220 gm, were fasted for approximately 20 hours prior to experimentation.

At t=-30, PYY(3-36) or saline was injected s.c. At t=0, a 1 ml gavage of absolute ethanol (ethyl alcohol-200 proof dehydrated alcohol, U.S.P. punctilious) or saline was administered. At t=30, the rats were anesthetized with 5% isofluorane. A midline laparotomy incision was made. The stomach was exposed and ligated at the pyloric and lower esophageal sphincters. The stomach was excised, opened along the lesser curvature and everted to expose the mucosa. The mucosa was gently rinsed with saline and assessed for damage (ulcerations, dilated blood vessels, sloughing off of the mucosal lining) by observers blinded to the treatment. Mucosal damage was scored between 0 (no damage) and 5 (100% of stomach covered by hyperemia and ulceration).

Treatment Groups:
Group A: saline 100 μl s.c. at t=-30, gavage 1 ml H2O at t=0, n=4.
Group B: saline 100 μl s.c. at t=-30, gavage 1 ml absolute ethanol at t=0, n=6.
Group C: PYY(3-36) 1 μg/kg at t=-30, gavage 1 ml absolute ethanol at t=0, n=5.
Group D: PYY(3-36) 10 μg/kg at t=-30, gavage 1 ml absolute ethanol at t=0, n=4.
Group E: PYY(3-36) 100 μg/kg at t=-30, gavage 1 ml absolute ethanol at t=0, n=5.
Group F: PYY(3-36) 300 μg/kg at t=-30, gavage 1 ml absolute ethanol at t=0, n=5.

Figure 20:
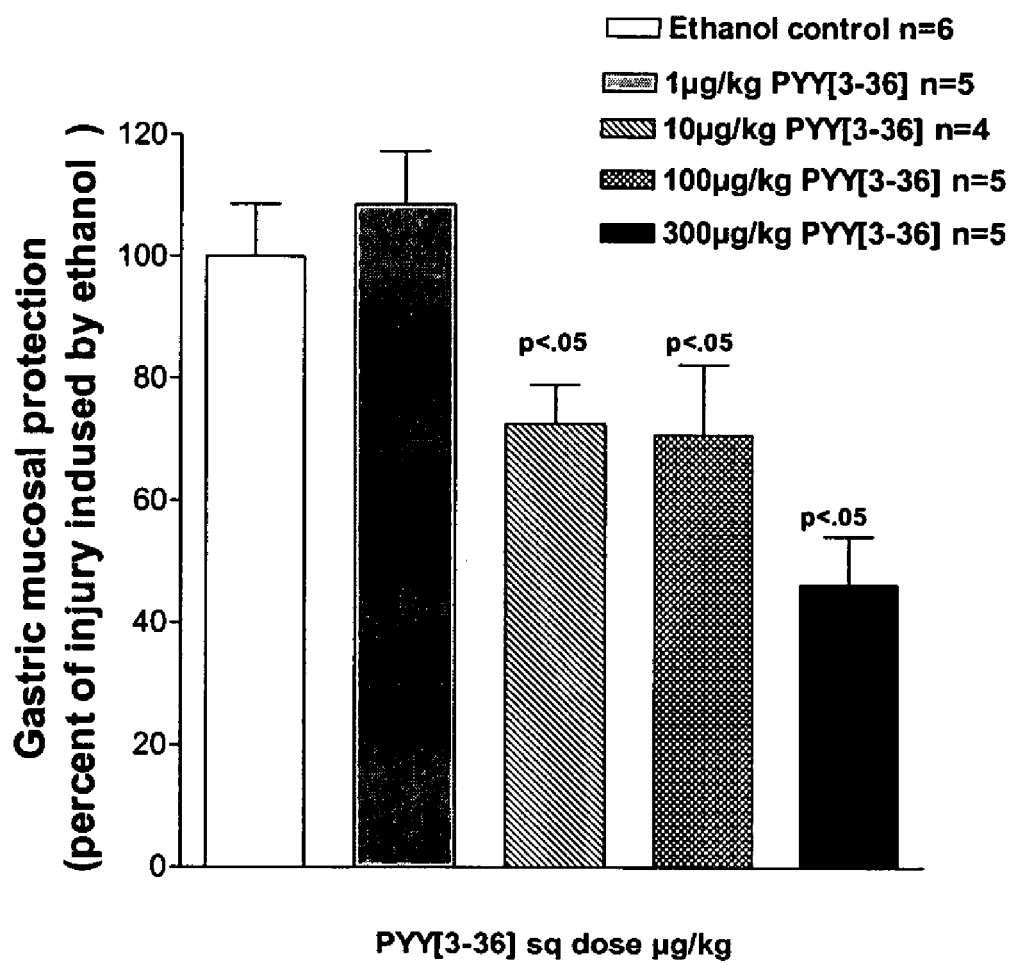
FIG. 20 demonstrates the activity of PPF polypeptides of the invention on gastric mucosal protection.

PYY(3-36) dose dependently reduced the injury score by 27.4±6.4, 29.3±11.6 and 53.7±7.9% (n=4,5,5, p<0.05 ANOVA) after injection of 10, 100, and 300 μg/kg of PYY (3-36), respectively (FIG. 20). PYY [3-36] showed a gastroprotective effect, in rats. Endogenously circulating PYY [3-36] may play a physiologic role in controlling gastric acid secretion and protecting the gastric mucosa.

Examples 7-10

Effects of PPF Polypeptides on Food Intake, Body Weight Gain, Metabolic Rate and Body Composition In rodents, weight reduction following administration of PYY(3-36) may be attributable to decreased food consumption or other processes impacting energy balance (including energy expenditure, tissue-level fuel partitioning, and/or gut nutrient uptake). The effects of continuous subcutaneous infusion of PYY(3-36) (1 mg/kg/day, up to 7 days) on metabolic rate, fat combustion, and/or fecal energy loss in diet-induced obese (DIO) mice were examined.

Animal Care and Housing

Examples 7-10 utilized a diet-induced obese (DIO) mouse model for metabolic disease. Prior to the treatment period, male C57BL/6J mice were fed a high-fat diet (#D12331, 58% of calories from fat; Research Diets, Inc.) for 6 weeks beginning at 4 weeks of age. During the study, the mice remained on this high-fat diet in powdered form throughout the treatment period unless otherwise noted. Water was provided ad libitum throughout the study. Animals were housed under a 12 hr:12 hr light-dark cycle at 21-23° C., and allowed ad libitum access to food pre- and post-treatment. In some embodiments, eight wk-old male NIH Swiss (non-obese) mice (HarlanTeklad, Indianapolis, Ind., USA) fed a standard chow diet (Teklad #LM7012, Madison, Wis.) were used in gallbladder emptying experiments. Where noted, one group of similarly-aged nonobese mice were fed a low-fat diet (#D12329, 11% of calories from fat) for purposes of comparing metabolic parameters to DIO groups.

Peptide Source

In some embodiments, the trifluoroacetic acid salt of human PYY(3-36) (>98% purity) was synthesized using standard methods (Peptisyntha, Torrance, Calif.), and its identity confirmed using mass spectroscopy.

Experimental Designs, Blood and Tissue Collection for Body Composition Analyses.

Studies of metabolic parameters [Study A], nutrient uptake by the gut [Studies B and C], food intake and body composition [Studies B and C] used mice that were housed singly for 1 week prior to treatment. Throughout the experiments, food intake and body weight were monitored daily. During the treatment period, vehicle (50% dimethylsulfoxide in water) and PYY(3-36) (1 mg/kg/day) were administered by continuous subcutaneous (s.c.) infusion using Alzet® osmotic pumps (Durect Corp., Cupertino, Calif.; Models 1003D, 2001, & 2004 for 3, 7, & 28 day studies, respectively) placed in the intrascapular region under isoflurane anesthesia. At the end of each study, animals were sacrificed after a 2-4 hr fast by isoflurane overdose. Blood was collected into Na-heparin-flushed syringes by cardiac puncture, and plasma was immediately frozen. In some studies (Studies B and C), body composition was determined using dual-energy X-ray absorptiometry (DEXA; PixiMus, GE Lunar). Bilateral epididymal fat pads and intrascapular brown adipose tissue (BAT) were dissected and weights determined. Excised liver samples were placed in RNALater (Ambion, Austin, Tex.), and stored at $-20°$ C.

Indirect Calorimetry [Study A]. DIO mice were acclimated to indirect calorimetry cages for 4 days prior to measuring post-treatment metabolic rate and RQ (Oxymax; software version 2.52; Columbus Instruments, Columbus, Ohio). The within-animal CV % during the 2-day pre-treatment baseline, averaged 4.6±0.8% & 4.0±0.8% for light & dark cycle energy expenditure, respectively, indicating adequate acclimation. Following osmotic pump implantation (vehicle controls, n=13; PYY(3-36) at 1 mg/kg/day, n=12), calorimetric measurements were made continuously over 7 days. Heat production was calculated by the instrument software (based on Lusk, G., (1928) The Elements of the Science of Nutrition, 4th Ed., W.B. Saunders Company, Philadelphia.) and is reported relative to body mass measured on each treatment day.

Fecal Energy Analysis [Studies B and C]. Mice were acclimated to metabolic cages (Diuresis Cages; Nalge Nunc Int'l Corp., Rochester, N.Y.; Study B), or to standard cages with raised wire mesh flooring [Study C], and to powdered high-fat chow for 4 days prior to treatment. In Study B, fecal energy content was determined using bomb calorimetry (Covance Labs; Madison, Wis.). To collect sufficient material, a pooling strategy was used for each mouse: pooled samples from individuals' 2 day baseline period, early treatment period (Days 1, 2, 3) and late treatment period (Days 5, 6, 7) were compared. In Study C, fecal energy content was determined in samples collected over the final 24 hr from cage bottoms lined with absorbant paper.

Long-term effects of PYY(3-36) on Body Weight in DIO Mice. Vehicle (n=18) or PYY(3-36) (n=24; 300 μg/kg/day, the estimated $ED_{50}$ for weight change in a prior study in this model (Pittner, et al., (2004) Int. J. Obes. Relat. Metab. Disord. 28: 963-71) were administered to DIO mice by Alzet s.c. osmotic pumps. At 28 days, pumps were replaced: controls continued to receive vehicle, and half of the PYY(3-36) group (n=12) continued to receive the peptide. The other half of the PYY(3-36) group (n=12), which had received PYY(3-36) for the initial treatment period, received new pumps containing vehicle to test the effect of peptide withdrawal. Mice were fed pelleted high-fat diet, and body weights and food intake were recorded weekly.

Gallbladder Emptying in Mice. Non-obese mice in the postabsorptive state (3 hr fasted) were injected s.c. with saline (n=14) or PYY(3-36) at 1, 10, or 100 μg/kg (n=6, 11, 8, respectively). Animals were sacrificed by cervical dislocation at 30 min. post-injection, and gallbladders were removed and weighed as a measure of gallbladder emptying rate.

Biochemical Assays. Plasma β-hydroxybutyrate (Cat. #2440, STANBIO Laboratory, Boerne, Tex.), glycerol (Cat. #TR0100, Sigma, St. Louis, Mo.), and non-esterified fatty acids (NEFA C, Cat. #994-75409, Wako Chemicals, Richmond, Va.) were measured using standard colorimetric assays. Total PYY immunoreactivity in plasma was determined by Linco Diagnostic Services (St. Louis, Mo.) using a human PYY RIA displaying <0.1% cross-reactivity to mouse or rat PYY(3-36), and averaged 39.3 ng/ml (~10 nM) in mice treated with 1 mg/kg/day PYY(3-36). Ex vivo lipolysis (glycerol release over 1 hr) was measured in non-obese female mouse retroperitoneal fat pad preparations using the method of Heffernan (Heffernan, et al., (2000) Am. J. Physiol. Endocrinol. Metab. 279: E501-7). Fat pads were incubated with PYY(3-36) at concentrations ranging from the upper physiologic to pharmacologic plasma levels (0.05, 0.5, & 10 nM) Values were compared to basal rates from untreated adipose tissue.

Statistical comparisons between control and treated animals over time (Examples 7 and 8) were made using a two-way analysis of variance (ANOVA) determining the effects of time, treatment, and time x treatment interaction (Prism v. 4.01, GraphPad Software, San Diego, Calif.). Differences between control and treated groups were analyzed by t-tests. Differences were considered statistically significant at $p<0.05$. In some embodiments, differences between treatment group means for parameters determined over time were analyzed using a repeated measures analysis of variance; post-hoc tests within timepoints were tested for simple effects using pooled standard error (SPSS version 13.0, Chicago, Ill.). Two-group comparisons were carried out using a Student's t-test, and dose-response data were evaluated using a one-way ANOVA and Tukey's comparison. Data are presented as mean±SEM, with $p<0.05$ considered to be statistically significant.

Gene Expression Analyses. RNA for gene expression analyses was isolated from a subset of tissues per manufacturer's instructions (RiboPure kit #1924; Ambion). One-step quantitative real-time RT-PCR analysis was used to measure mRNA abundance (ABI 7900HT; Applied Biosystems, Inc., Foster City, Calif.). The 50 μL reaction conditions were: 2.5 μL Assay-on-Demand® primer/probe mix, 1× Master Mix, 1× Multiscribe/RNAse inhibitor mix, and 50 ng RNA. RT-PCR conditions were: 48° C. 30 min., 95° C. 10 min., then 40 cycles (95° C. 15 sec./60° C. 1 min.). For each gene, cycle numbers were corrected for loading variation by simultaneously assaying 18S RNA abundance using a commercially-available primer/probe set (ABI). The relative abundance of mRNAs corresponding to the following genes were determined using ABI Assay-on-Demand® primer/probe sets: liver-type carnitine palmitoyltransferase 1 (L-CPT1 or CPT1a; Mm00550438_m1), acetyl-CoA carboxylase 1 (ACC1; MmO1304257_m1), ACC2 (MmO1204677_m1), mitochondrial hydroxymethylglutaryl-CoA synthase (HMGCS2; Mm00550050_m1), malonyl-CoA decarboxylase (MCD or MLYCD; Mm01245664_m1), and uncoupling protein 1 (UCP1; Mm00494069_m1). The results of these gene expression analyses are shown in Table 3 below. mRNA abundance is expressed as fold-difference vs. vehicle-treated control values within a given treatment time. * $P<0.05$ vs. Vehicle.

TABLE 3

| | Treatment time | | | |
|---|---|---|---|---|
| | 3 Days | | 7 Days | |
| Genes and groups | Vehicle (n = 8) | PYY(3-36) (n = 9) | Vehicle (n = 8) | PYY(3-36) (n = 7) |
| L-CPT1 | 1.00 ± 0.08 | 0.93 ± 0.08 | 1.00 ± 0.05 | 1.17 ± 0.15 |
| ACC1 | 1.00 ± 0.11 | 1.02 ± 0.11 | 1.00 ± 0.10 | 1.36 ± 0.13* |
| ACC2 | 1.00 ± 0.13 | 0.86 ± 0.11 | 1.00 ± 0.09 | 1.47 ± 0.17* |
| MCD | 1.00 ± 0.09 | 0.77 ± 0.09 | 1.00 ± 0.10 | 0.89 ± 0.10 |
| HMGCS2 | 1.00 ± 0.11 | 0.68 ± 0.10* | 1.00 ± 0.05 | 1.04 ± 0.08 |

Example 7

Singly-housed DIO mice were implanted with subcutaneous (SC) intrascapular osmotic pumps to deliver either vehicle (50% dimethylsulfoxide [DMSO] in water) n=13 or synthetic human PYY(3-36) n=12. The pumps of the latter group were set to deliver 1000 µg/kg/d of PYY(3-36) for 7 days.

Body weights and food intake were measured over regular intervals throughout the study periods. Respiratory quotient (RQ, defined as $CO_2$ production, $O_2$ consumption) and metabolic rate were determined using whole-animal indirect calorimetry (Oxymax, Columbus Instruments, Columbus, Ohio).

The mice were euthanized by isoflurane overdose, and an index of adiposity (bilateral epididymal fat pad weight) was measured.

Example 8

This experiment essentially repeated the study described in Example 7, with n=9 per group (vehicle and PYY(3-36)). However, prior to determination of epididymal weight, body composition (lean mass, fat mass) for each mouse was analyzed using a Dual Energy X-ray Absorptiometry (DEXA) instrument per manufacturer's instructions (Lunar Piximus, GE Imaging System).

Figure 21A:
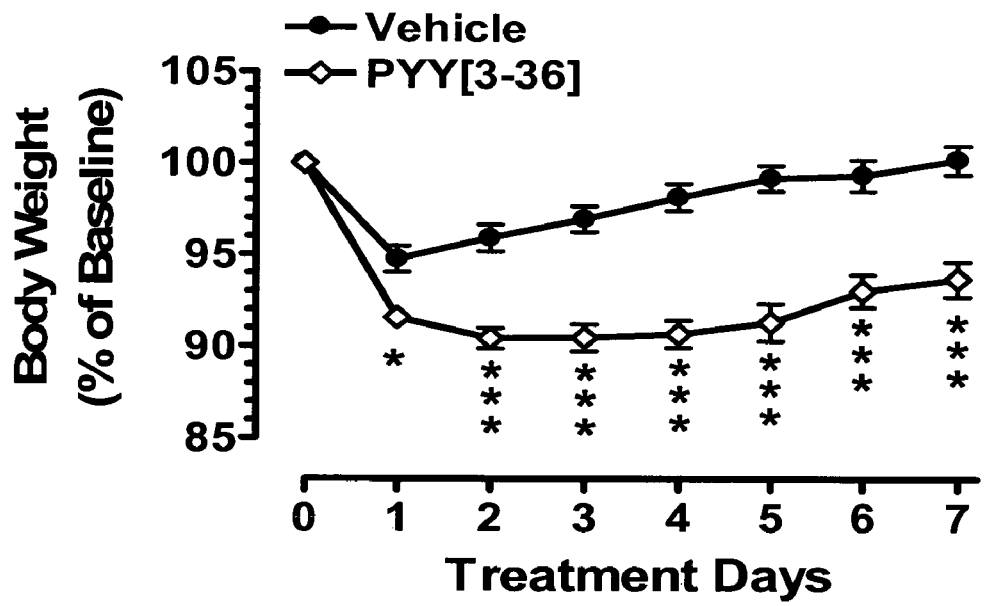
FIGS. 21A and 21B depict an exemplary effect of PYY(3-36) administration on body weight in DIO mice.
Figure 21B:
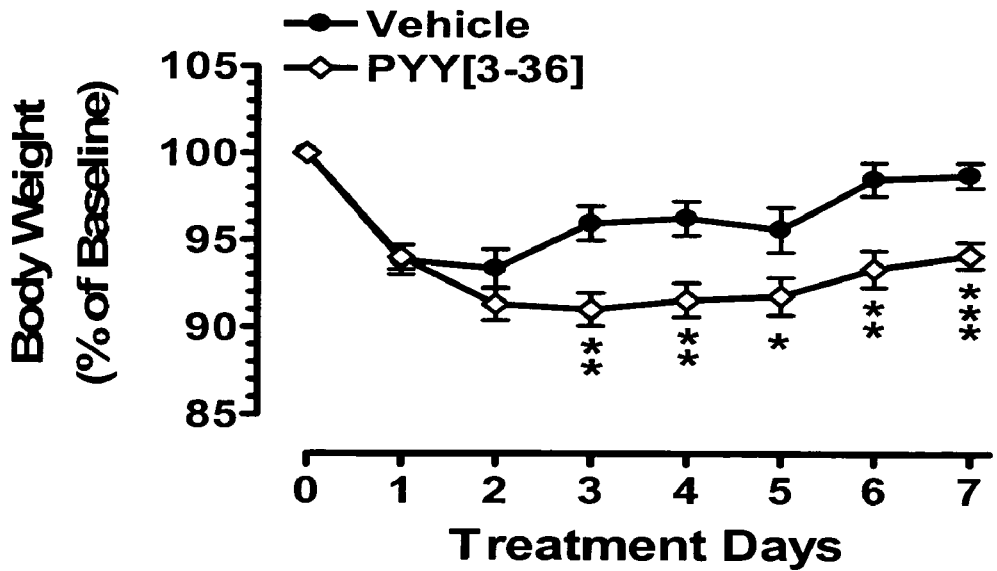

FIGS. 21A and 21B show the change in body weight as a percentage of baseline for DIO mice continuously administered vehicle or PYY(3-36) (1000 µg/kg/d) for 7 days. FIG. 21A shows the results of Example 7 and FIG. 21B shows the results of Example 8, and significance is denoted as $*p<0.05$, $p<0.01$, $*p<0.001$ vs. controls.

Figure 22A:
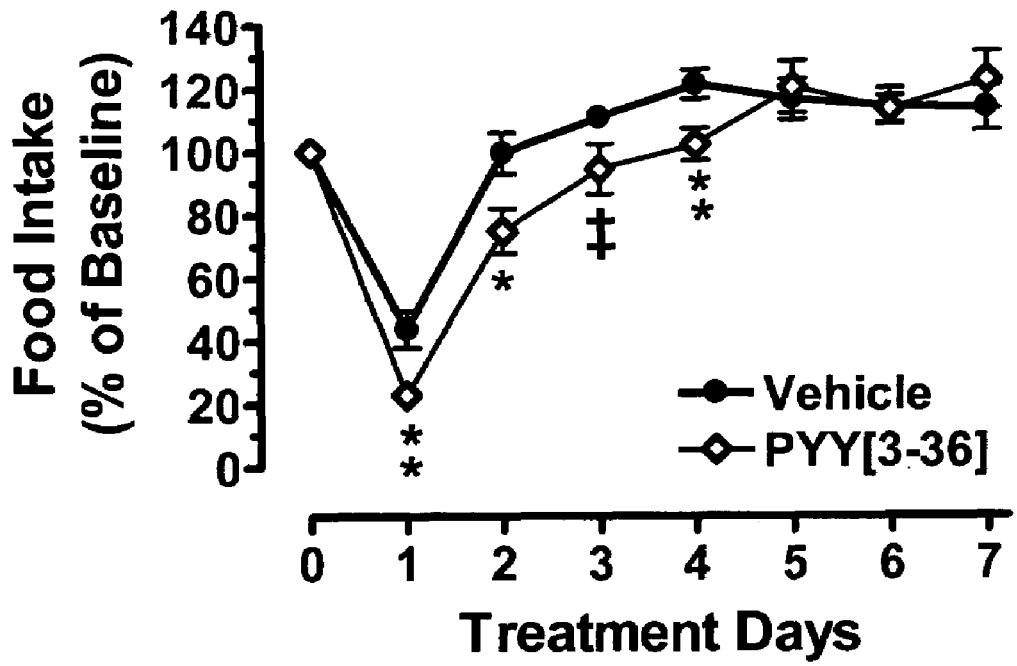
FIGS. 22A and 22B depict an exemplary effect of PYY(3-36) administration on food intake in the mice of FIGS. 21A and 21B, respectively.
Figure 22B:
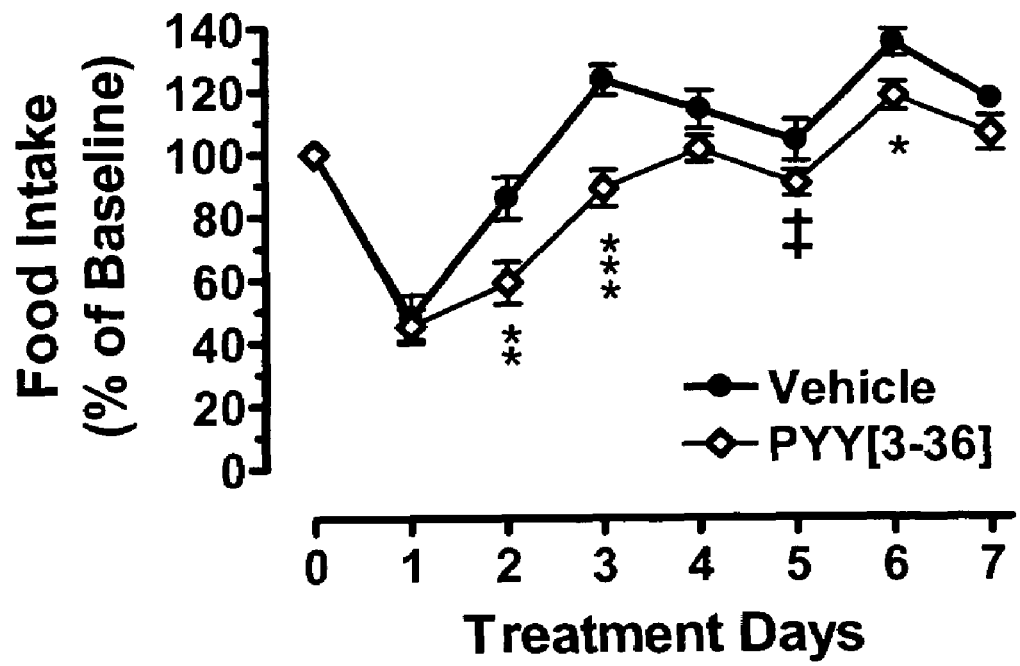

FIGS. 22A and 22B show the change in food intake as a percentage of baseline for DIO mice continuously administered vehicle or PYY(3-36) (1000 µg/kg/d) for 7 days. FIG. 22A shows the results of Example 7 and FIG. 22B shows the results of Example 8, and significance is denoted as $*p<0.05$, $p<0.01$, $*p<0.001$ vs. controls. There appears to be a trend for reduced food intake at Day 3 (‡ indicates p=0.06) in FIG. 22A and Day 5 (‡ indicates p=0.1) in FIG. 22B.

Figure 23A:
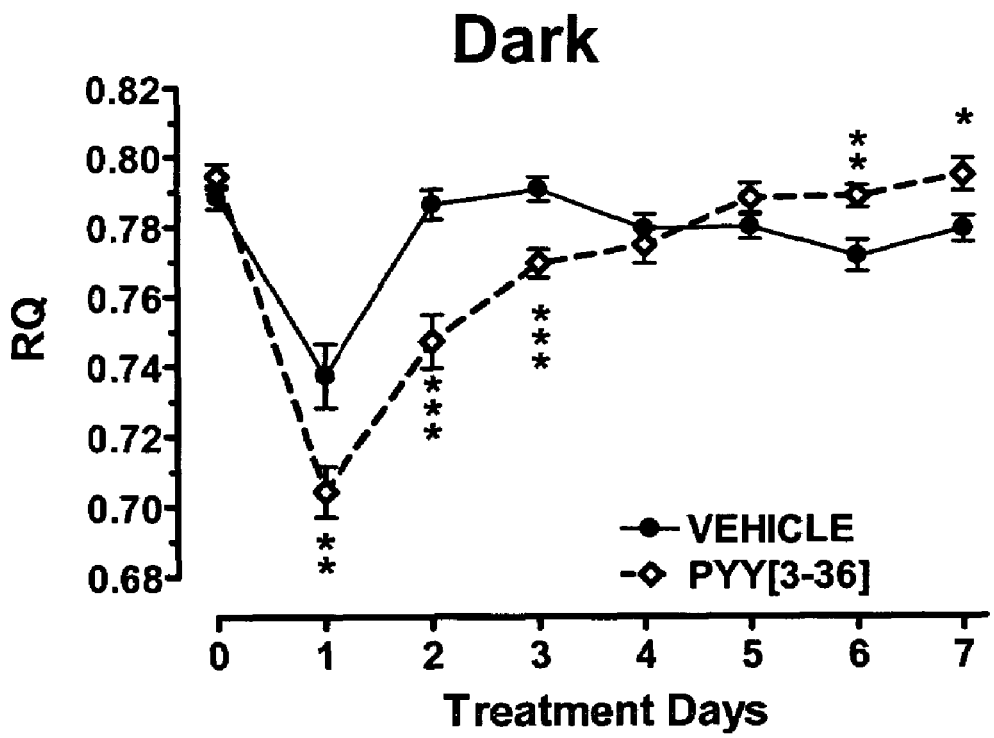
FIGS. 23A and 23B depict an exemplary effect of PYY(3-36) administration on respiratory quotient (RQ) during light and dark cycles in the mice of FIG. 21A.
Figure 23B:
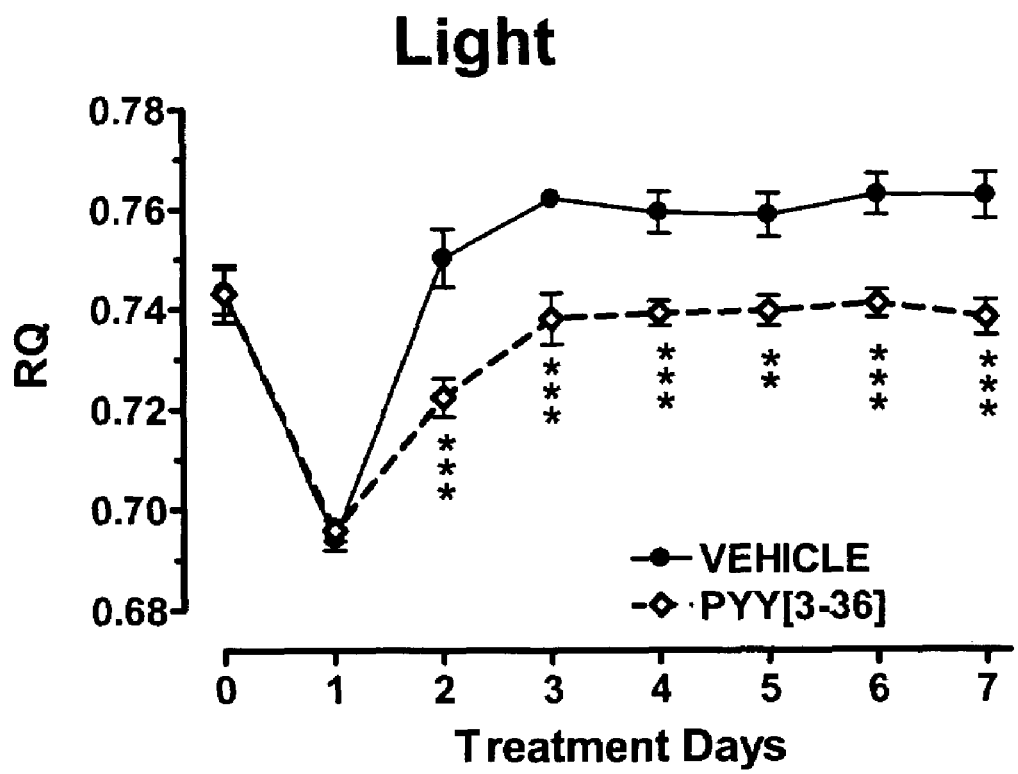

The respiratory quotient (RQ) of the mice in Example 7 was measured and compared. The RQ in PYY(3-36)-administered DIO mice was reduced during several dark cycle periods, and was lower during the light cycle throughout the study period. An RQ value near 0.70 is indicative of reliance upon fat catabolism to meet the energy requirements of the animal; thus, the relatively lower RQ in PYY(3-36)-administered animals is consistent with increased fat utilization for energy vs. control mice ($*p<0.05$, $p<0.01$, $*p<0.001$ vs. controls). This effect is especially persistent during the light cycle when animals are in a postabsorptive state (reduced food intake relative to the dark cycle) (see FIGS. 23A and 23B). These results indicate that PYY(3-36) has properties which drive fat combustion to meet caloric requirements which may lead to a preferential loss of fat over protein.

Morover, the reduced RQ observed with PYY(3-36) administration in DIO mice relative to vehicle-administered control is indicative of improved fat utilization for energy at the tissue- and cell-level (increased fatty acid β-oxidation). The majority of metabolic rate and RQ is influenced by metabolism in non-adipose tissues, such as liver and skeletal muscle. It follows then that PYY, PYY(3-36) and agonists thereof could be therapeutically useful in situations in which improved fatty acid β-oxidation in non-adipose tissues is desirable, with maintenance of lean body mass. Examples of such conditions include, but are not limited to, nonalcoholic steatohepatitis and lipodystrophy. A more specific example may be in the treatment of AIDS patients who are taking protease inhibitors. These patients may suffer from lipodystrophy (irregular fat distribution) that tends to increase central, truncal girth while at the same time decrease fat in the arms and legs. The treatment goal would be the reduction of central fat and an increase in peripheral muscle mass.

Figure 24A:
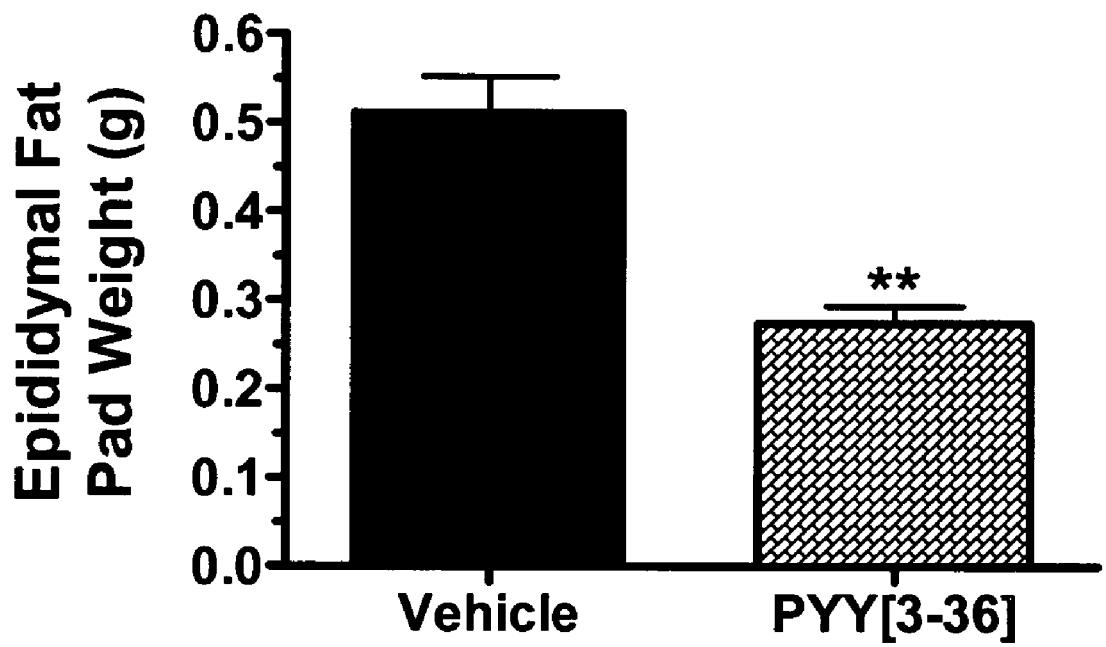
FIGS. 24A and 24B depict an exemplary effect of PYY(3-36) administration on epididymal fat pad weight in the mice of FIGS. 21A and 21B, respectively.
Figure 24B:
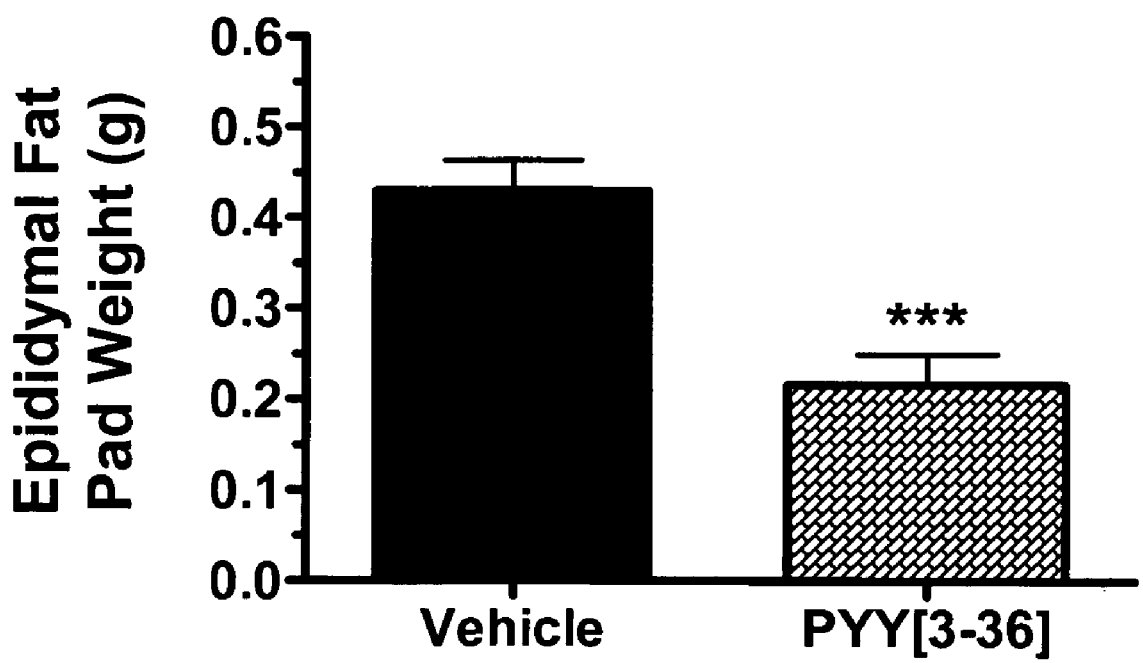
Figure 25A:
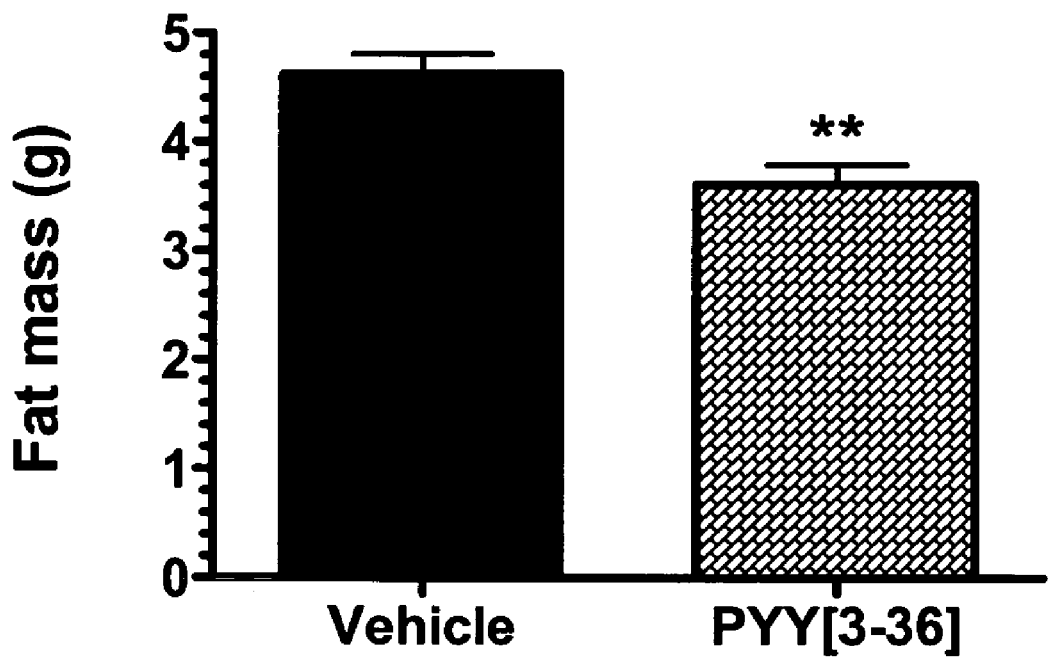
FIGS. 25A and 25B depict an exemplary effect of PYY(3-36) administration on fat and lean tissue mass in the mice of FIG. 21B.
Figure 25B:
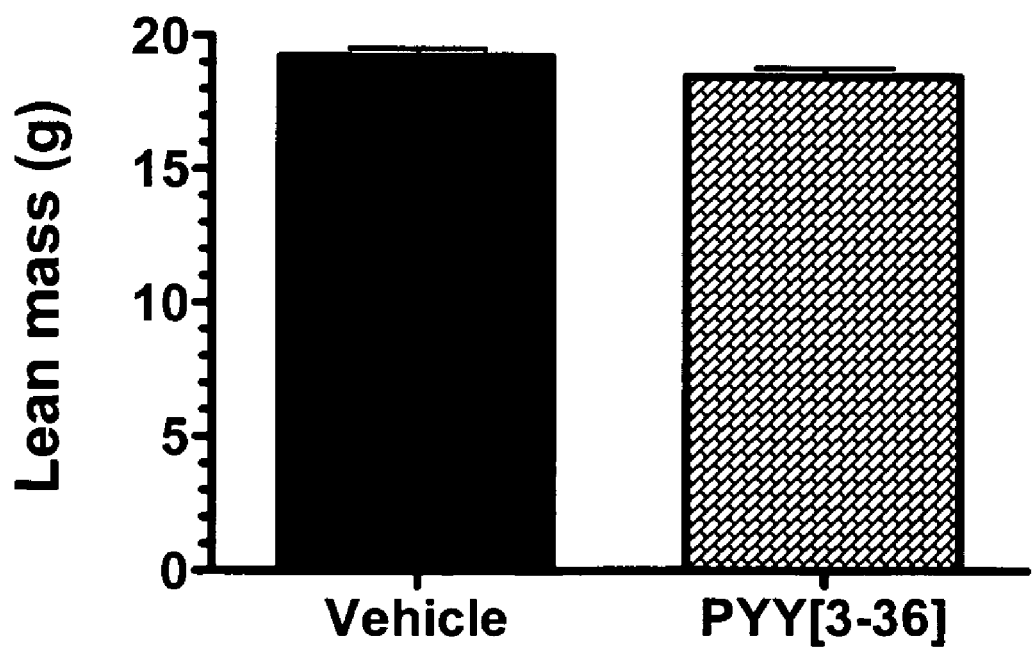

FIGS. 24A, 24B, 25A and 25B, for example, show evidence that PYY(3-36) and its agonists have the property of preferentially inducing the loss of fat over the loss of lean body tissue. Epididymal fat pads of Example 7 and Example 8 mice were weighed, and the reduced epididymal fat pad weights of the PYY(3-36)-administered mice over vehicle-administered mice, as shown in FIGS. 24A and 24B, Examples 7 and 8 respectively, indicate reduced adiposity in DIO mice administered PYY(3-36), ($p<0.01$, $*p<0.001$ vs. controls). In addition, reduced adiposity of PYY(3-36)-administered mice is supported by lower whole-animal fat mass determination by DEXA of Example 8 mice (FIG. 25A; $**p<0.01$ vs. controls). Of particular interest from the DEXA results is that despite significant weight loss (FIG. 21B) and fat loss (FIG. 24B and FIG. 25A), lean body mass was maintained in PYY(3-36)-administered mice, and did not differ much from those of vehicle-administered mice (FIG. 25B).

Example 9

In this experiment, the dose-effect of PYY(3-36) was studied and over a longer period than previous experiments. DIO mice were implanted with SC intrascapular osmotic pumps to deliver either vehicle (saline) or PYY(3-36). The pumps of the latter group were set to deliver a range of doses up to 1000 µg/kg/d for 28 days. Body weights and food intake were measured over regular intervals throughout the study periods.

Mice were housed two per cage. Sample sizes for body weight and food intake in this experiment were n=20, n=14, and n=12 for High-fat controls, Low-fat comparator group, and High-fat-fed PYY(3-36) groups, respectively. For body composition measures, sample sizes were n=18, n=14, and n=12 for High-fat controls, Low-fat comparator group, and High-fat-fed PYY(3-36) groups, respectively.

Figure 26:
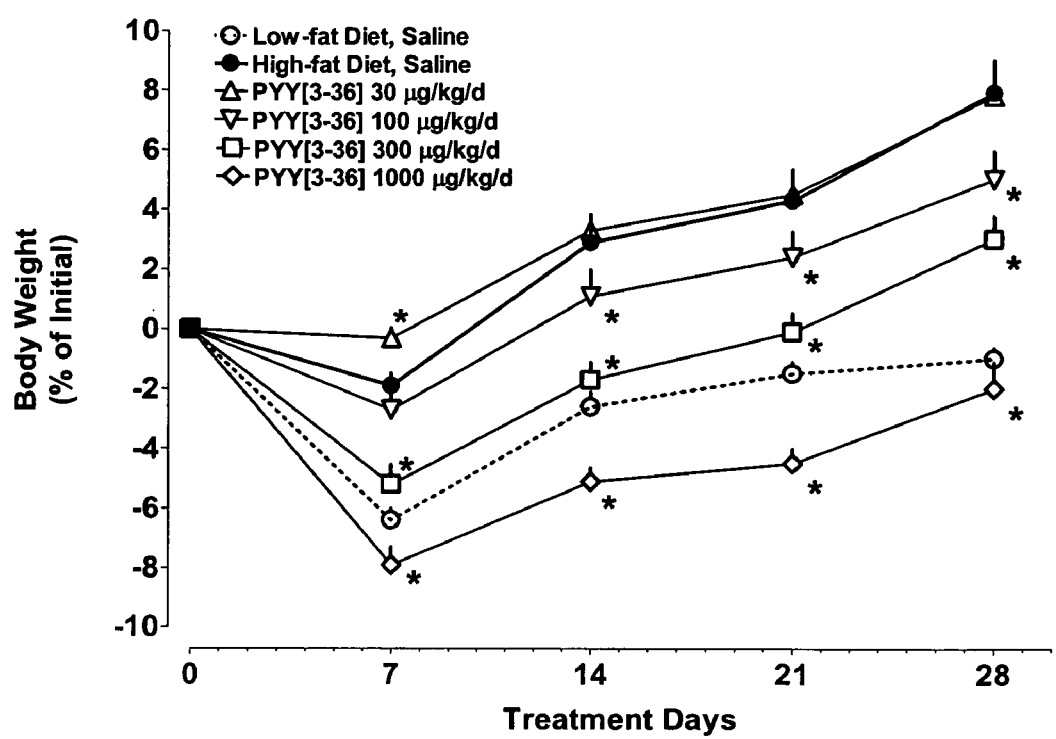
FIG. 26 depicts exemplary effects of PYY(3-36) administration on body weight at various doses in DIO mice versus high-fat fed and low-fat fed control mice.

FIG. 26 shows the change in body weight as a percentage of initial body weight of vehicle-administered mice fed low-fat chow, vehicle-administered DIO mice fed high-fat chow, and PYY(3-36)-administered DIO mice fed high-fat chow. Increasing doses of PYY(3-36) show an increasing effect on body weight ($*p<0.05$ vs. controls).

Figure 27:
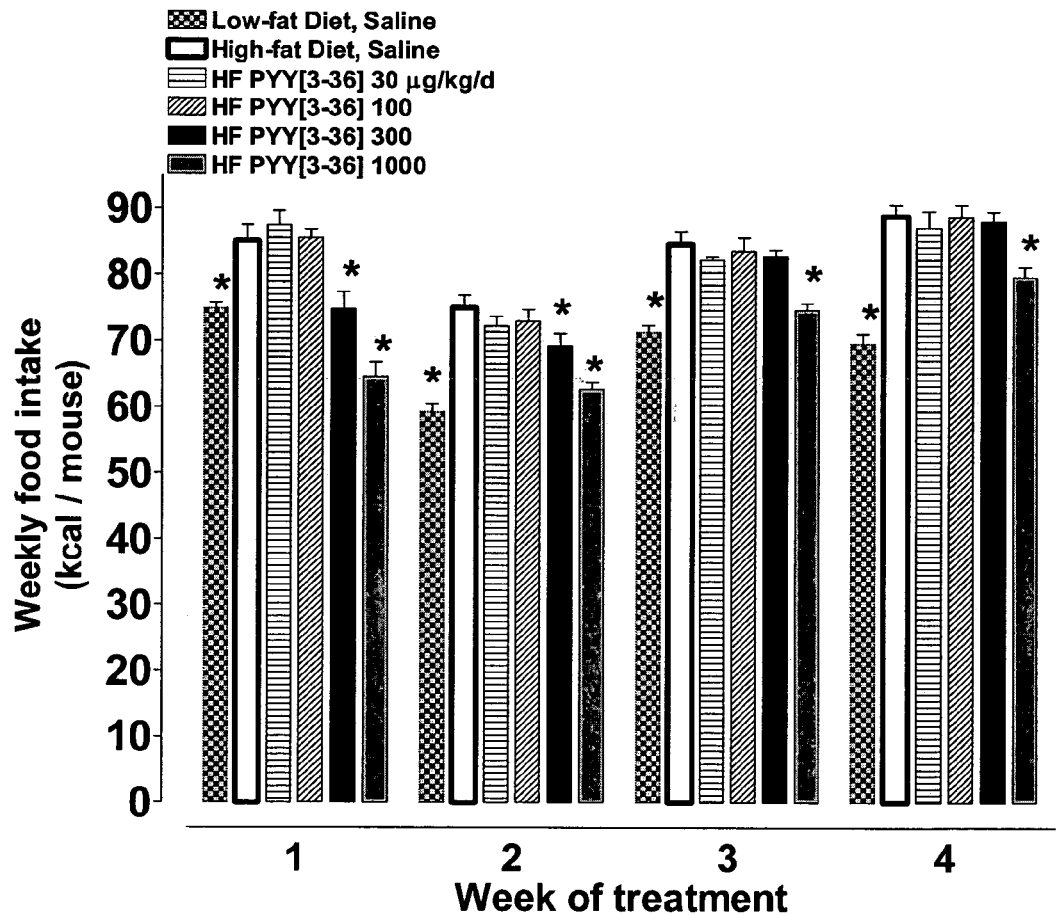
FIG. 27 depicts an exemplary effect of PYY(3-36) administration on weekly food intake in the mice of FIG. 26.

FIG. 27 shows the weekly food intake of the mice during four weeks of the study. The group of low-fat fed mice and the PYY(3-36) (1000 µg/kg/d) high-fat fed DIO mice consistently consumed significantly less food than the high-fat fed DIO mice controls during the four weeks of the study.

Figure 28A:
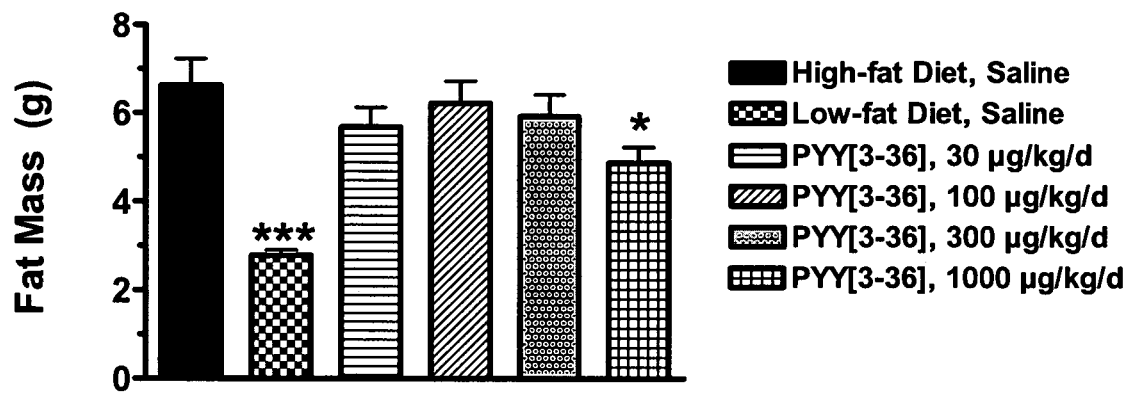
FIGS. 28A and 28B depict exemplary effects of PYY(3-36) administration on fat and lean tissue mass in the mice of FIG. 26.
Figure 28B:
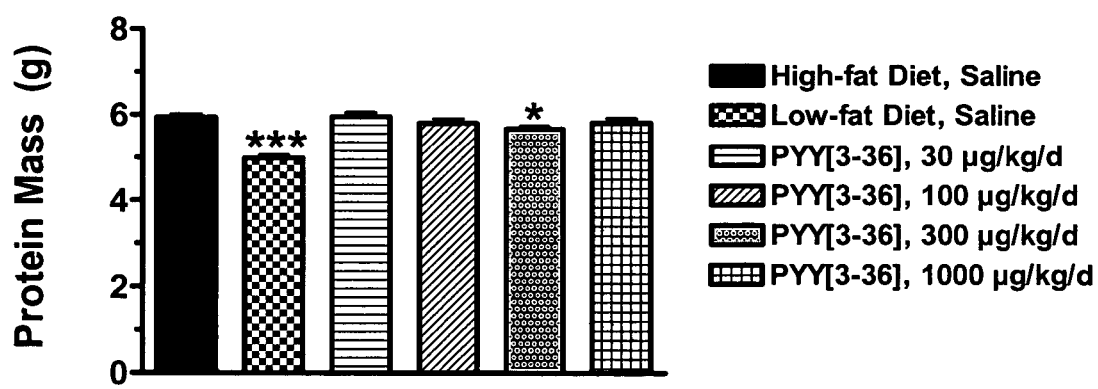

FIGS. 28A and 28B show that while fat mass was lower in low-fat fed mice and PYY(3-36) (1000 µg/kg/d) high-fat fed DIO mice ($*p<0.01$; $***p<0.001$ vs. vehicle-administered high-fat fed DIO mice controls), low-fat fed mice had significantly less protein mass whereas PYY(3-36) (1000 µg/kg/d)-administered DIO mice did not have significantly less protein mass than the high-fat fed controls. Whole carcass body composition was determined by proximate analysis using standard methods (Covance Laboratories, Madison, Wis.).

Example 10

In another study similar to those carried out in Examples 7 and 8, singly-housed DIO mice were implanted with subcutaneous (SC) intrascapular osmotic pumps to deliver either vehicle (50% dimethylsulfoxide [DMSO] in water) n=10 or synthetic human PYY(3-36) n=10. The pumps of the latter group were set to deliver 1000 µg/kg/d of PYY(3-36) for 3 days.

Figure 29A:
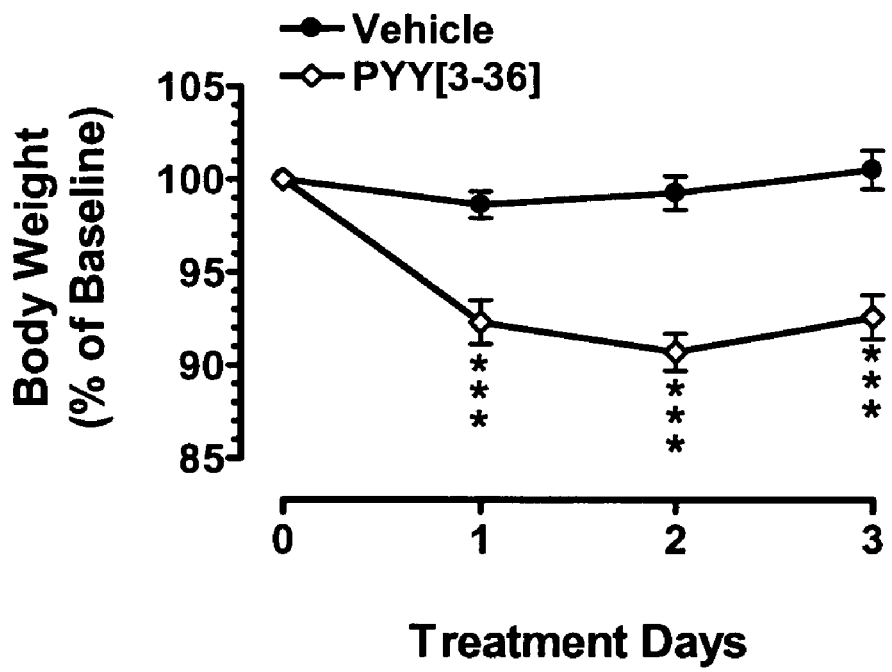
FIGS. 29A and 29B depict exemplary effects of PYY(3-36) administration on body weight and food intake in DIO mice.
Figure 29B:
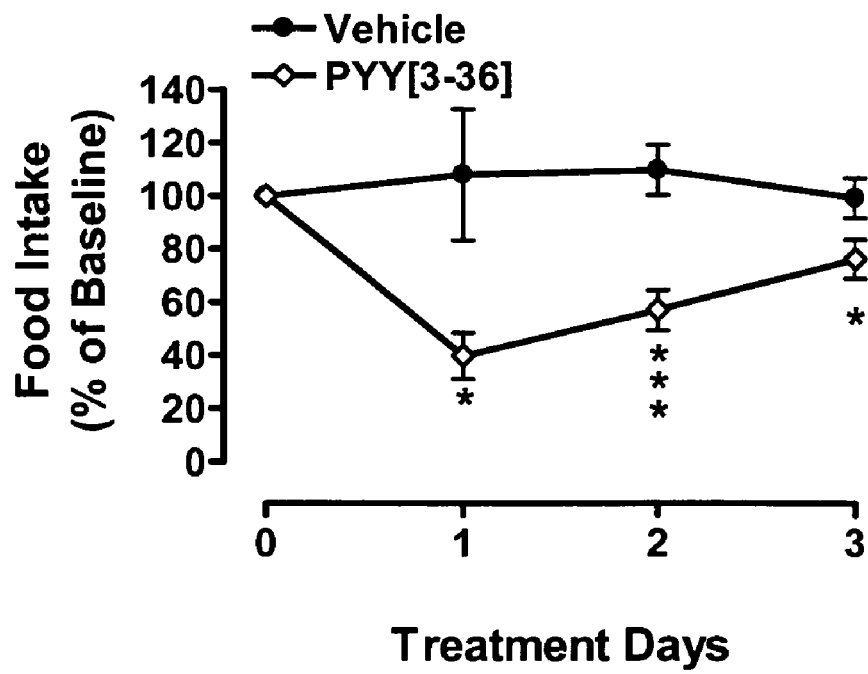

FIGS. 29A and 29B show the change in body weight and food intake, respectively, as a percentage of baseline for DIO mice continuously administered vehicle or PYY(3-36) (1000 µg/kg/d) for 3 days. FIGS. 29A and 29B show significant reduction in body weight and food intake in the DIO mice administered PYY(3-36) over the course of the treatment period (*$p<0.05$, $p<0.01$, *$p<0.001$ vs. controls).

Figure 30:
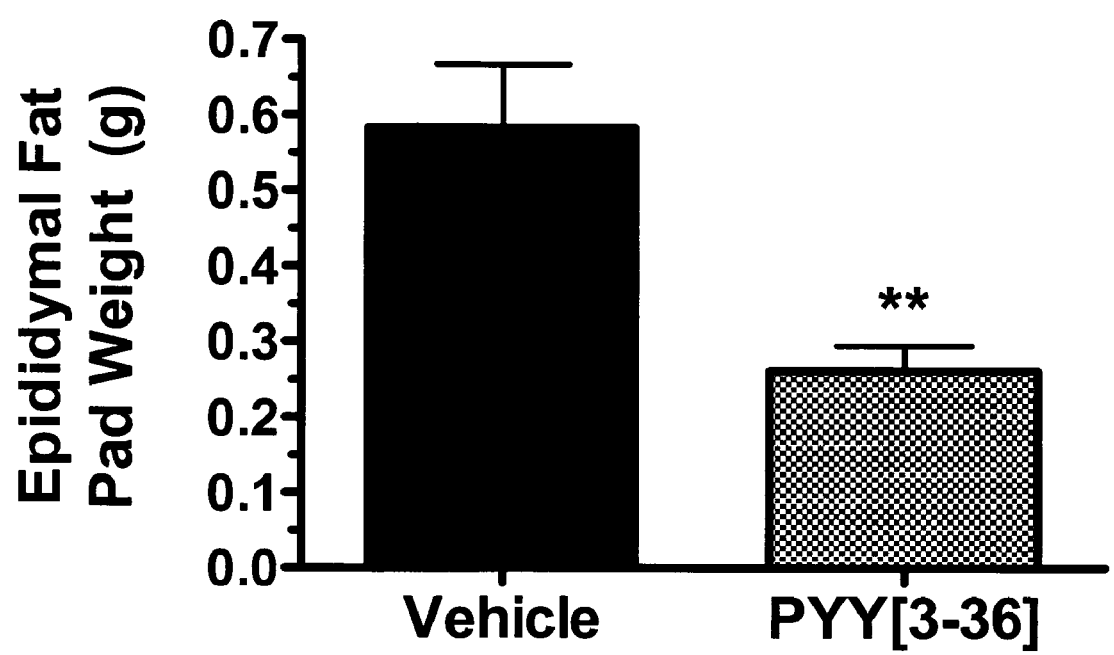
FIG. 30 depicts an exemplary effect of PYY(3-36) administration on epididymal fat pad weight in the mice of FIGS. 29A and 29B.
Figure 31A:
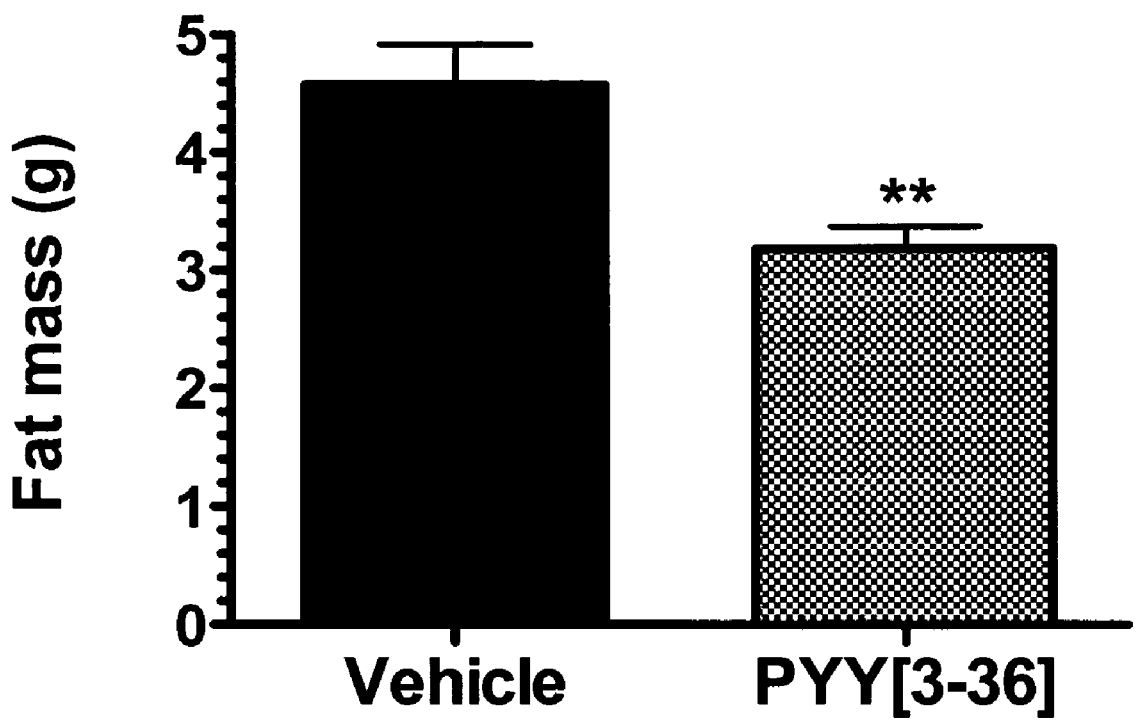
FIGS. 31A and 31B depict exemplary effects of PYY(3-36) administration on fat and lean tissue mass in the mice of FIGS. 29A and 29B.
Figure 31B:
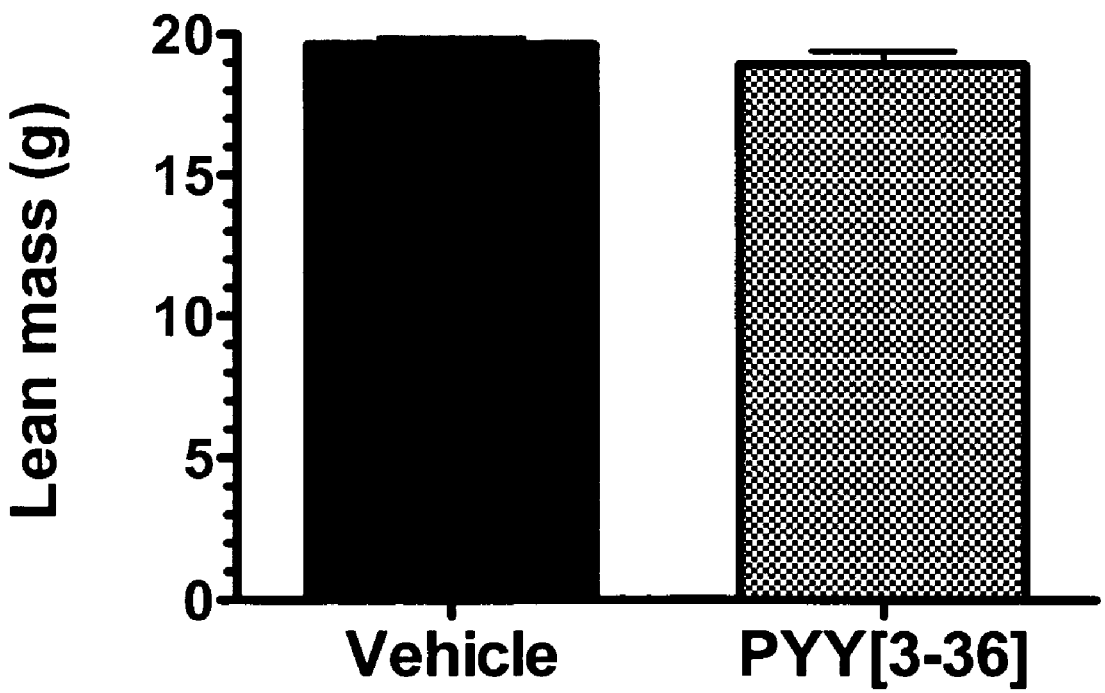

FIG. 30 shows significantly less adiposity in DIO mice administered PYY(3-36) over controls as indicated by lower epididymal fat pad weight ($p<0.01$ vs. control). FIG. 31A shows significantly less adiposity in DIO mice administered PYY(3-36) over controls as indicated by lower whole-animal fat mass determination by DEXA, as described in Example 8 ($p<0.01$ vs. control). While DIO mice administered PYY(3-36) significantly lost body weight and reduced food intake and had less adiposity over controls, FIG. 31B shows that the lean body mass of the PYY(3-36)-administered mice did not differ significantly from controls.

Figure 32A:
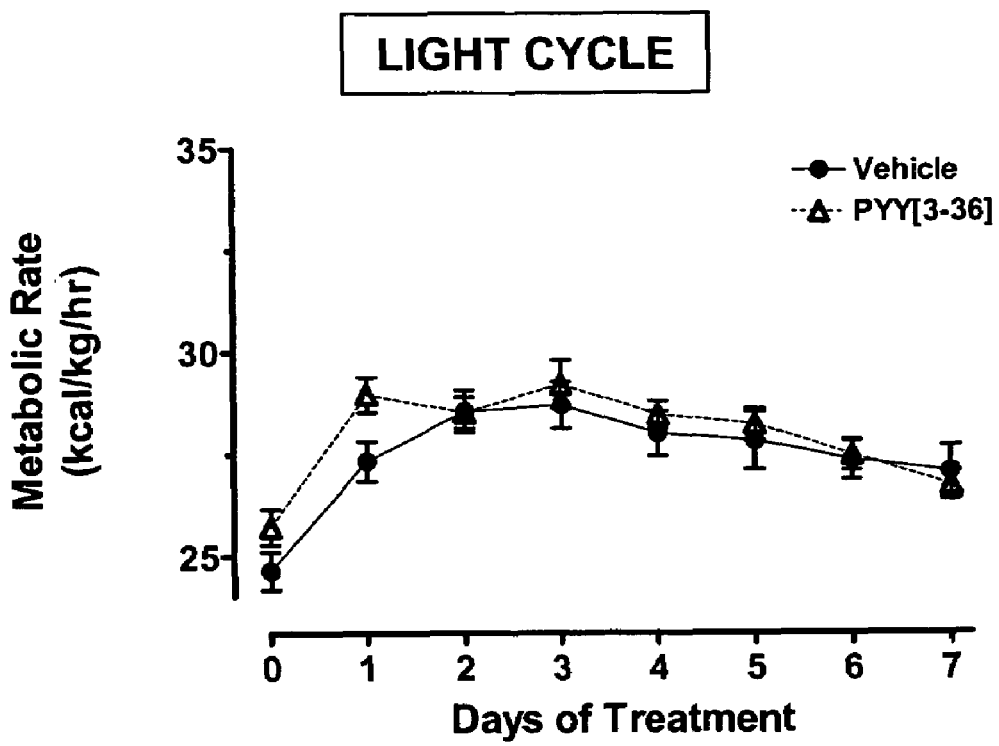
FIGS. 32A and 32B depict exemplary effects of PYY(3-36) administration on metabolic rate during light and dark cycles in DIO mice.
Figure 32B:
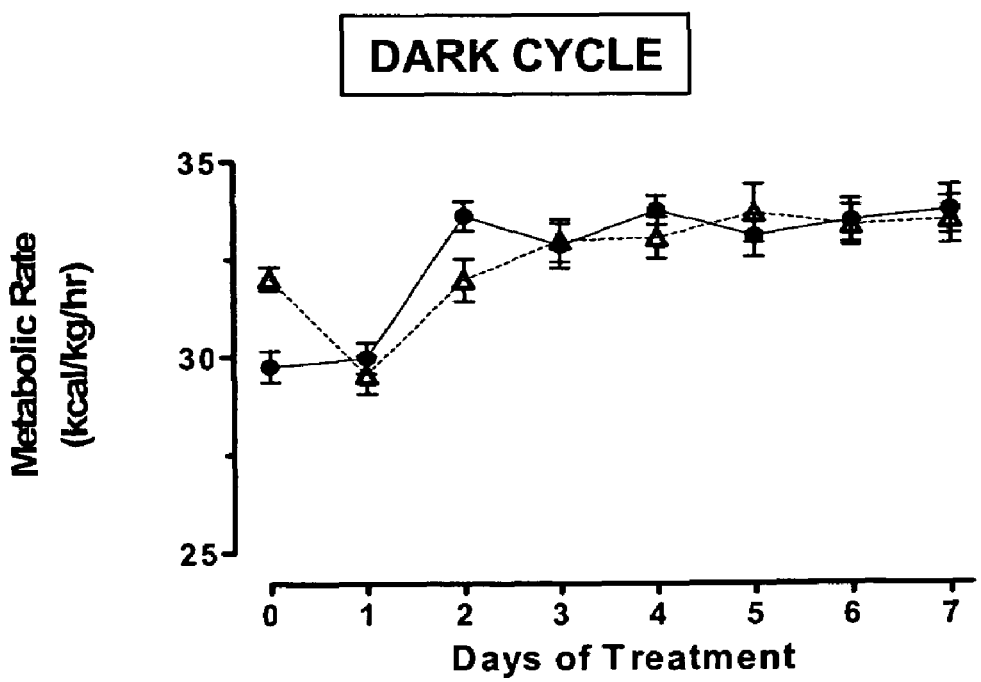

FIGS. 32A and 32B show the effects of administration of vehicle or PYY(3-36) on metabolic rate during the light cycle (top panel) and dark cycle (bottom panel) in DIO mice. Symbols: closed circles, vehicle-treated controls; open diamonds, PYY(3-36)-treated (1 mg/kg/day, continuous subcutaneous infusion). Day 0 represents the baseline (pre-treatment) mean value (25.2±0.3 kcal/kg/hr & 30.8±0.3 kcal/kg/hr for the light and dark cycle, respectively).

Figure 33:
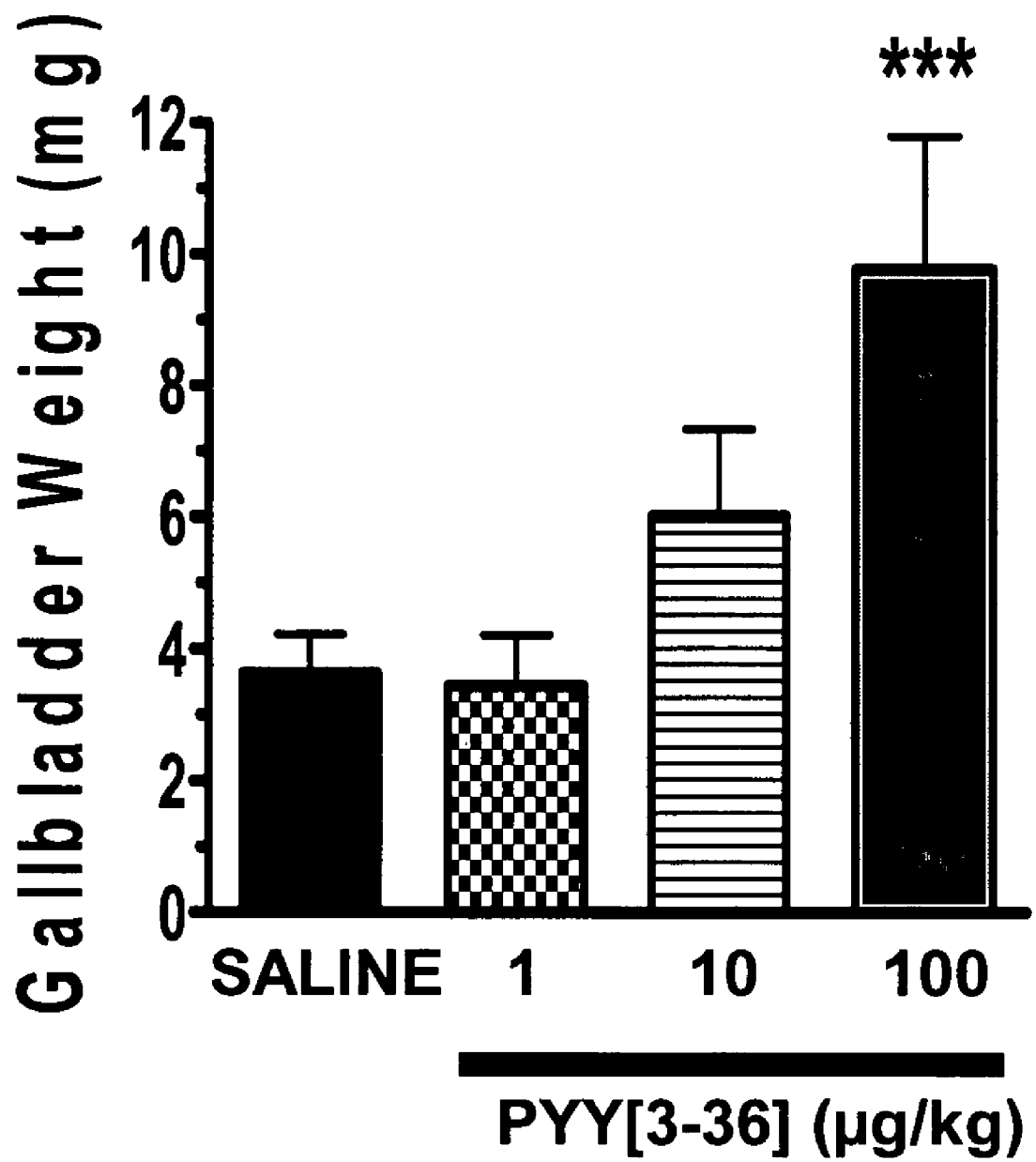
FIG. 33 depicts exemplary effects of various PYY(3-36) concentrations on gallbladder weight in non-obese mice.

FIG. 33 shows the acute effects of i.p. PYY(3-36) injection on gallbladder emptying in non-obese mice. Gallbladder weights measured at 30 min. post-injection are depicted, with a higher weight reflective of reduced basal gallbladder emptying rate. ***$p<0.001$, significantly different vs. saline-treated controls.

Figure 34A:
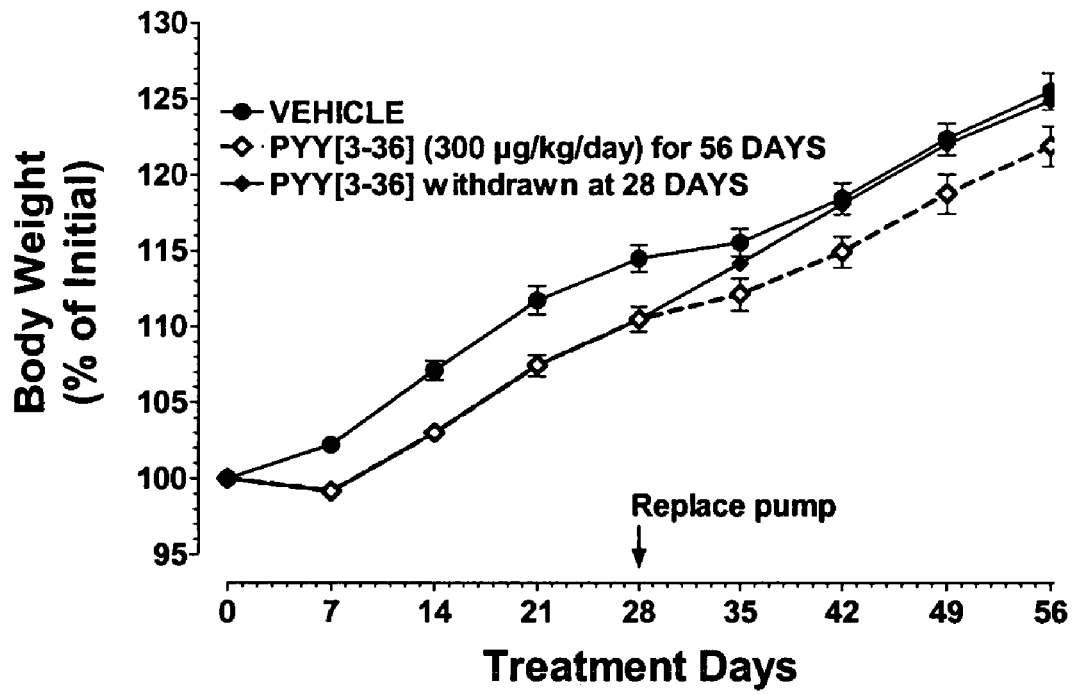
FIGS. 34A and 34B depict exemplary effects of prolonged PYY(3-36) administration and withdrawl in DIO mice.
Figure 34B:
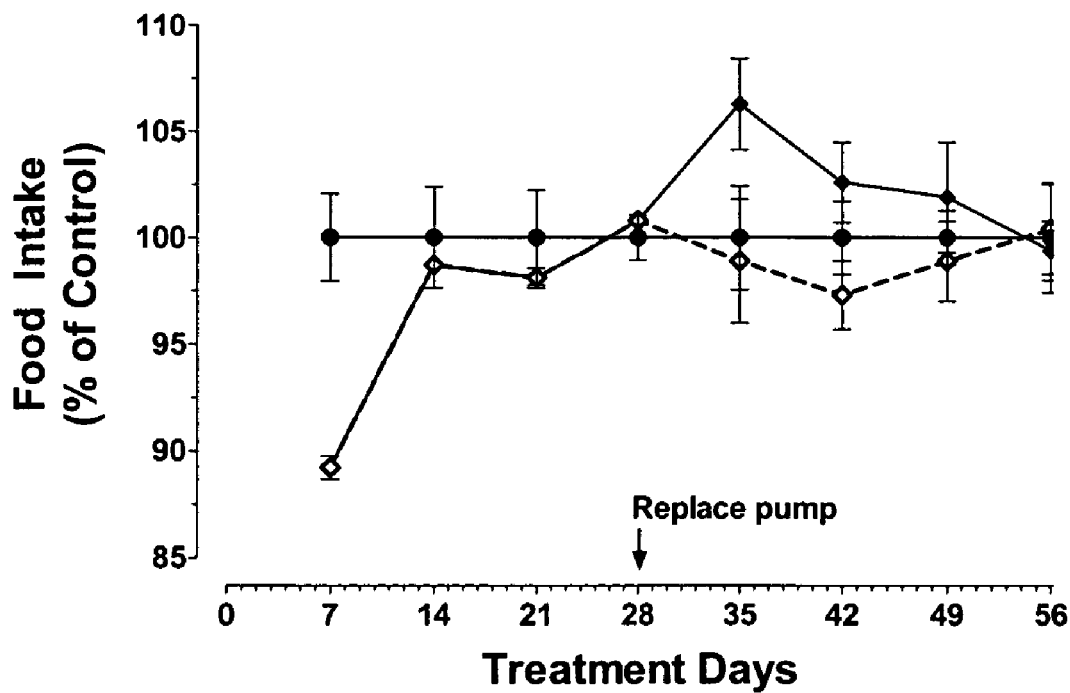

FIGS. 34A and 34B show the effect of prolonged PYY(3-36) administration and withdrawal in DIO mice on body weight and food intake, respectively. DIO mice were treated with PYY(3-36) (300 µg/kg/day) or vehicle for up to 56 days; PYY(3-36) was withdrawn from some animals after 28 days and replaced with vehicle. Symbols: closed circles, vehicle-treated controls; open diamonds, PYY(3-36)-treated; closed diamonds, PYY(3-36) days 0-28 followed by vehicle days 28-56. The initial (pre-treatment) mean weight was 24.7±1.6 g. Body weight differed significantly in PYY(3-36)-treated mice at all timepoints ($p<0.001$ vs vehicle control); body weight in mice withdrawn from PYY(3-36) did not differ from controls by day 35 or thereafter.

Overall, continuous subcutaneous infusion of PYY(3-36) (1 mg/kg/day, up to 7 days) was observed to increase metabolic rate, fat combustion, and/or fecal energy loss in diet-induced obese (DIO) mice. PYY(3-36) transiently reduced food intake (e.g., 25-43% lower at Day 2 relative to pre-treatment baseline) and decreased body weight (e.g., 9-10% reduced at Day 2 vs. baseline). The effect on body weight was durable, persisting throughout a 56-day study. Withdrawal of PYY(3-36) after 28 days of treatment was associated with transiently increased food intake, and regain of weight to the control level. Mass-specific metabolic rate (kcal/kg/hr) did not differ from controls. Light cycle RQ was reduced by PYY(3-36) throughout the study (averaging 0.730±0.006 vs. 0.750±0.009 in controls; $p<0.001$). Dark cycle respiratory quotient (RQ) was transiently decreased in PYY(3-36)-treated mice (e.g., Day 2, 0.747±0.008 vs. 0.786±0.004 in controls; $p<0.001$). Epididymal fat pad weight in PYY(3-36)-treated mice was decreased by approximately 50%. Fat pad lipolysis ex vivo was not stimulated by PYY(3-36), nor were there changes in the expression of hepatic genes relevant to lipid metabolism. PYY(3-36) decreased basal gallbladder emptying in non-obese mice; however, fecal energy density (kcal/100 g) did not change sufficiently to impact energy balance.

In some embodiments, in-bred male DIO prone rats were obtained from Charles Rivers Laboratories. These rats were developed from a line of Crl:CD®(SD)BR rats that are prone to become obese on a diet relatively high in fat and energy. These animals rapidly gain weight and body fat resulting in a hyper-triglyceridemic, -leptinemic and -insulinemic state. They were housed individually in shoebox cages at 22° C. in a 12:12-hour light dark cycle. Rats were maintained ad-libitum on a moderately high fat diet (32% kcal from fat; Research Diets D1226B) for 6 weeks prior to drug treatment. At the end of the fattening period their body weights were ~500 g. Chronic administration of test compounds was by subcutaneous osmotic pump. Indirect calorimetry was performed at 1 week. Plasma analytes were analyzed on day 14 after an overnight fast. Analyses of food intake, body weight, body weight gain, body composition, metabolic rate, RQ, EE, gastric acid secretion, gastric emptying, gallbladder emptying, and statistical comparisons were performed as described above.

Figure 35:
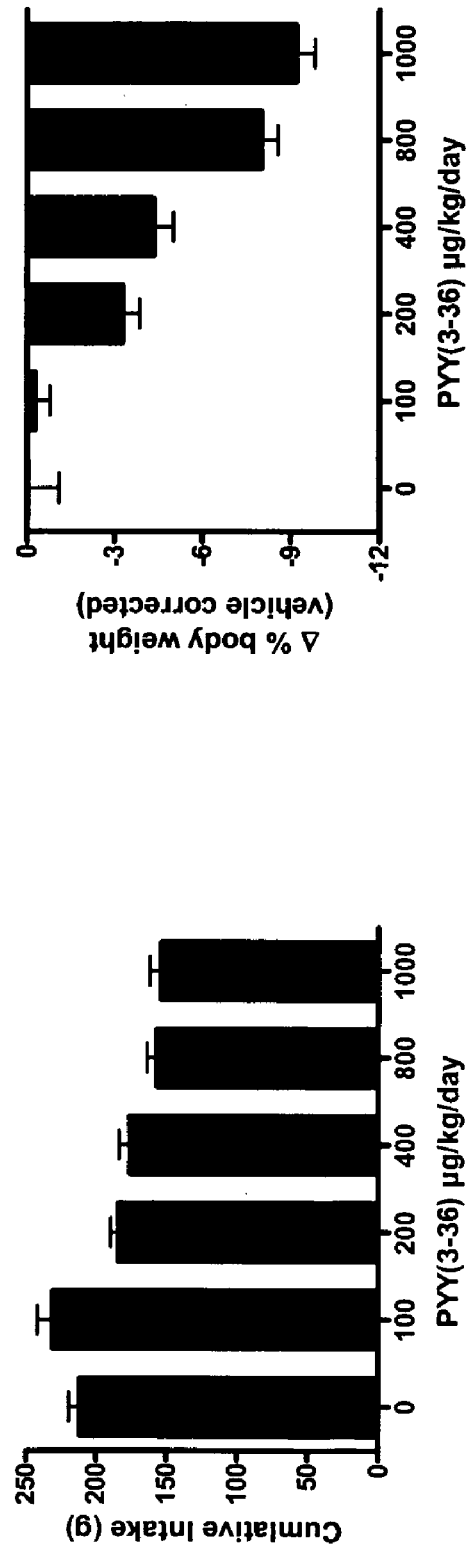
FIG. 35 depicts PYY(3-36) dose responsive decreases in food intake and body weight in DIO prone rats.

FIG. 35 depicts an example of the dose-dependent decrease in cumulative food intake and percent change in body weight observed upon administration of PYY(3-36) in inbred DIO prone rats at day 14. Based on these data, a dose of 500 µg/kg/day of PYY(3-36) was chosen for experiments exploring the effects of combining PYY(3-36) with other agents marketed for the treatment of obesity, appetite control or altering body composition, such as, for example, but not limited to, an amylin, amylin agonist or amylin analog agonist, salmon calcitonin, a cholecystokinin (CCK) or CCK agonist, a leptin (OB protein) or leptin agonist, an exendin or exendin analog agonist, a glucagon-like peptide-1 (GLP-1), GLP-1 agonist or GLP-1 analog agonist, CCK, CCK agonists, calcitonin, calcitonin agonists, small molecule cannabinoid CB1 receptor antagonists, rimonabant, 11 beta-hydroxysteroid dehydrogenase-1 inhibitors, phentermine, or sibutramine. In some embodiments, a dose of 500 µg/kg/day of PYY(3-36) was combined with a dose of 100 µg/kg/day of amylin. In some embodiments, a dose of 200 µg/kg/day of PYY(3-36) was combined with a dose of 100 µg/kg/day of amylin.

Figure 36:
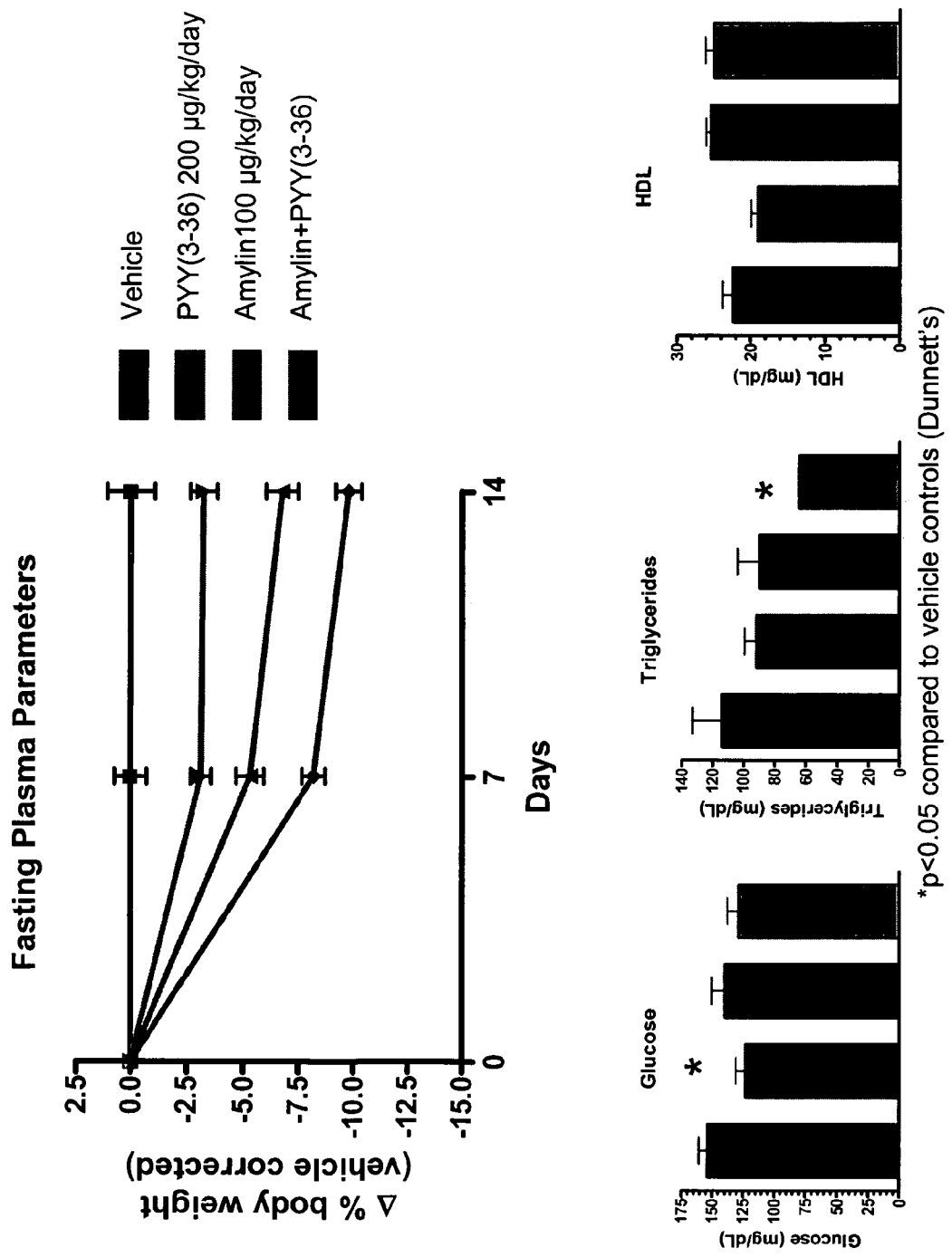
FIG. 36 depicts exemplary effects of PYY(3-36) with and without co-administration of amylin on fasting plasma parameters in DIO prone rats.
Figure 37:
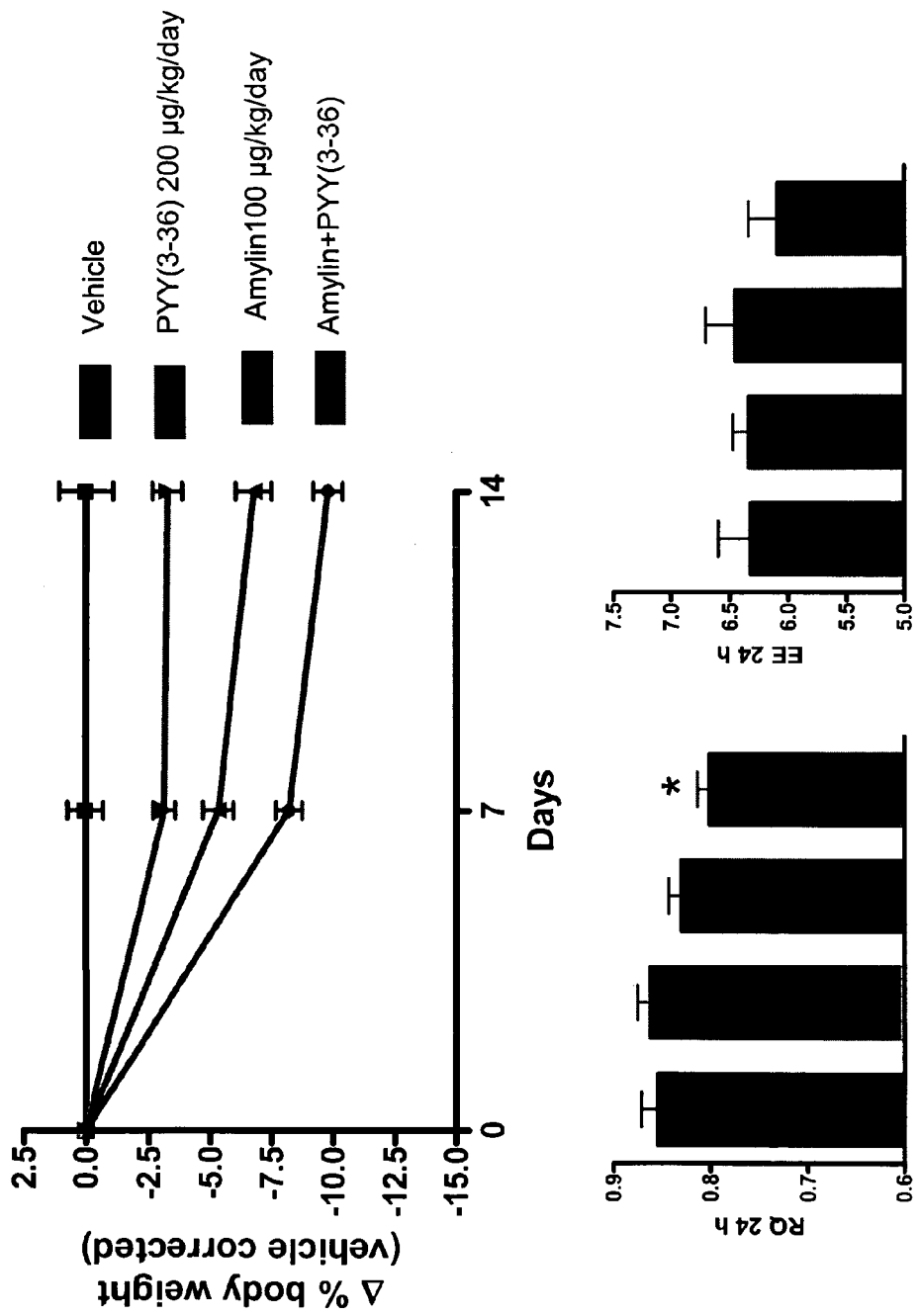
FIG. 37 depicts exemplary effects of PYY(3-36) with and without co-administration of amylin on respiratory quotient (RQ) and energy expenditure (EE) in DIO prone rats.

For example, FIG. 36 depicts exemplary effects of administering 200 µg/kg/day of PYY(3-36) with and without co-administration of 100 µg/kg/day of amylin on body weight as well as on fasting plasma parameters in DIO prone rats. Co-administration of PYY(3-36) was found to have an additive effect in reducing body weight. A glucose-lowering effect of administration of PYY(3-36) alone was also observed. Furthermore, co-administration of amylin and PYY(3-36) reduced triglyceride levels in an additive manner, without reducing HDL cholesterol levels. The additive effect on weight loss observed upon co-administration of PYY(3-36) and amylin was accompanied by a reduction in respiratory quotient (RQ) without a significant reduction in energy expenditure (EE) in these DIO prone rats (see FIG. 37).

Figure 38:
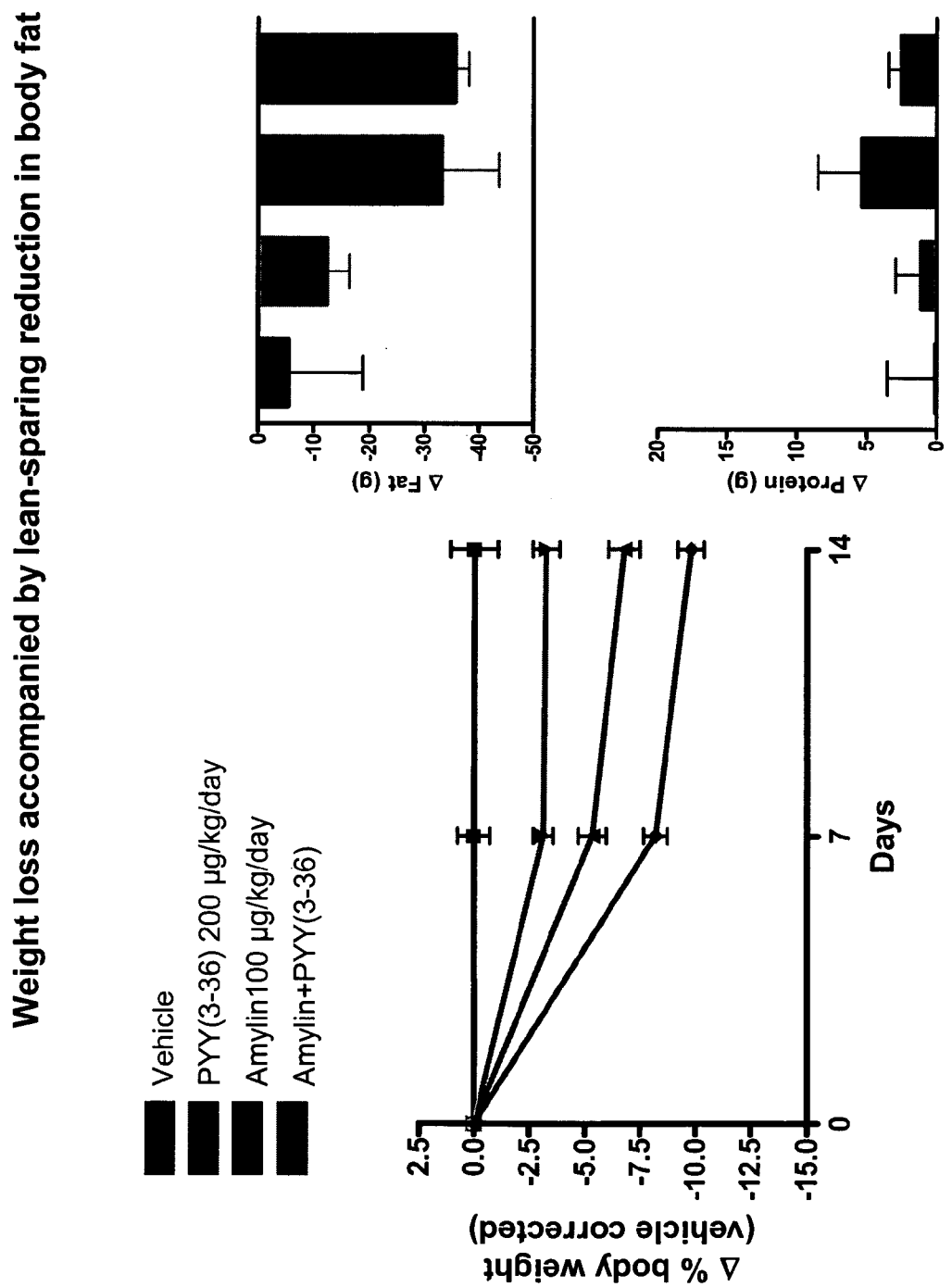
FIG. 38 depicts exemplary effects of PYY(3-36) with and without co-administration of amylin on body composition in DIO prone rats.

The additive effect on weight loss observed upon co-administration of PYY(3-36) and amylin was also accompanied by significant reduction in fat tissue mass, without concomitant reduction in protein mass relative to vehicle (see FIG. 38). Thus, the combination of PYY(3-36) and amylin appears to be effective in altering body composition via lean-sparing body fat reduction.

Figure 39:
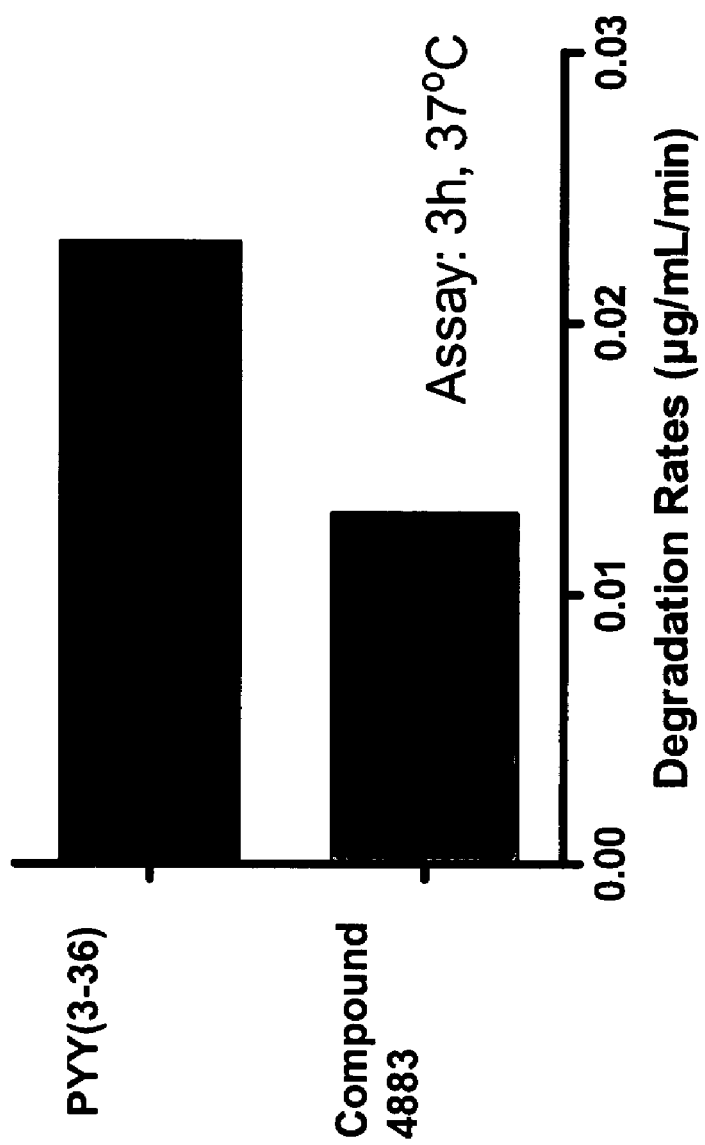
FIG. 39 compares the calculated rate of degradation of an exemplary PPF polypeptide to that of PYY(3-36).
Figure 54:
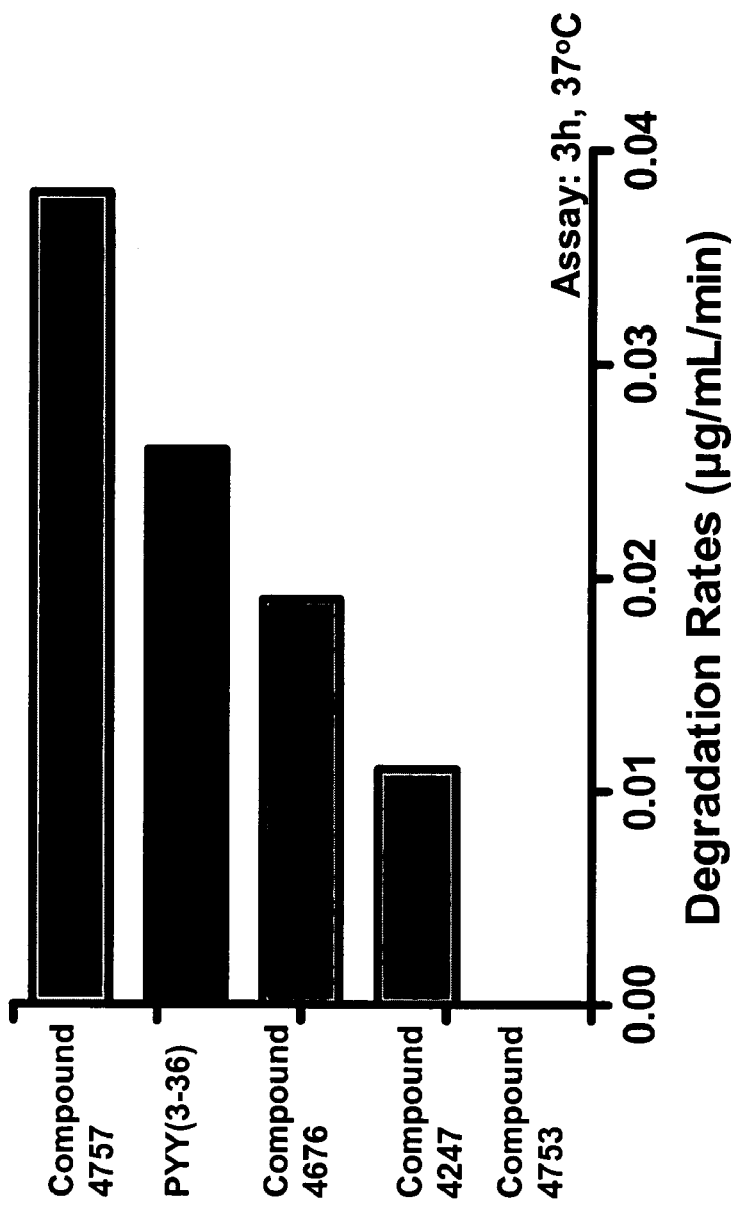
FIG. 54 compares the calculated rates of degradation of several PPF polypeptides to that of PYY(3-36).

The stability of several PPF polypeptides in human plasma was tested and compared to the plasma stability of PYY(3-36). To assess in vitro degradation, each of the PPF polypeptides or PYY(3-36) was incubated in human plasma at 37° C. for three hours, and aliquots were removed at specified timepoints and analyzed for peptide concentration. The peptide concentration was determined by comparison with a standard curve, and the degradation rates were determined by calculating the slope of the change in concentration over time. A comparison between the degradation rate of a PPF polypeptide and that of PYY(3-36) is shown in FIG. 39. In this example, PPF polypeptide compound 4883 has enhanced plasma stability as compared to PYY(3-36). FIG. 54 compares the calculated rates of degradation of several other PPF polypeptides to that of PYY(3-36). It was observed that compounds 4676, 4247 and 4753 have enhanced plasma stability in this assay as compared to PYY(3-36), whereas compound 4757 is less stable than PYY(3-36).

Figure 41:
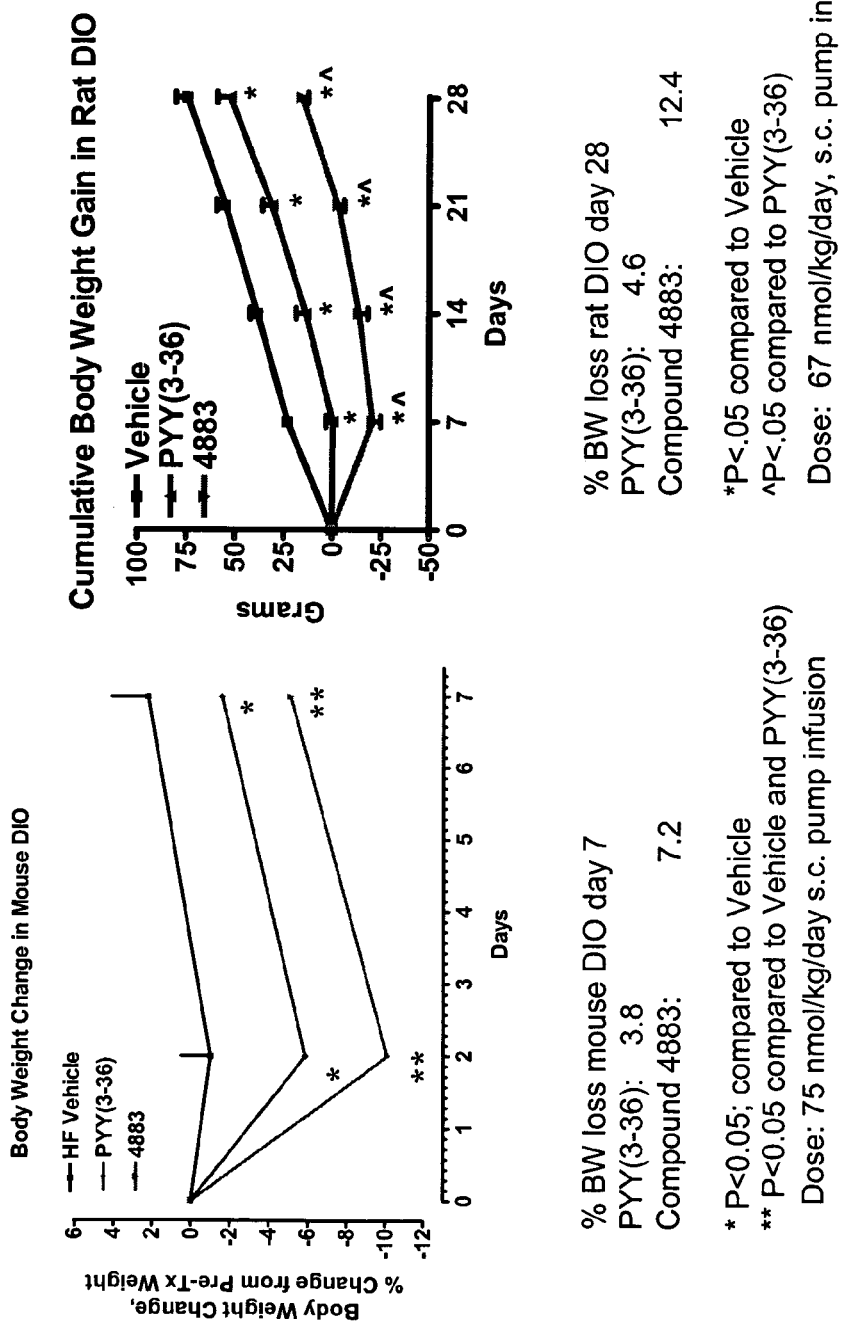
FIG. 41 demonstrates exemplary effects of chronic administration of a PPF polypeptide on body weight in rodent DIO models, as compared to PYY(3-36).

In mouse and rat DIO models, chronic administration of PPF polypeptide compound 4883 was found to have increased efficacy in reducing body weight as compared to PYY(3-36) (see FIG. 41).

Figure 43:
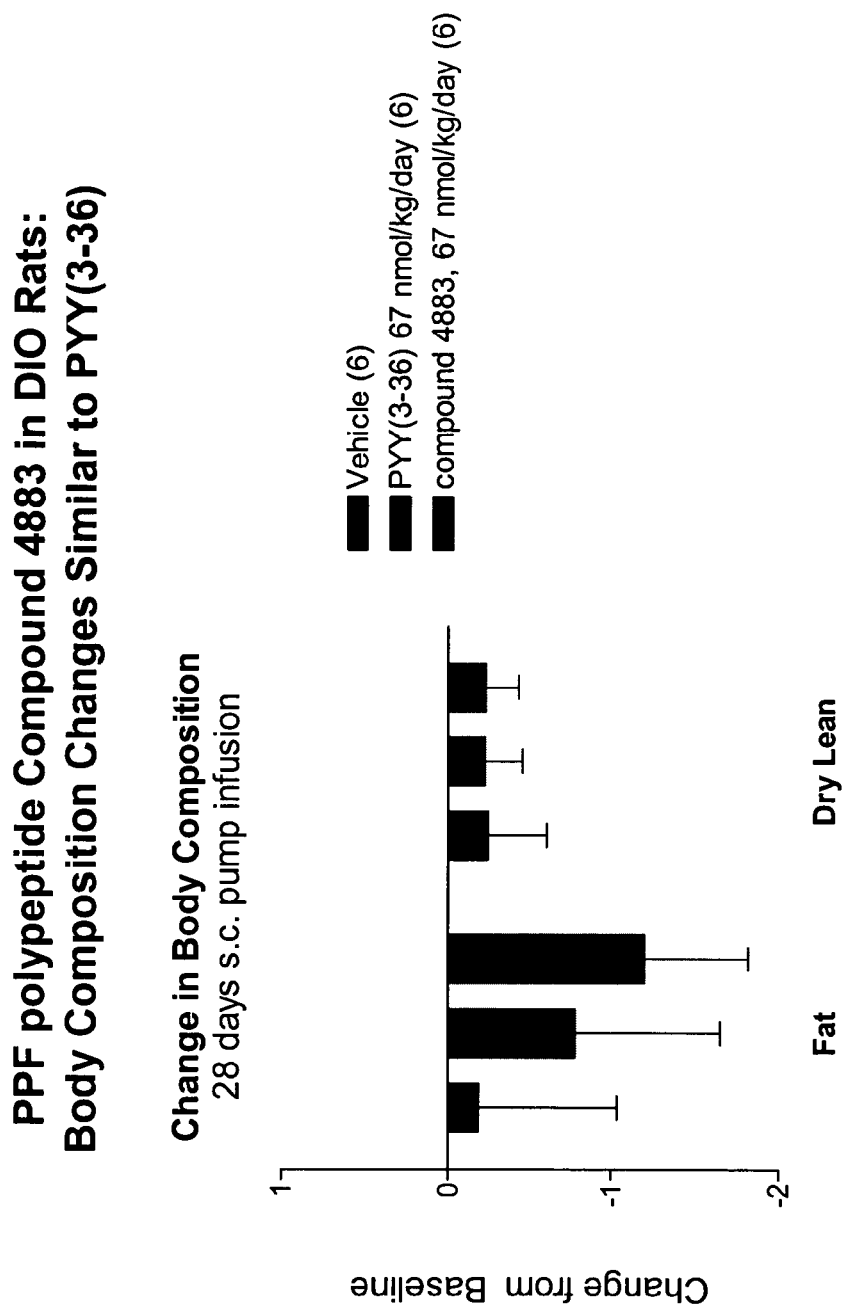
FIG. 43 depicts effects of administration of an exemplary PPF polypeptide on body composition, as compared to PYY(3-36), in DIO rats.
Figure 44:
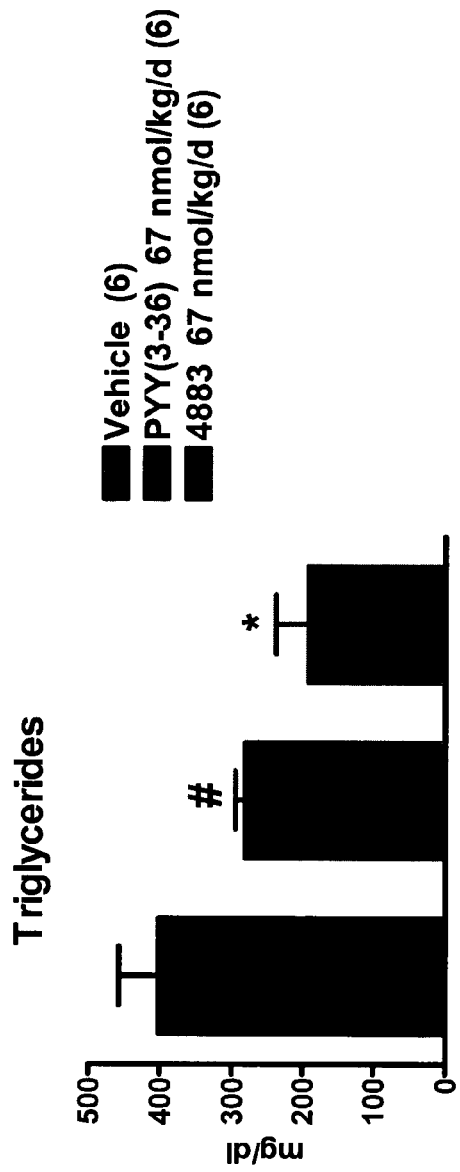
FIG. 44 depicts effects of administration of an exemplary PPF polypeptide on triglyceride levels, as compared to PYY(3-36), in DIO rats.

In some embodiments, a PPF polypeptide can preferentially lower plasma triglycerides, without changing other plasma analytes, such as HDL cholesterol, glucose or HbA1C levels. In some embodiments, a PPF polypeptide can lower plasma triglycerides and amylase levels, without changing other plasma analytes, such as HDL cholesterol, glucose or HbA1C levels. In some embodiments, the reduction in plasma triglyceride levels is greater than than the reduction in cholesterol levels. In some embodiments, plasma triglyceride levels are lowered and LDL cholesterol levels are lowered to a lesser extent. FIG. 43 demonstrates that chronic administration of PPF polypeptide compound 4883 in DIO rats over 28 days alters body composition by reducing fat tissue mass without changing lean tissue mass, and FIG. 44 depicts the preferential lowering of triglyceride levels by administration of PPF polypeptide compound 4883.

Figure 48:
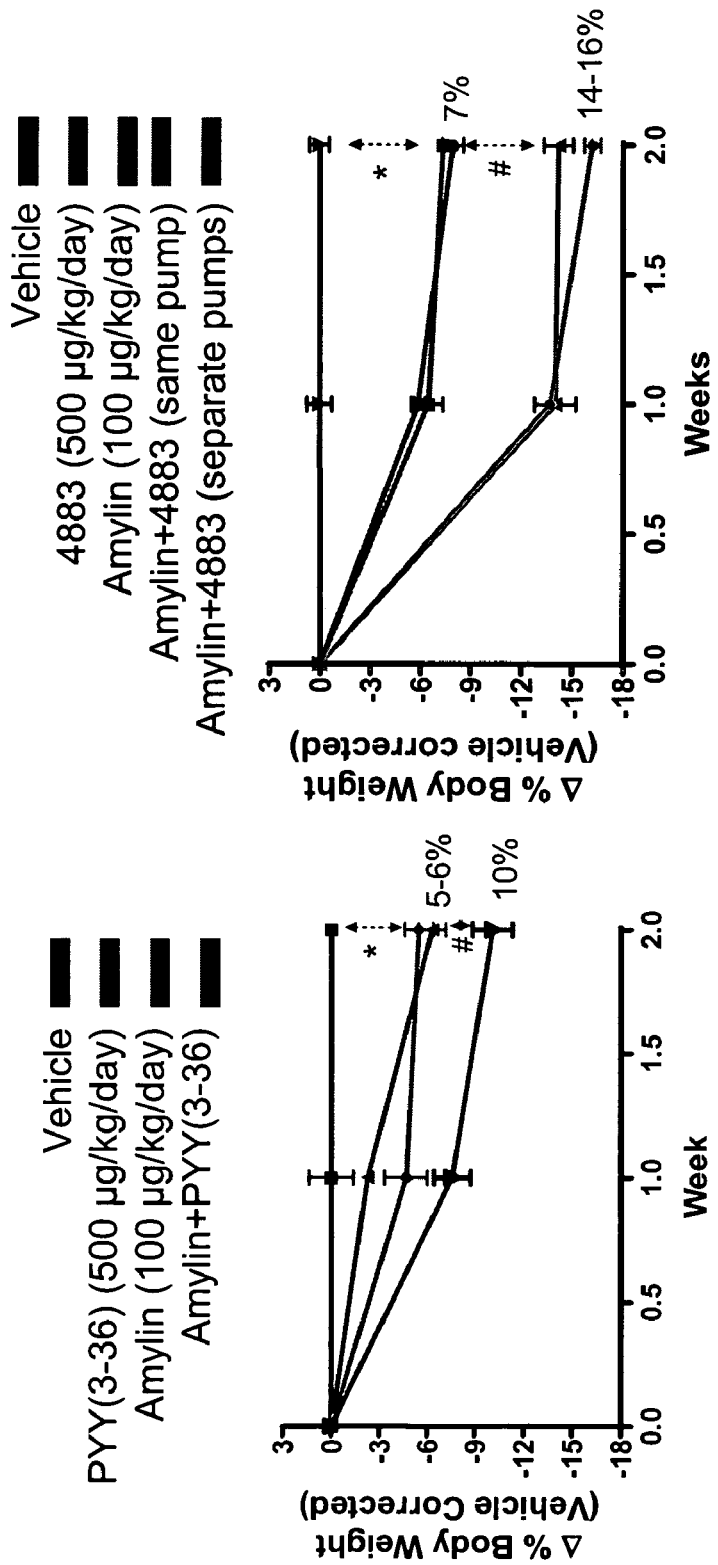
FIG. 48 depicts effects of an exemplary PPF polypeptide, as compared to PYY(3-36) with and without co-administration of amylin on body weight in DIO prone rats.
Figure 49:
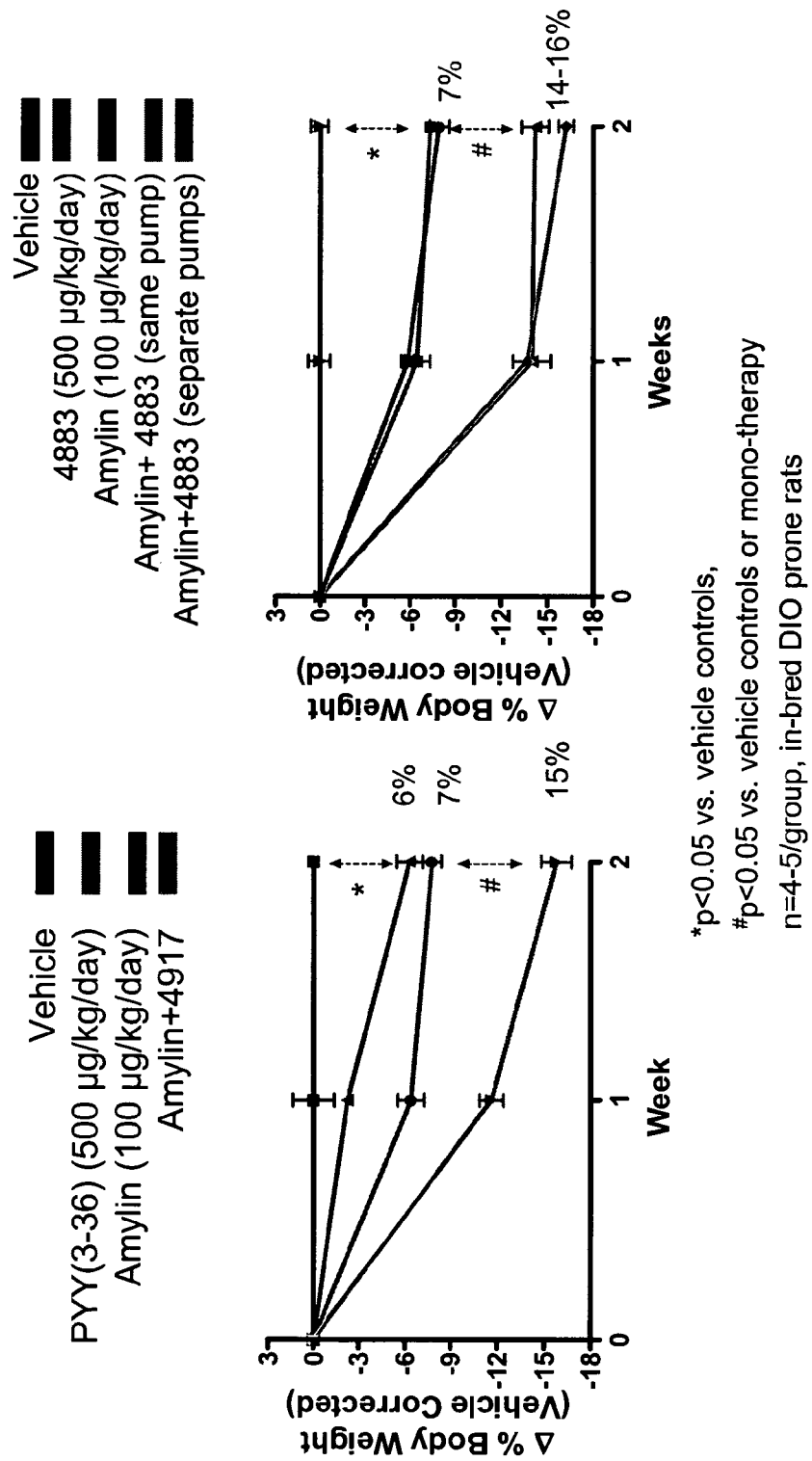
FIG. 49 depicts effects of two exemplary PPF polypeptides with and without co-administration of amylin on body weight in DIO prone rats.
Figure 53:
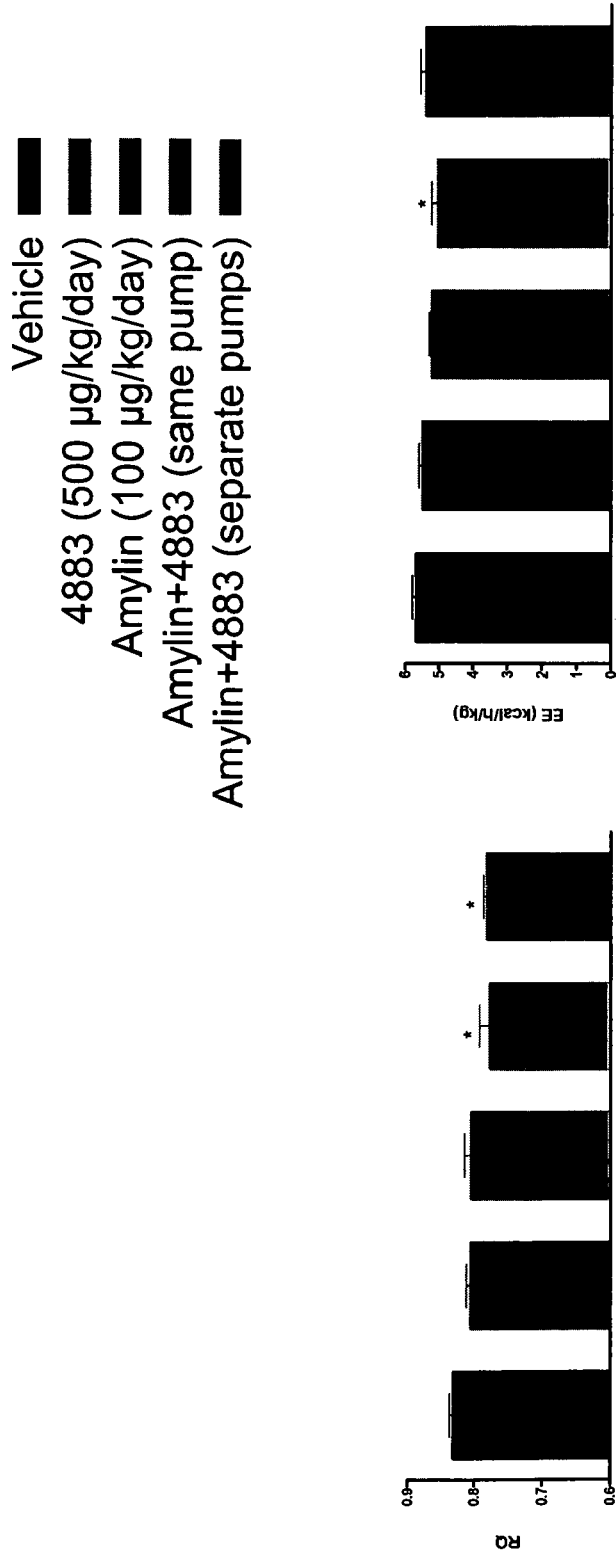
FIG. 53 depicts effects of an exemplary PPF polypeptide with and without co-administration of amylin on RQ and EE in rats.

In some embodiments, the PPF polypeptide and another agent, such as amylin, are administered via the same subcutaneous pump. In some embodiments, the PPF polypeptide and another agent, such as amylin, are administered through separate subcutaneous pumps. FIG. 48 depicts exemplary effects of administering 500 µg/kg/day of PYY(3-36) or a PPF polypeptide with and without co-administration of 100 µg/kg/day of amylin on body weight in DIO prone rats. Co-administration of 500 µg/kg/day of PYY(3-36) and 100 µg/kg/day of amylin was found to have an additive effect in reducing body weight. FIGS. 48 and 49 show that PPF polypeptide compounds 4883 and 4917 are more potent than PYY(3-36) in reducing body weight. FIGS. 48 and 49 also show that co-administration of 500 µg/kg/day of PPF polypeptide compound 4883 or compound 4917 plus 100 µg/kg/day of amylin have a correspondingly greater additive effect in reducing body weight as compared to the additive effect of PYY(3-36) plus amylin. The additive effect on weight loss observed upon co-administration of PPF polypeptide compound 4883 plus amylin was accompanied by a reduction in respiratory quotient (RQ) and energy expenditure (EE) in these DIO prone rats (see FIG. 53).

Figure 50:
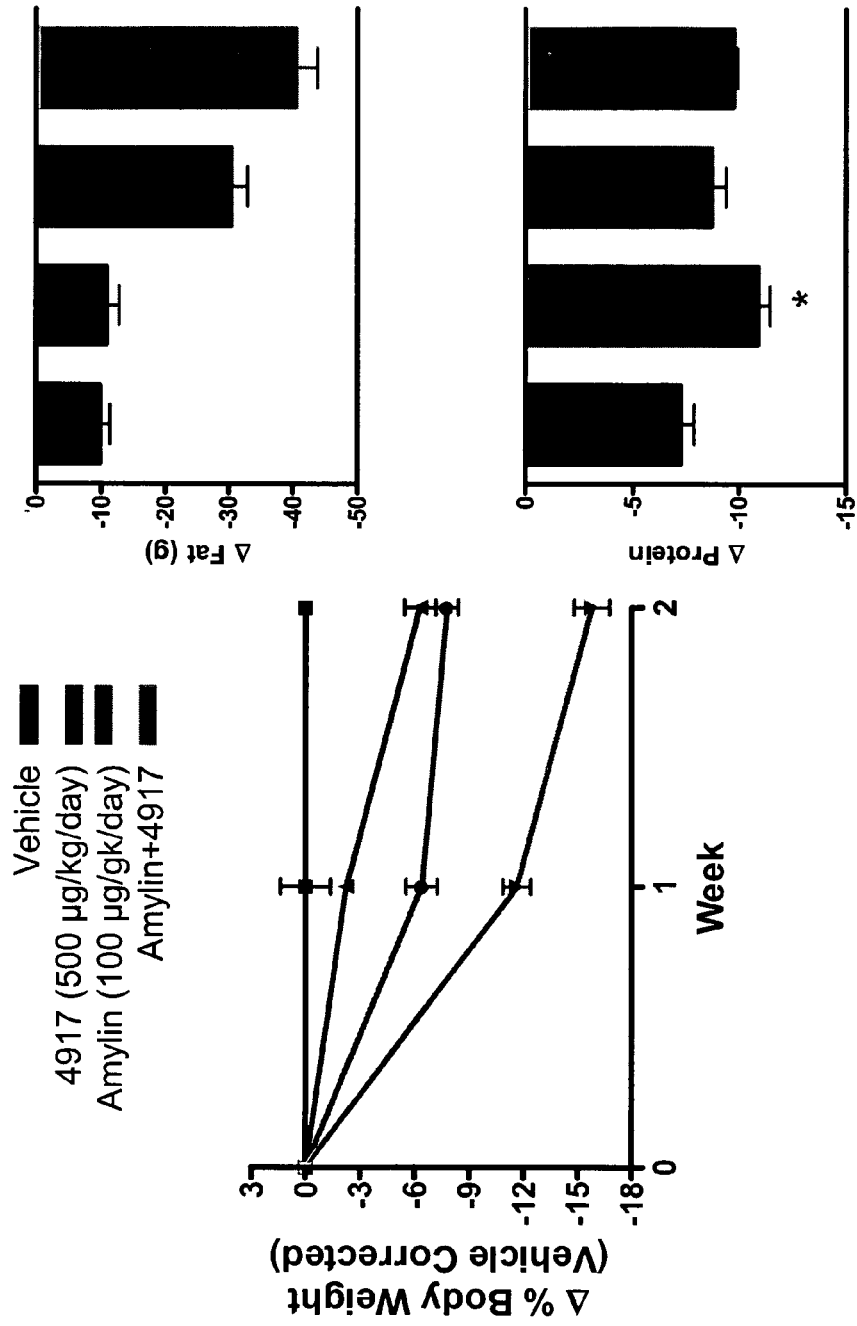
FIG. 50 depicts effects of an exemplary PPF polypeptide with and without co-administration of amylin on body composition in DIO prone rats.
Figure 51:
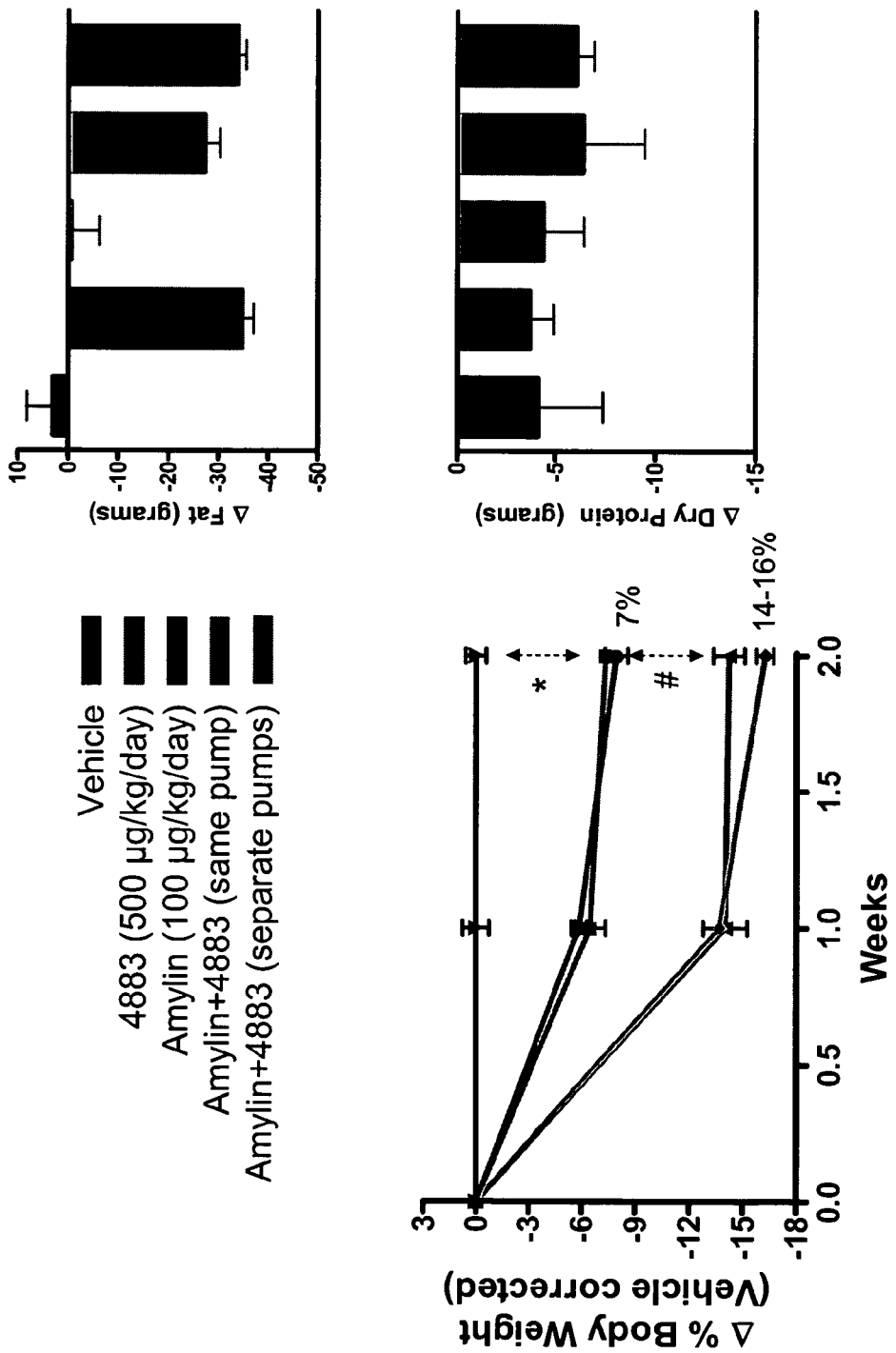
FIG. 51 depicts effects of an exemplary PPF polypeptide with and without co-administration of amylin on body composition in DIO prone rats.

The additive effect on reduction of body weight in DIO prone rats observed upon co-administration of amylin plus PPF polypeptide compound 4883 or 4917 was accompanied by a significant reduction in fat tissue mass, without a significant loss of lean tissue (see FIGS. 50 and 51). The co-administration of compound 4883 and amylin appears to have a synergistic effect on reducing body weight (FIG. 51). Overall, these data demonstrate that co-administration of amylin plus a PPF polypeptide is an effective means of altering body composition via lean-sparing body fat reduction.

Figure 52:
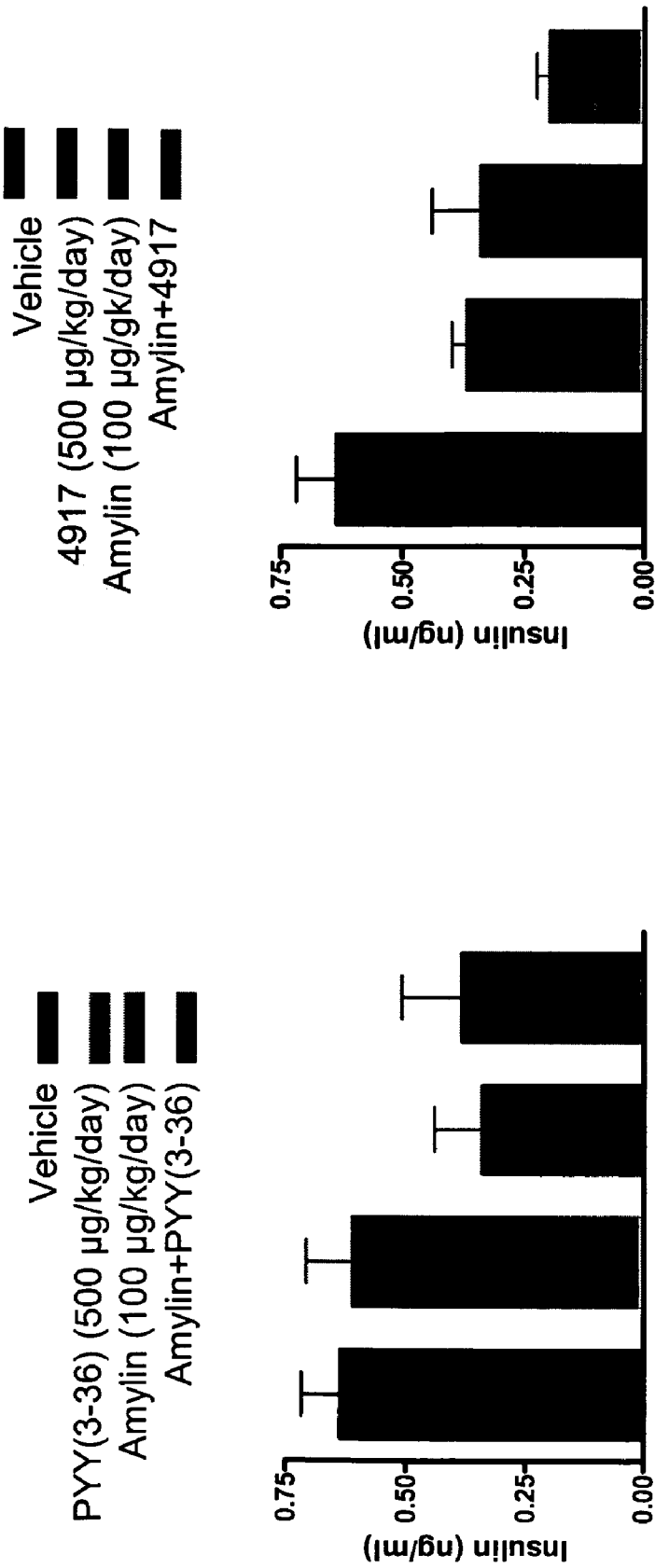
FIG. 52 depicts effects of PYY(3-36) or an exemplary PPF polypeptide with and without co-administration of amylin on fasting insulin levels in rats.

FIG. 52 shows that PPF polypeptide compound 4917, with or without co-administration of amylin, is more effective than PYY(3-36) at lowering fasting insulin levels in DIO rats.

Certain PPF polypeptides are shown in Table 4 below, although other polypeptides are envisioned. The following abbreviations may be used: hK=homolysine, hR=homoarginine, hS=homoserine, hP=homoproline, G(oct)=octylglycine, Aib=2-aminoisobutyric acid, Cit=citruline, Dap=diaminopropionic acid, Sar=sarcosine.

TABLE 4

| ID | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| 1 | A | P | L | E | P | V | Y | P | G | D | N | A | T | P | E | Q | M | A | Q | Y |
| 2 | Y | P | I | K | P | E | A | P | G | E | D | A | S | P | E | E | L | N | R | Y |
| 3 |   |   | I | K | P | E | N | P | G | E | D | A | S | P | E | D | L | N | R | Y |
| 4 | Y |   | S | E | P | D | Y | P | G | D | D | A | T | P | E | Q | M | A | R | Y |
| 5 | A | P | L | E | P | V | Y | P | G | D | D | A | T | P | E | Q | M | A | R | Y |
| 6 | A | P | L | K | P | V | S | P | G | D | N | A | T | P | A | E | L | A | K | Y |
| 7 | Y | P | P | K | P | E | H | P | G | E | D | A | P | A | E | D | L | A | K | Y |
| 8 |   |   | P | K | P | E | N | P | G | E | D | A | P | A | E | D | V | A | K | Y |
| 9 | A |   | P | K | P | E | S | P | G | D | D | A | P | P | E | D | L | A | K | Y |
| 10 |   |   | P | K | P | E | N | P | G | E | A | A | P | P | E | D | I | A | K | Y |
| 11 |   |   | P | K | P | E | N | P | G | E | D | A | S | P | E | D | L | A | Q | Y |
| 12 |   |   | P | K | P | D | S | P | G | S | D | A | S | P | Q | E | L | A | K | Y |
| 13 | Y |   | P | K | P | D | N | P | G | D | D | A | S | P | P | E | L | s | K | Y |
| 14 | M |   | P | K | P | E | N | P | G | S | N | A | S | P | E | E | L | s | K | Y |
| 15 |   |   | P | K | P | E | N | P | G | D | D | A | S | P | E | E | M | A | K | Y |
| 16 |   |   | T | K | P | D | N | P | G | E | D | A | S | P | E | E | M | A | K | Y |
| 17 |   |   | P | K | P | E | N | P | G | E | D | A | S | P | E | E | M | T | K | Y |
| 18 | Y |   | P | K | P | E | A | P | G | E | D | A | P | P | E | E | L | T | R | Y |
| 19 |   | P | I | K | P | E | N | P | G | E | D | A | P | P | E | D | V | A | K | Y |
| 20 |   |   | S | K | P | E | H | P | G | E | D | A | P | P | E | D | V | N | R | Y |
| 21 |   |   | P | K | P | E | H | P | G | E | D | A | S | A | E | D | V | N | Q | Y |
| 22 |   |   | P |   | P | E | H | P | G | E | D | A | P | A | E | D | V | N | R | Y |
| 23 |   |   | P | K | P | E | H | P | G | E | D | A | P | P | E | D | V | A | R | Y |
| 24 |   |   | P | K | P | E | A | P | G | D | D | A | P | P | E | D | L | A | K | Y |
| 25 |   |   | P | K | P | E | A | P | G | E | D | A | P | A | E | Q | L | A | Q | Y |
| 26 | Y |   | A | K |   |   |   |   |   |   |   |   |   |   |   |   |   |   |   |   |
| 27 |   |   |   |   |   |   |   |   |   |   |   |   |   |   |   |   |   |   |   |   |
| 28 |   |   |   |   |   |   |   |   |   |   |   |   |   |   |   |   |   |   |   |   |
| 29 | FORMULA I |   |   |   |   |   |   |   |   |   |   |   |   |   |   |   |   |   |   |   |
| 30 | Y | P | I | hK | P | E | A | P | G | E | D | A | S | P | E | E | L | N | R | Y |
| 31 | Y | P | I | K | P | E | A | P | G | E | D | A | S | P | E | E | L | N | R | Y |
| 32 | Y | P | I | K | P | E | A | P | G | E | D | A | S | P | E | E | L | N | R | Y |
| 33 | Y | P | I | K | P | E | A | P | G | A | A | A | S | P | E | E | L | N | R | Y |
| 34 | Y | P | I | K | P | E | A | P | G | E | D | A | A | P | E | E | L | N | R | Y |
| 35 | Y | P | I | K | P | E | A | P | G | E | D | A | S | A | E | E | L | N | R | Y |
| 36 | Y | P | I | K | P | E | A | P | G | E | D | A | S | P | A | E | L | N | R | Y |
| 37 | Y | P | I | K | P | E | A | P | G | E | D | A | S | P | E | A | L | N | R | Y |
| 38 | Y | P | I | K | P | E | A | P | G | E | D | A | S | P | E | E | A | N | R | Y |
| 39 | Y | P | I | K | P | E | A | P | G | E | D | A | S | P | E | E | L | N | R | Y |
| 40 | Y | P | I | K | P | E | A | P | G | E | D | A | A | P | E | E | L | N | R | Y |
| 41 | Y | P | I | K | P | E | A | P | G | E | D | A | S | A | E | E | L | N | R | Y |
| 42 | Y | P | I | K | P | E | A | P | G | E | D | A | S | P | A | E | L | N | R | Y |
| 43 | Y | P | I | K | P | E | A | P | G | E | D | A | S | P | E | A | L | N | R | Y |
| 44 | Y | P | I | K | P | E | A | P | G | E | D | A | S | P | E | E | A | N | R | Y |
| 45 | Y | P | I | K | P | E | A | P | G | E | D | A | S | P | E | E | L | N | R | Y |
| 46 | Y | P | I | K | P | E | A | P | G | E | D | A | S | P | E | E | L | A | R | Y |
| 47 | Y | P | I | K | P | E | A | P | G | E | D | A | A | A | E | E | L | A | R | Y |
| 48 | Y | P | I | K | P | E | A | P | G | E | D | A | S | P | E | E | L | A | R | Y |
| 49 | Y | P | I | K | P | E | A | P | G | E | D | A | S | A | E | E | L | A | R | Y |

TABLE 4-continued

| 50 | A | P |   | I | K | P | E | A | P | G | E | D | A | S | P | E | L | N | R | Y |
| 51 | F | P |   | I | K | P | E | A | P | G | E | D | A | S | P | E | L | N | R | Y |
| 52 | Y | dA |   | I | K | P | E | A | P | G | E | D | A | S | P | E | L | L | N | Y |
| 53 | Y | G |   | I | I | P | E | A | P | G | E | D | A | S | P | E | E | L | N | R |
| 54 | A | Y |   | P | I | K | A | E | P | A | P | E | D | A | A | P | E | L | L | R |
| 55 | A | A |   | P | I | A | P | E | A | P | G | E | D | A | S | P | E | E | L | R |
| 56 | Y | P |   | A | I | K | P | E | A | P | G | E | D | A | S | S | P | E | L | R |
| 57 | Y | P |   | I | A | K | P | E | A | P | G | E | D | A | S | S | P | E | L | R |
| 58 | Y | P |   | I | K | K | P | E | A | P | G | E | D | A | A | S | P | E | L | R |
| 59 | Y | P |   | I | K | K | P | E | A | P | G | E | D | D | A | S | P | E | L | R |
| 60 | Y | P |   | I | K | A | P | E | A | P | G | E | D | D | A | S | P | E | L | R |
| 61 | Y | P |   | I | K | P | A | E | A | P | A | E | D | D | A | S | P | E | L | R |
| 62 | Y | P |   | I | K | P | E | A | A | P | G | A | D | D | A | S | P | E | L | R |
| 63 | Y | P |   | I | K | P | E | E | A | P | G | E | D | D | A | S | P | E | L | R |
| 64 | Y | P |   | I | K | P | E | A | A | P | G | E

TABLE 4-continued

| # | Mod | | | | | | | | | | | | | | | | | | |
|---|---|---|---|---|---|---|---|---|---|---|---|---|---|---|---|---|---|---|---|
| 102 | | I | K | P | E | A | P | G | E | D | A | S | A | E | A | L | N | R | Y |
| 103 | | I | K | P | E | A | P | G | E | D | A | S | P | E | E | L | N | R | Y |
| 104 | | I | K | P | E | A | P | G | E | D | A | S | P | A | A | A | A | R | Y |
| 105 | | I | K | P | E | A | P | G | E | D | A | S | P | E | E | L | A | R | Y |
| 106 | | I | K | P | E | A | P | G | E | D | A | S | P | E | E | L | N | R | Y |
| 107 | | I | K | P | E | A | P | G | E | D | A | S | P | E | E | L | A | K(NMe)A | Y |
| 108 | | I | K | P | E | A | P | G | E | D | A | S | P | E | E | L | N | R | Y |
| 109 | | I | K | P | E | A | P | G | E | D | A | S | P | E | E | L | N | R | Y |
| 110 | | I | K | P | E | A | P | G | E | D | A | S | P | E | E | L | N | R | Y |
| 111 | | I | K | P | E | A | P | G | E | D | A | S | P | E | E | L | N | R | Y |
| 112 | | I | K | P | E | A | P | G | E | D | A | S | P | E | E | L | N | R | Y |
| 113 | | I | K | P | E | A | P | G | E | D | A | S | P | E | E | L | N | R | Y |
| 114 | | I | K | P | E | A | P | G | E | D | A | S | P | E | E | L | N | R | Y |
| 115 | | I | K | P | E | A | P | G | E | D | A | S | P | E | E | L | N | R | Y |
| 116 | | I | K | P | E | A | P | G | E | D | A | S | P | E | E | L | N | R | Y |
| 117 | | I | K | P | E | A | P | G | E | D | A | S | P | E | E | L | N | R | Y |
| 118 | | I | K | P | E | A | P | G | E | D | A | S | P | E | E | L | N | R | Y |
| 119 | | I | K | P | E | A | P | G | E | D | A | S | P | E | E | L | N | R | Y |
| 120 | | I | K | P | E | A | P | G | E | D | A | S | P | E | E | L | N | R | Y |
| 121 | | I | K | P | E | A | P | G | E | D | A | S | P | E | E | L | N | R | Y |
| 122 | | I | K | P | E | A | P | G | E | D | A | S | P | E | E | L | N | R | Y |
| 123 | | I | K | P | E | A | P | G | E | D | A | S | P | E | E | L | N | R | Y |
| 124 | | I | K | P | E | A | P | G | E | D | A | S | P | E | E | L | N | R | Y |
| 125 | | I | K | P | E | A | P | G | E | D | A | S | P | E | E | L | N | R | Y |
| 126 | | I | K | P | E | A | P | G | E | D | A | S | P | E | E | L | N | R | Y |
| 127 | | I | K | P | E | N | P | G | E | D | A | S | P | E | E | L | N | R | Y |
| 128 | | I | K | P | D | A | P | G | E | D | A | P | A | D | E | M | A | R | Y |
| 129 | isocap | S | K | P | E | A | P | G | E | D | A | S | P | E | E | L | N | R | Y |
| 130 | AC | P | K | P | E | A | P | G | E | D | A | S | P | E | E | L | N | R | Y |
| 131 | | P | K | P | E | A | P | G | E | D | A | S | P | E | E | L | N | R | Y |
| 132 | | I | K | P | E | A | P | G | E | D | A | S | P | E | E | L | N | R | Y |
| 133 | | I | K | P | E | A | P | G | E | D | A | S | P | E | E | L | N | R | Y |
| 134 | | I | K | P | E | A | P | G | E | D | A | S | P | E | E | L | N | R | Y |
| 135 | | I | K | P | E | A | P | G | E | D | A | S | P | E | E | L | N | R | Y |
| 136 | | I | K | P | E | A | P | G | E | D | A | S | P | E | E | L | N | R | Y |
| 137 | | I | K | P | E | A | P | G | E | D | A | S | P | E | E | L | N | R | Y |
| 138 | | I | K | P | E | A | P | G | E | D | A | S | P | E | E | L | N | R | Y |
| 139 | | I | K | P | E | A | P | G | E | D | A | S | P | E | E | L | N | R | Y |
| 140 | | I | K | P | E | A | P | G | E | D | A | S | A | E | E | L | A | R | Y |
| 141 | | I | K | P | E | A | P | G | E | D | A | S | P | E | E | L | N | R | Y |
| 142 | | I | K | P | E | A | P | G | E | D | A | S | A | E | E | L | A | R | Y |
| 143 | | I | K | P | E | A | P | G | E | D | A | S | A | E | E | L | N | R | Y |
| 144 | | I | hK | P | E | A | P | G | E | D | A | S | P | E | E | L | N | R | Y |
| 145 | | I | K | P | E | A | P | G | E | D | A | S(Ac) | P | E | E | L | N | R | Y |
| 146 | | I | K(FmocSO3H) | P | E | A | P | G | E | D | A | S | P | E | E | L | N | R | Y |
| 147 | | I | K | P | E | A | P | G | E | D | A | S | P | E | E | L | N | R | Y |
| 148 | | I | K | P | E | A | P | G | E | D | A | S | P | E | E | L | N | R | Y |
| 149 | | I | K | P | E | A | P | G | E | D | A | S | P | E | E | L | N | hR | Y |
| 150 | FmocSO3H | I | K | P | E | A | P | G | E | D | A | S | P | E | E | L | N | R | Y |
| 151 | isocaproyl | I | K | P | E | A | P | G | E | D | A | S | P | E | E | L | A | R | Y |
| 152 | Fmoc | I | K | P | E | A | P | G | E | D | A | S | P | E | E | L | A | R | Y |
| 153 | isobutyloxycarbonyl | I | K | P | E | A | P | G | E | D | A | S | P | E | E | L | A | R | Y |

TABLE 4-continued

| | | | | | | | | | | | | | | | | |
|---|---|---|---|---|---|---|---|---|---|---|---|---|---|---|---|---|
| 154 | isopropyloxycarbonyl | | I | K | P | E | A | P | G | E | D | A | S | P | E | L | A | R | Y |
| 155 | n-butyloxycarbonyl | | I | K | P | E | A | P | G | E | D | A | S | P | E | L | A | R | Y |
| 156 | ethoxycarbonyl | | I | K | P | E | A | P | G | E | D | A | S | P | E | L | A | R | Y |
| 157 | | | I | K | P | E | A | P | G | E | D | A | S | P | E | L | A | R | Y |
| 158 | | | I | K | P | E | A | P | G | E | D | A | S | P | E | L | s | R | Y |
| 159 | | | I | K | P | E | A | P | G | E | D | A | S | P | E | L | nV | R | Y |
| 160 | isocapryl | | I | K | P | E | A | P | G | E | D | A | S | P | E | L | A | R | Y |
| 161 | | | I | hK | P | E | A | P | G | E | D | A | S | P | E | L | A | hR | Y |
| 162 | isocaproyl | | I | K | P | E | A | P | G | E | D | A | S | P | E | L | A | hR | Y |
| 163 | | | I | hK | P | E | A | P | G | E | D | A | S | P | E | L | A | hR | Y |
| 164 | isocaproyl | | I | K | P | E | A | P | G | E | D | A | S | P | E | L | A | R | Y |
| 165 | | | I | hK | P | E | A | P | G | E | D | A | S | P | E | M | A | hR | Y |
| 166 | | | I | K | P | E | A | P | G | E | D | A | S | A | E | L | A | R | Y |
| 167 | | | I | hK | P | E | A | P | G | E | D | A | S | A | E | L | A | hR | Y |
| 168 | | | L | hK | P | E | A | P | G | E | D | A | hS | A | E | L | A | R | Y |
| 169 | | | I | hK | P | E | C | P | G | E | D | A | S | A | E | L | A | R | Y |
| 170 | | | I | KA | P | E | C | P | G | E | D | A | S | P | Q | L | C | R | Y |
| 171 | | | I | K | P | E | V | P | G | E | D | A | S | P | E | L | A | R | Y |
| 172 | | | L | E | P | E | V | P | G | E | D | A | S | P | E | L | N | R | Y |
| 173 | | | L | E | P | E | Y | P | G | E | D | A | S | P | E | L | A | R | Y |
| 174 | | | I | K | P | E | Y | P | G | E | D | A | S | P | E | L | N | R | Y |
| 175 | | | | | | | Y | A | P | G | E | D | A | S | P | E | L | N | R | Y |
| 176 | | | | | | | | | Aminocaproyl | | | | | | | | | | |
| 177 | | | | | | | | | Aminocaproyl | | | | | | | | | | |
| 178 | | | | | | | | | Aminocaproyl | | | | | | | | | | |
| 179 | | | | | | | | | | | | | A | | | | | | |
| 180 | | Y | I | K | P | E | A | P | G | E | D | A | Ado | P | E | L | N | R | Y |
| 181 | | Y | I | K | P | E | A | P | G | E | D | A | S | P | E | L | N | R | Y |
| 182 | | Y | I | K | P | E | A | P | G | E | D | A | S | P | E | L | N | R | Y |
| 183 | | Y | I | K | P | | | | G | E | D | A | S | P | E | L | N | R | Y |
| 184 | | Y | I | K | P | E | A | P | G | E | D | A | S | P | E | L | N | R | Y |
| 185 | | Y | I | K | P | E | A | P | G | E | D | A | S | P | E | L | N | R | Y |
| 186 | | Y | I | K(PEG 5000) | P | E | A | P | G | E | D | A | S | P | E | L | N | R | Y |
| 187 | Fmoc | | I | K(PEG 5000) | P | | | | | | | | | | | | | K(PEG 5000) | Y |
| 188 | Fmoc | | I | K(PEG 5000) | | | | | | | | | | | | | | | |
| 189 | Fmoc | | I | A | P | E | A | P | G | E | D | A | S | P | E | L | N | R | Y |
| 190 | PEG 5000 | | I | A | | | | | | | | | | | | | | | |
| 191 | | | I | K | P | E | A | P | G | E | D | A | S(O-acylation w/FA) | P | E | L | N | R | Y |
| 192 | Fmoc | | I | K | P | E | A | P | G | E | D | A | S | P | E | L | N | R | Y |
| 193 | | | I | A | P | E | A | P | G | E | D | A | S | P | E | L | N | K(oct) | Y |
| 194 | octanoic acid | | I | A | P | E | A | P | G | E | D | A | S | P | E | L | N | K(oct) | Y |
| 195 | Fmoc | | I | A | P | E | A | P | G | E | D | A | S | P | E | L | A | R | Y |
| 196 | | | I | A | P | E | A | P | G | E | D | A | S | P | E | L | N | K(stea) | Y |
| 197 | | | I | A | P | E | A | P | G | E | D | A | S | P | E | L | N | K(stea) | Y |

TABLE 4-continued

| # | | | | | | | | | | | | | | | | | | | |
|---|---|---|---|---|---|---|---|---|---|---|---|---|---|---|---|---|---|---|---|
| 198 | | | | | | | | | | | Ac | E | D | A | S | P | E | L | N | R | Y |
| 199 | | | | | | | | | | | stearyl | E | D | A | S | P | E | L | N | R | Y |
| 200 | | | | | | | | | | | octyl | E | D | A | S | P | E | L | N | R | Y |
| 201 | | | | | | | | | | | succinyl | E | D | A | S | P | E | L | N | R | Y |
| 202 | | | | | | | | | | | | | | | | | | | | | Y |
| 203 | | | | | | | | | | | | | | | | | | | | | stearyl |
| 204 | | | | I | A | P | E | A | P | E | D | A | S | P | E | L | N | R | octyl |
| 205 | | Fmoc | | I | A | P | E | A | P | E | D | A | S | P | K(PEG) | L | N | R | Y |
| 206 | | | | I | K | P | E | A | P | G | E | D | A | S | P | K(Oct) | L | N | R | Y |
| 207 | | | | I | K | P | E | A | P | G | E | D | A | S | P | K(Oct) | L | N | R | Y |
| 208 | | | | I | K | P | E | A | P | G | E | D | A | S | P | E | L | N | R | Y |
| 209 | | | | I | K | P | E | A | P | G | E | D | A | S | P | E | L | N | R | Y |
| 210 | | | | I | K | P | E | A | P | G | E | D | A | S | P | E | L | N | R | Y |
| 211 + 352 | | | | I | K | P | E | A | mimic A | E | D | A | S | P | E | L | N | R | Y |
| 212 + 353 | | | | I | K | P | E | A | P | mimic A | D | A | S | P | E | L | N | R | Y |
| 213 + 354 | | | | I | K | P | E | A | P | G | mimic A | A | S | P | E | L | N | R | Y |
| 214 + 355 | | | | I | K | P | E | A | P | G | E | mimic A | S | P | E | L | N | R | Y |
| 215 + 356 | | | | I | K | P | E | A | P | G | E | D | mimic A | P | E | L | N | R | Y |
| 216 + 357 | | | | I | K | P | E | A | P | G | E | D | A | mimic A | E | L | N | R | Y |
| 217 + 358 | | | | I | K | P | E | A | P | G | E | D | A | S | mimic A | L | N | R | Y |
| 218 | | | | I | K | P | E | A | Aib | G | E | D | A | S | P | E | L | N | R | Y |
| 219 | | | | I | K | P | E | A | P | Aib | E | D | A | S | P | E | L | N | R | Y |
| 220 | | | | I | K | P | E | A | P | G | Aib | D | A | S | P | E | L | N | R | Y |
| 221 | | | | I | K | P | E | A | P | G | E | Aib | A | S | P | E | L | N | R | Y |
| 222 | | | | I | K | P | E | A | P | G | E | D | Aib | S | P | E | L | N | R | Y |
| 223 | | | | I | K | P | E | A | P | G | E | D | A | Aib | P | E | L | N | R | Y |
| 224 | | | | I | K | P | E | A | P | G | E | D | A | S | Aib | E | L | N | R | Y |
| 225 | | | | I | K | P | E | A | P | A | E | D | A | S | P | E | L | N | R | Y |
| 226 | | | | I | K | P | E | A | P | P | E | D | A | S | P | E | L | N | R | Y |
| 227 | | | | I | K | P | E | A | P | G | A | D | A | S | P | E | L | N | R | Y |
| 228 | | | | I | K | P | E | A | P | G | E | P | A | S | P | E | L | N | R | Y |
| 229 | | | | I | K | P | E | A | P | G | E | D | P | S | P | E | L | N | R | Y |
| 230 | | | | I | K | P | E | A | P | G | E | D | A | P | P | E | L | N | R | Y |
| 231 + 359 | | | | I | K | P | E | A | mimic B | E | D | A | S | P | E | L | N | R | Y |
| 232 + 360 | | | | I | K | P | E | A | P | mimic B | D | A | S | P | E | L | N | R | Y |
| 233 + 361 | | | | I | K | P | E | A | P | G | mimic B | A | S | P | E | L | N | R | Y |
| 234 + 362 | | | | I | K | P | E | A | P | G | E | mimic B | S | P | E | L | N | R | Y |
| 235 + 363 | | | | I | K | P | E | A | P | G | E | D | mimic B | P | E | L | N | R | Y |
| 236 + 364 | | | | I | K | P | E | A | P | G | E | D | A | mimic B | E | L | N | R | Y |
| 237 + 365 | | | | I | K | P | E | A | P | G | E | D | A | S | mimic B | L | N | R | Y |
| 238 | A | | | L | E | P | E | Y | P | G | D | N | T | P | E | L | M | A | R | Y |
| 239 | Y | P | | I | K | P | E | A | P | G | E | A | P | E | Q | L | A | K | Y |
| 240 | | P | | I | | P | E | A | P | G | E | D | A | S | P | E | L | A | R | Y |
| 241 | | | | I | | P | E | A | P | G | E | D | A | S | P | E | L | A | R | Y |
| 242 | | | isocap | I | | P | E | A | P | G | E | D | A | S | P | E | L | A | R | Y |
| 243 | | | | I | K | P | E | A | P | G | E | D | A | S | P | E | L | A | R | Y |
| 244 | Y | P | | I | K | P | E | A | P | G | E | D | A | S | P | E | L | A | R | Y |
| 245 | Y | P | | I | K | P | E | A | P | G | E | D | A | S | P | E | L | A | K | Y |
| 246 | Y | P | | I | K | P | E | A | P | G | E | D | A | S | P | E | L | A | R | Y |
| 247 | Y | P | | I | K | P | E | A | P | G | E | D | A | S | P | E | L | A | R | Y |
| 248 | Y | P | | I | K | P | E | A | P | G | E | D | A | S | P | E | L | A | R | Y |
| 249 | Y | P | | I | hK | P | E | A | P | G | E | D | A | S | P | E | L | A | R | Y |

TABLE 4-continued

| # | | | | | | | | | | | | | | | | | | | | |
|---|---|---|---|---|---|---|---|---|---|---|---|---|---|---|---|---|---|---|---|---|
| 250 | | | I | hK | P | E | A | P | G | E | D | A | S | P | E | E | L | A | R | Y |
| 251 | Y | | I | hK | P | E | A | P | G | E | D | A | S | P | E | E | L | A | R | Y |
| 252 | | P | I | hK | P | E | A | P | G | E | D | A | S | P | E | E | L | A | R | Y |
| 253 | | | P | hK | P | E | A | P | G | E | D | A | S | P | E | E | L | A | R | Y |
| 254 | isocap | | P | K | P | E | A | P | G | E | D | A | S | P | E | E | L | A | R | Y |
| 255 | | | P | K | P | E | A | P | G | E | D | A | S | P | E | E | L | A | R | Y |
| 256 | | | P | K | P | E | A | P | G | E | D | A | P | P | E | E | L | A | R | Y |
| 257 | Y | | I | hK | P | E | A | P | G | E | D | A | S | P | E | E | L | A | R | Y |
| 258 | | P | I | hK | P | E | A | P | G | E | D | A | S | P | E | E | L | A | R | Y |
| 259 | Y | | I | hK | P | E | A | P | G | E | D | A | S | P | E | E | L | A | R | Y |
| 260 | | P | P | hK | P | E | A | P | G | E | D | A | S | P | E | E | L | A | R | Y |
| 261 | isocap | | P | K | P | E | A | P | G | E | D | A | S | P | E | E | L | A | R | Y |
| 262 | | | P | K | P | E | H | P | G | E | D | A | S | P | E | E | L | A | R | Y |
| 263 | | | P | K | P | E | A | P | G | E | D | A | S | P | E | E | L | A | R | Y |
| 264 | isocap | | P | K | P | E | H | P | G | E | D | A | S | P | E | E | L | A | R | Y |
| 265 | | | P | R | P | E | A | P | G | E | D | A | S | P | E | E | L | A | R | Y |
| 266 | Y | P | I | R | P | E | A | P | G | E | D | A | S | P | E | E | L | A | R | Y |
| 267 | Y | P | I | R | P | E | A | P | G | E | D | A | S | P | E | E | L | A | R | Y |
| 268 | | | P | R | P | E | A | P | G | E | D | A | S | P | E | E | L | A | R | Y |
| 269 | 8-amino octanoyl | | I | R | P | E | A | P | G | E | D | A | S | P | E | E | L | A | R | Y |
| 270 | Y | P | I | K | P | E | A | P | G | E | D | A | S | P | E | E | L | A | R | Y |
| 271 | Y | P | I | K | P | E | A | P | G | E | D | A | S | P | E | E | L | A | R | Y |
| 272 | 8-amino octanoyl | | I | K | P | E | A | P | G | E | D | A | S | P | E | E | L | A | R | Y |
| 273 | Y | P | | K | P | E | A | P | G | E | D | A | S | P | E | E | L | A | R | Y |
| 274 | | isocap | P | K | P | E | A | P | G | E | D | A | P | A | E | E | L | A | R | Y |
| 275 | | P | I | K | P | E | A | P | G | E | D | A | P | A | E | E | L | A | R | Y |
| 276 | isocap | | I | K | P | E | A | P | G | E | D | A | P | A | E | E | L | A | R | Y |
| 277 | | G(Oct) | P | K | P | E | A | P | G | E | D | A | P | A | E | E | L | A | R | Y |
| 278 | Fmoc-G(Oct) | | G(Oct) | K | P | E | A | P | G | E | D | A | P | A | E | E | L | A | R | Y |
| 279 | | P | S | E | P | D | N | P | G | E | D | A | P | A | D | E | L | A | R | Y |
| 280 | Y | | L | E | P | V | Y | P | G | D | N | A | T | P | Q | E | M | N | R | Y |
| 281 | A | P | L | E | P | V | Y | P | G | D | N | A | T | P | Q | E | M | N | R | Y |
| 282 | A | P | L | E | P | V | Y | P | G | D | N | A | T | P | Q | E | M | N | R | Y |
| 283 | A | P | L | E | P | V | Y | P | G | D | N | A | T | P | Q | E | M | N | R | Y |
| 284 | A | P | L | E | P | V | Y | P | G | D | N | A | T | P | Q | E | M | N | R | Y |
| 285 | A | P | L | E | P | V | Y | P | G | D | N | A | T | P | Q | E | M | N | R | Y |
| 286 | A | P | L | E | P | V | Y | P | G | D | N | A | T | P | Q | E | M | A | R | Y |
| 287 | A | P | L | E | P | V | Y | P | G | D | N | A | S | P | Q | E | M | N | R | K |
| 288 | A | P | L | E | P | V | Y | P | G | D | N | A | T | P | Q | E | L | N | R | Y |
| 289 | A | P | L | E | P | V | Y | P | G | D | N | A | T | P | E | E | L | L | R | Y |
| 290 | A | P | L | E | P | V | A | P | G | D | D | A | S | P | E | E | L | L | R | Y |
| 291 | A | P | L | E | P | E | A | P | G | E | D | A | S | P | E | E | L | L | R | Y |

TABLE 4-continued

| # | | | | | | | | | | | | | | | | | | | | | |
|---|---|---|---|---|---|---|---|---|---|---|---|---|---|---|---|---|---|---|---|---|---|
| 302 | A | | P | L | K | P | E | A | P | G | E | D | A | S | P | E | E | L | N | R | Y |
| 303 | isocap A | | P | L | E | P | E | Y | A | P | G | D | D | A | T | P | E | Q | M | N | R | Y |
| 304 | A | | P | L | E | P | E | A | P | G | D | N | A | T | P | E | Q | M | N | hR | Y |
| 305 | isocap A | | P | L | E | P | E | Y | A | P | G | D | N | A | T | P | E | Q | M | N | hR | Y |
| 306 | A | | P | M | E | P | E | V | A | P | G | D | N | A | T | P | E | Q | M | N | hK | Y |
| 307 | A | | P | L | E | P | E | V | A | P | G | D | N | A | T | P | E | Q | M | N | R | Y |
| 308 | Y | | P | L | K | P | E | V | A | P | G | D | D | A | S | P | E | Q | L | N | R | Y |
| 309 | | | | I | K | P | E | A | P | G | E | D | A | S | P | E | E | L | N | Q | Y |
| 310 | | P | I | K | P | E | A | P | G | E | D | A | S | P | E | E | L | A | Q | Y |
| 311 | Y | | P | I | K | P | E | A | P | G | E | D | A | S | P | E | E | L | A | Q | Y |
| 312 | Y | | P | I | K | P | E | A | P | G | E | D | A | S | P | E | E | L | A | Q | Y |
| 313 | Y | | P | I | K | P | E | A | P | G | E | D | A | S | P | E | E | L | A | Q | Y |
| 314 | Y | | P | I | K | P | E | A | P | G | E | D | A | S | P | E | E | L | A | Q | Y |
| 315 | Y | | P | I | K | P | E | A | P | G | E | D | A | S | P | E | E | L | A | Q | Y |
| 316 | Y | | P | I | K | P | E | A | P | G | E | D | A | S | P | E | E | L | A | Q | Y |
| 317 | Y | | dA | I | K | P | E | A | P | G | E | D | A | S | P | E | E | L | A | Q | Y |
| 318 | Y | | P | I | K | P | E | A | P | G | E | D | A | S | P | E | E | L | A | Q | Y |
| 319 | isocap Y | | P | I | K | P | E | A | P | G | E | D | A | S | P | E | E | L | A | Q | Y |
| 320 | Y | | P | I | K | P | E | A | P | G | E | D | A | S | P | E | E | L | A | Q | Y |
| 321 | Y | | P | I | K | P | E | A | P | G | E | D | A | S | P | E | E | L | A | Q | Y |
| 322 | Y | | P | I | K | P | E | A | P | G | E | D | A | S | P | E | E | L | A | Q | Y |
| 323 | Y | | P | I | K | P | E | A | P | G | E | D | A | S | P | E | E | L | A | Q | Y |
| 324 | Y | | P | I | K | P | E | A | P | G | E | D | A | S | P | E | E | L | A | Q | Y |
| 325 | Y | | P | I | K | P | E | A | P | G | E | D | A | S | P | E | E | L | A | Q | Y |
| 326 | Y | | P | I | K | P | E | A | P | G | E | D | A | S | P | E | E | L | A | Q | Y |
| 327 | Y | | P | I | K | P | E | A | P | G | E | D | A | S | P | E | E | L | A | Q | Y |
| 328 | Y | | P | I | K | P | E | A | P | G | E | D | A | S | P | E | E | L | A | Q | Y |
| 329 | Y | | P | I | hK | P | E | A | P | G | E | D | A | S | P | E | E | L | A | Q | Y |
| 330 | Y | | P | I | hR | P | E | A | P | G | E | D | A | S | P | E | E | L | A | Q | Y |
| 331 | isocap Y | | P | I | hR | P | E | A | hP | G | E | D | A | S | hP | E | E | L | A | Q | Y |
| 332 | Y | | P | I | K | P | E | A | hP | G | E | D | A | S | Aib | E | E | L | A | Q | Y |
| 333 | Y | | P | I | K | P | E | A | Aib | Sar | E | D | A | S | P | E | E | L | A | Q | Y |
| 334 | Y | | P | I | K | P | E | A | G | P | E | D | A | S | P | E | E | L | A | Q | Y |
| 335 | Y | | P | I | K | P | E | A | P | G | E | D | A | S | P | E | E | L | A | Q | Y |
| 336 | Y | | P | I | K | P | E | A | P | G | E | D | A | hS | P | E | E | L | A | Q | Y |
| 337 | Y | | P | I | K | P | E | A | P | G | E | D | A | Dap | P | E | E | L | A | Q | Y |
| 338 | Y | | P | I | K | P | E | A | P | G | E | D | A | S | P | Q | E | L | A | Q | Y |
| 339 | Y | | P | I | K | P | E | A | P | G | E | D | A | S | P | D | E | L | A | Q | Y |
| 340 | Y | | P | I | K | P | E | A | P | G | E | D | A | S | A | E | E | L | A | Q | Y |
| 341 | Y | | P | I | K | P | E | A | P | G | E | D | A | S | A | Q | E | M | A | Q | Y |
| 342 | Y | | P | I | K | P | E | A | P | G | E | D | A | S | A | S | E | L | A | Q | Y |
| 343 | Y | | P | I | K | P | E | A | P | G | E | D | A | S | P | Q | E | L | A | Q | Y |
| 344 | Y | | P | I | hK | P | E | A | P | G | E | D | A | S | P | E | E | M | A | Q | Y |
| 345 | Y | | P | I | K | P | E | A | P | G | E | D | A | S | P | E | E | L | A | Q | Y |
| 346 | Y | | P | I | hK | P | E | A | P | G | E | D | A | S | P | E | E | M | A | Q | Y |
| 347 | Y | | P | I | hK | P | E | A | P | G | E | D | A | S | P | E | E | L | A | Q | Y |
| 348 | Formula III | | | | | | | | | | | | | | | | | | | | | |
| 349 | Formula IV | | | | | | | | | | | | | | | | | | | | | |
| 350 | Formula V | | | | | | | | | | | | | | | | | | | | | |
| 351 | hPYY C-terminal Motiff - 32-35 | | | | | | | | | | | | | | | | | | | | | |
| 436 | | | P | P | K | P | E | A | P | G | E | D | A | S | P | E | E | L | N | R | Y |
| 437 | isocap | | P | P | K | P | E | A | P | G | E | D | A | S | P | E | E | L | A | R | Y |

TABLE 4-continued

| | | | | | | | | | | | | | | | | | | |
|---|---|---|---|---|---|---|---|---|---|---|---|---|---|---|---|---|---|---|
| 438 | | | K | P | E | H | P | G | E | D | A | R | S | P | E | E | L | A | R | Y |
| 439 | | | K | P | E | H | P | G | E | D | A | R | S | P | E | E | L | A | R | Y |
| 440 | isocap | | K | P | E | A | P | G | E | D | A | H | S | P | E | E | L | A | K | Y |
| 441 | | | K | I | E | H | P | G | E | D | A | H | S | A | E | E | L | N | K | Y |
| 442 | | | K | P | E | A | P | G | E | D | A | R | S | P | E | E | L | N | R | Y |
| 443 | isobutyloxycarbonyl | | K | P | E | H | P | G | E | D | A | H | S | A | E | E | L | N | R | Y |
| 444 | | | K | P | E | A | P | G | E | D | A | H | S | P | E | E | L | N | R | Y |
| 445 | isocap | | K | P | E | A | P | G | E | D | A | H | S | P | E | E | L | N | R | Y |
| 446 | isocap | | K | P | E | H | P | G | E | D | A | R | S | P | E | E | L | N | R | Y |
| 447 | isocap | | K | P | E | A | P | G | E | D | A | R | S | P | E | E | L | N | R | Y |
| 448 | | | K | I | E | A | P | G | E | D | A | R | S | P | E | E | L | N | R | Y |
| 449 | | | K | P | E | A | P | G | E | D | A | R | S | P | E | E | L | N | R | Y |
| 450 | | | K | P | E | A | P | G | E | D | A | R | S | P | E | E | L | N | A(NMe) | Y |
| 451 | Dansyl | | K | P | E | A | P | G | E | D | A | R | S | P | E | E | L | A | R | Y |
| 452 | I | | A | I | E | A | P | G | E | D | A | R | P | P | E | E | L | A | R | Y |
| 453 | isocap | | K | K | E | H | P | G | E | D | A | R | S | P | E | E | L | A | R | Y |
| 454 | octanoyl | | K | P | E | A | P | G | E | D | A | R | S | P | E | E | L | A | R | Y |
| 455 | isobutyloxycarbonyl | | K | P | E | A | P | G | E | D | A | R | S | P | E | D | L | A | R | Y |
| 456 | octylGly | | K | P | E | A | P | G | E | D | A | R | S | P | E | E | L | A | R | Y |
| 457 | isocap | | K | P | E | A | P | A | E | D | A | R | S | A | E | E | L | A | R | Y |
| 458 | isocap | | K | P | E | A | P | G | E | D | A | R | S | A | E | E | L | A | R | Y |
| 459 | | | K | P | E | G | P | G | E | D | A | R | S | A | E | E | L | A | R | Y |
| 460 | isocap | | K | P | E | A | P | G | E | D | P | R | P | P | E | E | L | A | R | Y |
| 461 | isocap | | S | P | E | A | P | G | E | D | A | P | P | A | E | E | L | A | R | Y |
| 462 | isocap | | K | P | E | A | P | G | E | D | A | R | S | S | E | E | L | A | K | Y |
| 463 | | | K | V | E | A | P | G | E | D | A | R | P | A | E | E | L | A | R | Y |
| 464 | isocap | | K | P | E | H | P | G | E | D | A | R | S | P | E | E | L | A | R | Y |
| 465 | | | K | P | E | A | P | G | E | D | A | R | S | P | E | E | L | A | R | Y |
| 466 | | | K | P | E | A | P | G | E | D | A | R | S | P | E | E | L | A | R | Y |
| 467 | isocap | | K | I | E | H | P | G | E | D | A | R | S | P | E | E | L | A | R | Y |
| 468 | isocap | | A | I | E | A | P | G | E | D | A | R | S | P | E | E | L | A | K | Y |
| 469 | isocap | | K | I | E | A | P | G | E | D | A | R | S | P | E | E | L | A | K | Y |
| 470 | isocaproyl | | K | I | E | A | P | G | E | D | A | R | S | P | E | E | L | A | R | Y |
| 471 | 8-amino octanoyl | P | A | I | E | A | P | G | E | D | A | R | S | P | E | E | L | A | Q | Y |
| 472 | BH modified-Y | | A | I | E | A | P | G | E | D | A | R | S | P | E | E | L | A | Q | Y |
| 473 | BH modified-Y | P | K-(BH modified) | I | E | A | P | G | E | D | A | R | P | P | E | E | L | A | Q | Y |
| 474 | BH modified-P | | K | P | E | A | P | G | E | D | A | R | S | P | E | E | L | A | R | Y |
| 475 | BH modified-P | | A | P | E | A | P | G | E | D | A | R | S | P | E | E | L | A | R | Y |

| ID | 21 | 22 | 23 | 24 | 25 | 26 | 27 | 28 | 29 | 30 | 31 | 32 | 33 | 34 | 35 | 36 | 37 |
|---|---|---|---|---|---|---|---|---|---|---|---|---|---|---|---|---|---|
| 1 | A | A | D | L | R | R | Y | I | N | M | L | T | R | P | R | Y | |
| 2 | Y | A | S | L | R | H | L | L | N | L | V | T | R | Q | R | Y | |
| 3 | Y | A | S | L | R | H | Y | L | N | L | V | T | R | Q | R | Y | |

Formula VI — 481
Formula VII — 482

TABLE 4-continued

| | | | | | | | | | | | | | | | | |
|---|---|---|---|---|---|---|---|---|---|---|---|---|---|---|---|---|
| 4 | Y | S | A | L | R | H | Y | I | N | L | I | T | R | Q | R | Y |
| 5 | Y | S | A | L | R | H | Y | I | N | L | I | Aib | R | Q | R | Y |
| 6 | Y | S | A | L | R | H | Y | I | N | L | A | T | R | Q | R | Y |
| 7 | I | I | A | D | R | H | Y | I | N | L | I | T | R | Q | R | Y |
| 8 | I | T | A | D | R | H | Y | I | N | L | V | T | R | Q | R | Y |
| 9 | Y | T | A | L | R | H | Y | I | N | L | I | T | R | Q | R | Y |
| 10 | Y | S | A | L | R | H | Y | I | N | L | I | T | R | Q | R | Y |
| 11 | F | S | A | L | R | H | Y | I | N | L | V | T | R | Q | R | Y |
| 12 | M | L | A | V | R | H | Y | I | N | L | I | T | R | Q | R | Y |
| 13 | M | L | A | V | R | H | Y | I | N | L | I | T | R | Q | R | Y |
| 14 | K | A | A | L | R | N | Y | I | N | L | I | T | R | Q | R | Y |
| 15 | F | S | A | L | R | H | Y | I | N | L | V | T | R | Q | R | Y |
| 16 | M | T | A | L | R | H | Y | I | N | L | I | T | R | Q | R | Y |
| 17 | L | T | A | L | R | H | Y | I | N | L | I | T | R | Q | R | Y |
| 18 | L | T | A | L | R | H | Y | I | N | L | V | T | R | Q | R | Y |
| 19 | Y | A | A | L | R | A | Y | V | N | L | I | T | R | Q | R | Y |
| 20 | Y | A | S | L | R | R | Y | I | N | M | L | T | R | Q | R | Y |
| 21 | Y | A | A | L | R | A | Y | L | N | L | I | T | R | Q | R | Y |
| 22 | A | A | D | L | R | H | Y | L | N | L | I | T | R | Q | R | Y |
| 23 | Y | S | A | L | R | A | Y | I | N | L | I | T | R | Q | R | Y |
| 24 | Y | S | A | L | R | H | Y | I | N | L | I | T | R | Q | R | Y |
| 25 | Y | A | A | L | R | A | Y | V | N | L | I | T | R | Q | R | Y |
| 26 | L | T | A | L | R | H | Y | I | N | L | V | T | R | Q | R | Y |
| 27 | | | | | | | | | | | | | | | | |
| 28 | | | | | | | | | | | | | | | | |
| 29 | | | | | | | | | | | | | | | | |
| 30 | | | | | | | | | | | | | | | | |
| 31 | Y | A | S | L | R | H | Y | L | N | L | V | T | R | Q | R | Y |
| 32 | Y | A | S | L | R | H | Y | L | N | L | V | T | R | Q | R | Y |
| 33 | Y | A | S | L | R | H | Y | L | N | L | V | T | R | Q | R | Y |
| 34 | Y | A | S | L | R | H | Y | L | N | L | V | T | R | Q | R | Y |
| 35 | Y | A | S | L | R | H | Y | L | N | L | V | T | R | Q | R | Y |
| 36 | Y | A | S | L | R | H | Y | L | N | L | V | T | R | Q | R | Y |
| 37 | Y | A | S | L | R | H | Y | L | N | L | V | T | R | Q | R | Y |
| 38 | Y | A | S | L | R | H | Y | L | N | L | V | T | R | Q | R | Y |
| 39 | Y | A | S | L | R | H | Y | L | N | L | V | T | R | Q | R | Y |
| 40 | Y | A | S | L | R | H | Y | L | N | L | V | T | R | Q | R | Y |
| 41 | Y | A | S | L | R | H | Y | L | N | L | V | T | R | Q | R | Y |
| 42 | Y | A | S | L | R | H | Y | L | N | L | V | T | R | Q | R | Y |
| 43 | Y | A | A | L | R | A | Y | L | N | L | V | T | R | Q | R | Y |
| 44 | Y | A | S | L | R | H | Y | L | N | A | V | T | R | Q | R | Y |
| 45 | Y | A | S | L | R | H | Y | L | N | L | V | T | R | Q | R | Y |
| 46 | Y | A | S | L | R | H | Y | L | N | L | V | T | R | Q | R | Y |
| 47 | Y | A | A | L | R | A | Y | L | N | L | V | T | R | Q | R | Y |
| 48 | Y | A | S | L | R | H | Y | L | N | L | V | T | R | Q | R | Y |
| 49 | Y | A | S | L | R | H | Y | L | N | L | V | T | R | Q | R | Y |
| 50 | Y | A | S | L | R | H | Y | L | N | L | V | T | R | Q | R | Y |
| 51 | Y | A | S | L | R | H | Y | L | N | L | V | T | R | Q | R | Y |
| 52 | Y | A | A | L | R | R | Y | H | L | N | L | T | R | Q | R | Y |
| 53 | Y | Y | A | S | L | L | H | Y | L | L | L | V | T | T | R | R |
| 54 | Y | Y | A | S | L | L | R | H | Y | L | N | V | V | T | T | Q | R | Y |
| 55 | Y | Y | A | A | S | R | H | Y | N | N | L | V | R | Q | R | Y |

TABLE 4-continued

| Pos | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| 56 | Y | Y | A | S | L | R | H | Y | L | N | L | V | T | R | Q | R | Y |
| 57 | Y | Y | A | S | L | R | H | Y | L | N | L | V | T | R | Q | R | Y |
| 58 | Y | Y | A | S | L | R | H | Y | L | N | L | V | T | R | Q | R | Y |
| 59 | Y | Y | A | S | L | R | H | Y | L | N | L | V | T | R | Q | R | Y |
| 60 | Y | Y | A | S | L | R | H | Y | L | N | L | V | T | R | Q | R | Y |
| 61 | Y | Y | A | S | L | R | H | Y | L | N | L | V | T | R | Q | R | Y |
| 62 | Y | Y | A | S | L | R | H | Y | L | N | L | V | T | R | Q | R | Y |
| 63 | Y | Y | A | S | L | R | H | Y | L | N | L | V | T | R | Q | R | Y |
| 64 | Y | Y | A | S | L | R | H | Y | L | N | L | V | T | R | Q | R | Y |
| 65 | Y | Y | A | S | L | R | H | Y | L | N | L | V | T | R | Q | R | Y |
| 66 | Y | Y | A | S | L | R | H | Y | L | N | L | V | T | R | Q | R | Y |
| 67 | Y | Y | A | S | L | R | H | Y | L | N | L | V | T | R | Q | R | Y |
| 68 | Y | Y | A | S | L | R | H | Y | L | N | L | V | T | R | Q | R | Y |
| 69 | Y | Y | A | S | L | R | H | Y | L | N | L | V | T | R | Q | R | Y |
| 70 | Y | Y | A | S | L | R | H | Y | L | N | L | V | T | R | Q | R | Y |
| 71 | Y | Y | A | S | L | R | H | Y | L | N | L | V | T | R | Q | R | Y |
| 72 | Y | A | A | S | L | R | H | Y | L | N | L | V | T | R | Q | R | Y |
| 73 | Y | Y | A | S | L | R | H | Y | L | N | L | V | T | R | Q | R | Y |
| 74 | Y | Y | A | S | L | R | H | A | L | N | L | V | T | R | Q | R | Y |
| 75 | Y | Y | S | L | A | R | H | Y | L | N | L | V | T | R | Q | R | Y |
| 76 | Y | A | S | L | R | H | A | Y | N | L | L | V | T | R | Q | R | Y |
| 77 | Y | A | S | L | R | H | Y | L | N | L | V | T | R | Q | R | Y | Y |
| 78 | Y | A | S | L | R | H | Y | L | N | L | V | T | R | Q | R | Y | Y |
| 79 | Y | A | S | L | R | H | Y | L | N | L | V | T | R | Q | R | Y | Y |
| 80 | Y | A | S | L | R | H | Y | L | N | L | V | T | R | Q | R | Y | Y |
| 81 | Y | A | S | L | R | H | Y | L | N | L | V | T | R | Q | R | Y | Y |
| 82 | Y | A | S | L | R | H | Y | L | N | L | V | T | R | Q | R | Y | Y |
| 83 | Y | A | S | L | R | H | Y | L | N | L | V | T | R | Q | R | Y | Y |
| 84 | Y | A | S | L | R | H | Y | L | N | L | V | T | R | Q | R | Y | Y |
| 85 | Y | A | S | L | R | H | Y | L | N | L | V | T | A | Q | Q | A | Y |
| 86 | Y | A | S | L | R | H | Y | L | N | L | V | T | R | Q | R | Y | Y |
| 87 | Y | A | S | L | R | H | Y | L | N | L | V | T | R | Q | R | Y | Y |
| 88 | | | S | L | R | H | Y | L | N | L | V | T | R | Q | R | Y | Y |
| 89 | | | S | L | R | H | Y | L | N | L | V | T | R | Q | R | Y | Y |
| 90 | | | S | L | R | H | Y | L | N | L | V | T | R | Q | R | Y | Y |
| 91 | | | S | L | R | H | Y | L | N | L | V | T | R | Q | R | Y | Y |
| 92 | | | S | L | R | H | Y | L | N | L | V | T | R | Q | R | Y | Y |
| 93 | | | S | L | R | H | Y | L | N | L | V | T | R | Q | R | Y | Y |
| 94 | | | S | L | R | H | Y | L | N | L | V | T | R | Q | R | Y | Y |
| 95 | | | S | L | R | H | Y | L | N | L | V | T | R | Q | R | Y | Y |
| 96 | | | S | L | R | H | Y | L | N | L | V | T | R | Q | R | Y | Y |
| 97 | | | S | L | R | H | Y | L | N | L | V | T | R | Q | R | Y | Y |
| 98 | | | S | L | R | H | Y | L | N | L | V | T | R | Q | R | Y | Y |
| 99 | | | S | L | R | H | Y | L | N | L | V | T | R | Q | R | Y | Y |
| 100 | | | S | L | R | H | Y | L | N | L | V | T | R | Q | R | Y | Y |
| 101 | | | S | L | R | H | Y | L | N | L | V | T | R | Q | R | Y | Y |
| 102 | | | S | L | R | H | Y | L | N | L | V | T | R | Q | R | Y | Y |
| 103 | | | S | L | R | H | Y | L | N | L | V | T | R | Q | R | Y | Y |
| 104 | | | S | L | R | H | Y | L | N | L | V | T | R | Q | R | Y | Y |
| 105 | | | S | L | R | H | Y | L | N | L | V | T | R | Q | R | Y | Y |
| 106 | | | S | L | R | H | Y | L | N | L | V | T | R | Q | R | Y | Y |
| 107 | | | S | L | R | H | Y | L | N | L | V | T | R | Q | R | Y | Y |

TABLE 4-continued

| # | 1 | 2 | 3 | 4 | 5 | 6 | 7 | 8 | 9 | 10 | 11 | 12 | 13 | 14 | 15 | 16 |
|---|---|---|---|---|---|---|---|---|---|----|----|----|----|----|----|----|
| 108 | Y | A | S | L | R | H | Y | L | N | L | V | T | R | Q | R | Y |
| 109 | Y | A | S | L | R | H | Y | L | N | L | V | T | R | Q | R | Y |
| 110 | Y | A | S | L | R | H | Y | L | N | L | V | T | R | Q | R | Y |
| 111 | A | dA | S | L | R | H | Y | L | N | L | V | T | R | Q | R | Y |
| 112 | Y | A | A | L | R | H | Y | L | N | L | V | T | R | Q | R | Y |
| 113 | Y | A | A | L | A | H | Y | L | N | L | V | T | R | Q | R | Y |
| 114 | Y | A | S | L | A | A | Y | L | N | L | V | T | K | Q | R | Y |
| 115 | Y | A | S | L | R | K | A | Y | L | A | L | V | T | R | Q | R | Y |
| 116 | Y | A | S | L | R | H | Y | L | N | L | V | T

TABLE 4-continued

| # | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| 160 | Y | A | S | L | R | H | Y | L | N | L | V | T | R | Q | R | Y |
| 161 | Y | A | S | L | R | H | Y | L | N | L | V | T | R | Q | R | Y |
| 162 | Y | A | S | L | R | H | Y | L | N | L | V | T | R | Q | R | Y |
| 163 | Y | A | S | L | R | H | Y | L | N | L | V | T | R | Q | R | Y |
| 164 | Y | A | S | L | R | H | Y | L | N | L | V | T | R | Q | R | Y |
| 165 | Y | A | S | L | R | A | Y | L | N | L | V | T | R | Q | R | Y |
| 166 | Y | A | S | L | R | A | Y | L | N | L | V | T | R | Q | R | Y |
| 167 | Y | A | S | L | R | A | Y | L | N | L | V | T | R | Q | R | Y |
| 168 | Y | A | S | L | R | A | Y | L | N | L | V | T | R | Q | R | Y |
| 169 | Y | A | S | L | R | H | Y | L | N | L | V | T | R | Q | R | Y |
| 170 | Y | A | S | L | K | H | Y | L | N | L | V | T | R | Q | R | Y |
| 171 | Y | A | S | L | R | H | Y | L | N | L | I | T | R | Q | R | Y |
| 172 | Y | A | S | L | R | H | Y | L | N | L | V | T | R | Q | R | Y |
| 173 | Y | A | S | L | R | H | Y | L | N | L | V | T | R | Q | R | Y |
| 174 | YY | A | S | L | R | H | Y | L | N | L | V | T | R | Q | R | Y |
| 175 | Y | A | S | L | R | A | Y | L | N | L | V | T | R | Q | R | Y |
| 176 | Y | A | S | L | R | H | Y | L | N | L | V | T | R | Q | R | Y |
| 177 | Y | A | S | L | R | H | Y | L | N | L | V | T | R | Q | R | Y |
| 178 | Y | A | S | L | R | H | Y | L | N | L | V | T | R | Q | R | Y |
| 179 | | | S (O-acylation w/FA) | | | | | | | | | | | | | |
| 180 | Y | A | S | L | R | H | Y | L | N | L | V | T | R | Q | R | Y |
| 181 | Y | A | S | L | R | H | Y | L | N | L | V | T | R | Q | R | Y |
| 182 | Y | A | | L | R | H | Y | L | N | L | V | T | R | Q | R | Y |
| 183 | | | | | | | | | | | | | | | | |
| 184 | | A | S | L | R | H | Y | L | N | L | V | T | R | Q | R | Y |
| 185 | Y | A | S | L | R | H | Y | L | N | L | V | T | R | Q | R | Y |
| 186 | Y | A | S | L | R | H | Y | L | N | L | V | T | R | Q | R | Y |
| 187 | Y | A | S | L | R | H | Y | L | N | L | V | T | R | Q | R | Y |
| 188 | Y | A | S | L | R | H | Y | L | N | L | V | T | R | Q | R | Y |
| 189 | Y | A | S | L | R | H | Y | L | N | L | V | T | R | Q | R | Y |
| 190 | Y | A | S | L | R | H | Y | L | N | L | V | T | R | Q | R | Y |
| 191 | Y | A | S | L | R | H | Y | L | N | L | V | T | R | Q | R | Y |
| 192 | Y | A | S | L | R | H | Y | L | N | L | V | T | R | Q | R | Y |
| 193 | Y | A | S | L | R | H | Y | L | N | L | V | T | R | Q | R | Y |
| 194 | Y | A | S | L | R | H | Y | L | N | L | V | T | R | Q | R | Y |
| 195 | Y | A | S | L | R | H | Y | L | N | L | V | T | R | Q | R | Y |
| 196 | Y | A | S | L | R | H | Y | L | N | L | V | T | R | Q | R | Y |
| 197 | Y | A | S | L | R | H | Y | L | N | L | V | T | R | Q | R | Y |
| 198 | Y | A | S | L | R | H | Y | L | N | L | V | T | Q | R | R | Y |
| 199 | Y | A | S | L | R | H | Y | L | N | L | T | R | Q | Q | Y | Y |
| 200 | A | A | S | L | R | H | Y | L | L | L | T | T | Q | R | R | Y |
| 201 | A | A | L | R | R | H | Y | L | N | L | V | T | R | Q | R | Y |
| 202 | Y | S | L | L | L | Y | Y | N | L | V | T | T | R | Q | R | Y |
| 203 | Y | A | S | L | R | H | Y | L | N | L | V | T | R | Q | R | Y |
| 204 | Y | A | S | L | R | H | Y | L | N | L | V | T | R | Q | R | Y |
| 205 | Y | A | S | L | R | H | Y | L | N | L | V | T | R | Q | R | Y |
| 206 | Y | A | S | L | R | H | Y | L | N | L | V | T | R | Q | R | Y |
| 207 | Y | A | S | L | R | H | Y | L | N | L | V | T | R | Q | R | Y(8-Am-3,6-dioxaoct) |

TABLE 4-continued

| | | | | | | | | | | | | | | | |
|---|---|---|---|---|---|---|---|---|---|---|---|---|---|---|---|
| 208 | Y | A | S | L | R | H | Y | L | N | L | V | T | R | Q | R | Y(11-Am-undecanoyl) |
| 209 | Y | A | S | L | R | H | Y | L | N | L | V | T | R | Q | R | Y(12 Ado) |
| 210 | Y | A | S | L | R | H | Y | L | N | L | V | T | R | Q | R | Y(8-Oct) |
| 211 + 352 | Y | A | S | L | R | H | Y | L | N | L | V | T | R | Q | R | Y |
| 212 + 353 | Y | A | S | L | R | H | Y | L | N | L | V | T | R | Q | R | Y |
| 213 + 354 | Y | A | S | L | R | H | Y | L | N | L | V | T | R | Q | R | Y |
| 214 + 355 | Y | A | S | L | R | H | Y | L | N | L | V | T | R | Q | R | Y |
| 215 + 356 | Y | A | S | L | R | H | Y | L | N | L | V | T | R | Q | R | Y |
| 216 + 357 | Y | A | S | L | R | H | Y | L | N | L | V | T | R | Q | R | Y |
| 217 + 358 | Y | A | S | L | R | H | Y | L | N | L | V | T | R | Q | R | Y |
| 218 | Y | A | S | L | R | H | Y | L | N | L | V | T | R | Q | R | Y |
| 219 | Y | A | S | L | R | H | Y | L | N | L | V | T | R | Q | R | Y |
| 220 | Y | A | S | L | R | H | Y | L | N | L | V | T | R | Q | R | Y |
| 221 | Y | A | S | L | R | H | Y | L | N | L | V | T | R | Q | R | Y |
| 222 | Y | A | S | L | R | H | Y | L | N | L | V | T | R | Q | R | Y |
| 223 | Y | A | S | L | R | H | Y | L | N | L | V | T | R | Q | R | Y |
| 224 | Y | A | S | L | R | H | Y | L | N | L | V | T | R | Q | R | Y |
| 225 | Y | A | S | L | R | H | Y | L | N | L | V | T | R | Q | R | Y |
| 226 | Y | A | S | L | R | H | Y | L | N | L | V | T | R | Q | R | Y |
| 227 | Y | A | S | L | R | H | Y | L | N | L | V | T | R | Q | R | Y |
| 228 | Y | A | S | L | R | H | Y | L | N | L | V | T | R | Q | R | Y |
| 229 | Y | A | S | L | R | H | Y | L | N | L | V | T | R | Q | R | Y |
| 230 | Y | A | S | L | R | H | Y | L | N | L | V | T | R | Q | R | Y |
| 231 + 359 | Y | A | S | L | R | H | Y | L | N | L | V | T | R | Q | R | Y |
| 232 + 360 | Y | A | S | L | R | H | Y | L | N | L | V | T | R | Q | R | Y |
| 233 + 361 | Y | A | S | L | R | H | Y | L | N | L | V | T | R | Q | R | Y |
| 234 + 362 | Y | A | S | L | R | H | Y | L | N | L | V | T | R | Q | R | Y |
| 235 + 363 | Y | A | S | L | R | H | Y | L | N | L | V | T | R | Q | R | Y |
| 236 + 364 | Y | A | S | L | R | H | Y | L | N | L | V | T | R | Q | R | Y |
| 237 + 365 | Y | A | S | L | R | H | Y | L | N | L | V | T | R | Q | R | Y |
| 238 | Y | S | A | L | R | H | Y | I | N | L | A | T | R | Q | R | Y |
| 239 | Y | S | A | L | R | H | Y | I | N | L | I | T | R | Q | R | Y |
| 240 | Y | S | A | L | R | H | Y | I | N | L | I | T | R | Q | R | Y |
| 241 | Y | S | A | L | R | H | Y | I | N | L | I | T | R | Q | R | Y |
| 242 | Y | S | A | L | R | H | Y | I | N | L | I | T | R | Q | R | Y |
| 243 | Y | S | A | L | R | H | Y | I | N | L | I | T | R | Q | R | Y |
| 244 | Y | S | A | L | R | A | Y | I | N | L | I | T | R | Q | R | Y |
| 245 | Y | A | S | L | R | H | Y | I | N | L | I | T | R | Q | R | Y |
| 246 | Y | A | S | L | R | H | Y | I | N | L | I | T | R | Q | R | Y |
| 247 | Y | S | A | L | R | A | Y | I | N | L | I | T | R | Q | R | Y |
| 248 | Y | A | S | L | R | A | Y | I | N | L | I | T | R | Q | R | Y |
| 249 | Y | S | A | L | R | H | Y | I | N | L | I | T | R | Q | R | Y |
| 250 | Y | S | A | L | R | H | Y | I | N | L | I | T | R | Q | R | Y |
| 251 | Y | A | S | L | R | H | Y | I | N | L | I | T | R | Q | R | Y |
| 252 | Y | A | S | L | R | H | Y | I | N | L | I | T | R | Q | R | Y |
| 253 | Y | A | S | L | R | H | Y | I | N | L | I | T | R | Q | R | Y |
| 254 | Y | A | S | L | R | H | Y | I | N | L | I | T | R | Q | R | Y |
| 255 | Y | A | S | L | R | H | Y | I | N | L | I | T | R | Q | R | Y |
| 256 | Y | A | S | L | R | H | Y | I | N | L | I | T | R | Q | R | Y |
| 257 | Y | A | S | L | R | H | Y | I | N | L | I | T | R | Q | R | Y |
| 258 | Y | S | A | L | R | A | Y | I | N | L | I | T | R | Q | R | Y |

TABLE 4-continued

| # | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| 259 | Y | S | A | L | R | A | Y | I | N | L | I | T | R | Q | R | Y |
| 260 | Y | A | S | L | R | A | Y | I | N | L | I | T | R | Q | R | Y |
| 261 | Y | A | A | L | R | A | Y | I | N | L | I | T | R | Q | R | Y |
| 262 | Y | A | A | L | R | A | Y | I | N | L | I | T | R | Q | R | Y |
| 263 | Y | A | A | L | R | A | Y | I | N | L | I | T | R | Q | R | Y |
| 264 | Y | A | A | L | R | A | Y | I | N | L | I | T | R | Q | R | Y |
| 265 | Y | A | A | L | R | A | Y | I | N | L | I | T | R | Q | R | Y |
| 266 | Y | A | A | L | R | A | Y | I | N | L | I | T | R | Q | R | Y |
| 267 | Y | A | A | L | R | A | Y | I | N | L | I | T | R | Q | R | Y |
| 268 | Y | A | A | L | R | A | Y | I | N | L | I | T | R | Q | R | Y |
| 269 | Y | A | A | L | R | A | Y | I | N | L | I | T | R | Q | R | Y |
| 270 | Y | A | A | L | R | A | Y | I | N | L | I | T | R | Q | R | Y |
| 271 | Y | A | S | L | R | A | Y | I | N | L | I | T | R | Q | R | Y |
| 272 | Y | S | A | L | R | A | Y | I | N | L | I | T | R | Q | R | Y |
| 273 | Y | A | A | L | R | A | Y | I | N | L | I | T | R | Q | R | Y |
| 274 | Y | A | A | L | R | H | Y | I | N | L | I | T | R | Q | R | Y |
| 275 | Y | A | A | L | R | A | Y | I | N | L | I | T | R | Q | R | Y |
| 276 | Y | A | A | L | R | A | Y | I | N | L | I | T | R | Q | R | Y |
| 277 | Y | A | A | L | R | H | Y | I | N | L | I | T | R | Q | R | Y |
| 278 | Y | A | A | L | R | H | Y | I | N | L | I | T | R | Q | R | Y |
| 279 | Y | A | A | L | R | A | Y | I | N | L | I | T | R | Q | R | Y |
| 280 | Y | A | A | L | R | H | Y | I | N | L | I | T | R | Q | R | Y |
| 281 | Y | S | A | L | R | A | Y | I | N | L | I | T | R | Q | R | Y |
| 282 | Y | A | A | L | R | A | Y | I | N | L | I | T | R | Q | R | Y |
| 283 | Y | S | S | L | R | A | Y | I | N | L | I | T | R | Q | R | Y |
| 284 | Y | S | S | L | R | H | Y | I | N | L | I | T | R | Q | R | Y |
| 285 | Y | A | S | L | R | H | Y | I | N | L | I | T | R | Q | R | Y |
| 286 | Y | A | A | L | R | H | Y | I | N | L | I | T | R | Q | R | Y |
| 287 | Y | A | A | L | R | H | Y | I | N | L | I | T | R | Q | R | Y |
| 288 | Y | A | A | L | R | H | Y | I | N | L | I | T | R | Q | R | Y |
| 289 | Y | A | S | L | R | H | Y | F | N | L | I | T | R | Q | R | Y |
| 290 | Y | A | S | L | R | H | Y | I | L | L | V | T | R | Q | R | Y |
| 291 | Y | A | A | L | R | H | Y | I | L | L | A | T | R | Q | R | Y |
| 292 | Y | A | A | L | R | H | Y | I | L | L | A | T | R | Q | R | Y |
| 293 | Y | A | A | L | R | H | Y | I | L | L | A | T | R | Q | R | Y |
| 294 | Y | A | A | L | R | H | Y | I | L | L | V | P | R | Q | R | Y |
| 295 | Y | A | A | L | R | H | Y | I | L | L | V | Aib | R | Q | R | Y |
| 296 | Y | A | A | L | R | H | Y | I | L | L | V | Sar | R | Q | R | Y |
| 297 | Y | A | A | L | R | H | Y | I | L | L | V | T | R | Q | R | Y |
| 298 | Y | A | A | L | R | H | Y | I | L | L | V | T | R | Q | R | Y |
| 299 | Y | A | A | L | R | H | Y | I | L | L | V | T | R | Q | R | Y |
| 300 | Y | A | A | L | R | H | Y | I | L | L | V | T | R | Q | R | Y |
| 301 | Y | A | A | L | R | H | Y | I | L | L | V | T | R | Q | R | Y |
| 302 | Y | A | A | L | R | H | Y | I | L | L | V | T | R | Q | R | Y |
| 303 | Y | A | A | L | R | H | Y | I | L | L | V | T | R | Q | R | Y |
| 304 | Y | A | A | L | R | H | Y | I | L | L | V | T | R | Q | R | Y |
| 305 | Y | A | A | L | R | H | Y | I | L | L | V | T | R | Q | R | Y |
| 306 | Y | A | A | L | R | H | Y | I | L | L | V | T | R | Q | R | Y |
| 307 | Y | A | A | L | R | H | Y | I | L | L | V | T | R | Q | R | Y |
| 308 | Y | A | A | L | R | H | Y | I | N | L | M | T | R | Q | R | Y |
| 309 | A | A | D | L | R | R | Y | I | N | L | M | L | R | P | R | Y |
| 310 | A | D | D | L | R | R | Y | I | N | L | M | L | T | R | P | Y |

TABLE 4-continued

| | | | | | | | | | | | | | | |
|---|---|---|---|---|---|---|---|---|---|---|---|---|---|---|
| 311 | A | A | D | L | R | R | Y | I | N | M | L | T | R | Q | R | Y |
| 312 | A | A | D | L | R | R | Y | I | N | M | L | T | R | Q | R | Y |
| 313 | A | s | S | L | R | H | Y | I | N | M | L | T | R | Q | R | Y |
| 314 | s | A | A | L | R | H | Y | I | N | M | L | T | R | Q | R | Y |
| 315 | A | A | D | L | R | R | Y | I | N | M | L | T | R | Q | R | Y |
| 316 | A | A | D | L | R | R | Y | I | N | M | L | T | R | Q | R | Y |
| 317 | A | A | s | L | R | R | Y | I | N | M | L | T | R | Q | R | Y |
| 318 | A | A | D | L | R | R | Y | I | N | M | L | T | R | Q | R | Y |
| 319 | A | A | D | L | R | R | Y | I | N | M | L | T | R | Q | R | Y |
| 320 | A | A | D | L | hK | R | Y | I | N | M | L | T | R | Q | R | Y |
| 321 | A | A | D | L | hR | R | Y | I | N | M | L | T | R | Q | R | Y |
| 322 | A | A | D | L | Om | R | Y | I | N | M | L | T | R | Q | R | Y |
| 323 | A | A | D | L | Cit | R | Y | I | N | M | L | T | R | Q | R | Y |
| 324 | A | A | D | L | R | hK | Y | I | N | M | L | T | R | Q | R | Y |
| 325 | A | A | D | L | R | hR | Y | I | N | M | L | T | R | Q | R | Y |
| 326 | A | A | D | L | R | Om | Y | I | N | M | L | T | R | Q | R | Y |
| 327 | A | A | D | L | R | Cit | Y | I | N | M | L | T | R | Q | R | Y |
| 328 | A | A | D | L | R | hR | Y | I | N | M | L | T | R | Q | R | Y |
| 329 | A | A | D | L | hR | R | Y | I | N | M | L | T | R | Q | R | Y |
| 330 | A | A | D | L | R | R | Y | I | N | M | L | T | R | Q | R | Y |
| 331 | A | A | D | L | R | R | Y | I | N | M | L | T | R | Q | R | Y |
| 332 | A | A | D | L | R | R | Y | I | N | M | L | T | R | Q | R | Y |
| 333 | A | A | D | L | R | R | Y | I | N | M | L | T | R | Q | R | Y |
| 334 | A | A | D | L | R | R | Y | I | N | M | L | T | R | Q | R | Y |
| 335 | A | A | D | L | R | R | Y | I | N | M | L | T | R | Q | R | Y |
| 336 | A | A | D | L | R | R | Y | I | N | M | L | T | R | Q | R | Y |
| 337 | A | A | D | L | R | R | Y | I | N | M | L | T | R | Q | R | Y |
| 338 | A | A | D | L | R | R | Y | I | N | M | L | T | R | Q | R | Y |
| 339 | A | A | D | L | R | R | Y | I | N | M | L | T | R | Q | R | Y |
| 340 | A | A | D | L | R | R | Y | I | N | M | L | T | R | Q | R | Y |
| 341 | A | A | D | L | R | R | Y | I | N | M | L | T | R | Q | R | Y |
| 342 | A | A | D | L | R | R | Y | I | N | M | L | T | R | Q | R | Y |
| 343 | A | A | D | L | R | R | Y | I | N | M | L | T | R | Q | R | Y |
| 344 | A | A | D | L | R | R | Y | I | N | M | L | T | R | Q | R | Y |
| 345 | A | A | D | L | R | R | Y | I | N | M | L | T | R | Q | R | Y |
| 346 | A | A | D | L | R | R | Y | I | N | M | L | T | R | Q | R | Y |
| 347 | A | A | E | L | R | R | Y | I | Q | M | L | T | R | Q | R | Y |
| 348 | | | | | | | | | | | | | | | | |
| 349 | | | | | | | | | | | | | | | | |
| 350 | | | | | | | | | | | | | | | | |
| 351 | | | | | | | | | | | | | | | | |
| 436 | Y | A | S | L | R | H | Y | L | N | L | V | T | R | Q | R | Y |
| 437 | Y | A | S | L | R | A | Y | I | N | L | L | T | R | Q | R | Y |
| 438 | Y | A | S | L | R | A | Y | I | N | L | L | T | R | Q | R | Y |
| 439 | Y | A | S | L | R | A | Y | I | N | L | L | T | R | Q | R | Y |
| 440 | Y | A | S | L | R | A | Y | I | N | L | L | T | R | Q | R | Y |
| 441 | Y | A | S | L | R | A | Y | I | N | L | L | T | R | Q | K | Y |
| 442 | Y | A | S | L | R | H | Y | L | N | L | V | T | R | Q | R | Y |
| 443 | Y | A | S | L | R | H | Y | L | N | L | V | T | R | Q | R | Y |
| 444 | Y | A | S | L | R | A | Y | I | N | L | V | T | R | Q | R | Y |
| 445 | Y | A | S | L | R | A | Y | I | N | L | L | T | R | Q | R | Y |
| 446 | F | A | S | L | R | A | Y | I | N | L | V | T | R | Q | R | Y |

TABLE 4-continued

| | | | | | | | | | | | | | | |
|---|---|---|---|---|---|---|---|---|---|---|---|---|---|---|
| 447 | K | A | S | L | R | A | Y | I | N | L | V | T | R | Q | R | Y |
| 448 | F | A | S | L | R | A | Y | L | N | L | V | T | R | Q | R | Y |
| 449 | K | A | S | L | R | A | Y | L | N | L | V | T | R | Q | R | Y |
| 450 | Y | A | S | L | R | A | Y | L | N | L | V | T | R | Q | R | W |
| 451 | Y | A | S | L | R | H | Y | L | N | L | V | T | R | Q | R | Y |
| 452 | Y | A | S | L | R | N | Y | L | N | L | V | T | R | Q | R | Y |
| 453 | Y | A | S | L | R | H | Y | L | N | L | V | T | R | Q | R | Y |
| 454 | K | A | S | L | R | A | Y | L | N | L | I | T | R | Q | R | Y |
| 455 | Y | A | S | L | R | A | Y | L | N | L | I | T | R | Q | R | Y |
| 456 | Y | A | S | L | R | A | Y | L | N | L | I | T | R | Q | R | Y |
| 457 | Y | A | S | L | R | A | Y | L | N | L | I | T | R | Q | R | F |
| 458 | Y | A | S | L | R | A | Y | L | N | L | I | T | R | Q | R | W |
| 459 | Y | A | S | L | R | A | Y | L | N | L | I | T | R | Q | R | Y |
| 460 | Y | A | S | L | R | A | Y | L | N | L | I | T | R | Q | R | Y |
| 461 | Y | A | S | L | R | A | Y | L | N | L | I | T | R | Q | R | Y |
| 462 | Y | A | S | L | R | A | Y | L | N | L | I | T | R | Q | R | Y |
| 463 | Y | A | S | L | R | A | Y | L | N | L | I | T | R | Q | R | Y |
| 464 | Y | A | S | L | R | A | Y | I | N | L | I | T | R | Q | R | Y |
| 465 | Y | A | S | L | R | A | Y | I | N | L | I | T | R | Q | R | Y |
| 466 | Y | A | S | L | R | A | Y | I | N | L | I | T | R | Q | R | Y |
| 467 | Y | A | S | L | R | A | Y | I | N | L | I | T | R | Q | R | Y |
| 468 | Y | A | S | L | R | A | Y | I | N | L | I | T | R | Q | R | Y |
| 469 | Y | A | S | L | R | A | Y | I | N | L | I | T | R | Q | R | Y |
| 470 | Y | A | S | L | R | A | Y | I | N | L | I | T | R | Q | R | Y |
| 471 | Y | A | S | L | R | A | Y | I | N | L | I | T | R | Q | R | Y |
| 472 | Y | A | S | L | R | A | Y | I | N | L | I | T | R | Q | R | Y |
| 473 | Y | A | S | L | R | A | Y | I | N | L | I | T | R | Q | R | Y |
| 474 | Y | A | D | L | R | A | Y | I | N | L | I | T | R | Q | R | Y |
| 475 | A | A | D | L | R | R | Y | I | N | L | L | T | R | Q | R | Y |
| 476 | A | A | D | L | R | R | Y | I | N | M | M | T | R | Q | R | Y |
| 477 | A | A | D | L | R | R | Y | I | N | M | M | T | R | Q | R | Y |
| 478 | A | A | S | L | R | A | Y | I | N | L | L | T | R | Q | R | Y |
| 479 | Y | A | S | L | R | A | Y | I | N | L | I | T | R | Q | R | Y |
| 480 | Y | A | | | | | | | | | | | | | | Y |
| 481 | | | | | | | | | | | | | | | | |
| 482 | | | | | | | | | | | | | | | | |

While the present invention has been described in terms of several and embodiments, it is understood that variations and modifications will occur skilled in the art. Therefore, it is intended that the appended claims cover all valent variations which come within the scope of the invention as claimed.

---

What is claimed is:

1. A PPF polypeptide comprising an amino acid sequence selected from the group consisting of SEQ ID NOs: 266, 267, 274, 282, 320, 436, 437, 438, 439, 440, 441, 442, 443, 444, 445, 446, 447, 448, 449, 450, 451, 453, 454, 455, 456, 457, 458, 459, 460, 461, 462, 463, 464, 465, 466, 467, 468, 469, 470, 471, 472, 473, 474, 475, 476, 477, 478, 479 and 480.

2. The PPF polypeptide of claim 1, wherein said polypeptide comprises an amino acid sequence selected from the group consisting of SEQ ID NOs: 282, 320, 437, 441, 444, 445 to 447, 452, 454 to 459, 461 to 464, 466, 468 to 470 and 472 to 480.

3. The PPF polypeptide of claim 1, wherein said polypeptide comprises an amino acid sequence selected from the group consisting of SEQ ID NOs: 266, 437, 438, 439, 442, 462, 469, 470, 471 and 472.

4. The PPF polypeptide of claim 1, wherein said polypeptide comprises an amino acid sequence selected from the group consisting of SEQ ID NOs: 437, 462, 469, 470 and 472.

5. A PPF polypeptide comprising SEQ ID NO: 266.
6. A PPF polypeptide comprising SEQ ID NO: 267.
7. A PPF polypeptide comprising SEQ ID NO: 274.
8. A PPF polypeptide comprising SEQ ID NO: 282.
9. A PPF polypeptide comprising SEQ ID NO: 320.
10. A PPF polypeptide comprising SEQ ID NO: 436.
11. A PPF polypeptide comprising SEQ ID NO: 437.
12. A PPF polypeptide comprising SEQ ID NO: 438.
13. A PPF polypeptide comprising SEQ ID NO: 439.
14. A PPF polypeptide comprising SEQ ID NO: 440.
15. A PPF polypeptide comprising SEQ ID NO: 441.
16. A PPF polypeptide comprising SEQ ID NO: 442.
17. A PPF polypeptide comprising SEQ ID NO: 474.
18. A PPF polypeptide comprising SEQ ID NO: 443.
19. A PPF polypeptide comprising SEQ ID NO: 444.
20. A PPF polypeptide comprising SEQ ID NO: 445.
21. A PPF polypeptide comprising SEQ ID NO: 446.
22. A PPF polypeptide comprising SEQ ID NO: 447.
23. A PPF polypeptide comprising SEQ ID NO: 448.
24. A PPF polypeptide comprising SEQ ID NO: 449.
25. A PPF polypeptide comprising SEQ ID NO: 450.
26. A PPF polypeptide comprising SEQ ID NO: 451.
27. A PPF polypeptide comprising SEQ ID NO: 453.
28. A PPF polypeptide comprising SEQ ID NO: 454.
29. A PPF polypeptide comprising SEQ ID NO: 455.
30. A PPF polypeptide comprising SEQ ID NO: 456.
31. A PPF polypeptide comprising SEQ ID NO: 457.
32. A PPF polypeptide comprising SEQ ID NO: 458.
33. A PPF polypeptide comprising SEQ ID NO: 459.
34. A PPF polypeptide comprising SEQ ID NO: 460.
35. A PPF polypeptide comprising SEQ ID NO: 461.
36. A PPF polypeptide comprising SEQ ID NO: 462.
37. A PPF polypeptide comprising SEQ ID NO: 463.
38. A PPF polypeptide comprising SEQ ID NO: 464.
39. A PPF polypeptide comprising SEQ ID NO: 465.
40. A PPF polypeptide comprising SEQ ID NO: 466.
41. A PPF polypeptide comprising SEQ ID NO: 467.
42. A PPF polypeptide comprising SEQ ID NO: 468.
43. A PPF polypeptide comprising SEQ ID NO: 469.
44. A PPF polypeptide comprising SEQ ID NO: 470.
45. A PPF polypeptide comprising SEQ ID NO: 471.
46. A PPF polypeptide comprising SEQ ID NO: 472.
47. A PPF polypeptide comprising SEQ ID NO: 473.
48. A PPF polypeptide comprising SEQ ID NO: 475.
49. A PPF polypeptide comprising SEQ ID NO: 476.
50. A PPF polypeptide comprising SEQ ID NO: 477.
51. A PPF polypeptide comprising SEQ ID NO: 478.
52. A PPF polypeptide comprising SEQ ID NO: 479.
53. A PPF polypeptide comprising SEQ ID NO: 480.

* * * * *

UNITED STATES PATENT AND TRADEMARK OFFICE
CERTIFICATE OF CORRECTION

| | | |
|---|---|---|
| PATENT NO. | : 7,723,471 B2 | Page 1 of 1 |
| APPLICATION NO. | : 11/301744 | |
| DATED | : May 25, 2010 | |
| INVENTOR(S) | : Levy et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 695 days.

Signed and Sealed this

Fifteenth Day of February, 2011

David J. Kappos
*Director of the United States Patent and Trademark Office*

UNITED STATES PATENT AND TRADEMARK OFFICE
CERTIFICATE OF CORRECTION

PATENT NO. : 7,723,471 B2
APPLICATION NO. : 11/301744
DATED : May 25, 2010
INVENTOR(S) : Odile Levy et al.

Page 1 of 1

It is certified that error appears in the above-identified patent and that said Letters Patent is hereby corrected as shown below:

Title Page, Item (56) "Related U.S. Application Data," replace the entire paragraph with the following priority claim information:

--Continuation-in part of application No. 11/055,098, filed on Feb., 2005, which claims benefit of priority from provisional application No. 60/635,897, filed on Dec. 13, 2004, and from provisional application No. 60,543,406, filed on Feb. 11, 2004, and from provisional application No. 60/543,407, filed on Feb. 11, 2004.--

Signed and Sealed this
Ninth Day of August, 2011

David J. Kappos
*Director of the United States Patent and Trademark Office*

SEQUENCE LISTING

```
<160> NUMBER OF SEQ ID NOS: 482

<210> SEQ ID NO 1
<211> LENGTH: 36
<212> TYPE: PRT
<213> ORGANISM: Homo sapiens

<400> SEQUENCE: 1

Ala Pro Leu Glu Pro Val Tyr Pro Gly Asp Asn Ala Thr Pro Glu Gln
1               5                   10                  15

Met Ala Gln Tyr Ala Ala Asp Leu Arg Arg Tyr Ile Asn Met Leu Thr
            20                  25                  30

Arg Pro Arg Tyr
        35

<210> SEQ ID NO 2
<211> LENGTH: 36
<212> TYPE: PRT
<213> ORGANISM: Homo sapiens

<400> SEQUENCE: 2

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 3
<211> LENGTH: 34
<212> TYPE: PRT
<213> ORGANISM: Homo sapiens

<400> SEQUENCE: 3

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 4
<211> LENGTH: 36
<212> TYPE: PRT
<213> ORGANISM: Homo sapiens

<400> SEQUENCE: 4

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35
```

```
<210> SEQ ID NO 5
<211> LENGTH: 36
<212> TYPE: PRT
<213> ORGANISM: Homo sapiens
<220> FEATURE:
<221> NAME/KEY: MOD_RES
<222> LOCATION: (32)
<223> OTHER INFORMATION: Aib

<400> SEQUENCE: 5

Ala Pro Leu Glu Pro Val Tyr Pro Gly Asp Asn Ala Thr Pro Glu Gln
1               5                   10                  15

Met Ala Arg Tyr Tyr Ser Ala Leu Arg His Tyr Ile Asn Leu Ala Xaa
            20                  25                  30

Arg Gln Arg Tyr
        35

<210> SEQ ID NO 6
<211> LENGTH: 36
<212> TYPE: PRT
<213> ORGANISM: Homo sapiens

<400> SEQUENCE: 6

Ala Pro Leu Glu Pro Val Tyr Pro Gly Asp Asn Ala Thr Pro Glu Gln
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 7
<211> LENGTH: 36
<212> TYPE: PRT
<213> ORGANISM: Raja rhina

<400> SEQUENCE: 7

Tyr Pro Pro Lys Pro Glu Ser Pro Gly Glu Asn Ala Thr Pro Glu Glu
1               5                   10                  15

Leu Ala Lys Tyr Ile Ser Ala Asp Arg His Tyr Ile Asn Leu Val Thr
            20                  25                  30

Arg Gln Arg Tyr
        35

<210> SEQ ID NO 8
<211> LENGTH: 34
<212> TYPE: PRT
<213> ORGANISM: Raja rhina

<400> SEQUENCE: 8

Pro Lys Pro Glu Ser Pro Gly Glu Asn Ala Thr Pro Glu Glu Leu Ala
1               5                   10                  15

Lys Tyr Ile Ser Ala Asp Arg His Tyr Ile Asn Leu Val Thr Arg Gln
            20                  25                  30

Arg Tyr

<210> SEQ ID NO 9
<211> LENGTH: 36
<212> TYPE: PRT
<213> ORGANISM: Danio rerio

<400> SEQUENCE: 9

Ala Pro Pro Lys Pro Glu His Pro Gly Asp Asp Ala Pro Ala Glu Asp
```

```
                1               5                  10                 15
Val Ala Lys Tyr Tyr Thr Ala Leu Arg His Tyr Ile Asn Leu Ile Thr
                       20                  25                 30

Arg Gln Arg Tyr
        35

<210> SEQ ID NO 10
<211> LENGTH: 34
<212> TYPE: PRT
<213> ORGANISM: Danio rerio

<400> SEQUENCE: 10

Pro Lys Pro Glu His Pro Gly Asp Asp Ala Pro Ala Glu Asp Val Ala
1               5                  10                 15

Lys Tyr Tyr Thr Ala Leu Arg His Tyr Ile Asn Leu Ile Thr Arg Gln
                20                 25                 30

Arg Tyr

<210> SEQ ID NO 11
<211> LENGTH: 34
<212> TYPE: PRT
<213> ORGANISM: Raja rhina

<400> SEQUENCE: 11

Pro Lys Pro Glu Asn Pro Gly Glu Asp Ala Pro Glu Glu Leu Ala
1               5                  10                 15

Lys Tyr Tyr Ser Ala Leu Arg His Tyr Ile Asn Leu Ile Thr Arg Gln
                20                 25                 30

Arg Tyr

<210> SEQ ID NO 12
<211> LENGTH: 37
<212> TYPE: PRT
<213> ORGANISM: Gallus gallus

<400> SEQUENCE: 12

Ala Tyr Pro Pro Lys Pro Glu Ser Pro Gly Asp Ala Ala Ser Pro Glu
1               5                  10                 15

Glu Ile Ala Gln Tyr Phe Ser Ala Leu Arg His Tyr Ile Asn Leu Val
                20                 25                 30

Thr Arg Gln Arg Tyr
        35

<210> SEQ ID NO 13
<211> LENGTH: 36
<212> TYPE: PRT
<213> ORGANISM: Rana ridibunda

<400> SEQUENCE: 13

Met Pro Pro Lys Pro Asp Asn Pro Ser Ser Asp Ala Ser Pro Glu Glu
1               5                  10                 15

Leu Ser Lys Tyr Met Leu Ala Val Arg Asn Tyr Ile Asn Leu Ile Thr
                20                 25                 30

Arg Gln Arg Tyr
        35

<210> SEQ ID NO 14
<211> LENGTH: 34
<212> TYPE: PRT
<213> ORGANISM: Rana ridibunda
```

-continued

<400> SEQUENCE: 14

Pro Lys Pro Asp Asn Pro Ser Ser Asp Ala Ser Pro Glu Glu Leu Ser
1               5                   10                  15

Lys Tyr Met Leu Ala Val Arg Asn Tyr Ile Asn Leu Ile Thr Arg Gln
            20                  25                  30

Arg Tyr

<210> SEQ ID NO 15
<211> LENGTH: 34
<212> TYPE: PRT
<213> ORGANISM: Ichthyomyzon gagei

<400> SEQUENCE: 15

Pro Lys Pro Asp Asn Pro Gly Asp Asn Ala Ser Pro Glu Gln Met Ala
1               5                   10                  15

Arg Tyr Lys Ala Ala Val Arg His Tyr Ile Asn Leu Ile Thr Arg Gln
            20                  25                  30

Arg Tyr

<210> SEQ ID NO 16
<211> LENGTH: 34
<212> TYPE: PRT
<213> ORGANISM: Raja rhina

<400> SEQUENCE: 16

Pro Lys Pro Glu Asn Pro Gly Asp Asn Ala Ser Pro Glu Glu Met Ala
1               5                   10                  15

Lys Tyr Phe Ser Ala Leu Arg His Tyr Ile Asn Leu Val Thr Arg Gln
            20                  25                  30

Arg Tyr

<210> SEQ ID NO 17
<211> LENGTH: 34
<212> TYPE: PRT
<213> ORGANISM: Rana ridibunda

<400> SEQUENCE: 17

Thr Lys Pro Glu Asn Pro Gly Asn Asp Ala Ser Pro Gln Glu Met Ala
1               5                   10                  15

Lys Tyr Met Thr Ala Leu Arg His Tyr Val Asn Leu Ile Thr Arg Gln
            20                  25                  30

Arg Tyr

<210> SEQ ID NO 18
<211> LENGTH: 36
<212> TYPE: PRT
<213> ORGANISM: Rana ridibunda

<400> SEQUENCE: 18

Tyr Pro Pro Lys Pro Glu Asn Pro Gly Glu Asp Ala Ser Pro Glu Glu
1               5                   10                  15

Met Thr Lys Tyr Leu Thr Ala Leu Arg His Tyr Ile Asn Leu Val Thr
            20                  25                  30

Arg Gln Arg Tyr
        35

<210> SEQ ID NO 19
<211> LENGTH: 34

```
<212> TYPE: PRT
<213> ORGANISM: Rana ridibunda

<400> SEQUENCE: 19

Pro Lys Pro Glu Asn Pro Gly Glu Asp Ala Ser Pro Glu Glu Met Thr
1               5                   10                  15

Lys Tyr Leu Thr Ala Leu Arg His Tyr Ile Asn Leu Val Thr Arg Gln
            20                  25                  30

Arg Tyr

<210> SEQ ID NO 20
<211> LENGTH: 34
<212> TYPE: PRT
<213> ORGANISM: Danio rerio

<400> SEQUENCE: 20

Ile Lys Pro Glu Ala Pro Gly Glu Asp Ala Ser Pro Glu Glu Leu Ala
1               5                   10                  15

Lys Tyr Tyr Thr Ala Leu Arg His Tyr Ile Asn Leu Ile Thr Arg Gln
            20                  25                  30

Arg Tyr

<210> SEQ ID NO 21
<211> LENGTH: 34
<212> TYPE: PRT
<213> ORGANISM: Amia calva

<400> SEQUENCE: 21

Ser Lys Pro Asp Asn Pro Gly Glu Asp Ala Pro Ala Glu Asp Met Ala
1               5                   10                  15

Lys Tyr Tyr Thr Ala Leu Arg His Tyr Ile Asn Leu Ile Thr Arg Gln
            20                  25                  30

Arg Tyr

<210> SEQ ID NO 22
<211> LENGTH: 34
<212> TYPE: PRT
<213> ORGANISM: Homo sapiens

<400> SEQUENCE: 22

Pro Lys Pro Glu His Pro Gly Asp Asp Ala Pro Ala Glu Asp Val Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 23
<211> LENGTH: 34
<212> TYPE: PRT
<213> ORGANISM: Ovis Aries

<400> SEQUENCE: 23

Pro Lys Pro Glu His Pro Gly Asp Asp Ala Pro Ala Glu Asp Val Asn
1               5                   10                  15

Arg Tyr Tyr Ala Ala Leu Arg Ala Tyr Leu Asn Leu Val Thr Arg Gln
            20                  25                  30

Arg Tyr

<210> SEQ ID NO 24
```

```
<211> LENGTH: 34
<212> TYPE: PRT
<213> ORGANISM: Ovis Aries

<400> SEQUENCE: 24

Pro Lys Pro Glu His Pro Gly Asp Asp Ala Pro Ala Glu Asp Val Ala
1               5                   10                  15

Gln Tyr Ala Ala Asp Leu Arg Arg Tyr Ile Asn Met Leu Thr Arg Gln
            20                  25                  30

Arg Tyr

<210> SEQ ID NO 25
<211> LENGTH: 33
<212> TYPE: PRT
<213> ORGANISM: Ovis Aries

<400> SEQUENCE: 25

Ile Pro Glu His Pro Gly Asp Asp Ala Pro Ala Glu Asp Val Ala Arg
1               5                   10                  15

Tyr Tyr Ser Ala Leu Arg Ala Tyr Ile Asn Leu Ile Thr Arg Gln Arg
            20                  25                  30

Tyr

<210> SEQ ID NO 26
<211> LENGTH: 34
<212> TYPE: PRT
<213> ORGANISM: Ovis Aries

<400> SEQUENCE: 26

Pro Lys Pro Glu His Pro Gly Asp Asp Ala Pro Ala Glu Asp Val Ala
1               5                   10                  15

Arg Tyr Tyr Ser Ala Leu Arg His Tyr Ile Asn Leu Ile Thr Arg Gln
            20                  25                  30

Arg Tyr

<210> SEQ ID NO 27
<211> LENGTH: 34
<212> TYPE: PRT
<213> ORGANISM: Ovis Aries

<400> SEQUENCE: 27

Pro Lys Pro Glu His Pro Gly Asp Asp Ala Pro Ala Glu Asp Val Ala
1               5                   10                  15

Arg Tyr Tyr Ser Ala Leu Arg Ala Tyr Ile Asn Leu Ile Thr Arg Gln
            20                  25                  30

Arg Tyr

<210> SEQ ID NO 28
<211> LENGTH: 36
<212> TYPE: PRT
<213> ORGANISM: Raja rhina

<400> SEQUENCE: 28

Tyr Pro Pro Lys Pro Glu Ala Pro Gly Glu Asp Ala Ser Pro Glu Glu
1               5                   10                  15

Leu Ala Lys Tyr Tyr Ala Ala Leu Arg His Tyr Ile Asn Leu Val Thr
            20                  25                  30

Arg Gln Arg Tyr
        35
```

-continued

<210> SEQ ID NO 29
<211> LENGTH: 34
<212> TYPE: PRT
<213> ORGANISM: Rana ridibunda

<400> SEQUENCE: 29

Ala Lys Pro Glu Asn Pro Gly Asp Asn Ala Pro Ala Glu Gln Met Ala
1               5                   10                  15

Lys Tyr Leu Thr Ala Leu Arg Ala Tyr Val Asn Leu Ile Thr Arg Gln
            20                  25                  30

Arg Tyr

<210> SEQ ID NO 30
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Tyr, Ala, Phe, Trp, or absent
<220> FEATURE:
<221> NAME/KEY: MOD_RES
<222> LOCATION: (2)
<223> OTHER INFORMATION: Pro, Gly, d-Ala, homoPro, hydroxyPro, or absent
<220> FEATURE:
<221> NAME/KEY: MOD_RES
<222> LOCATION: (3)
<223> OTHER INFORMATION: Ile, Ala, NorVal, Val, Leu, Pro, Ser, Thr,
      or absent
<220> FEATURE:
<221> NAME/KEY: MOD_RES
<222> LOCATION: (4)
<223> OTHER INFORMATION: Lys, Ala, Gly, Arg, d-Ala, homoLys, homo-Arg,
      Glu, Asp, or absent
<220> FEATURE:
<221> NAME/KEY: MOD_RES
<222> LOCATION: (6)
<223> OTHER INFORMATION: Glu, Ala, Val, Asp, Asn, or Gln
<220> FEATURE:
<221> NAME/KEY: MOD_RES
<222> LOCATION: (7)
<223> OTHER INFORMATION: Ala, Asn, His, Ser, or Tyr
<220> FEATURE:
<221> NAME/KEY: MOD_RES
<222> LOCATION: (9)
<223> OTHER INFORMATION: Gly, Ala, Ser, Sarcosine, Pro, or Aib
<220> FEATURE:
<221> NAME/KEY: MOD_RES
<222> LOCATION: (10)
<223> OTHER INFORMATION: Glu, Ala, Asp, Asn, Gln, Pro, Aib, or Gly
<220> FEATURE:
<221> NAME/KEY: MOD_RES
<222> LOCATION: (11)
<223> OTHER INFORMATION: Asp, Ala, Glu, Asn, Gln, Pro, Aib, or Gly
<220> FEATURE:
<221> NAME/KEY: MOD_RES
<222> LOCATION: (12)
<223> OTHER INFORMATION: Ala or d-Ala
<220> FEATURE:
<221> NAME/KEY: MOD_RES
<222> LOCATION: (13)
<223> OTHER INFORMATION: Ser, Ala, Thr, Pro, or homoSer
<220> FEATURE:
<221> NAME/KEY: MOD_RES
<222> LOCATION: (14)
<223> OTHER INFORMATION: Pro, Ala, homoPro, hydroxyPro, Aib, or Gly
<220> FEATURE:
<221> NAME/KEY: MOD_RES
<222> LOCATION: (15)
<223> OTHER INFORMATION: Glu, Ala, Asp, Asn, Gln, Pro, Aib, or Gly
<220> FEATURE:

```
<221> NAME/KEY: MOD_RES
<222> LOCATION: (16)
<223> OTHER INFORMATION: Glu, Ala, Asp, Asn, or Gln
<220> FEATURE:
<221> NAME/KEY: MOD_RES
<222> LOCATION: (17)
<223> OTHER INFORMATION: Leu, Ala, Met, Trp, Ile, Val, or NorVal
<220> FEATURE:
<221> NAME/KEY: MOD_RES
<222> LOCATION: (18)
<223> OTHER INFORMATION: Asn, Asp, Ala, Glu, Gln, Ser, or Thr
<220> FEATURE:
<221> NAME/KEY: MOD_RES
<222> LOCATION: (19)
<223> OTHER INFORMATION: Arg, Tyr, Lys, Ala, Gln, or N(Me)Ala
<220> FEATURE:
<221> NAME/KEY: MOD_RES
<222> LOCATION: (21)
<223> OTHER INFORMATION: Tyr, Ala, Met, Phe, or Leu
<220> FEATURE:
<221> NAME/KEY: MOD_RES
<222> LOCATION: (22)
<223> OTHER INFORMATION: Ala, Ser, Thr, or d-Ala
<220> FEATURE:
<221> NAME/KEY: MOD_RES
<222> LOCATION: (23)
<223> OTHER INFORMATION: Ser, Ala, Asp, Thr, or homoSer
<220> FEATURE:
<221> NAME/KEY: MOD_RES
<222> LOCATION: (25)
<223> OTHER INFORMATION: Arg, homoArg, Lys, homoLys, Orn, or Cit
<220> FEATURE:
<221> NAME/KEY: MOD_RES
<222> LOCATION: (26)
<223> OTHER INFORMATION: His, Ala, Arg, homoArg, homoLys, Orn, or Cit
<220> FEATURE:
<221> NAME/KEY: MOD_RES
<222> LOCATION: (27)
<223> OTHER INFORMATION: Tyr or Phe
<220> FEATURE:
<221> NAME/KEY: MOD_RES
<222> LOCATION: (28)
<223> OTHER INFORMATION: Leu, Ile, Val, or Ala
<220> FEATURE:
<221> NAME/KEY: MOD_RES
<222> LOCATION: (29)
<223> OTHER INFORMATION: Asn or Gln
<220> FEATURE:
<221> NAME/KEY: MOD_RES
<222> LOCATION: (30)
<223> OTHER INFORMATION: Leu, Ala, NorVal, Val, Ile, or Met
<220> FEATURE:
<221> NAME/KEY: MOD_RES
<222> LOCATION: (31)
<223> OTHER INFORMATION: Ala, Val, Ile, or Leu
<220> FEATURE:
<221> NAME/KEY: MOD_RES
<222> LOCATION: (36)
<223> OTHER INFORMATION: Tyr, N(Me)Tyr, His, Trp, or Phe

<400> SEQUENCE: 30

Xaa Xaa Xaa Xaa Pro Xaa Xaa Pro Xaa Xaa Xaa Xaa Xaa Xaa Xaa Xaa
1               5                   10                  15

Xaa Xaa Xaa Tyr Xaa Xaa Xaa Leu Xaa Xaa Xaa Xaa Xaa Xaa Xaa Thr
            20                  25                  30

Arg Gln Arg Xaa
        35

<210> SEQ ID NO 31
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
```

```
<220> FEATURE:
<221> NAME/KEY: MOD_RES
<222> LOCATION: (4)
<223> OTHER INFORMATION: homo-Lys

<400> SEQUENCE: 31

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
            35

<210> SEQ ID NO 32
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 32

Tyr Pro Ile Lys Pro Ala Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
            35

<210> SEQ ID NO 33
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 33

Tyr Pro Ile Lys Pro Glu Ala Pro Ala Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
            35

<210> SEQ ID NO 34
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 34

Tyr Pro Ile Lys Pro Glu Ala Pro Gly Ala Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
            35

<210> SEQ ID NO 35
<211> LENGTH: 36
```

```
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 35

Tyr Pro Ile Lys Pro Glu Ala Pro Gly Glu Ala Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
            35

<210> SEQ ID NO 36
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 36

Tyr Pro Ile Lys Pro Glu Ala Pro Gly Glu Asp Ala Ala Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
            35

<210> SEQ ID NO 37
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 37

Tyr Pro Ile Lys Pro Glu Ala Pro Gly Glu Asp Ala Ser Ala Glu Glu
1               5                   10                  15

Leu Asn Arg Tyr Tyr Ala Ser Leu Arg His Tyr Leu Asn Leu Val Thr
            20                  25                  30

Arg Gln Arg Tyr
            35

<210> SEQ ID NO 38
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 38

Tyr Pro Ile Lys Pro Glu Ala Pro Gly Glu Asp Ala Ser Pro Ala Glu
1               5                   10                  15

Leu Asn Arg Tyr Tyr Ala Ser Leu Arg His Tyr Leu Asn Leu Val Thr
            20                  25                  30

Arg Gln Arg Tyr
            35

<210> SEQ ID NO 39
```

```
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 39

Tyr Pro Ile Lys Pro Glu Ala Pro Gly Glu Asp Ala Ser Pro Glu Ala
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 40
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 40

Tyr Pro Ile Lys Pro Glu Ala Pro Gly Glu Asp Ala Ser Pro Glu Glu
1               5                   10                  15

Ala Asn Arg Tyr Tyr Ala Ser Leu Arg His Tyr Leu Asn Leu Val Thr
            20                  25                  30

Arg Gln Arg Tyr
        35

<210> SEQ ID NO 41
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 41

Tyr Pro Ile Lys Pro Glu Ala Pro Gly Glu Asp Ala Ser Pro Glu Glu
1               5                   10                  15

Leu Ala Arg Tyr Tyr Ala Ser Leu Arg His Tyr Leu Asn Leu Val Thr
            20                  25                  30

Arg Gln Arg Tyr
        35

<210> SEQ ID NO 42
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 42

Tyr Pro Ile Lys Pro Glu Ala Pro Gly Glu Asp Ala Ser Pro Glu Glu
1               5                   10                  15

Leu Asn Lys Tyr Tyr Ala Ser Leu Arg His Tyr Leu Asn Leu Val Thr
            20                  25                  30

Arg Gln Arg Tyr
        35
```

```
<210> SEQ ID NO 43
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 43

Tyr Pro Ile Lys Pro Glu Ala Pro Gly Glu Asp Ala Ser Pro Glu Glu
1               5                   10                  15

Leu Asn Arg Tyr Ala Ala Ser Leu Arg His Tyr Leu Asn Leu Val Thr
            20                  25                  30

Arg Gln Arg Tyr
        35

<210> SEQ ID NO 44
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 44

Tyr Pro Ile Lys Pro Glu Ala Pro Gly Glu Asp Ala Ser Pro Glu Glu
1               5                   10                  15

Leu Asn Arg Tyr Tyr Ala Ala Leu Arg His Tyr Leu Asn Leu Val Thr
            20                  25                  30

Arg Gln Arg Tyr
        35

<210> SEQ ID NO 45
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 45

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg Ala Tyr Leu Asn Leu Val Thr
            20                  25                  30

Arg Gln Arg Tyr
        35

<210> SEQ ID NO 46
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 46

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Ala Val Thr
            20                  25                  30

Arg Gln Arg Tyr
        35
```

```
<210> SEQ ID NO 47
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 47

Tyr Pro Ile Lys Pro Glu Ala Pro Gly Glu Asp Ala Ser Ala Glu Glu
1               5                   10                  15

Leu Ala Arg Tyr Tyr Ala Ser Leu Arg His Tyr Leu Asn Leu Val Thr
            20                  25                  30

Arg Gln Arg Tyr
        35

<210> SEQ ID NO 48
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 48

Tyr Pro Ile Lys Pro Glu Ala Pro Gly Glu Asp Ala Ser Pro Glu Glu
1               5                   10                  15

Leu Ala Arg Tyr Tyr Ala Ser Leu Arg Ala Tyr Leu Asn Leu Val Thr
            20                  25                  30

Arg Gln Arg Tyr
        35

<210> SEQ ID NO 49
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 49

Tyr Pro Ile Lys Pro Glu Ala Pro Gly Glu Asp Ala Ser Ala Glu Glu
1               5                   10                  15

Leu Ala Arg Tyr Tyr Ala Ser Leu Arg Ala Tyr Leu Asn Leu Val Thr
            20                  25                  30

Arg Gln Arg Tyr
        35

<210> SEQ ID NO 50
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 50

Ala Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35
```

```
<210> SEQ ID NO 51
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 51

Phe Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 52
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)
<223> OTHER INFORMATION: d-Ala

<400> SEQUENCE: 52

Tyr Ala Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 53
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 53

Tyr Gly Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 54
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 54

Ala Tyr Pro Ile Lys Pro Glu Ala Pro Gly Glu Asp Ala Ser Pro Glu
1               5                   10                  15
```

Glu Leu Asn Arg Tyr Tyr Ala Ser Leu Arg His Tyr Leu Asn Leu Val
            20                  25                  30

Thr Arg Gln Arg Tyr
        35

<210> SEQ ID NO 55
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 55

Tyr Ala Pro Ile Lys Pro Glu Ala Pro Gly Glu Asp Ala Ser Pro Glu
1               5                   10                  15

Glu Leu Asn Arg Tyr Tyr Ala Ser Leu Arg His Tyr Leu Asn Leu Val
            20                  25                  30

Thr Arg Gln Arg Tyr
        35

<210> SEQ ID NO 56
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 56

Tyr Pro Ala Ile Lys Pro Glu Ala Pro Gly Glu Asp Ala Ser Pro Glu
1               5                   10                  15

Glu Leu Asn Arg Tyr Tyr Ala Ser Leu Arg His Tyr Leu Asn Leu Val
            20                  25                  30

Thr Arg Gln Arg Tyr
        35

<210> SEQ ID NO 57
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 57

Tyr Pro Ile Ala Lys Pro Glu Ala Pro Gly Glu Asp Ala Ser Pro Glu
1               5                   10                  15

Glu Leu Asn Arg Tyr Tyr Ala Ser Leu Arg His Tyr Leu Asn Leu Val
            20                  25                  30

Thr Arg Gln Arg Tyr
        35

<210> SEQ ID NO 58
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 58

Tyr Pro Ile Lys Ala Pro Glu Ala Pro Gly Glu Asp Ala Ser Pro Glu
1               5                   10                  15

Glu Leu Asn Arg Tyr Tyr Ala Ser Leu Arg His Tyr Leu Asn Leu Val
            20                  25                  30

Thr Arg Gln Arg Tyr
        35

<210> SEQ ID NO 59
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 59

Tyr Pro Ile Lys Pro Ala Glu Ala Pro Gly Glu Asp Ala Ser Pro Glu
1               5                   10                  15

Glu Leu Asn Arg Tyr Tyr Ala Ser Leu Arg His Tyr Leu Asn Leu Val
            20                  25                  30

Thr Arg Gln Arg Tyr
        35

<210> SEQ ID NO 60
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 60

Tyr Pro Ile Lys Pro Glu Ala Ala Pro Gly Glu Asp Ala Ser Pro Glu
1               5                   10                  15

Glu Leu Asn Arg Tyr Tyr Ala Ser Leu Arg His Tyr Leu Asn Leu Val
            20                  25                  30

Thr Arg Gln Arg Tyr
        35

<210> SEQ ID NO 61
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 61

Tyr Pro Ile Lys Pro Glu Ala Pro Ala Gly Glu Asp Ala Ser Pro Glu
1               5                   10                  15

Glu Leu Asn Arg Tyr Tyr Ala Ser Leu Arg His Tyr Leu Asn Leu Val
            20                  25                  30

Thr Arg Gln Arg Tyr
        35

<210> SEQ ID NO 62
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 62

Tyr Pro Ile Lys Pro Glu Ala Pro Gly Ala Glu Asp Ala Ser Pro Glu

```
                1               5                  10                  15
Glu Leu Asn Arg Tyr Tyr Ala Ser Leu Arg His Tyr Leu Asn Leu Val
                    20                  25                  30

Thr Arg Gln Arg Tyr
        35

<210> SEQ ID NO 63
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 63

Tyr Pro Ile Lys Pro Glu Ala Pro Gly Glu Ala Asp Ala Ser Pro Glu
1               5                   10                  15

Glu Leu Asn Arg Tyr Tyr Ala Ser Leu Arg His Tyr Leu Asn Leu Val
                    20                  25                  30

Thr Arg Gln Arg Tyr
        35

<210> SEQ ID NO 64
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 64

Tyr Pro Ile Lys Pro Glu Ala Pro Gly Glu Asp Ala Ala Ser Pro Glu
1               5                   10                  15

Glu Leu Asn Arg Tyr Tyr Ala Ser Leu Arg His Tyr Leu Asn Leu Val
                    20                  25                  30

Thr Arg Gln Arg Tyr
        35

<210> SEQ ID NO 65
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 65

Tyr Pro Ile Lys Pro Glu Ala Pro Gly Glu Asp Ala Ser Ala Pro Glu
1               5                   10                  15

Glu Leu Asn Arg Tyr Tyr Ala Ser Leu Arg His Tyr Leu Asn Leu Val
                    20                  25                  30

Thr Arg Gln Arg Tyr
        35

<210> SEQ ID NO 66
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 66
```

Tyr Pro Ile Lys Pro Glu Ala Pro Gly Glu Asp Ala Ser Pro Ala Glu
1               5                   10                  15

Glu Leu Asn Arg Tyr Tyr Ala Ser Leu Arg His Tyr Leu Asn Leu Val
            20                  25                  30

Thr Arg Gln Arg Tyr
        35

<210> SEQ ID NO 67
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 67

Tyr Pro Ile Lys Pro Glu Ala Pro Gly Glu Asp Ala Ser Pro Glu Ala
1               5                   10                  15

Glu Leu Asn Arg Tyr Tyr Ala Ser Leu Arg His Tyr Leu Asn Leu Val
            20                  25                  30

Thr Arg Gln Arg Tyr
        35

<210> SEQ ID NO 68
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 68

Tyr Pro Ile Lys Pro Glu Ala Pro Gly Glu Asp Ala Ser Pro Glu Glu
1               5                   10                  15

Ala Leu Asn Arg Tyr Tyr Ala Ser Leu Arg His Tyr Leu Asn Leu Val
            20                  25                  30

Thr Arg Gln Arg Tyr
        35

<210> SEQ ID NO 69
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 69

Tyr Pro Ile Lys Pro Glu Ala Pro Gly Glu Asp Ala Ser Pro Glu Glu
1               5                   10                  15

Leu Ala Asn Arg Tyr Tyr Ala Ser Leu Arg His Tyr Leu Asn Leu Val
            20                  25                  30

Thr Arg Gln Arg Tyr
        35

<210> SEQ ID NO 70
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 70

Tyr Pro Ile Lys Pro Glu Ala Pro Gly Glu Asp Ala Ser Pro Glu Glu
1               5                   10                  15

Leu Asn Ala Arg Tyr Tyr Ala Ser Leu Arg His Tyr Leu Asn Leu Val
            20                  25                  30

Thr Arg Gln Arg Tyr
        35

<210> SEQ ID NO 71
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 71

Tyr Pro Ile Lys Pro Glu Ala Pro Gly Glu Asp Ala Ser Pro Glu Glu
1               5                   10                  15

Leu Asn Arg Ala Tyr Tyr Ala Ser Leu Arg His Tyr Leu Asn Leu Val
            20                  25                  30

Thr Arg Gln Arg Tyr
        35

<210> SEQ ID NO 72
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 72

Tyr Pro Ile Lys Pro Glu Ala Pro Gly Glu Asp Ala Ser Pro Glu Glu
1               5                   10                  15

Leu Asn Arg Tyr Ala Tyr Ala Ser Leu Arg His Tyr Leu Asn Leu Val
            20                  25                  30

Thr Arg Gln Arg Tyr
        35

<210> SEQ ID NO 73
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 73

Tyr Pro Ile Lys Pro Glu Ala Pro Gly Glu Asp Ala Ser Pro Glu Glu
1               5                   10                  15

Leu Asn Arg Tyr Tyr Ala Ala Ser Leu Arg His Tyr Leu Asn Leu Val
            20                  25                  30

Thr Arg Gln Arg Tyr
        35

<210> SEQ ID NO 74
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

```
<400> SEQUENCE: 74

Tyr Pro Ile Lys Pro Glu Ala Pro Gly Glu Asp Ala Ser Pro Glu Glu
1               5                   10                  15

Leu Asn Arg Tyr Tyr Ala Ser Ala Leu Arg His Tyr Leu Asn Leu Val
            20                  25                  30

Thr Arg Gln Arg Tyr
        35

<210> SEQ ID NO 75
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 75

Tyr Pro Ile Lys Pro Glu Ala Pro Gly Glu Asp Ala Ser Pro Glu Glu
1               5                   10                  15

Leu Asn Arg Tyr Tyr Ala Ser Leu Ala Arg His Tyr Leu Asn Leu Val
            20                  25                  30

Thr Arg Gln Arg Tyr
        35

<210> SEQ ID NO 76
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 76

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg Ala His Tyr Leu Asn Leu Val
            20                  25                  30

Thr Arg Gln Arg Tyr
        35

<210> SEQ ID NO 77
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 77

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Ala Tyr Leu Asn Leu Val
            20                  25                  30

Thr Arg Gln Arg Tyr
        35

<210> SEQ ID NO 78
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct
```

<400> SEQUENCE: 78

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Ala Leu Asn Leu Val
            20                  25                  30

Thr Arg Gln Arg Tyr
        35

<210> SEQ ID NO 79
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 79

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Ala Asn Leu Val
            20                  25                  30

Thr Arg Gln Arg Tyr
        35

<210> SEQ ID NO 80
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 80

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Ala Leu Val
            20                  25                  30

Thr Arg Gln Arg Tyr
        35

<210> SEQ ID NO 81
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 81

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Ala Val
            20                  25                  30

Thr Arg Gln Arg Tyr
        35

<210> SEQ ID NO 82
<211> LENGTH: 37
<212> TYPE: PRT
<213> ORGANISM: Artificial Sequence
<220> FEATURE:
<223> OTHER INFORMATION: Description of Artificial Sequence: Synthetic -continued peptide construct

<400> SEQUENCE: 82

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Ala
            20                  25                  30

Thr Arg Gln Arg Tyr
        35

<210> SEQ ID NO 83
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 83

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Ala Arg Gln Arg Tyr
        35

<210> SEQ ID NO 84
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 84

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Ala Gln Arg Tyr
        35

<210> SEQ ID NO 85
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 85

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Ala Arg Tyr
        35

<210> SEQ ID NO 86
<211> LENGTH: 37
<212> TYPE: PRT
<213> ORGANISM: Artificial Sequence
<220> FEATURE:

<223> OTHER INFORMATION: Description of Artificial Sequence: Synthetic
      peptide construct

<400> SEQUENCE: 86

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
                20                  25                  30

Arg Gln Arg Ala Tyr
            35

<210> SEQ ID NO 87
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 87

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
                20                  25                  30

Arg Gln Arg Tyr Ala
            35

<210> SEQ ID NO 88
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Tyr, Ala, Phe, Trp, or absent
<220> FEATURE:
<221> NAME/KEY: MOD_RES
<222> LOCATION: (2)
<223> OTHER INFORMATION: Pro, Gly, d-Ala, homoPro, hydroxy-Pro, or
      absent
<220> FEATURE:
<221> NAME/KEY: MOD_RES
<222> LOCATION: (3)
<223> OTHER INFORMATION: Ile, Ala, NorVal, Val, Leu, Pro, Ser, or Thr
<220> FEATURE:
<221> NAME/KEY: MOD_RES
<222> LOCATION: (4)
<223> OTHER INFORMATION: Lys, Ala, Gly, Arg, d-Ala, homoLys, homoArg,
      Glu, or Asp
<220> FEATURE:
<221> NAME/KEY: MOD_RES
<222> LOCATION: (6)
<223> OTHER INFORMATION: Glu, Ala, Val, Asp, Asn, or Gln
<220> FEATURE:
<221> NAME/KEY: MOD_RES
<222> LOCATION: (7)
<223> OTHER INFORMATION: Ala, Asn, His, Ser, or Tyr
<220> FEATURE:
<221> NAME/KEY: MOD_RES
<222> LOCATION: (9)
<223> OTHER INFORMATION: Gly, Ala, Ser, Sarcosine, Pro, or Aib
<220> FEATURE:
<221> NAME/KEY: MOD_RES
<222> LOCATION: (10)
<223> OTHER INFORMATION: Glu, Ala, Asp, Asn, Gln, Pro, Aib, or Gly
<220> FEATURE:
<221> NAME/KEY: MOD_RES
<222> LOCATION: (11)

```
<223> OTHER INFORMATION: Asp, Ala, Glu, Asn, Gln, Pro, Aib, or Gly
<220> FEATURE:
<221> NAME/KEY: MOD_RES
<222> LOCATION: (12)
<223> OTHER INFORMATION: Ala or d-Ala
<220> FEATURE:
<221> NAME/KEY: MOD_RES
<222> LOCATION: (13)
<223> OTHER INFORMATION: Ser, Ala, Thr, or homoSer
<220> FEATURE:
<221> NAME/KEY: MOD_RES
<222> LOCATION: (14)
<223> OTHER INFORMATION: Pro, Ala, homoPro, hydroxyPro, Aib, or Gly
<220> FEATURE:
<221> NAME/KEY: MOD_RES
<222> LOCATION: (15)
<223> OTHER INFORMATION: Glu, Ala, Asp, Asn, Gln, Pro, Aib, or Gly
<220> FEATURE:
<221> NAME/KEY: MOD_RES
<222> LOCATION: (16)
<223> OTHER INFORMATION: Glu, Ala, Asp, Asn, or Gln
<220> FEATURE:
<221> NAME/KEY: MOD_RES
<222> LOCATION: (17)
<223> OTHER INFORMATION: Leu, Ala, Met, Trp, Ile, Val, or NorVal
<220> FEATURE:
<221> NAME/KEY: MOD_RES
<222> LOCATION: (18)
<223> OTHER INFORMATION: Asn, Asp, Ala, Glu, Gln, Ser, or Thr
<220> FEATURE:
<221> NAME/KEY: MOD_RES
<222> LOCATION: (19)
<223> OTHER INFORMATION: Arg, Tyr, Lys, Ala, Gln, or N(Me)Ala
<220> FEATURE:
<221> NAME/KEY: MOD_RES
<222> LOCATION: (21)
<223> OTHER INFORMATION: Tyr, Ala, Met, Phe, or Leu
<220> FEATURE:
<221> NAME/KEY: MOD_RES
<222> LOCATION: (22)
<223> OTHER INFORMATION: Ala, Ser, Thr, or d-Ala
<220> FEATURE:
<221> NAME/KEY: MOD_RES
<222> LOCATION: (23)
<223> OTHER INFORMATION: Ser, Ala, Thr, or homoSer
<220> FEATURE:
<221> NAME/KEY: MOD_RES
<222> LOCATION: (26)
<223> OTHER INFORMATION: His or Ala
<220> FEATURE:
<221> NAME/KEY: MOD_RES
<222> LOCATION: (28)
<223> OTHER INFORMATION: Leu, Ile, Val, or Ala
<220> FEATURE:
<221> NAME/KEY: MOD_RES
<222> LOCATION: (30)
<223> OTHER INFORMATION: Leu, Ala, NorVal, Val, Ile, or Met
<220> FEATURE:
<221> NAME/KEY: MOD_RES
<222> LOCATION: (31)
<223> OTHER INFORMATION: Ala, Val, Ile, or Leu
<220> FEATURE:
<221> NAME/KEY: MOD_RES
<222> LOCATION: (36)
<223> OTHER INFORMATION: Tyr, N(Me)Tyr, His, Trp, or Phe

<400> SEQUENCE: 88

Xaa Xaa Xaa Xaa Pro Xaa Xaa Pro Xaa Xaa Xaa Xaa Xaa Xaa Xaa
1               5                   10                  15

Xaa Xaa Xaa Tyr Xaa Xaa Xaa Leu Arg Xaa Tyr Xaa Asn Xaa Xaa Thr
            20                  25                  30

Arg Gln Arg Xaa
        35

<210> SEQ ID NO 89
```

```
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 89

Ala Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 90
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 90

Ile Ala Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 91
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 91

Ile Gly Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 92
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)
<223> OTHER INFORMATION: d-Ala

<400> SEQUENCE: 92

Ile Ala Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr
```

<210> SEQ ID NO 93
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 93

Ile Lys Ala Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 94
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 94

Ile Lys Pro Ala Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 95
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (5)
<223> OTHER INFORMATION: d-Ala

<400> SEQUENCE: 95

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 96
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 96

Ile Lys Pro Glu Ala Ala Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

```
<210> SEQ ID NO 97
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 97

Ile Lys Pro Glu Ala Pro Ala Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 98
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 98

Ile Lys Pro Glu Ala Pro Gly Ala Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 99
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 99

Ile Lys Pro Glu Ala Pro Gly Glu Ala Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 100
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (10)
<223> OTHER INFORMATION: d-Ala

<400> SEQUENCE: 100

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr
```

<210> SEQ ID NO 101
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 101

Ile Lys Pro Glu Ala Pro Gly Glu Asp Ala Ala Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 102
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 102

Ile Lys Pro Glu Ala Pro Gly Glu Asp Ala Ser Ala Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 103
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 103

Ile Lys Pro Glu Ala Pro Gly Glu Asp Ala Ser Pro Ala Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 104
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 104

Ile Lys Pro Glu Ala Pro Gly Glu Asp Ala Ser Pro Glu Ala Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 105

<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 105

Ile Lys Pro Glu Ala Pro Gly Glu Asp Ala Ser Pro Glu Glu Ala Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 106
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 106

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 107
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 107

Ile Lys Pro Glu Ala Pro Gly Glu Asp Ala Ser Pro Glu Glu Leu Asn
1               5                   10                  15

Ala Tyr Tyr Ala Ser Leu Arg His Tyr Leu Asn Leu Val Thr Arg Gln
            20                  25                  30

Arg Tyr

<210> SEQ ID NO 108
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 108

Ile Lys Pro Glu Ala Pro Gly Glu Asp Ala Ser Pro Glu Glu Leu Asn
1               5                   10                  15

Lys Tyr Tyr Ala Ser Leu Arg His Tyr Leu Asn Leu Val Thr Arg Gln
            20                  25                  30

Arg Tyr

<210> SEQ ID NO 109
<211> LENGTH: 34
<212> TYPE: PRT
<213> ORGANISM: Artificial Sequence

```
<220> FEATURE:
<223> OTHER INFORMATION: Description of Artificial Sequence: Synthetic
      peptide construct
<220> FEATURE:
<221> NAME/KEY: MOD_RES
<222> LOCATION: (17)
<223> OTHER INFORMATION: (NMe)Ala

<400> SEQUENCE: 109

Ile Lys Pro Glu Ala Pro Gly Glu Asp Ala Ser Pro Glu Glu Leu Asn
1               5                   10                  15

Ala Tyr Tyr Ala Ser Leu Arg His Tyr Leu Asn Leu Val Thr Arg Gln
            20                  25                  30

Arg Tyr

<210> SEQ ID NO 110
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 110

Ile Lys Pro Glu Ala Pro Gly Glu Asp Ala Ser Pro Glu Glu Leu Asn
1               5                   10                  15

Arg Ala Tyr Ala Ser Leu Arg His Tyr Leu Asn Leu Val Thr Arg Gln
            20                  25                  30

Arg Tyr

<210> SEQ ID NO 111
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 111

Ile Lys Pro Glu Ala Pro Gly Glu Asp Ala Ser Pro Glu Glu Leu Asn
1               5                   10                  15

Arg Tyr Ala Ala Ser Leu Arg His Tyr Leu Asn Leu Val Thr Arg Gln
            20                  25                  30

Arg Tyr

<210> SEQ ID NO 112
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (20)
<223> OTHER INFORMATION: d-Ala

<400> SEQUENCE: 112

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr
```

<210> SEQ ID NO 113
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 113

Ile Lys Pro Glu Ala Pro Gly Glu Asp Ala Ser Pro Glu Glu Leu Asn
1               5                   10                  15

Arg Tyr Tyr Ala Ala Leu Arg His Tyr Leu Asn Leu Val Thr Arg Gln
            20                  25                  30

Arg Tyr

<210> SEQ ID NO 114
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 114

Ile Lys Pro Glu Ala Pro Gly Glu Asp Ala Ser Pro Glu Glu Leu Asn
1               5                   10                  15

Arg Tyr Tyr Ala Ser Ala Arg His Tyr Leu Asn Leu Val Thr Arg Gln
            20                  25                  30

Arg Tyr

<210> SEQ ID NO 115
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 115

Ile Lys Pro Glu Ala Pro Gly Glu Asp Ala Ser Pro Glu Glu Leu Asn
1               5                   10                  15

Arg Tyr Tyr Ala Ser Leu Ala His Tyr Leu Asn Leu Val Thr Arg Gln
            20                  25                  30

Arg Tyr

<210> SEQ ID NO 116
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 116

Ile Lys Pro Glu Ala Pro Gly Glu Asp Ala Ser Pro Glu Glu Leu Asn
1               5                   10                  15

Arg Tyr Tyr Ala Ser Leu Lys His Tyr Leu Asn Leu Val Thr Arg Gln
            20                  25                  30

Arg Tyr

<210> SEQ ID NO 117
<211> LENGTH: 34

```
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 117

Ile Lys Pro Glu Ala Pro Gly Glu Asp Ala Ser Pro Glu Glu Leu Asn
1               5                   10                  15

Arg Tyr Tyr Ala Ser Leu Arg Ala Tyr Leu Asn Leu Val Thr Arg Gln
            20                  25                  30

Arg Tyr

<210> SEQ ID NO 118
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 118

Ile Lys Pro Glu Ala Pro Gly Glu Asp Ala Ser Pro Glu Glu Leu Asn
1               5                   10                  15

Arg Tyr Tyr Ala Ser Leu Arg His Ala Leu Asn Leu Val Thr Arg Gln
            20                  25                  30

Arg Tyr

<210> SEQ ID NO 119
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 119

Ile Lys Pro Glu Ala Pro Gly Glu Asp Ala Ser Pro Glu Glu Leu Asn
1               5                   10                  15

Arg Tyr Tyr Ala Ser Leu Arg His Tyr Ala Asn Leu Val Thr Arg Gln
            20                  25                  30

Arg Tyr

<210> SEQ ID NO 120
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 120

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Ala Leu Val Thr Arg Gln
            20                  25                  30

Arg Tyr

<210> SEQ ID NO 121
<211> LENGTH: 34
<212> TYPE: PRT
<213> ORGANISM: Artificial Sequence
<220> FEATURE:
```

```
<223> OTHER INFORMATION: Description of Artificial Sequence: Synthetic
      peptide construct

<400> SEQUENCE: 121

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Ala Val Thr Arg Gln
            20                  25                  30

Arg Tyr

<210> SEQ ID NO 122
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 122

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Ala Thr Arg Gln
            20                  25                  30

Arg Tyr

<210> SEQ ID NO 123
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 123

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Ala Arg Gln
            20                  25                  30

Arg Tyr

<210> SEQ ID NO 124
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 124

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Ala Gln
            20                  25                  30

Arg Tyr

<210> SEQ ID NO 125
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
```

```
<400> SEQUENCE: 125

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Lys Gln
            20                  25                  30

Arg Tyr

<210> SEQ ID NO 126
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 126

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Ala
            20                  25                  30

Arg Tyr

<210> SEQ ID NO 127
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 127

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Ala Tyr

<210> SEQ ID NO 128
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 128

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Ala

<210> SEQ ID NO 129
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 129

Ser Lys Pro Asp Asn Pro Gly Glu Asp Ala Pro Ala Glu Asp Met Ala
```

```
1               5                  10                  15
Arg Tyr Tyr Ser Ala Leu Arg His Tyr Ile Asn Leu Ile Thr Arg Gln
            20                  25                  30

Arg Tyr

<210> SEQ ID NO 130
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 130

Pro Lys Pro Glu Ala Pro Gly Glu Asp Ala Ser Pro Glu Glu Leu Asn
1               5                  10                  15

Arg Tyr Tyr Ala Ser Leu Arg Ala Tyr Leu Asn Leu Val Thr Arg Gln
            20                  25                  30

Arg Tyr

<210> SEQ ID NO 131
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Pro

<400> SEQUENCE: 131

Pro Lys Pro Glu Ala Pro Gly Glu Asp Ala Ser Pro Glu Glu Leu Asn
1               5                  10                  15

Arg Tyr Tyr Ala Ser Leu Arg His Tyr Leu Asn Leu Val Thr Arg Gln
            20                  25                  30

Arg Tyr

<210> SEQ ID NO 132
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Ac-Pro

<400> SEQUENCE: 132

Pro Lys Pro Glu Ala Pro Gly Glu Asp Ala Ser Pro Glu Glu Leu Asn
1               5                  10                  15

Arg Tyr Tyr Ala Ser Leu Arg His Tyr Leu Asn Leu Val Thr Arg Gln
            20                  25                  30

Arg Tyr

<210> SEQ ID NO 133
<211> LENGTH: 34
<212> TYPE: PRT
<213> ORGANISM: Artificial Sequence
<220> FEATURE:
<223> OTHER INFORMATION: Description of Artificial Sequence: Synthetic
```

```
        peptide construct
<220> FEATURE:
<221> NAME/KEY: MOD_RES
<222> LOCATION: (34)
<223> OTHER INFORMATION: (NMe)Tyr

<400> SEQUENCE: 133

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 134
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 134

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg His

<210> SEQ ID NO 135
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 135

Ile Lys Pro Glu Ala Pro Gly Glu Asp Ala Ser Pro Glu Glu Leu Asn
1               5                   10                  15

Arg Tyr Tyr Ala Ser Leu Arg Ala Tyr Leu Asn Leu Val Thr Arg Gln
            20                  25                  30

Arg His

<210> SEQ ID NO 136
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 136

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Trp

<210> SEQ ID NO 137
<211> LENGTH: 34
<212> TYPE: PRT
<213> ORGANISM: Artificial Sequence
<220> FEATURE:
```

```
<223> OTHER INFORMATION: Description of Artificial Sequence: Synthetic
      peptide construct

<400> SEQUENCE: 137

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Phe

<210> SEQ ID NO 138
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 138

Ile Lys Pro Glu Ala Pro Gly Glu Asp Ala Ser Pro Glu Glu Leu Asn
1               5                   10                  15

Arg Tyr Tyr Ala Ser Leu Arg Ala Tyr Leu Asn Leu Val Thr Arg Gln
            20                  25                  30

Arg Phe

<210> SEQ ID NO 139
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (34)
<223> OTHER INFORMATION: Tyr(CH2SO3)

<400> SEQUENCE: 139

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 140
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (34)
<223> OTHER INFORMATION: Pro(OH)

<400> SEQUENCE: 140

Ile Lys Pro Glu Ala Pro Gly Glu Asp Ala Ser Pro Glu Glu Leu Asn
1               5                   10                  15

Arg Tyr Tyr Ala Ser Leu Arg Ala Tyr Leu Asn Leu Val Thr Arg Gln
            20                  25                  30

Arg Pro
```

```
<210> SEQ ID NO 141
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (33)
<223> OTHER INFORMATION: homo-Arg

<400> SEQUENCE: 141

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 142
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 142

Ile Lys Pro Glu Ala Pro Gly Glu Asp Ala Ser Ala Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 143
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 143

Ile Lys Pro Glu Ala Pro Gly Glu Asp Ala Ser Pro Glu Glu Leu Ala
1               5                   10                  15

Arg Tyr Tyr Ala Ser Leu Arg Ala Tyr Leu Asn Leu Val Thr Arg Gln
            20                  25                  30

Arg Tyr

<210> SEQ ID NO 144
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 144

Ile Lys Pro Glu Ala Pro Gly Glu Asp Ala Ser Ala Glu Glu Leu Ala
1               5                   10                  15

Arg Tyr Tyr Ala Ser Leu Arg Ala Tyr Leu Asn Leu Val Thr Arg Gln
            20                  25                  30

Arg Tyr
```

```
<210> SEQ ID NO 145
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)
<223> OTHER INFORMATION: homo-Lys

<400> SEQUENCE: 145

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 146
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (11)
<223> OTHER INFORMATION: Ser(Ac)

<400> SEQUENCE: 146

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 147
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (21)
<223> OTHER INFORMATION: Ser(Ac)

<400> SEQUENCE: 147

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 148
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
```

```
<222> LOCATION: (17)
<223> OTHER INFORMATION: homo-Arg

<400> SEQUENCE: 148

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 149
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (23)
<223> OTHER INFORMATION: homo-Arg

<400> SEQUENCE: 149

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 150
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: FmocSO3H-Ile
<220> FEATURE:
<221> NAME/KEY: MOD_RES
<222> LOCATION: (2)
<223> OTHER INFORMATION: Lys(FmocSO3H)

<400> SEQUENCE: 150

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 151
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Ile

<400> SEQUENCE: 151

Ile Lys Pro Glu Ala Pro Gly Glu Asp Ala Ser Pro Glu Glu Leu Ala
```

```
                1               5                   10                  15
Arg Tyr Tyr Ala Ser Leu Arg His Tyr Leu Asn Leu Val Thr Arg Gln
                20                  25                  30

Arg Tyr

<210> SEQ ID NO 152
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Fmoc-Ile

<400> SEQUENCE: 152

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
                20                  25                  30

Arg Tyr

<210> SEQ ID NO 153
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isobutyloxycarbonyl-Ile

<400> SEQUENCE: 153

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
                20                  25                  30

Arg Tyr

<210> SEQ ID NO 154
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isopropyloxycarbonyl-Ile

<400> SEQUENCE: 154

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
                20                  25                  30

Arg Tyr

<210> SEQ ID NO 155
<211> LENGTH: 34
```

```
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: N-butyloxycarbonyl-Ile

<400> SEQUENCE: 155

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 156
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Ethoxycarbonyl-Ile

<400> SEQUENCE: 156

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 157
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 157

Ile Lys Pro Glu Ala Pro Gly Glu Asp Ala Ser Pro Glu Glu Leu Ser
1               5                   10                  15

Arg Tyr Tyr Ala Ser Leu Arg His Tyr Leu Asn Leu Val Thr Arg Gln
            20                  25                  30

Arg Tyr

<210> SEQ ID NO 158
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (16)
<223> OTHER INFORMATION: NorVal

<400> SEQUENCE: 158

Ile Lys Pro Glu Ala Pro Gly Glu Asp Ala Ser Pro Glu Glu Leu Xaa
1               5                   10                  15
```

Arg Tyr Tyr Ala Ser Leu Arg His Tyr Leu Asn Leu Val Thr Arg Gln
            20                  25                  30

Arg Tyr

<210> SEQ ID NO 159
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)
<223> OTHER INFORMATION: homo-Lys

<400> SEQUENCE: 159

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 160
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Ile
<220> FEATURE:
<221> NAME/KEY: MOD_RES
<222> LOCATION: (2)
<223> OTHER INFORMATION: homo-Lys

<400> SEQUENCE: 160

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 161
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (17)
<223> OTHER INFORMATION: homo-Arg

<400> SEQUENCE: 161

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

-continued

<210> SEQ ID NO 162
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Ile
<220> FEATURE:
<221> NAME/KEY: MOD_RES
<222> LOCATION: (17)
<223> OTHER INFORMATION: homo-Arg

<400> SEQUENCE: 162

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 163
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)
<223> OTHER INFORMATION: homo-Lys
<220> FEATURE:
<221> NAME/KEY: MOD_RES
<222> LOCATION: (17)
<223> OTHER INFORMATION: homo-Arg

<400> SEQUENCE: 163

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 164
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Ile
<220> FEATURE:
<221> NAME/KEY: MOD_RES
<222> LOCATION: (2)
<223> OTHER INFORMATION: homo-Lys
<220> FEATURE:
<221> NAME/KEY: MOD_RES
<222> LOCATION: (17)
<223> OTHER INFORMATION: homo-Arg

<400> SEQUENCE: 164

Ile Lys Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 165
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 165

Ile Lys Pro Glu Ala Pro Gly Glu Asp Ala Ser Pro Glu Glu Met Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 166
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)
<223> OTHER INFORMATION: homo-Lys

<400> SEQUENCE: 166

Ile Lys Pro Glu Ala Pro Gly Glu Asp Ala Ser Ala Glu Glu Leu Ala
1               5                   10                  15

Arg Tyr Tyr Ala Ser Leu Arg Ala Tyr Leu Asn Leu Val Thr Arg Gln
            20                  25                  30

Arg Tyr

<210> SEQ ID NO 167
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)
<223> OTHER INFORMATION: homo-Lys
<220> FEATURE:
<221> NAME/KEY: MOD_RES
<222> LOCATION: (17)
<223> OTHER INFORMATION: homo-Arg

<400> SEQUENCE: 167

Ile Lys Pro Glu Ala Pro Gly Glu Asp Ala Ser Ala Glu Glu Leu Ala
1               5                   10                  15

Arg Tyr Tyr Ala Ser Leu Arg Ala Tyr Leu Asn Leu Val Thr Arg Gln
            20                  25                  30

Arg Tyr

<210> SEQ ID NO 168
<211> LENGTH: 34
<212> TYPE: PRT

```
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)
<223> OTHER INFORMATION: homo-Lys
<220> FEATURE:
<221> NAME/KEY: MOD_RES
<222> LOCATION: (11)
<223> OTHER INFORMATION: homo-Ser
<220> FEATURE:
<221> NAME/KEY: MOD_RES
<222> LOCATION: (17)
<223> OTHER INFORMATION: homo-Arg

<400> SEQUENCE: 168

Leu Lys Pro Glu Ala Pro Gly Glu Asp Ala Ser Ala Glu Glu Leu Ala
1               5                  10                  15

Arg Tyr Tyr Ala Ser Leu Arg Ala Tyr Leu Asn Leu Val Thr Arg Gln
            20                  25                  30

Arg Tyr

<210> SEQ ID NO 169
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)
<223> OTHER INFORMATION: homo-Lys

<400> SEQUENCE: 169

Ile Lys Pro Glu Ala Pro Gly Glu Asp Ala Ser Ala Gln Glu Leu Ala
1               5                  10                  15

Arg Tyr Tyr Ala Ser Leu Arg Ala Tyr Leu Asn Leu Val Thr Arg Gln
            20                  25                  30

Arg Tyr

<210> SEQ ID NO 170
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 170

Ile Lys Ala Pro Glu Ala Pro Gly Glu Asp Ala Ser Pro Glu Glu Leu
1               5                  10                  15

Asn Arg Tyr Tyr Ala Ser Leu Lys His Tyr Leu Asn Leu Val Thr Arg
            20                  25                  30

Gln Arg Tyr
        35

<210> SEQ ID NO 171
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
```

```
<400> SEQUENCE: 171

Ile Lys Pro Glu Cys Pro Gly Glu Asp Ala Ser Pro Glu Glu Cys Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 172
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 172

Leu Glu Pro Val Tyr Pro Gly Glu Asp Ala Ser Pro Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 173
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 173

Leu Glu Pro Val Tyr Pro Gly Glu Asp Ala Ser Pro Glu Glu Leu Ala
1               5                   10                  15

Arg Tyr Tyr Ala Ser Leu Arg His Tyr Ile Asn Leu Ile Thr Arg Gln
            20                  25                  30

Arg Tyr

<210> SEQ ID NO 174
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 174

Ile Lys Pro Glu Ala Pro Gly Glu Asp Ala Ser Pro Glu Glu Leu Asn
1               5                   10                  15

Arg Tyr Tyr Tyr Ala Ser Leu Arg His Tyr Leu Asn Ala Val Thr Arg
            20                  25                  30

Gln Arg Tyr
        35

<210> SEQ ID NO 175
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 175
```

```
Pro Glu Ala Pro Gly Glu Asp Ala Ser Pro Glu Glu Leu Asn Arg Tyr
1               5                   10                  15

Tyr Ala Ser Leu Arg His Tyr Leu Asn Leu Val Thr Arg Gln Arg Tyr
            20                  25                  30
```

<210> SEQ ID NO 176
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 176

```
Glu Asp Ala Ser Pro Glu Glu Leu Asn Arg Tyr Tyr Ala Ser Leu Arg
1               5                   10                  15

His Tyr Leu Asn Leu Val Thr Arg Gln Arg Tyr
            20                  25
```

<210> SEQ ID NO 177
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 177

```
Glu Glu Leu Asn Arg Tyr Tyr Ala Ser Leu Arg His Tyr Leu Asn Leu
1               5                   10                  15

Val Thr Arg Gln Arg Tyr
            20
```

<210> SEQ ID NO 178
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 178

```
Tyr Tyr Ala Ser Leu Arg His Tyr Leu Asn Leu Val Thr Arg Gln Arg
1               5                   10                  15

Tyr
```

<210> SEQ ID NO 179
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 179

```
Arg His Tyr Leu Asn Leu Val Thr Arg Gln Arg Tyr
1               5                   10
```

<210> SEQ ID NO 180
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:

<221> NAME/KEY: MOD_RES
<222> LOCATION: (5)
<223> OTHER INFORMATION: Aca

<400> SEQUENCE: 180

Tyr Pro Ile Lys Xaa Pro Glu Glu Leu Asn Arg Tyr Tyr Ala Ser Leu
1               5                   10                  15
Arg His Tyr Leu Asn Leu Val Thr Arg Gln Arg Tyr
            20                  25

<210> SEQ ID NO 181
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (5)
<223> OTHER INFORMATION: Aca

<400> SEQUENCE: 181

Tyr Pro Ile Lys Xaa Glu Glu Leu Asn Arg Tyr Tyr Ala Ser Leu Arg
1               5                   10                  15
His Tyr Leu Asn Leu Val Thr Arg Gln Arg Tyr
            20                  25

<210> SEQ ID NO 182
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (5)
<223> OTHER INFORMATION: Aca

<400> SEQUENCE: 182

Tyr Pro Ile Lys Xaa Glu Leu Asn Arg Tyr Tyr Ala Ser Leu Arg His
1               5                   10                  15
Tyr Leu Asn Leu Val Thr Arg Gln Arg Tyr
            20                  25

<210> SEQ ID NO 183
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (5)
<223> OTHER INFORMATION: Aca

<400> SEQUENCE: 183

Tyr Pro Ile Lys Xaa Ala Ser Leu Arg His Tyr Leu Asn Leu Val Thr
1               5                   10                  15
Arg Gln Arg Tyr
            20

<210> SEQ ID NO 184
<211> LENGTH: 17
<212> TYPE: PRT

```
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (5)
<223> OTHER INFORMATION: Aca

<400> SEQUENCE: 184

Tyr Pro Ile Lys Xaa Arg His Tyr Leu Asn Leu Val Thr Arg Gln Arg
1               5                   10                  15

Tyr

<210> SEQ ID NO 185
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 185

Tyr Pro Ile Lys Pro Glu Ala Pro Gly Glu Ala Asn Arg Tyr Tyr Ala
1               5                   10                  15

Ser Leu Arg His Tyr Leu Asn Leu Val Thr Arg Gln Arg Tyr
            20                  25                  30

<210> SEQ ID NO 186
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (11)
<223> OTHER INFORMATION: Ado

<400> SEQUENCE: 186

Tyr Pro Ile Lys Pro Glu Ala Pro Gly Glu Xaa Asn Arg Tyr Tyr Ala
1               5                   10                  15

Ser Leu Arg His Tyr Leu Asn Leu Val Thr Arg Gln Arg Tyr
            20                  25                  30

<210> SEQ ID NO 187
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Fmoc-Ile
<220> FEATURE:
<221> NAME/KEY: MOD_RES
<222> LOCATION: (2)
<223> OTHER INFORMATION: Lys(PEG5000)

<400> SEQUENCE: 187

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30
```

Arg Tyr

<210> SEQ ID NO 188
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Fmoc-Lys(PEG5000)

<400> SEQUENCE: 188

Lys Pro Glu Ala Pro Gly Glu Asp Ala Ser Pro Glu Glu Leu Asn Arg
1               5                   10                  15

Tyr Tyr Ala Ser Leu Arg His Tyr Leu Asn Leu Val Thr Arg Gln Arg
            20                  25                  30

Tyr

<210> SEQ ID NO 189
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Fmoc-Ile
<220> FEATURE:
<221> NAME/KEY: MOD_RES
<222> LOCATION: (17)
<223> OTHER INFORMATION: Lys(PEG5000)

<400> SEQUENCE: 189

Ile Ala Pro Glu Ala Pro Gly Glu Asp Ala Ser Pro Glu Glu Leu Asn
1               5                   10                  15

Lys Tyr Tyr Ala Ser Leu Arg His Tyr Leu Asn Leu Val Thr Arg Gln
            20                  25                  30

Arg Tyr

<210> SEQ ID NO 190
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: PEG5000-Ile

<400> SEQUENCE: 190

Ile Ala Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 191
<211> LENGTH: 34
<212> TYPE: PRT

<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (11)
<223> OTHER INFORMATION: Ser(OAc)

<400> SEQUENCE: 191

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 192
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (21)
<223> OTHER INFORMATION: Ser(OAc)

<400> SEQUENCE: 192

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 193
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Fmoc-Ile
<220> FEATURE:
<221> NAME/KEY: MOD_RES
<222> LOCATION: (17)
<223> OTHER INFORMATION: Lys(Oct)

<400> SEQUENCE: 193

Ile Ala Pro Glu Ala Pro Gly Glu Asp Ala Ser Pro Glu Glu Leu Asn
1               5                   10                  15

Lys Tyr Tyr Ala Ser Leu Arg His Tyr Leu Asn Leu Val Thr Arg Gln
            20                  25                  30

Arg Tyr

<210> SEQ ID NO 194
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES

```
<222> LOCATION: (17)
<223> OTHER INFORMATION: Lys(Oct)

<400> SEQUENCE: 194

Ile Ala Pro Glu Ala Pro Gly Glu Asp Ala Ser Pro Glu Glu Leu Asn
1               5                   10                  15

Lys Tyr Tyr Ala Ser Leu Arg His Tyr Leu Asn Leu Val Thr Arg Gln
            20                  25                  30

Arg Tyr

<210> SEQ ID NO 195
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Octanoic acid-Ile

<400> SEQUENCE: 195

Ile Ala Pro Glu Ala Pro Gly Glu Asp Ala Ser Pro Glu Glu Leu Ala
1               5                   10                  15

Arg Tyr Tyr Ala Ser Leu Arg His Tyr Leu Asn Leu Val Thr Arg Gln
            20                  25                  30

Arg Tyr

<210> SEQ ID NO 196
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Fmoc-Ile
<220> FEATURE:
<221> NAME/KEY: MOD_RES
<222> LOCATION: (17)
<223> OTHER INFORMATION: Lys(stearyl)

<400> SEQUENCE: 196

Ile Ala Pro Glu Ala Pro Gly Glu Asp Ala Ser Pro Glu Glu Leu Asn
1               5                   10                  15

Lys Tyr Tyr Ala Ser Leu Arg His Tyr Leu Asn Leu Val Thr Arg Gln
            20                  25                  30

Arg Tyr

<210> SEQ ID NO 197
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (17)
<223> OTHER INFORMATION: Lys(stearyl)

<400> SEQUENCE: 197

Ile Ala Pro Glu Ala Pro Gly Glu Asp Ala Ser Pro Glu Glu Leu Asn
```

```
                1               5                  10                 15
Lys Tyr Tyr Ala Ser Leu Arg His Tyr Leu Asn Leu Val Thr Arg Gln
                20                 25                 30

Arg Tyr

<210> SEQ ID NO 198
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Ac-Glu

<400> SEQUENCE: 198

Glu Asp Ala Ser Pro Glu Glu Leu Asn Arg Tyr Tyr Ala Ser Leu Arg
1               5                  10                 15

His Tyr Leu Asn Leu Val Thr Arg Gln Arg Tyr
                20                 25

<210> SEQ ID NO 199
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Stearyl-Glu

<400> SEQUENCE: 199

Glu Asp Ala Ser Pro Glu Glu Leu Asn Arg Tyr Tyr Ala Ser Leu Arg
1               5                  10                 15

His Tyr Leu Asn Leu Val Thr Arg Gln Arg Tyr
                20                 25

<210> SEQ ID NO 200
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Octyl-Glu

<400> SEQUENCE: 200

Glu Asp Ala Ser Pro Glu Glu Leu Asn Arg Tyr Tyr Ala Ser Leu Arg
1               5                  10                 15

His Tyr Leu Asn Leu Val Thr Arg Gln Arg Tyr
                20                 25

<210> SEQ ID NO 201
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
```

```
<221> NAME/KEY: MOD_RES
<222> LOCATION: (1)
<223> OTHER INFORMATION: Succinyl-Glu

<400> SEQUENCE: 201

Glu Asp Ala Ser Pro Glu Glu Leu Asn Arg Tyr Tyr Ala Ser Leu Arg
1               5                   10                  15

His Tyr Leu Asn Leu Val Thr Arg Gln Arg Tyr
            20                  25

<210> SEQ ID NO 202
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Stearyl-Ala

<400> SEQUENCE: 202

Ala Ser Leu Arg His Tyr Leu Asn Leu Val Thr Arg Gln Arg Tyr
1               5                   10                  15

<210> SEQ ID NO 203
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Octyl-Ala

<400> SEQUENCE: 203

Ala Ser Leu Arg His Tyr Leu Asn Leu Val Thr Arg Gln Arg Tyr
1               5                   10                  15

<210> SEQ ID NO 204
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (14)
<223> OTHER INFORMATION: Lys(PEG)

<400> SEQUENCE: 204

Ile Ala Pro Glu Ala Pro Gly Glu Asp Ala Ser Pro Glu Lys Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 205
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
```

```
<220> FEATURE:
<221> NAME/KEY: MOD_RES
<222> LOCATION: (14)
<223> OTHER INFORMATION: Lys(Oct)

<400> SEQUENCE: 205

Ile Ala Pro Glu Ala Pro Gly Glu Asp Ala Ser Pro Glu Lys Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 206
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Fmoc-Ile
<220> FEATURE:
<221> NAME/KEY: MOD_RES
<222> LOCATION: (14)
<223> OTHER INFORMATION: Lys(Oct)

<400> SEQUENCE: 206

Ile Ala Pro Glu Ala Pro Gly Glu Asp Ala Ser Pro Glu Lys Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 207
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (34)
<223> OTHER INFORMATION: Tyr(8-Am-3,6-dioxaoct)

<400> SEQUENCE: 207

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 208
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (34)
<223> OTHER INFORMATION: Tyr(11-Am-undecanoyl)

<400> SEQUENCE: 208
```

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 209
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (34)
<223> OTHER INFORMATION: Tyr(12 Ado)

<400> SEQUENCE: 209

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 210
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (34)
<223> OTHER INFORMATION: Tyr(8-Oct)

<400> SEQUENCE: 210

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 211
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: C-term Mimic A linker to SEQ ID NO: 352

<400> SEQUENCE: 211

Ile Lys Pro Glu Ala
1               5

<210> SEQ ID NO 212
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide construct

```
<220> FEATURE:
<223> OTHER INFORMATION: C-term Mimic A linker to SEQ ID NO: 353

<400> SEQUENCE: 212

Ile Lys Pro Glu Ala Pro
1               5

<210> SEQ ID NO 213
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: C-term Mimic A linker to SEQ ID NO: 354

<400> SEQUENCE: 213

Ile Lys Pro Glu Ala Pro Gly
1               5

<210> SEQ ID NO 214
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: C-term Mimic A linker to SEQ ID NO: 355

<400> SEQUENCE: 214

Ile Lys Pro Glu Ala Pro Gly Glu
1               5

<210> SEQ ID NO 215
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: C-term Mimic A linker to SEQ ID NO: 356

<400> SEQUENCE: 215

Ile Lys Pro Glu Ala Pro Gly Glu Asp
1               5

<210> SEQ ID NO 216
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: C-term Mimic A linker to SEQ ID NO: 357

<400> SEQUENCE: 216

Ile Lys Pro Glu Ala Pro Gly Glu Asp Ala
1               5                   10

<210> SEQ ID NO 217
<211> LENGTH: 11
<212> TYPE: PRT
<213> ORGANISM: Artificial Sequence
<220> FEATURE:
<223> OTHER INFORMATION: Description of Artificial Sequence: Synthetic
```

```
                                 peptide construct
<220> FEATURE:
<223> OTHER INFORMATION: C-term Mimic A linker to SEQ ID NO: 358

<400> SEQUENCE: 217

Ile Lys Pro Glu Ala Pro Gly Glu Asp Ala Ser
1               5                   10

<210> SEQ ID NO 218
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (7)
<223> OTHER INFORMATION: Aib

<400> SEQUENCE: 218

Ile Lys Pro Glu Ala Ala Xaa Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 219
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (8)
<223> OTHER INFORMATION: Aib

<400> SEQUENCE: 219

Ile Lys Pro Glu Ala Pro Ala Xaa Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 220
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (9)
<223> OTHER INFORMATION: Aib

<400> SEQUENCE: 220

Ile Lys Pro Glu Ala Pro Gly Ala Xaa Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr
```

```
<210> SEQ ID NO 221
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (10)
<223> OTHER INFORMATION: Aib

<400> SEQUENCE: 221

Ile Lys Pro Glu Ala Pro Gly Glu Ala Xaa Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 222
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (11)
<223> OTHER INFORMATION: Aib

<400> SEQUENCE: 222

Ile Lys Pro Glu Ala Pro Gly Glu Asp Ala Xaa Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 223
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (12)
<223> OTHER INFORMATION: Aib

<400> SEQUENCE: 223

Ile Lys Pro Glu Ala Pro Gly Glu Asp Ala Ala Xaa Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 224
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (13)
```

<223> OTHER INFORMATION: Aib

<400> SEQUENCE: 224

Ile Lys Pro Glu Ala Pro Gly Glu Asp Ala Ser Ala Xaa Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 225
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 225

Ile Lys Pro Glu Ala Ala Pro Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 226
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 226

Ile Lys Pro Glu Ala Pro Ala Pro Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 227
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 227

Ile Lys Pro Glu Ala Pro Gly Ala Pro Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 228
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 228

Ile Lys Pro Glu Ala Pro Gly Glu Ala Pro Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 229
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 229

Ile Lys Pro Glu Ala Pro Gly Glu Asp Ala Pro Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 230
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 230

Ile Lys Pro Glu Ala Pro Gly Glu Asp Ala Ser Ala Pro Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 231
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: C-term Mimic B linker to SEQ ID NO: 359

<400> SEQUENCE: 231

Ile Lys Pro Glu Ala
1               5

<210> SEQ ID NO 232
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: C-term Mimic B linker to SEQ ID NO: 360

<400> SEQUENCE: 232

Ile Lys Pro Glu Ala Pro
1               5

```
<210> SEQ ID NO 233
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: C-term Mimic B linker to SEQ ID NO: 361

<400> SEQUENCE: 233

Ile Lys Pro Glu Ala Pro Gly
1               5

<210> SEQ ID NO 234
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: C-term Mimic B linker to SEQ ID NO: 362

<400> SEQUENCE: 234

Ile Lys Pro Glu Ala Pro Gly Glu
1               5

<210> SEQ ID NO 235
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: C-term Mimic B linker to SEQ ID NO: 363

<400> SEQUENCE: 235

Ile Lys Pro Glu Ala Pro Gly Glu Asp
1               5

<210> SEQ ID NO 236
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: C-term Mimic B linker to SEQ ID NO: 364

<400> SEQUENCE: 236

Ile Lys Pro Glu Ala Pro Gly Glu Asp Ala
1               5                   10

<210> SEQ ID NO 237
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: C-term Mimic B linker to SEQ ID NO: 365

<400> SEQUENCE: 237

Ile Lys Pro Glu Ala Pro Gly Glu Asp Ala Ser
1               5                   10
```

<210> SEQ ID NO 238
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 238

Ala Pro Leu Glu Pro Val Tyr Pro Gly Asp Asn Ala Thr Pro Glu Gln
1               5                   10                  15

Met Ala Arg Tyr Tyr Ser Ala Leu Arg His Tyr Ile Asn Leu Ala Thr
            20                  25                  30

Arg Gln Arg Tyr
        35

<210> SEQ ID NO 239
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 239

Tyr Pro Ile Lys Pro Glu Ala Pro Gly Glu Asp Ala Ser Pro Glu Glu
1               5                   10                  15

Leu Ala Arg Tyr Tyr Ser Ala Leu Arg His Tyr Ile Asn Leu Ile Thr
            20                  25                  30

Arg Gln Arg Tyr
        35

<210> SEQ ID NO 240
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 240

Ile Lys Pro Glu Ala Pro Gly Glu Asp Ala Ser Pro Glu Glu Leu Ala
1               5                   10                  15

Arg Tyr Tyr Ser Ala Leu Arg His Tyr Ile Asn Leu Ile Thr Arg Gln
            20                  25                  30

Arg Tyr

<210> SEQ ID NO 241
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 241

Ile Lys Pro Glu Ala Pro Gly Glu Asp Ala Ser Pro Glu Glu Leu Ala
1               5                   10                  15

Lys Tyr Tyr Ser Ala Leu Arg His Tyr Ile Asn Leu Ile Thr Arg Gln
            20                  25                  30

Arg Tyr

<210> SEQ ID NO 242
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Ile

<400> SEQUENCE: 242

Ile Lys Pro Glu Ala Pro Gly Glu Asp Ala Ser Pro Glu Glu Leu Ala
1               5                   10                  15

Lys Tyr Tyr Ser Ala Leu Arg His Tyr Ile Asn Leu Ile Thr Arg Gln
            20                  25                  30

Arg Tyr

<210> SEQ ID NO 243
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 243

Ile Pro Glu Ala Pro Gly Glu Asp Ala Ser Pro Glu Glu Leu Ala Arg
1               5                   10                  15

Tyr Tyr Ser Ala Leu Arg His Tyr Ile Asn Leu Ile Thr Arg Gln Arg
            20                  25                  30

Tyr

<210> SEQ ID NO 244
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 244

Tyr Pro Ile Pro Glu Ala Pro Gly Glu Asp Ala Ser Ala Glu Glu Leu
1               5                   10                  15

Ala Arg Tyr Tyr Ser Ala Leu Arg Ala Tyr Ile Asn Leu Ile Thr Arg
            20                  25                  30

Gln Arg Tyr
        35

<210> SEQ ID NO 245
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 245

Tyr Pro Ile Lys Pro Glu Ala Pro Gly Glu Asp Ala Ser Pro Glu Glu
1               5                   10                  15

Leu Ala Arg Tyr Tyr Ala Ser Leu Arg His Tyr Ile Asn Leu Ile Thr
            20                  25                  30

-continued

Arg Gln Arg Tyr
        35

<210> SEQ ID NO 246
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 246

Ile Lys Pro Glu Ala Pro Gly Glu Asp Ala Ser Pro Glu Glu Leu Ala
1               5                   10                  15

Arg Tyr Tyr Ala Ser Leu Arg His Tyr Ile Asn Leu Ile Thr Arg Gln
            20                  25                  30

Arg Tyr

<210> SEQ ID NO 247
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 247

Tyr Pro Ile Lys Pro Glu Ala Pro Gly Glu Asp Ala Ser Ala Glu Glu
1               5                   10                  15

Leu Ala Arg Tyr Tyr Ser Ala Leu Arg Ala Tyr Ile Asn Leu Ile Thr
            20                  25                  30

Arg Gln Arg Tyr
        35

<210> SEQ ID NO 248
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 248

Tyr Pro Ile Lys Pro Glu Ala Pro Gly Glu Asp Ala Ser Ala Glu Glu
1               5                   10                  15

Leu Ala Arg Tyr Tyr Ala Ser Leu Arg Ala Tyr Ile Asn Leu Ile Thr
            20                  25                  30

Arg Gln Arg Tyr
        35

<210> SEQ ID NO 249
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (4)
<223> OTHER INFORMATION: homo-Lys

<400> SEQUENCE: 249

Tyr Pro Ile Lys Pro Glu Ala Pro Gly Glu Asp Ala Ser Pro Glu Glu
1               5                   10                  15

Leu Ala Arg Tyr Tyr Ser Ala Leu Arg His Tyr Ile Asn Leu Ile Thr
            20                  25                  30

Arg Gln Arg Tyr
        35

<210> SEQ ID NO 250
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)
<223> OTHER INFORMATION: homo-Lys

<400> SEQUENCE: 250

Ile Lys Pro Glu Ala Pro Gly Glu Asp Ala Ser Pro Glu Glu Leu Ala
1               5                   10                  15

Arg Tyr Tyr Ser Ala Leu Arg His Tyr Ile Asn Leu Ile Thr Arg Gln
            20                  25                  30

Arg Tyr

<210> SEQ ID NO 251
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (4)
<223> OTHER INFORMATION: homo-Lys

<400> SEQUENCE: 251

Tyr Pro Ile Lys Pro Glu Ala Pro Gly Glu Asp Ala Ser Pro Glu Glu
1               5                   10                  15

Leu Ala Arg Tyr Tyr Ala Ser Leu Arg His Tyr Ile Asn Leu Ile Thr
            20                  25                  30

Arg Gln Arg Tyr
        35

<210> SEQ ID NO 252
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)
<223> OTHER INFORMATION: homo-Lys

<400> SEQUENCE: 252

Ile Lys Pro Glu Ala Pro Gly Glu Asp Ala Ser Pro Glu Glu Leu Ala
1               5                   10                  15

Arg Tyr Tyr Ala Ser Leu Arg His Tyr Ile Asn Leu Ile Thr Arg Gln
            20                  25                  30

Arg Tyr

<210> SEQ ID NO 253

```
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)
<223> OTHER INFORMATION: homo-Lys

<400> SEQUENCE: 253

Pro Lys Pro Glu Ala Pro Gly Glu Asp Ala Ser Pro Glu Glu Leu Ala
1               5                   10                  15

Arg Tyr Tyr Ala Ser Leu Arg His Tyr Ile Asn Leu Ile Thr Arg Gln
            20                  25                  30

Arg Tyr

<210> SEQ ID NO 254
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 254

Pro Lys Pro Glu Ala Pro Gly Glu Asp Ala Ser Pro Glu Glu Leu Ala
1               5                   10                  15

Arg Tyr Tyr Ala Ser Leu Arg His Tyr Ile Asn Leu Ile Thr Arg Gln
            20                  25                  30

Arg Tyr

<210> SEQ ID NO 255
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Pro

<400> SEQUENCE: 255

Pro Lys Pro Glu Ala Pro Gly Glu Asp Ala Ser Pro Glu Glu Leu Ala
1               5                   10                  15

Arg Tyr Tyr Ala Ser Leu Arg His Tyr Ile Asn Leu Ile Thr Arg Gln
            20                  25                  30

Arg Tyr

<210> SEQ ID NO 256
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 256

Pro Lys Pro Glu His Pro Gly Glu Asp Ala Pro Ala Glu Glu Leu Ala
1               5                   10                  15

Arg Tyr Tyr Ala Ser Leu Arg His Tyr Ile Asn Leu Ile Thr Arg Gln
            20                  25                  30
```

-continued

Arg Tyr

<210> SEQ ID NO 257
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 257

Pro Lys Pro Glu Ala Pro Gly Glu Asp Ala Pro Ala Glu Glu Leu Ala
1               5                   10                  15

Arg Tyr Tyr Ala Ser Leu Arg His Tyr Ile Asn Leu Ile Thr Arg Gln
            20                  25                  30

Arg Tyr

<210> SEQ ID NO 258
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (4)
<223> OTHER INFORMATION: homo-Lys

<400> SEQUENCE: 258

Tyr Pro Ile Lys Pro Glu Ala Pro Gly Glu Asp Ala Ser Pro Glu Glu
1               5                   10                  15

Leu Ala Arg Tyr Tyr Ser Ala Leu Arg Ala Tyr Ile Asn Leu Ile Thr
            20                  25                  30

Arg Gln Arg Tyr
        35

<210> SEQ ID NO 259
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)
<223> OTHER INFORMATION: homo-Lys

<400> SEQUENCE: 259

Ile Lys Pro Glu Ala Pro Gly Glu Asp Ala Ser Pro Glu Glu Leu Ala
1               5                   10                  15

Arg Tyr Tyr Ser Ala Leu Arg Ala Tyr Ile Asn Leu Ile Thr Arg Gln
            20                  25                  30

Arg Tyr

<210> SEQ ID NO 260
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES

```
<222> LOCATION: (4)
<223> OTHER INFORMATION: homo-Lys

<400> SEQUENCE: 260

Tyr Pro Ile Lys Pro Glu Ala Pro Gly Glu Asp Ala Ser Pro Glu Glu
1               5                   10                  15

Leu Ala Arg Tyr Tyr Ala Ser Leu Arg Ala Tyr Ile Asn Leu Ile Thr
            20                  25                  30

Arg Gln Arg Tyr
        35

<210> SEQ ID NO 261
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)
<223> OTHER INFORMATION: homo-Lys

<400> SEQUENCE: 261

Ile Lys Pro Glu Ala Pro Gly Glu Asp Ala Ser Pro Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 262
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)
<223> OTHER INFORMATION: homo-Lys

<400> SEQUENCE: 262

Pro Lys Pro Glu Ala Pro Gly Glu Asp Ala Ser Pro Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 263
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 263

Pro Lys Pro Glu Ala Pro Gly Glu Asp Ala Ser Pro Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr
```

<210> SEQ ID NO 264
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 264

Pro Pro Lys Pro Glu Ala Pro Gly Glu Asp Ala Ser Pro Glu Glu Leu
1               5                   10                  15

Ala Arg Tyr Tyr Ala Ser Leu Arg Ala Tyr Ile Asn Leu Ile Thr Arg
            20                  25                  30

Gln Arg Tyr
        35

<210> SEQ ID NO 265
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Pro

<400> SEQUENCE: 265

Pro Lys Pro Glu Ala Pro Gly Glu Asp Ala Ser Pro Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 266
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 266

Pro Lys Pro Glu His Pro Gly Glu Asp Ala Pro Ala Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 267
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 267

Tyr Pro Ile Arg Pro Glu Ala Pro Gly Glu Asp Ala Ser Pro Glu Glu
1               5                   10                  15

Leu Ala Arg Tyr Tyr Ala Ser Leu Arg His Tyr Ile Asn Leu Ile Thr
            20                  25                  30

-continued

Arg Gln Arg Tyr
        35

<210> SEQ ID NO 268
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 268

Tyr Pro Ile Arg Pro Glu Ala Pro Gly Glu Asp Ala Ser Pro Glu Glu
1               5                   10                  15

Leu Ala Arg Tyr Tyr Ala Ser Leu Arg Ala Tyr Ile Asn Leu Ile Thr
            20                  25                  30

Arg Gln Arg Tyr
        35

<210> SEQ ID NO 269
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 269

Ile Arg Pro Glu Ala Pro Gly Glu Asp Ala Ser Pro Glu Glu Leu Ala
1               5                   10                  15

Arg Tyr Tyr Ala Ser Leu Arg His Tyr Ile Asn Leu Ile Thr Arg Gln
            20                  25                  30

Arg Tyr

<210> SEQ ID NO 270
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 270

Pro Arg Pro Glu Ala Pro Gly Glu Asp Ala Ser Pro Glu Glu Leu Ala
1               5                   10                  15

Arg Tyr Tyr Ala Ser Leu Arg His Tyr Ile Asn Leu Ile Thr Arg Gln
            20                  25                  30

Arg Tyr

<210> SEQ ID NO 271
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: 8-amino-octanoyl-Ile

<400> SEQUENCE: 271

Ile Arg Pro Glu Ala Pro Gly Glu Asp Ala Ser Pro Glu Glu Leu Ala
1               5                   10                  15

```
Arg Tyr Tyr Ala Ser Leu Arg His Tyr Ile Asn Leu Ile Thr Arg Gln
            20                  25                  30

Arg Tyr

<210> SEQ ID NO 272
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 272

Tyr Pro Ile Arg Pro Glu Ala Pro Gly Glu Asp Ala Ser Pro Glu Glu
1               5                   10                  15

Leu Ala Arg Tyr Tyr Ser Ala Leu Arg His Tyr Ile Asn Leu Ile Thr
            20                  25                  30

Arg Gln Arg Tyr
        35

<210> SEQ ID NO 273
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 273

Tyr Pro Ile Lys Pro Glu Ala Pro Gly Glu Asp Ala Pro Ala Glu Glu
1               5                   10                  15

Leu Ala Arg Tyr Tyr Ala Ser Leu Arg Ala Tyr Ile Asn Leu Ile Thr
            20                  25                  30

Arg Gln Arg Tyr
        35

<210> SEQ ID NO 274
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 274

Ile Lys Pro Glu Ala Pro Gly Glu Asp Ala Pro Ala Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 275
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 275

Pro Tyr Pro Ile Lys Pro Glu Ala Pro Gly Glu Asp Ala Pro Ala Glu
1               5                   10                  15

Glu Leu Ala Arg Tyr Tyr Ala Ser Leu Arg Ala Tyr Ile Asn Leu Ile
```

```
                    20                  25                  30

Thr Arg Gln Arg Tyr
        35

<210> SEQ ID NO 276
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: 8-amino-octanoyl-Lys

<400> SEQUENCE: 276

Lys Pro Glu Ala Pro Gly Glu Asp Ala Pro Ala Glu Glu Leu Ala Arg
1               5                   10                  15

Tyr Tyr Ala Ser Leu Arg Ala Tyr Ile Asn Leu Ile Thr Arg Gln Arg
            20                  25                  30

Tyr

<210> SEQ ID NO 277
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 277

Pro Lys Pro Glu Ala Pro Gly Glu Asp Ala Pro Ala Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 278
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 278

Pro Lys Pro Glu Ala Pro Gly Glu Asp Ala Pro Ala Glu Glu Leu Ala
1               5                   10                  15

Arg Tyr Tyr Ala Ser Leu Arg His Tyr Ile Asn Leu Ile Thr Arg Gln
            20                  25                  30

Arg Tyr

<210> SEQ ID NO 279
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Pro
```

```
<400> SEQUENCE: 279

Pro Lys Pro Glu Ala Pro Gly Glu Asp Ala Pro Ala Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 280
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Tyr

<400> SEQUENCE: 280

Tyr Pro Ile Lys Pro Glu Ala Pro Gly Glu Asp Ala Ser Pro Glu Glu
1               5                   10                  15

Leu Ala Arg Tyr Tyr Ala Ser Leu Arg His Tyr Ile Asn Leu Ile Thr
            20                  25                  30

Arg Gln Arg Tyr
        35

<210> SEQ ID NO 281
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Ile

<400> SEQUENCE: 281

Ile Lys Pro Glu Ala Pro Gly Glu Asp Ala Ser Pro Glu Glu Leu Ala
1               5                   10                  15

Arg Tyr Tyr Ser Ala Leu Arg His Tyr Ile Asn Leu Ile Thr Arg Gln
            20                  25                  30

Arg Tyr

<210> SEQ ID NO 282
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Gly(Oct)

<400> SEQUENCE: 282

Gly Ile Lys Pro Glu Ala Pro Gly Glu Asp Ala Ser Pro Glu Glu Leu
1               5                   10                  15

Ala Arg Tyr Tyr Ser Ala Leu Arg His Tyr Ile Asn Leu Ile Thr Arg
            20                  25                  30

Gln Arg Tyr
```

-continued

```
<210> SEQ ID NO 283
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Fmoc-Gly(Oct)

<400> SEQUENCE: 283

Gly Ile Lys Pro Glu Ala Pro Gly Glu Asp Ala Ser Pro Glu Leu
1               5                   10                  15

Ala Arg Tyr Tyr Ser Ala Leu Arg His Tyr Ile Asn Leu Ile Thr Arg
            20                  25                  30

Gln Arg Tyr
        35

<210> SEQ ID NO 284
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Gly(Oct)

<400> SEQUENCE: 284

Gly Lys Pro Glu Ala Pro Gly Glu Asp Ala Ser Pro Glu Glu Leu Ala
1               5                   10                  15

Arg Tyr Tyr Ser Ala Leu Arg His Tyr Ile Asn Leu Ile Thr Arg Gln
            20                  25                  30

Arg Tyr

<210> SEQ ID NO 285
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 285

Tyr Pro Ser Lys Pro Asp Asn Pro Gly Glu Asp Ala Pro Ala Glu Asp
1               5                   10                  15

Met Ala Arg Tyr Tyr Ala Ser Leu Arg His Tyr Leu Asn Leu Val Thr
            20                  25                  30

Arg Gln Arg Tyr
        35

<210> SEQ ID NO 286
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 286
```

```
Ala Pro Leu Glu Pro Val Tyr Pro Gly Asp Asn Ala Thr Pro Glu Gln
1               5                   10                  15

Met Asn Arg Tyr Tyr Ala Ser Leu Arg His Tyr Leu Asn Leu Val Thr
            20                  25                  30

Arg Gln Arg Tyr
        35

<210> SEQ ID NO 287
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 287

Leu Glu Pro Val Tyr Pro Gly Asp Asn Ala Thr Pro Glu Gln Met Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 288
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 288

Ala Pro Leu Glu Pro Val Tyr Pro Gly Asp Asn Ala Thr Pro Glu Gln
1               5                   10                  15

Met Asn Arg Tyr Tyr Ala Ser Leu Arg His Phe Leu Asn Leu Val Thr
            20                  25                  30

Arg Gln Arg Tyr
        35

<210> SEQ ID NO 289
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 289

Ala Pro Leu Glu Pro Val Tyr Pro Gly Asp Asn Ala Thr Pro Glu Gln
1               5                   10                  15

Met Asn Arg Tyr Tyr Ala Ser Leu Arg His Tyr Leu Asn Leu Ala Pro
            20                  25                  30

Arg Gln Arg Tyr
        35

<210> SEQ ID NO 290
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
```

```
<222> LOCATION: (32)
<223> OTHER INFORMATION: Aib

<400> SEQUENCE: 290

Ala Pro Leu Glu Pro Val Tyr Pro Gly Asp Asn Ala Thr Pro Glu Gln
1               5                   10                  15

Met Asn Arg Tyr Tyr Ala Ser Leu Arg His Tyr Leu Asn Leu Ala Xaa
            20                  25                  30

Arg Gln Arg Tyr
        35

<210> SEQ ID NO 291
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (32)
<223> OTHER INFORMATION: Sar

<400> SEQUENCE: 291

Ala Pro Leu Glu Pro Val Tyr Pro Gly Asp Asn Ala Thr Pro Glu Gln
1               5                   10                  15

Met Asn Arg Tyr Tyr Ala Ser Leu Arg His Tyr Leu Asn Leu Ala Xaa
            20                  25                  30

Arg Gln Arg Tyr
        35

<210> SEQ ID NO 292
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 292

Ala Pro Leu Glu Pro Val Tyr Pro Gly Asp Asn Ala Thr Pro Glu Gln
1               5                   10                  15

Met Asn Arg Tyr Tyr Ser Ala Leu Arg His Tyr Leu Asn Leu Val Thr
            20                  25                  30

Arg Gln Arg Tyr
        35

<210> SEQ ID NO 293
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 293

Ala Pro Leu Glu Pro Val Tyr Pro Gly Asp Asn Ala Thr Pro Glu Gln
1               5                   10                  15

Met Asn Lys Tyr Tyr Ala Ser Leu Arg His Tyr Leu Asn Leu Val Thr
            20                  25                  30

Arg Gln Arg Tyr
        35
```

-continued

<210> SEQ ID NO 294
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 294

Ala Pro Leu Glu Pro Val Tyr Pro Gly Asp Asn Ala Thr Pro Glu Gln
1               5                   10                  15

Met Ala Arg Tyr Tyr Ala Ser Leu Arg His Tyr Leu Asn Leu Val Thr
            20                  25                  30

Arg Gln Arg Tyr
        35

<210> SEQ ID NO 295
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 295

Ala Pro Leu Glu Pro Val Tyr Pro Gly Asp Asn Ala Thr Pro Glu Gln
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 296
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 296

Ala Pro Leu Glu Pro Val Tyr Pro Gly Asp Asn Ala Thr Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 297
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 297

Ala Pro Leu Glu Pro Val Tyr Pro Gly Asp Asn Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

-continued

```
<210> SEQ ID NO 298
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 298

Ala Pro Leu Glu Pro Val Tyr Pro Gly Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 299
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 299

Ala Pro Leu Glu Pro Val Tyr Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 300
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 300

Ala Pro Leu Glu Pro Val Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 301
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 301

Ala Pro Leu Glu Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35
```

```
<210> SEQ ID NO 302
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 302

Ala Pro Leu Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 303
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Ala

<400> SEQUENCE: 303

Ala Pro Leu Glu Pro Val Tyr Pro Gly Asp Asn Ala Thr Pro Glu Gln
1               5                   10                  15

Met Asn Arg Tyr Tyr Ala Ser Leu Arg His Tyr Leu Asn Leu Val Thr
            20                  25                  30

Arg Gln Arg Tyr
        35

<210> SEQ ID NO 304
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (19)
<223> OTHER INFORMATION: homo-Arg

<400> SEQUENCE: 304

Ala Pro Leu Glu Pro Val Tyr Pro Gly Asp Asn Ala Thr Pro Glu Gln
1               5                   10                  15

Met Asn Arg Tyr Tyr Ala Ser Leu Arg His Tyr Leu Asn Leu Val Thr
            20                  25                  30

Arg Gln Arg Tyr
        35

<210> SEQ ID NO 305
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
```

```
<222> LOCATION: (1)
<223> OTHER INFORMATION: Isocaproyl-Ala
<220> FEATURE:
<221> NAME/KEY: MOD_RES
<222> LOCATION: (19)
<223> OTHER INFORMATION: homo-Arg

<400> SEQUENCE: 305

Ala Pro Leu Glu Pro Val Tyr Pro Gly Asp Asn Ala Thr Pro Glu Gln
1               5                   10                  15

Met Asn Arg Tyr Tyr Ala Ser Leu Arg His Tyr Leu Asn Leu Val Thr
            20                  25                  30

Arg Gln Arg Tyr
        35

<210> SEQ ID NO 306
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (19)
<223> OTHER INFORMATION: homo-Lys

<400> SEQUENCE: 306

Ala Pro Leu Glu Pro Val Tyr Pro Gly Asp Asn Ala Thr Pro Glu Gln
1               5                   10                  15

Met Asn Lys Tyr Tyr Ala Ser Leu Arg His Tyr Leu Asn Leu Val Thr
            20                  25                  30

Arg Gln Arg Tyr
        35

<210> SEQ ID NO 307
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 307

Ala Pro Met Glu Pro Val Tyr Pro Gly Asp Asn Ala Thr Pro Glu Gln
1               5                   10                  15

Met Asn Arg Tyr Tyr Ala Ser Leu Arg His Tyr Leu Asn Leu Val Thr
            20                  25                  30

Arg Gln Arg Tyr
        35

<210> SEQ ID NO 308
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 308

Ala Pro Leu Glu Pro Val Tyr Pro Gly Asp Asn Ala Thr Pro Glu Gln
1               5                   10                  15

Met Asn Arg Tyr Tyr Ala Ser Leu Arg Ala Tyr Leu Asn Leu Val Thr
            20                  25                  30
```

-continued

Arg Gln Arg Tyr
        35

<210> SEQ ID NO 309
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 309

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Pro Arg Tyr
        35

<210> SEQ ID NO 310
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 310

Ile Lys Pro Glu Ala Pro Gly Glu Asp Ala Ser Pro Glu Glu Leu Ala
1               5                   10                  15

Gln Tyr Ala Ala Asp Leu Arg Arg Tyr Ile Asn Met Leu Thr Arg Pro
            20                  25                  30

Arg Tyr

<210> SEQ ID NO 311
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 311

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 312
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 312

Ile Lys Pro Glu Ala Pro Gly Glu Asp Ala Ser Pro Glu Glu Leu Ala
1               5                   10                  15

Gln Tyr Ala Ala Asp Leu Arg Arg Tyr Ile Asn Met Leu Thr Arg Gln
            20                  25                  30

Arg Tyr

<210> SEQ ID NO 313
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 313

Tyr Pro Ile Lys Pro Glu Ala Pro Gly Glu Asp Ala Ser Pro Glu Glu
1               5                   10                  15

Leu Ala Gln Tyr Ala Ala Ser Leu Arg His Tyr Ile Asn Met Leu Thr
            20                  25                  30

Arg Gln Arg Tyr
        35

<210> SEQ ID NO 314
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 314

Tyr Pro Ile Lys Pro Glu Ala Pro Gly Glu Asp Ala Ser Pro Glu Glu
1               5                   10                  15

Leu Ala Gln Tyr Ala Ser Ala Leu Arg His Tyr Ile Asn Met Leu Thr
            20                  25                  30

Arg Gln Arg Tyr
        35

<210> SEQ ID NO 315
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 315

Tyr Pro Ile Lys Pro Glu Ala Pro Gly Glu Asp Ala Ser Pro Glu Glu
1               5                   10                  15

Leu Ala Gln Tyr Ala Ala Asp Leu Arg His Tyr Ile Asn Met Leu Thr
            20                  25                  30

Arg Gln Arg Tyr
        35

<210> SEQ ID NO 316
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 316

Tyr Pro Ile Lys Pro Glu Ala Pro Gly Glu Asp Ala Ser Pro Glu Glu
1               5                   10                  15

Leu Asn Gln Tyr Ala Ala Asp Leu Arg Arg Tyr Ile Asn Met Leu Thr
            20                  25                  30

Arg Gln Arg Tyr
        35

<210> SEQ ID NO 317
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 317

Tyr Pro Ile Lys Pro Glu Ala Pro Gly Glu Asp Ala Ser Pro Glu Glu
1               5                   10                  15

Leu Asn Gln Tyr Ala Ala Ser Leu Arg Arg Tyr Ile Asn Met Leu Thr
            20                  25                  30

Arg Gln Arg Tyr
        35

<210> SEQ ID NO 318
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)
<223> OTHER INFORMATION: d-Ala

<400> SEQUENCE: 318

Tyr Ala Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 319
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 319

Ala Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 320
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Tyr

```
<400> SEQUENCE: 320

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 321
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (25)
<223> OTHER INFORMATION: homo-Lys

<400> SEQUENCE: 321

Tyr Pro Ile Lys Pro Glu Ala Pro Gly Glu Asp Ala Ser Pro Glu Glu
1               5                   10                  15

Leu Ala Gln Tyr Ala Ala Asp Leu Lys Arg Tyr Ile Asn Met Leu Thr
            20                  25                  30

Arg Gln Arg Tyr
        35

<210> SEQ ID NO 322
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (25)
<223> OTHER INFORMATION: homo-Arg

<400> SEQUENCE: 322

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 323
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (25)
<223> OTHER INFORMATION: Orn

<400> SEQUENCE: 323

Tyr Pro Ile Lys Pro Glu Ala Pro Gly Glu Asp Ala Ser Pro Glu Glu
1               5                   10                  15

Leu Ala Gln Tyr Ala Ala Asp Leu Xaa Arg Tyr Ile Asn Met Leu Thr
```

```
            20                  25                  30

Arg Gln Arg Tyr
        35

<210> SEQ ID NO 324
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (25)
<223> OTHER INFORMATION: Cit

<400> SEQUENCE: 324

Tyr Pro Ile Lys Pro Glu Ala Pro Gly Glu Asp Ala Ser Pro Glu Glu
1               5                   10                  15

Leu Ala Gln Tyr Ala Ala Asp Leu Xaa Arg Tyr Ile Asn Met Leu Thr
            20                  25                  30

Arg Gln Arg Tyr
        35

<210> SEQ ID NO 325
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (26)
<223> OTHER INFORMATION: homo-Lys

<400> SEQUENCE: 325

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Lys Tyr Ile Asn Met Leu Thr
            20                  25                  30

Arg Gln Arg Tyr
        35

<210> SEQ ID NO 326
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (26)
<223> OTHER INFORMATION: homo-Arg

<400> SEQUENCE: 326

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 327
```

```
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (26)
<223> OTHER INFORMATION: Orn

<400> SEQUENCE: 327

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Xaa Tyr Ile Asn Met Leu Thr
            20                  25                  30

Arg Gln Arg Tyr
        35

<210> SEQ ID NO 328
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (26)
<223> OTHER INFORMATION: Cit

<400> SEQUENCE: 328

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Xaa Tyr Ile Asn Met Leu Thr
            20                  25                  30

Arg Gln Arg Tyr
        35

<210> SEQ ID NO 329
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (25)..(26)
<223> OTHER INFORMATION: homo-Arg

<400> SEQUENCE: 329

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 330
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
```

```
<221> NAME/KEY: MOD_RES
<222> LOCATION: (4)
<223> OTHER INFORMATION: homo-Lys

<400> SEQUENCE: 330

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 331
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Tyr
<220> FEATURE:
<221> NAME/KEY: MOD_RES
<222> LOCATION: (4)
<223> OTHER INFORMATION: homo-Lys

<400> SEQUENCE: 331

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 332
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (4)
<223> OTHER INFORMATION: homo-Arg

<400> SEQUENCE: 332

Tyr Pro Ile Arg Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 333
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (8)
<223> OTHER INFORMATION: homo-Pro
```

<400> SEQUENCE: 333

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 334
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (8)
<223> OTHER INFORMATION: Aib

<400> SEQUENCE: 334

Tyr Pro Ile Lys Pro Glu Ala Xaa Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 335
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 335

Tyr Pro Ile Lys Pro Glu Ala Gly Pro Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 336
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (14)
<223> OTHER INFORMATION: homo-Pro

<400> SEQUENCE: 336

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

```
<210> SEQ ID NO 337
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (14)
<223> OTHER INFORMATION: Aib

<400> SEQUENCE: 337

Tyr Pro Ile Lys Pro Glu Ala Pro Gly Glu Asp Ala Ser Xaa Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 338
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (9)
<223> OTHER INFORMATION: Sar

<400> SEQUENCE: 338

Tyr Pro Ile Lys Pro Glu Ala Pro Xaa Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 339
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (13)
<223> OTHER INFORMATION: homo-Ser

<400> SEQUENCE: 339

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 340
<211> LENGTH: 36
<212> TYPE: PRT
<213> ORGANISM: Artificial Sequence
<220> FEATURE:
```

```
<223> OTHER INFORMATION: Description of Artificial Sequence: Synthetic
      peptide construct
<220> FEATURE:
<221> NAME/KEY: MOD_RES
<222> LOCATION: (13)
<223> OTHER INFORMATION: Dap

<400> SEQUENCE: 340

Tyr Pro Ile Lys Pro Glu Ala Pro Gly Glu Asp Ala Xaa Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 341
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 341

Tyr Pro Ile Lys Pro Glu Ala Pro Gly Glu Asp Ala Ser Pro Gln Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 342
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 342

Tyr Pro Ile Lys Pro Glu Ala Pro Gly Glu Asp Ala Ser Pro Asp Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 343
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 343

Tyr Pro Ile Lys Pro Glu Ala Pro Gly Glu Asp Ala Ser Pro Glu Glu
1               5                   10                  15

Met Ala Gln Tyr Ala Ala Asp Leu Arg Arg Tyr Ile Asn Met Leu Thr
            20                  25                  30

Arg Gln Arg Tyr
        35
```

```
<210> SEQ ID NO 344
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (4)
<223> OTHER INFORMATION: homo-Lys

<400> SEQUENCE: 344

Tyr Pro Ile Lys Pro Glu Ala Pro Gly Glu Asp Ala Ser Ala Gln Glu
1               5                   10                  15

Leu Ala Gln Tyr Ala Ala Asp Leu Arg Arg Tyr Ile Asn Met Leu Thr
                20                  25                  30

Arg Gln Arg Tyr
            35

<210> SEQ ID NO 345
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (4)
<223> OTHER INFORMATION: homo-Lys

<400> SEQUENCE: 345

Tyr Pro Ile Lys Pro Glu Ala Pro Gly Glu Asp Ala Ser Ala Ser Glu
1               5                   10                  15

Leu Ala Gln Tyr Ala Ala Asp Leu Arg Arg Tyr Ile Asn Met Leu Thr
                20                  25                  30

Arg Gln Arg Tyr
            35

<210> SEQ ID NO 346
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (4)
<223> OTHER INFORMATION: homo-Lys

<400> SEQUENCE: 346

Tyr Pro Ile Lys Pro Glu Ala Pro Gly Glu Asp Ala Ser Ala Gln Glu
1               5                   10                  15

Met Ala Gln Tyr Ala Ala Asp Leu Arg Arg Tyr Ile Asn Met Leu Thr
                20                  25                  30

Arg Gln Arg Tyr
            35

<210> SEQ ID NO 347
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
```

<400> SEQUENCE: 347

Tyr Pro Ile Lys Pro Glu Ala Pro Gly Glu Asp Ala Ser Pro Glu Glu
1               5                   10                  15

Leu Ala Gln Tyr Ala Ala Glu Leu Arg Arg Tyr Ile Gln Met Leu Thr
            20                  25                  30

Arg Gln Arg Tyr
        35

<210> SEQ ID NO 348
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Tyr, Phe, Trp, or absent
<220> FEATURE:
<221> NAME/KEY: MOD_RES
<222> LOCATION: (2)
<223> OTHER INFORMATION: Pro, Gly, d-Ala, homo-Pro, hyroxy-Pro, or
      absent
<220> FEATURE:
<221> NAME/KEY: MOD_RES
<222> LOCATION: (3)
<223> OTHER INFORMATION: Ile, Ala, NorVal, Val, Leu, Pro, Ser, or Thr
<220> FEATURE:
<221> NAME/KEY: MOD_RES
<222> LOCATION: (4)
<223> OTHER INFORMATION: Lys, Ala, Gly, Arg, d-Ala, homo-Lys, homo-Arg,
      Glu, or Asp
<220> FEATURE:
<221> NAME/KEY: MOD_RES
<222> LOCATION: (6)
<223> OTHER INFORMATION: Glu, Ala, Val, Asp, Asn, or Gln
<220> FEATURE:
<221> NAME/KEY: MOD_RES
<222> LOCATION: (7)
<223> OTHER INFORMATION: Ala, Asn, His, Ser, or Tyr
<220> FEATURE:
<221> NAME/KEY: MOD_RES
<222> LOCATION: (9)
<223> OTHER INFORMATION: Gly, Ala, Ser, Sarcosine, Pro, or Aib
<220> FEATURE:
<221> NAME/KEY: MOD_RES
<222> LOCATION: (10)
<223> OTHER INFORMATION: Glu, Ala, Asp, Asn, Gln, Pro, Aib, or Gly
<220> FEATURE:
<221> NAME/KEY: MOD_RES
<222> LOCATION: (11)
<223> OTHER INFORMATION: Asp, Ala, Glu, Asn, Gln, Pro, Aib, or Gly
<220> FEATURE:
<221> NAME/KEY: MOD_RES
<222> LOCATION: (12)
<223> OTHER INFORMATION: Ala or d-Ala
<220> FEATURE:
<221> NAME/KEY: MOD_RES
<222> LOCATION: (13)
<223> OTHER INFORMATION: Ser, Ala, Thr, Pro, or homo-Ser
<220> FEATURE:
<221> NAME/KEY: MOD_RES
<222> LOCATION: (14)
<223> OTHER INFORMATION: Pro, Ala, homo-Pro, hydroxy-Pro, Aib, or Gly
<220> FEATURE:
<221> NAME/KEY: MOD_RES
<222> LOCATION: (15)
<223> OTHER INFORMATION: Glu, Ala, Asp, Asn, Gln, Pro, Aib, or Gly
<220> FEATURE:
<221> NAME/KEY: MOD_RES
<222> LOCATION: (16)
<223> OTHER INFORMATION: Glu, Ala, Asp, Asn, or Gln
<220> FEATURE:

```
<221> NAME/KEY: MOD_RES
<222> LOCATION: (17)
<223> OTHER INFORMATION: Leu, Ala, Met, Trp, Ile, Val, or NorVal
<220> FEATURE:
<221> NAME/KEY: MOD_RES
<222> LOCATION: (18)
<223> OTHER INFORMATION: Asn, Asp, Ala, Glu, Gln, Ser, or Thr
<220> FEATURE:
<221> NAME/KEY: MOD_RES
<222> LOCATION: (19)
<223> OTHER INFORMATION: Arg, Tyr, Lys, Ala, Gln, or N(Me)Ala
<220> FEATURE:
<221> NAME/KEY: MOD_RES
<222> LOCATION: (21)
<223> OTHER INFORMATION: Tyr, Ala, Met, Phe, or Leu
<220> FEATURE:
<221> NAME/KEY: MOD_RES
<222> LOCATION: (22)
<223> OTHER INFORMATION: Ala, Ser, Thr, or d-Ala
<220> FEATURE:
<221> NAME/KEY: MOD_RES
<222> LOCATION: (23)
<223> OTHER INFORMATION: Ser, Ala, Thr, or homo-Ser
<220> FEATURE:
<221> NAME/KEY: MOD_RES
<222> LOCATION: (26)
<223> OTHER INFORMATION: His or Ala
<220> FEATURE:
<221> NAME/KEY: MOD_RES
<222> LOCATION: (28)
<223> OTHER INFORMATION: Leu, Ile, Val, or Ala
<220> FEATURE:
<221> NAME/KEY: MOD_RES
<222> LOCATION: (30)
<223> OTHER INFORMATION: Leu, Ala, NorVal, Val, Ile, or Met
<220> FEATURE:
<221> NAME/KEY: MOD_RES
<222> LOCATION: (31)
<223> OTHER INFORMATION: Ala, Val, Ile, or Leu
<220> FEATURE:
<221> NAME/KEY: MOD_RES
<222> LOCATION: (36)
<223> OTHER INFORMATION: Tyr, N(Me)Tyr, His, Trp, or Phe

<400> SEQUENCE: 348

Xaa Xaa Xaa Xaa Pro Xaa Xaa Pro Xaa Xaa Xaa Xaa Xaa Xaa Xaa
1               5                   10                  15

Xaa Xaa Xaa Tyr Xaa Xaa Xaa Leu Arg Xaa Tyr Xaa Asn Xaa Xaa Thr
            20                  25                  30

Arg Gln Arg Xaa
        35

<210> SEQ ID NO 349
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Tyr, Phe, Trp, or absent
<220> FEATURE:
<221> NAME/KEY: MOD_RES
<222> LOCATION: (2)
<223> OTHER INFORMATION: Pro, Gly, d-Ala, homo-Pro, hydroxy-Pro, or
      absent
<220> FEATURE:
<221> NAME/KEY: MOD_RES
<222> LOCATION: (3)
<223> OTHER INFORMATION: Ile, Ala, NorVal, Val, Leu, Pro, Ser, or Thr
<220> FEATURE:
<221> NAME/KEY: MOD_RES
<222> LOCATION: (4)
```

```
<223> OTHER INFORMATION: Lys, Ala, Gly, Arg, d-Ala, homo-Lys, homo-Arg,
      Glu, or Asp
<220> FEATURE:
<221> NAME/KEY: MOD_RES
<222> LOCATION: (6)
<223> OTHER INFORMATION: Glu, Ala, Val, Asp, Asn, or Gln
<220> FEATURE:
<221> NAME/KEY: MOD_RES
<222> LOCATION: (7)
<223> OTHER INFORMATION: Ala, Asn, His, Ser, or Tyr
<220> FEATURE:
<221> NAME/KEY: MOD_RES
<222> LOCATION: (9)
<223> OTHER INFORMATION: Gly, Ala, Ser, Sarcosine, Pro, or Aib
<220> FEATURE:
<221> NAME/KEY: MOD_RES
<222> LOCATION: (10)
<223> OTHER INFORMATION: Glu, Ala, Asp, Asn, Gln, Pro, Aib, or Gly
<220> FEATURE:
<221> NAME/KEY: MOD_RES
<222> LOCATION: (11)
<223> OTHER INFORMATION: Asp Ala, Glu, Asn, Gln, Pro, Aib, or Gly
<220> FEATURE:
<221> NAME/KEY: MOD_RES
<222> LOCATION: (12)
<223> OTHER INFORMATION: Ala or d-Ala
<220> FEATURE:
<221> NAME/KEY: MOD_RES
<222> LOCATION: (13)
<223> OTHER INFORMATION: Ser, Ala, Thr, or homo-Ser
<220> FEATURE:
<221> NAME/KEY: MOD_RES
<222> LOCATION: (14)
<223> OTHER INFORMATION: Pro, Ala, homo-Pro, hydroxy-Pro, Aib, or Gly
<220> FEATURE:
<221> NAME/KEY: MOD_RES
<222> LOCATION: (15)
<223> OTHER INFORMATION: Glu, Ala, Asp, Asn, Gln, Pro, Aib, or Gly
<220> FEATURE:
<221> NAME/KEY: MOD_RES
<222> LOCATION: (16)
<223> OTHER INFORMATION: Glu, Ala, Asp, Asn, or Gln
<220> FEATURE:
<221> NAME/KEY: MOD_RES
<222> LOCATION: (17)
<223> OTHER INFORMATION: Leu, Ala, Met, Trp, Ile, Val, or NorVal
<220> FEATURE:
<221> NAME/KEY: MOD_RES
<222> LOCATION: (18)
<223> OTHER INFORMATION: Asn, Asp, Ala, Glu, Gln, Ser, or Thr
<220> FEATURE:
<221> NAME/KEY: MOD_RES
<222> LOCATION: (19)
<223> OTHER INFORMATION: Arg, Tyr, Lys, Ala, Gln, or N(Me)Ala
<220> FEATURE:
<221> NAME/KEY: MOD_RES
<222> LOCATION: (21)
<223> OTHER INFORMATION: Tyr, Ala, Met, Phe, or Leu
<220> FEATURE:
<221> NAME/KEY: MOD_RES
<222> LOCATION: (22)
<223> OTHER INFORMATION: Ala, Ser, Thr, or d-Ala
<220> FEATURE:
<221> NAME/KEY: MOD_RES
<222> LOCATION: (23)
<223> OTHER INFORMATION: Ser, Ala, Thr, or homo-Ser
<220> FEATURE:
<221> NAME/KEY: MOD_RES
<222> LOCATION: (26)
<223> OTHER INFORMATION: His or Ala
<220> FEATURE:
<221> NAME/KEY: MOD_RES
<222> LOCATION: (28)
<223> OTHER INFORMATION: Leu, Ile, Val, or Ala
<220> FEATURE:
<221> NAME/KEY: MOD_RES
<222> LOCATION: (30)
<223> OTHER INFORMATION: Leu, Ala, NorVal, Val, Ile, or Met
<220> FEATURE:
```

```
<221> NAME/KEY: MOD_RES
<222> LOCATION: (31)
<223> OTHER INFORMATION: Ala, Val, Ile, or Leu
<220> FEATURE:
<221> NAME/KEY: MOD_RES
<222> LOCATION: (36)
<223> OTHER INFORMATION: Tyr, N(Me)Tyr, His, Trp, or Phe

<400> SEQUENCE: 349

Xaa Xaa Xaa Xaa Pro Xaa Xaa Pro Xaa Xaa Xaa Xaa Xaa Xaa Xaa
1               5                   10                  15

Xaa Xaa Xaa Tyr Xaa Xaa Xaa Leu Arg Xaa Tyr Xaa Asn Xaa Xaa Thr
            20                  25                  30

Arg Gln Arg Xaa
        35

<210> SEQ ID NO 350
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Ile, Ala, Pro, Ser, Thr, or NorVal
<220> FEATURE:
<221> NAME/KEY: MOD_RES
<222> LOCATION: (2)
<223> OTHER INFORMATION: Lys, Ala, Gly, Glu, Asp, d-Ala, homo-Lys, or
      homo-Arg
<220> FEATURE:
<221> NAME/KEY: MOD_RES
<222> LOCATION: (4)
<223> OTHER INFORMATION: Glu, Ala, Val, Asp, Asn, or Gln
<220> FEATURE:
<221> NAME/KEY: MOD_RES
<222> LOCATION: (5)
<223> OTHER INFORMATION: Ala, Asn, His, Ser, or Tyr
<220> FEATURE:
<221> NAME/KEY: MOD_RES
<222> LOCATION: (7)
<223> OTHER INFORMATION: Gly, Ala, Ser, Sarcosine, Pro, or Aib
<220> FEATURE:
<221> NAME/KEY: MOD_RES
<222> LOCATION: (8)
<223> OTHER INFORMATION: Glu, Ala, Asp, Asn, Gln, Pro, Aib, or Gly
<220> FEATURE:
<221> NAME/KEY: MOD_RES
<222> LOCATION: (9)
<223> OTHER INFORMATION: Asp, Ala, Glu, Asn, Gln, Pro, Aib, or Gly
<220> FEATURE:
<221> NAME/KEY: MOD_RES
<222> LOCATION: (10)
<223> OTHER INFORMATION: Ala or d-Ala
<220> FEATURE:
<221> NAME/KEY: MOD_RES
<222> LOCATION: (11)
<223> OTHER INFORMATION: Ser, Ala, Thr, or homo-Ser
<220> FEATURE:
<221> NAME/KEY: MOD_RES
<222> LOCATION: (12)
<223> OTHER INFORMATION: Pro, Ala, homo-Pro, hydroxy-Pro, Aib, or Gly
<220> FEATURE:
<221> NAME/KEY: MOD_RES
<222> LOCATION: (13)
<223> OTHER INFORMATION: Glu, Ala, Asp, Asn, Gln, Pro, Aib, or Gly
<220> FEATURE:
<221> NAME/KEY: MOD_RES
<222> LOCATION: (14)
<223> OTHER INFORMATION: Glu, Ala, Asp, Asn, or Gln
<220> FEATURE:
<221> NAME/KEY: MOD_RES
<222> LOCATION: (15)
```

```
<223> OTHER INFORMATION: Leu, Ala, Met, Trp, Ile, Val, or NorVal
<220> FEATURE:
<221> NAME/KEY: MOD_RES
<222> LOCATION: (16)
<223> OTHER INFORMATION: Asn, Asp, Ala, Glu, Gln, Ser or Thr
<220> FEATURE:
<221> NAME/KEY: MOD_RES
<222> LOCATION: (17)
<223> OTHER INFORMATION: Arg, Tyr, Lys, Ala, Gln, or N(Me)Ala
<220> FEATURE:
<221> NAME/KEY: MOD_RES
<222> LOCATION: (19)
<223> OTHER INFORMATION: Tyr, Ala, Met, Phe, or Leu
<220> FEATURE:
<221> NAME/KEY: MOD_RES
<222> LOCATION: (20)
<223> OTHER INFORMATION: Ala, Ser, Thr, or d-Ala
<220> FEATURE:
<221> NAME/KEY: MOD_RES
<222> LOCATION: (21)
<223> OTHER INFORMATION: Ser, Ala, Thr, or homo-Ser
<220> FEATURE:
<221> NAME/KEY: MOD_RES
<222> LOCATION: (24)
<223> OTHER INFORMATION: His or Ala
<220> FEATURE:
<221> NAME/KEY: MOD_RES
<222> LOCATION: (26)
<223> OTHER INFORMATION: Leu or Ala
<220> FEATURE:
<221> NAME/KEY: MOD_RES
<222> LOCATION: (28)
<223> OTHER INFORMATION: Leu, Ala, NorVal, or Ile
<220> FEATURE:
<221> NAME/KEY: MOD_RES
<222> LOCATION: (29)
<223> OTHER INFORMATION: Ala or Val
<220> FEATURE:
<221> NAME/KEY: MOD_RES
<222> LOCATION: (34)
<223> OTHER INFORMATION: Tyr, N(Me)Tyr, His, or Trp

<400> SEQUENCE: 350

Xaa Xaa Pro Xaa Xaa Pro Xaa Xaa Xaa Xaa Xaa Xaa Xaa Xaa Xaa
1               5                   10                  15

Xaa Tyr Xaa Xaa Xaa Leu Arg Xaa Tyr Xaa Asn Xaa Xaa Thr Arg Gln
            20                  25                  30

Arg Xaa

<210> SEQ ID NO 351
<211> LENGTH: 4
<212> TYPE: PRT
<213> ORGANISM: Homo sapiens

<400> SEQUENCE: 351

Thr Arg Gln Arg
1

<210> SEQ ID NO 352
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: N-term Mimic A linker to SEQ ID NO: 211

<400> SEQUENCE: 352

Glu Asp Ala Ser Pro Glu Glu Leu Asn Arg Tyr Tyr Ala Ser Leu Arg
1               5                   10                  15
```

His Tyr Leu Asn Leu Val Thr Arg Gln Arg Tyr
            20                  25

<210> SEQ ID NO 353
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: N-term Mimic A linker to SEQ ID NO: 212

<400> SEQUENCE: 353

Asp Ala Ser Pro Glu Glu Leu Asn Arg Tyr Tyr Ala Ser Leu Arg His
1               5                   10                  15

Tyr Leu Asn Leu Val Thr Arg Gln Arg Tyr
            20                  25

<210> SEQ ID NO 354
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: N-term Mimic A linker to SEQ ID NO: 213

<400> SEQUENCE: 354

Ala Ser Pro Glu Glu Leu Asn Arg Tyr Tyr Ala Ser Leu Arg His Tyr
1               5                   10                  15

Leu Asn Leu Val Thr Arg Gln Arg Tyr
            20                  25

<210> SEQ ID NO 355
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: N-term Mimic A linker to SEQ ID NO: 214

<400> SEQUENCE: 355

Ser Pro Glu Glu Leu Asn Arg Tyr Tyr Ala Ser Leu Arg His Tyr Leu
1               5                   10                  15

Asn Leu Val Thr Arg Gln Arg Tyr
            20

<210> SEQ ID NO 356
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: N-term Mimic A linker to SEQ ID NO: 215

<400> SEQUENCE: 356

Pro Glu Glu Leu Asn Arg Tyr Tyr Ala Ser Leu Arg His Tyr Leu Asn
1               5                   10                  15

Leu Val Thr Arg Gln Arg Tyr
            20

```
<210> SEQ ID NO 357
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: N-term Mimic A linker to SEQ ID NO: 216

<400> SEQUENCE: 357

Glu Glu Leu Asn Arg Tyr Tyr Ala Ser Leu Arg His Tyr Leu Asn Leu
1               5                   10                  15

Val Thr Arg Gln Arg Tyr
            20

<210> SEQ ID NO 358
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: N-term Mimic A linker to SEQ ID NO: 217

<400> SEQUENCE: 358

Glu Leu Asn Arg Tyr Tyr Ala Ser Leu Arg His Tyr Leu Asn Leu Val
1               5                   10                  15

Thr Arg Gln Arg Tyr
            20

<210> SEQ ID NO 359
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: N-term Mimic B linker to SEQ ID NO: 231

<400> SEQUENCE: 359

Glu Asp Ala Ser Pro Glu Glu Leu Asn Arg Tyr Tyr Ala Ser Leu Arg
1               5                   10                  15

His Tyr Leu Asn Leu Val Thr Arg Gln Arg Tyr
            20                  25

<210> SEQ ID NO 360
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: N-term Mimic B linker to SEQ ID NO: 232

<400> SEQUENCE: 360

Asp Ala Ser Pro Glu Glu Leu Asn Arg Tyr Tyr Ala Ser Leu Arg His
1               5                   10                  15

Tyr Leu Asn Leu Val Thr Arg Gln Arg Tyr
            20                  25

<210> SEQ ID NO 361
<211> LENGTH: 25
```

```
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: N-term Mimic B linker to SEQ ID NO: 233

<400> SEQUENCE: 361

Ala Ser Pro Glu Glu Leu Asn Arg Tyr Tyr Ala Ser Leu Arg His Tyr
1               5                   10                  15

Leu Asn Leu Val Thr Arg Gln Arg Tyr
            20                  25

<210> SEQ ID NO 362
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: N-term Mimic B linker to SEQ ID NO: 234

<400> SEQUENCE: 362

Ser Pro Glu Glu Leu Asn Arg Tyr Tyr Ala Ser Leu Arg His Tyr Leu
1               5                   10                  15

Asn Leu Val Thr Arg Gln Arg Tyr
            20

<210> SEQ ID NO 363
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: N-term Mimic B linker to SEQ ID NO: 235

<400> SEQUENCE: 363

Pro Glu Glu Leu Asn Arg Tyr Tyr Ala Ser Leu Arg His Tyr Leu Asn
1               5                   10                  15

Leu Val Thr Arg Gln Arg Tyr
            20

<210> SEQ ID NO 364
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: N-term Mimic B linker to SEQ ID NO: 236

<400> SEQUENCE: 364

Glu Glu Leu Asn Arg Tyr Tyr Ala Ser Leu Arg His Tyr Leu Asn Leu
1               5                   10                  15

Val Thr Arg Gln Arg Tyr
            20

<210> SEQ ID NO 365
<211> LENGTH: 21
<212> TYPE: PRT
<213> ORGANISM: Artificial Sequence
<220> FEATURE:
```

```
<223> OTHER INFORMATION: Description of Artificial Sequence: Synthetic
      peptide construct
<220> FEATURE:
<223> OTHER INFORMATION: N-term Mimic B linker to SEQ ID NO: 237

<400> SEQUENCE: 365

Glu Leu Asn Arg Tyr Tyr Ala Ser Leu Arg His Tyr Leu Asn Leu Val
1               5                   10                  15

Thr Arg Gln Arg Tyr
            20

<210> SEQ ID NO 366
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 366

Pro Ser Lys Pro Asp Asn Pro Gly Glu Asp Ala Pro Ala Glu Asp Met
1               5                   10                  15

Ala Arg Tyr Tyr Ser Ala Leu Arg His Tyr Ile Asn Leu Ile Thr Arg
            20                  25                  30

Gln Arg Tyr
        35

<210> SEQ ID NO 367
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 367

Lys Pro Asp Asn Pro Gly Glu Asp Ala Pro Ala Glu Asp Met Ala Arg
1               5                   10                  15

Tyr Tyr Ser Ala Leu Arg His Tyr Ile Asn Leu Ile Thr Arg Gln Arg
            20                  25                  30

Tyr

<210> SEQ ID NO 368
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 368

Pro Ile Lys Pro Glu Ala Pro Gly Glu Asp Ala Ser Pro Glu Glu Leu
1               5                   10                  15

Asn Arg Tyr Tyr Ala Ser Leu Arg His Tyr Leu Asn Leu Val Thr Arg
            20                  25                  30

Gln Arg Tyr
        35

<210> SEQ ID NO 369
<211> LENGTH: 33
<212> TYPE: PRT
<213> ORGANISM: Artificial Sequence
<220> FEATURE:
<223> OTHER INFORMATION: Description of Artificial Sequence: Synthetic
```

```
                                       peptide construct

<400> SEQUENCE: 369

Lys Pro Glu Ala Pro Gly Glu Asp Ala Ser Pro Glu Leu Asn Arg
1               5                   10                  15

Tyr Tyr Ala Ser Leu Arg His Tyr Leu Asn Leu Val Thr Arg Gln Arg
                20                  25                  30

Tyr

<210> SEQ ID NO 370
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 370

Pro Leu Glu Pro Val Tyr Pro Gly Asp Asn Ala Thr Pro Glu Gln Met
1               5                   10                  15

Ala Gln Tyr Ala Ala Asp Leu Arg Arg Tyr Ile Asn Met Leu Thr Arg
                20                  25                  30

Pro Arg Tyr
        35

<210> SEQ ID NO 371
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 371

Glu Pro Val Tyr Pro Gly Asp Asn Ala Thr Pro Glu Gln Met Ala Gln
1               5                   10                  15

Tyr Ala Ala Asp Leu Arg Arg Tyr Ile Asn Met Leu Thr Arg Pro Arg
                20                  25                  30

Tyr

<210> SEQ ID NO 372
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 372

Ala Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
                20                  25                  30

Arg Gln Arg Tyr
        35

<210> SEQ ID NO 373
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
```

<400> SEQUENCE: 373

Tyr Pro Ala Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 374
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 374

Tyr Pro Ser Ala Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 375
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 375

Tyr Pro Ser Lys Pro Ala Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 376
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 376

Tyr Pro Ser Lys Pro Asp Ala Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 377
<211> LENGTH: 36
<212> TYPE: PRT
<213> ORGANISM: Artificial Sequence
<220> FEATURE:
<223> OTHER INFORMATION: Description of Artificial Sequence: Synthetic -continued

```
      peptide construct

<400> SEQUENCE: 377

Tyr Pro Ser Lys Pro Lys Tyr Pro Gly Glu Asp Ala Pro Ala Glu Asp
1               5                   10                  15

Leu Ala Arg Tyr Tyr Ser Ala Leu Arg His Tyr Ile Asn Leu Ile Thr
            20                  25                  30

Arg Gln Arg Tyr
        35

<210> SEQ ID NO 378
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 378

Tyr Pro Ser Lys Pro Asp Asn Pro Ala Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 379
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 379

Tyr Pro Ser Lys Pro Asp Asn Pro Gly Ala Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 380
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 380

Tyr Pro Ser Lys Pro Asp Asn Pro Gly Glu Ala Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 381
<211> LENGTH: 36
<212> TYPE: PRT
<213> ORGANISM: Artificial Sequence
<220> FEATURE:
```

<223> OTHER INFORMATION: Description of Artificial Sequence: Synthetic
      peptide construct

<400> SEQUENCE: 381

Tyr Pro Ser Lys Pro Asp Asn Pro Gly Glu Asp Ala Ala Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 382
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 382

Tyr Pro Ser Lys Pro Asp Asn Pro Gly Glu Asp Ala Pro Gly Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 383
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 383

Tyr Pro Ser Lys Pro Asp Asn Pro Gly Glu Asp Ala Pro Ala Ala Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 384
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 384

Tyr Pro Ser Lys Pro Asp Asn Pro Gly Glu Asp Ala Pro Ala Glu Ala
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 385
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 385

Tyr Pro Ser Lys Pro Asp Asn Pro Gly Glu Asp Ala Pro Ala Glu Asp
1               5                   10                  15

Ala Ala Arg Tyr Tyr Ser Ala Leu Arg His Tyr Ile Asn Leu Ile Thr
            20                  25                  30

Arg Gln Arg Tyr
        35

<210> SEQ ID NO 386
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 386

Tyr Pro Ser Lys Pro Asp Asn Pro Gly Glu Asp Ala Pro Ala Glu Asp
1               5                   10                  15

Met Ala Ala Tyr Tyr Ser Ala Leu Arg His Tyr Ile Asn Leu Ile Thr
            20                  25                  30

Arg Gln Arg Tyr
        35

<210> SEQ ID NO 387
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 387

Tyr Pro Ser Lys Pro Asp Asn Pro Gly Glu Asp Ala Pro Ala Glu Asp
1               5                   10                  15

Met Ala Lys Tyr Tyr Ser Ala Leu Arg His Tyr Ile Asn Leu Ile Thr
            20                  25                  30

Arg Gln Arg Tyr
        35

<210> SEQ ID NO 388
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 388

Tyr Pro Ser Lys Pro Asp Asn Pro Gly Glu Asp Ala Pro Ala Glu Asp
1               5                   10                  15

Met Ala Arg Tyr Ala Ser Ala Leu Arg His Tyr Ile Asn Leu Ile Thr
            20                  25                  30

Arg Gln Arg Tyr
        35

<210> SEQ ID NO 389
<211> LENGTH: 36
<212> TYPE: PRT

<213> ORGANISM: Artificial Sequence
<220> FEATURE:
<223> OTHER INFORMATION: Description of Artificial Sequence: Synthetic peptide construct

<400> SEQUENCE: 389

Tyr Pro Ser Lys Pro Asp Asn Pro Gly Glu Asp Ala Pro Ala Glu Asp
1               5                   10                  15

Met Ala Arg Tyr Tyr Ala Ala Leu Arg His Tyr Ile Asn Leu Ile Thr
            20                  25                  30

Arg Gln Arg Tyr
        35

<210> SEQ ID NO 390
<211> LENGTH: 36
<212> TYPE: PRT
<213> ORGANISM: Artificial Sequence
<220> FEATURE:
<223> OTHER INFORMATION: Description of Artificial Sequence: Synthetic peptide construct

<400> SEQUENCE: 390

Tyr Pro Ser Lys Pro Asp Asn Pro Gly Glu Asp Ala Pro Ala Glu Asp
1               5                   10                  15

Met Ala Arg Tyr Tyr Ser Ala Leu Lys His Tyr Ile Asn Leu Ile Thr
            20                  25                  30

Arg Gln Arg Tyr
        35

<210> SEQ ID NO 391
<211> LENGTH: 36
<212> TYPE: PRT
<213> ORGANISM: Artificial Sequence
<220> FEATURE:
<223> OTHER INFORMATION: Description of Artificial Sequence: Synthetic peptide construct

<400> SEQUENCE: 391

Tyr Pro Ser Lys Pro Asp Asn Pro Gly Glu Asp Ala Pro Ala Glu Asp
1               5                   10                  15

Met Ala Arg Tyr Tyr Ser Ala Leu Arg Ala Tyr Ile Asn Leu Ile Thr
            20                  25                  30

Arg Gln Arg Tyr
        35

<210> SEQ ID NO 392
<211> LENGTH: 36
<212> TYPE: PRT
<213> ORGANISM: Artificial Sequence
<220> FEATURE:
<223> OTHER INFORMATION: Description of Artificial Sequence: Synthetic peptide construct

<400> SEQUENCE: 392

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Phe Ile Asn Leu Ile Thr
            20                  25                  30

Arg Gln Arg Tyr
        35

<210> SEQ ID NO 393
<211> LENGTH: 36

```
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 393

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ala Asn Leu Ile Thr
            20                  25                  30

Arg Gln Arg Tyr
        35

<210> SEQ ID NO 394
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 394

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Gln Leu Ile Thr
            20                  25                  30

Arg Gln Arg Tyr
        35

<210> SEQ ID NO 395
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 395

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Ala Ile Thr
            20                  25                  30

Arg Gln Arg Tyr
        35

<210> SEQ ID NO 396
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 396

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ala Thr
            20                  25                  30

Arg Gln Arg Tyr
        35

<210> SEQ ID NO 397
```

```
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 397

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
                20                  25                  30

Arg Gln Arg Phe
        35

<210> SEQ ID NO 398
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 398

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
                20                  25                  30

Arg Gln Arg His
        35

<210> SEQ ID NO 399
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 399

Leu Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
                20                  25                  30

Arg Tyr

<210> SEQ ID NO 400
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 400

Val Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
                20                  25                  30

Arg Tyr

<210> SEQ ID NO 401
<211> LENGTH: 36
```

```
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 401

Tyr Pro Ile Lys Pro Glu Ala Pro Gly Glu Asp Ala Pro Ala Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 402
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 402

Ala Pro Leu Glu Pro Val Tyr Tyr Pro Ser Lys Pro Lys Asn Pro Gly
1               5                   10                  15

Glu Asp Ala Pro Ala Glu Asp Leu Ala Arg Tyr Tyr Ser Ala Leu Arg
            20                  25                  30

His Tyr Ile Asn Leu Ile Thr Arg Gln Arg Tyr
        35                  40

<210> SEQ ID NO 403
<211> LENGTH: 53
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 403

Ala Pro Leu Glu Pro Val Tyr Pro Gly Asp Asn Ala Thr Pro Glu Gln
1               5                   10                  15

Met Tyr Pro Ser Lys Pro Lys Asn Pro Gly Glu Asp Ala Pro Ala Glu
            20                  25                  30

Asp Leu Ala Arg Tyr Tyr Ser Ala Leu Arg His Tyr Ile Asn Leu Ile
        35                  40                  45

Thr Arg Gln Arg Tyr
    50

<210> SEQ ID NO 404
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 404

Gln Tyr Ala Ala Asp Tyr Pro Ser Lys Pro Lys Asn Pro Gly Glu Asp
1               5                   10                  15

Ala Pro Ala Glu Asp Leu Ala Arg Tyr Tyr Ser Ala Leu Arg His Tyr
            20                  25                  30

Ile Asn Leu Ile Thr Arg Gln Arg Tyr
        35                  40
```

<210> SEQ ID NO 405
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 405

Ile Lys Pro Glu Ala Pro Gly Glu Asp Ala Ser Pro Glu Glu Leu Asn
1               5                   10                  15

Arg Tyr Tyr Ala Ser Leu Arg His Phe Leu Asn Leu Val Thr Arg Gln
            20                  25                  30

Arg Tyr

<210> SEQ ID NO 406
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 406

Ile Lys Pro Glu Ala Pro Gly Glu Asp Ala Ser Pro Glu Glu Leu Asn
1               5                   10                  15

Arg Tyr Tyr Ala Ser Leu Arg His Tyr Ile Asn Leu Val Thr Arg Gln
            20                  25                  30

Arg Tyr

<210> SEQ ID NO 407
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 407

Ile Lys Pro Glu Ala Pro Gly Glu Asp Ala Ser Pro Glu Glu Leu Asn
1               5                   10                  15

Arg Tyr Tyr Ala Ser Leu Arg His Tyr Val Asn Leu Val Thr Arg Gln
            20                  25                  30

Arg Tyr

<210> SEQ ID NO 408
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 408

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Gln Leu Val Thr Arg Gln
            20                  25                  30

Arg Tyr

<210> SEQ ID NO 409

```
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 409

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Val Val Thr Arg Gln
            20                  25                  30

Arg Tyr

<210> SEQ ID NO 410
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 410

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Ile Thr Arg Gln
            20                  25                  30

Arg Tyr

<210> SEQ ID NO 411
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 411

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Leu Thr Arg Gln
            20                  25                  30

Arg Tyr

<210> SEQ ID NO 412
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 412

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Phe

<210> SEQ ID NO 413
<211> LENGTH: 34
<212> TYPE: PRT
<213> ORGANISM: Artificial Sequence
```

<220> FEATURE:
<223> OTHER INFORMATION: Description of Artificial Sequence: Synthetic
      peptide construct

<400> SEQUENCE: 413

Ile Lys Pro Glu Ala Pro Gly Glu Asp Ala Ser Pro Glu Glu Leu Asn
1               5                   10                  15

Arg Tyr Tyr Ala Ser Leu Lys His Phe Leu Asn Leu Val Thr Arg Gln
            20                  25                  30

Arg Tyr

<210> SEQ ID NO 414
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 414

Ile Lys Pro Glu Ala Pro Gly Glu Asp Ala Ser Pro Glu Glu Leu Asn
1               5                   10                  15

Arg Tyr Tyr Ala Ser Leu Lys His Tyr Ile Asn Leu Val Thr Arg Gln
            20                  25                  30

Arg Tyr

<210> SEQ ID NO 415
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 415

Ile Lys Pro Glu Ala Pro Gly Glu Asp Ala Ser Pro Glu Glu Leu Asn
1               5                   10                  15

Arg Tyr Tyr Ala Ser Leu Lys His Tyr Val Asn Leu Val Thr Arg Gln
            20                  25                  30

Arg Tyr

<210> SEQ ID NO 416
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 416

Ile Lys Pro Glu Ala Pro Gly Glu Asp Ala Ser Pro Glu Glu Leu Asn
1               5                   10                  15

Arg Tyr Tyr Ala Ser Leu Lys His Tyr Leu Gln Leu Val Thr Arg Gln
            20                  25                  30

Arg Tyr

<210> SEQ ID NO 417
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 417

Ile Lys Pro Glu Ala Pro Gly Glu Asp Ala Ser Pro Glu Glu Leu Asn
1               5                   10                  15

Arg Tyr Tyr Ala Ser Leu Lys His Tyr Leu Asn Val Val Thr Arg Gln
            20                  25                  30

Arg Tyr

<210> SEQ ID NO 418
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 418

Ile Lys Pro Glu Ala Pro Gly Glu Asp Ala Ser Pro Glu Glu Leu Asn
1               5                   10                  15

Arg Tyr Tyr Ala Ser Leu Lys His Tyr Leu Asn Leu Ile Thr Arg Gln
            20                  25                  30

Arg Tyr

<210> SEQ ID NO 419
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 419

Ile Lys Pro Glu Ala Pro Gly Glu Asp Ala Ser Pro Glu Glu Leu Asn
1               5                   10                  15

Arg Tyr Tyr Ala Ser Leu Lys His Tyr Leu Asn Leu Leu Thr Arg Gln
            20                  25                  30

Arg Tyr

<210> SEQ ID NO 420
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 420

Ile Lys Pro Glu Ala Pro Gly Glu Asp Ala Ser Pro Glu Glu Leu Asn
1               5                   10                  15

Arg Tyr Tyr Ala Ser Leu Lys His Tyr Leu Asn Leu Val Thr Arg Gln
            20                  25                  30

Arg Phe

<210> SEQ ID NO 421
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 421

-continued

```
Ile Lys Pro Glu Ala Pro Gly Glu Asp Ala Ser Pro Glu Glu Leu Asn
1               5                   10                  15

Arg Tyr Tyr Ala Ser Leu Arg His Phe Ile Asn Leu Val Thr Arg Gln
            20                  25                  30

Arg Tyr

<210> SEQ ID NO 422
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 422

Ile Lys Pro Glu Ala Pro Gly Glu Asp Ala Ser Pro Glu Glu Leu Asn
1               5                   10                  15

Arg Tyr Tyr Ala Ser Leu Arg His Phe Val Asn Leu Val Thr Arg Gln
            20                  25                  30

Arg Tyr

<210> SEQ ID NO 423
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 423

Ile Lys Pro Glu Ala Pro Gly Glu Asp Ala Ser Pro Glu Glu Leu Asn
1               5                   10                  15

Arg Tyr Tyr Ala Ser Leu Arg His Phe Leu Gln Leu Val Thr Arg Gln
            20                  25                  30

Arg Tyr

<210> SEQ ID NO 424
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 424

Ile Lys Pro Glu Ala Pro Gly Glu Asp Ala Ser Pro Glu Glu Leu Asn
1               5                   10                  15

Arg Tyr Tyr Ala Ser Leu Arg His Phe Leu Asn Val Val Thr Arg Gln
            20                  25                  30

Arg Tyr

<210> SEQ ID NO 425
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 425

Ile Lys Pro Glu Ala Pro Gly Glu Asp Ala Ser Pro Glu Glu Leu Asn
1               5                   10                  15
```

-continued

Arg Tyr Tyr Ala Ser Leu Arg His Phe Leu Asn Leu Ile Thr Arg Gln
            20                  25                  30

Arg Tyr

<210> SEQ ID NO 426
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 426

Ile Lys Pro Glu Ala Pro Gly Glu Asp Ala Ser Pro Glu Glu Leu Asn
1               5                   10                  15

Arg Tyr Tyr Ala Ser Leu Arg His Phe Leu Asn Leu Leu Thr Arg Gln
            20                  25                  30

Arg Tyr

<210> SEQ ID NO 427
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 427

Ile Lys Pro Glu Ala Pro Gly Glu Asp Ala Ser Pro Glu Glu Leu Asn
1               5                   10                  15

Arg Tyr Tyr Ala Ser Leu Arg His Phe Leu Asn Leu Val Thr Arg Gln
            20                  25                  30

Arg Phe

<210> SEQ ID NO 428
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 428

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Gln Val Val Thr Arg Gln
            20                  25                  30

Arg Tyr

<210> SEQ ID NO 429
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 429

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Gln Leu Ile Thr Arg Gln
            20                  25                  30

Arg Tyr

<210> SEQ ID NO 430
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 430

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Gln Leu Leu Thr Arg Gln
            20                  25                  30

Arg Tyr

<210> SEQ ID NO 431
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 431

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Gln Leu Val Thr Arg Gln
            20                  25                  30

Arg Phe

<210> SEQ ID NO 432
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 432

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Val Ile Thr Arg Gln
            20                  25                  30

Arg Tyr

<210> SEQ ID NO 433
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 433

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Val Leu Thr Arg Gln
            20                  25                  30

Arg Tyr

<210> SEQ ID NO 434
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 434

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Val Val Thr Arg Gln
            20                  25                  30

Arg Phe

<210> SEQ ID NO 435
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 435

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Leu Thr Arg Gln
            20                  25                  30

Arg Phe

<210> SEQ ID NO 436
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 436

Pro Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 437
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Pro

<400> SEQUENCE: 437

Pro Lys Pro Glu His Pro Gly Glu Asp Ala Ser Ala Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 438
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 438

Pro Lys Pro Glu His Pro Gly Glu Asp Ala Ser Pro Glu Glu Leu Ala
 1               5                  10                  15

Arg Tyr Tyr Ala Ser Leu Arg Ala Tyr Ile Asn Leu Ile Thr Arg Gln
            20                  25                  30

Arg Tyr

<210> SEQ ID NO 439
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 439

Pro Lys Pro Glu His Pro Gly Glu Asp Ala Ser Ala Glu Glu Leu Ala
 1               5                  10                  15

Arg Tyr Tyr Ala Ser Leu Arg Ala Tyr Ile Asn Leu Ile Thr Arg Gln
            20                  25                  30

Arg Tyr

<210> SEQ ID NO 440
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 440

Pro Lys Pro Glu Ala Pro Gly Glu Asp Ala Ser Pro Glu Glu Leu Ala
 1               5                  10                  15

Lys Tyr Tyr Ala Ser Leu Arg Ala Tyr Ile Asn Leu Ile Thr Arg Gln
            20                  25                  30

Arg Tyr

<210> SEQ ID NO 441
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Pro

<400> SEQUENCE: 441

Pro Lys Pro Glu Ala Pro Gly Glu Asp Ala Ser Pro Glu Glu Leu Ala
 1               5                  10                  15

Lys Tyr Tyr Ala Ser Leu Arg Ala Tyr Ile Asn Leu Ile Thr Arg Gln
            20                  25                  30

Arg Tyr

<210> SEQ ID NO 442
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 442

Pro Lys Pro Glu His Pro Gly Glu Asp Ala Pro Ala Glu Glu Leu Ala
 1               5                  10                  15

Lys Tyr Tyr Ala Ser Leu Arg Ala Tyr Ile Asn Leu Ile Thr Arg Gln
             20                  25                  30

Arg Tyr

<210> SEQ ID NO 443
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 443

Ile Lys Pro Glu Ala Pro Gly Glu Asp Ala Ser Pro Glu Glu Leu Asn
 1               5                  10                  15

Arg Tyr Tyr Ala Ser Leu Arg His Tyr Leu Asn Leu Val Thr Arg Gln
             20                  25                  30

Lys Tyr

<210> SEQ ID NO 444
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isobutyloxycarbonyl-Pro

<400> SEQUENCE: 444

Pro Lys Pro Glu Ala Pro Gly Glu Asp Ala Ser Pro Glu Glu Leu Asn
 1               5                  10                  15

Arg Tyr Tyr Ala Ser Leu Arg His Tyr Leu Asn Leu Val Thr Arg Gln
             20                  25                  30

Arg Tyr

<210> SEQ ID NO 445
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Pro

<400> SEQUENCE: 445

Pro Lys Pro Glu His Pro Gly Glu Asp Ala Ser Pro Glu Glu Leu Asn
 1               5                  10                  15

Arg Tyr Tyr Ala Ser Leu Arg Ala Tyr Ile Asn Leu Val Thr Arg Gln
            20                  25                  30

Arg Tyr

<210> SEQ ID NO 446
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Pro

<400> SEQUENCE: 446

Pro Lys Pro Glu Ala Pro Gly Glu Asp Ala Ser Pro Glu Glu Ile Asn
 1               5                  10                  15

Arg Tyr Phe Ala Ser Leu Arg Ala Tyr Ile Asn Leu Val Thr Arg Gln
            20                  25                  30

Arg Tyr

<210> SEQ ID NO 447
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Pro

<400> SEQUENCE: 447

Pro Lys Pro Glu Ala Pro Gly Glu Asp Ala Ser Pro Glu Glu Leu Asn
 1               5                  10                  15

Arg Tyr Lys Ala Ser Leu Arg Ala Tyr Leu Asn Leu Val Thr Arg Gln
            20                  25                  30

Arg Tyr

<210> SEQ ID NO 448
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 448

Pro Lys Pro Glu Ala Pro Gly Glu Asp Ala Ser Pro Glu Glu Ile Asn
 1               5                  10                  15

Arg Tyr Phe Ala Ser Leu Arg Ala Tyr Ile Asn Leu Val Thr Arg Gln
            20                  25                  30

Arg Tyr

<210> SEQ ID NO 449
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 449

Pro Lys Pro Glu Ala Pro Gly Glu Asp Ala Ser Pro Glu Glu Leu Asn
 1               5                  10                  15
Arg Tyr Lys Ala Ser Leu Arg Ala Tyr Leu Asn Leu Val Thr Arg Gln
            20                  25                  30
Arg Tyr

<210> SEQ ID NO 450
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 450

Ile Lys Pro Glu Ala Pro Gly Glu Asp Ala Ser Pro Glu Glu Leu Asn
 1               5                  10                  15
Arg Tyr Tyr Ala Ser Leu Arg Ala Tyr Leu Asn Leu Val Thr Arg Gln
            20                  25                  30
Arg Trp

<210> SEQ ID NO 451
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (17)
<223> OTHER INFORMATION: (NMe)Ala

<400> SEQUENCE: 451

Pro Lys Pro Glu Ala Pro Gly Glu Asp Ala Ser Pro Glu Glu Leu Asn
 1               5                  10                  15
Ala Tyr Tyr Ala Ser Leu Arg His Tyr Leu Asn Leu Val Thr Arg Gln
            20                  25                  30
Arg Tyr

<210> SEQ ID NO 452
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Dansyl-Ile

<400> SEQUENCE: 452

Ile Lys Pro Glu Ala Pro Gly Glu Asp Ala Ser Pro Glu Glu Leu Asn
 1               5                  10                  15
Arg Tyr Tyr Ala Ser Leu Arg His Tyr Leu Asn Leu Val Thr Arg Gln
            20                  25                  30
Arg Tyr

<210> SEQ ID NO 453
<211> LENGTH: 35

```
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 453

Ile Lys Ala Pro Glu Ala Pro Gly Glu Asp Ala Ser Pro Glu Glu Leu
1               5                   10                  15

Asn Arg Tyr Tyr Ala Ser Leu Arg His Tyr Leu Asn Leu Val Thr Arg
            20                  25                  30

Gln Arg Tyr
        35

<210> SEQ ID NO 454
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Pro

<400> SEQUENCE: 454

Pro Lys Pro Glu Ala Pro Gly Glu Asp Ala Ser Pro Glu Asp Leu Ala
1               5                   10                  15

Arg Tyr Lys Ala Ser Leu Arg Ala Tyr Ile Asn Leu Ile Thr Arg Gln
            20                  25                  30

Arg Tyr

<210> SEQ ID NO 455
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Octanoyl-Pro

<400> SEQUENCE: 455

Pro Lys Pro Glu Ala Pro Gly Glu Asp Ala Ser Pro Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 456
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isobutyloxycarbonyl-Pro

<400> SEQUENCE: 456

Pro Lys Pro Glu Ala Pro Gly Glu Asp Ala Ser Pro Glu Glu Leu Ala
```

-continued

```
                1               5                  10                 15
Arg Tyr Tyr Ala Ser Leu Arg Ala Tyr Ile Asn Leu Ile Thr Arg Gln
            20                  25                 30

Arg Tyr

<210> SEQ ID NO 457
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Octyl-Gly

<400> SEQUENCE: 457

Gly Pro Lys Pro Glu Ala Pro Gly Glu Asp Ala Ser Pro Glu Glu Leu
 1               5                  10                 15

Ala Arg Tyr Tyr Ala Ser Leu Arg Ala Tyr Ile Asn Leu Ile Thr Arg
            20                  25                 30

Gln Arg Tyr
        35

<210> SEQ ID NO 458
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Pro

<400> SEQUENCE: 458

Pro Lys Pro Glu Ala Pro Gly Glu Asp Ala Ser Pro Glu Glu Leu Ala
 1               5                  10                 15

Arg Tyr Tyr Ala Ser Leu Arg Ala Tyr Ile Asn Leu Ile Thr Arg Gln
            20                  25                 30

Arg Phe

<210> SEQ ID NO 459
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Pro

<400> SEQUENCE: 459

Pro Lys Pro Glu Ala Pro Gly Glu Asp Ala Ser Pro Glu Glu Leu Ala
 1               5                  10                 15

Arg Tyr Tyr Ala Ser Leu Arg Ala Tyr Ile Asn Leu Ile Thr Arg Gln
            20                  25                 30

Arg Trp

<210> SEQ ID NO 460
```

<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 460

Pro Lys Pro Glu Ala Pro Gly Glu Asp Ala Ser Ala Glu Glu Leu Ala
 1               5                  10                  15

Arg Tyr Tyr Ala Ser Leu Arg Ala Tyr Ile Asn Leu Ile Thr Arg Gln
            20                  25                  30

Arg Tyr

<210> SEQ ID NO 461
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Pro

<400> SEQUENCE: 461

Pro Lys Pro Glu Ala Pro Gly Glu Asp Ala Ser Ala Glu Glu Leu Ala
 1               5                  10                  15

Arg Tyr Tyr Ala Ser Leu Arg Ala Tyr Ile Asn Leu Ile Thr Arg Gln
            20                  25                  30

Arg Tyr

<210> SEQ ID NO 462
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Pro

<400> SEQUENCE: 462

Pro Lys Pro Glu His Pro Gly Glu Asp Ala Ser Pro Glu Glu Leu Ala
 1               5                  10                  15

Arg Tyr Tyr Ala Ser Leu Arg Ala Tyr Ile Asn Leu Ile Thr Arg Gln
            20                  25                  30

Arg Tyr

<210> SEQ ID NO 463
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Pro

<400> SEQUENCE: 463

Pro Ser Pro Glu Ala Pro Gly Glu Asp Ala Ser Pro Glu Glu Leu Ala

```
             1               5              10              15

Arg Tyr Tyr Ala Ser Leu Arg Ala Tyr Ile Asn Leu Ile Thr Arg Gln
            20              25              30

Arg Tyr

<210> SEQ ID NO 464
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Pro

<400> SEQUENCE: 464

Pro Lys Pro Glu Gly Pro Ala Glu Asp Ala Ser Pro Glu Glu Leu Ala
  1               5              10              15

Arg Tyr Tyr Ala Ser Leu Arg Ala Tyr Ile Asn Leu Ile Thr Arg Gln
            20              25              30

Arg Tyr

<210> SEQ ID NO 465
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 465

Pro Lys Pro Glu Ala Pro Gly Glu Asp Pro Ser Pro Glu Glu Leu Ala
  1               5              10              15

Arg Tyr Tyr Ala Ser Leu Arg Ala Tyr Ile Asn Leu Ile Thr Arg Gln
            20              25              30

Arg Tyr

<210> SEQ ID NO 466
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Pro

<400> SEQUENCE: 466

Pro Lys Pro Glu Ala Pro Gly Glu Asp Pro Ser Pro Glu Glu Leu Ala
  1               5              10              15

Arg Tyr Tyr Ala Ser Leu Arg Ala Tyr Ile Asn Leu Ile Thr Arg Gln
            20              25              30

Arg Tyr

<210> SEQ ID NO 467
<211> LENGTH: 34
<212> TYPE: PRT
<213> ORGANISM: Artificial Sequence
<220> FEATURE:
<223> OTHER INFORMATION: Description of Artificial Sequence: Synthetic
``` peptide construct

<400> SEQUENCE: 467

Val Lys Pro Glu Ala Pro Gly Glu Asp Ala Ser Pro Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 468
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Val

<400> SEQUENCE: 468

Val Lys Pro Glu Ala Pro Gly Glu Asp Ala Ser Pro Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 469
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Pro

<400> SEQUENCE: 469

Pro Lys Pro Glu His Pro Gly Glu Asp Ala Pro Ala Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 470
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Pro

<400> SEQUENCE: 470

Pro Lys Pro Glu His Pro Gly Glu Asp Ala Pro Ala Glu Glu Leu Ala
1               5                   10                  15

Lys Tyr Tyr Ala Ser Leu Arg Ala Tyr Ile Asn Leu Ile Thr Arg Gln
            20                  25                  30

Arg Tyr

<210> SEQ ID NO 471
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 471

Pro Lys Pro Glu His Pro Gly Glu Asp Ala Pro Ser Glu Glu Leu Ala
 1               5                  10                  15

Lys Tyr Tyr Ala Ser Leu Arg Ala Tyr Ile Asn Leu Ile Thr Arg Gln
            20                  25                  30

Arg Tyr

<210> SEQ ID NO 472
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Pro

<400> SEQUENCE: 472

Pro Lys Pro Glu His Pro Gly Glu Asp Ala Pro Ser Glu Glu Leu Ala
 1               5                  10                  15

Lys Tyr Tyr Ala Ser Leu Arg Ala Tyr Ile Asn Leu Ile Thr Arg Gln
            20                  25                  30

Arg Tyr

<210> SEQ ID NO 473
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Ile

<400> SEQUENCE: 473

Ile Lys Pro Glu Ala Pro Gly Glu Asp Ala Pro Ala Glu Glu Leu Ala
 1               5                  10                  15

Arg Tyr Tyr Ala Ser Leu Arg Ala Tyr Ile Asn Leu Ile Thr Arg Gln
            20                  25                  30

Arg Tyr

<210> SEQ ID NO 474
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: 8-amino octanoyl-Ile -continued

<400> SEQUENCE: 474

Ile Lys Pro Glu Ala Pro Gly Glu Asp Ala Pro Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 475
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: N-term BH modified

<400> SEQUENCE: 475

Tyr Pro Ile Lys Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 476
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: N-term BH modified

<400> SEQUENCE: 476

Tyr Pro Ile Ala Pro Glu Ala Pro Gly Glu Asp Ala Ser Pro Glu Glu
1               5                   10                  15

Leu Ala Gln Tyr Ala Ala Asp Leu Arg Arg Tyr Ile Asn Met Leu Thr
            20                  25                  30

Arg Gln Arg Tyr
        35

<210> SEQ ID NO 477
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: N-term BH modified

<400> SEQUENCE: 477

Ile Ala Pro Glu Ala Pro Gly Glu Asp Ala Ser Pro Glu Glu Leu Ala
1               5                   10                  15

Gln Tyr Ala Ala Asp Leu Arg Arg Tyr Ile Asn Met Leu Thr Arg Gln
            20                  25                  30

Arg Tyr

<210> SEQ ID NO 478
<211> LENGTH: 34

```
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Isocaproyl-Ile
<220> FEATURE:
<221> NAME/KEY: MOD_RES
<222> LOCATION: (2)
<223> OTHER INFORMATION: BH modified Lys

<400> SEQUENCE: 478

Ile Lys Pro Glu Ala Pro Gly Glu Asp Ala Ser Pro Glu Glu Leu Ala
 1               5                  10                  15

Gln Tyr Ala Ala Asp Leu Arg Arg Tyr Ile Asn Met Leu Thr Arg Gln
            20                  25                  30

Arg Tyr

<210> SEQ ID NO 479
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: N-term BH modified

<400> SEQUENCE: 479

Pro Lys Pro Glu Ala Pro Gly Glu Asp Ala Ser Pro Glu Glu Leu Ala
 1               5                  10                  15

Arg Tyr Tyr Ala Ser Leu Arg Ala Tyr Ile Asn Leu Ile Thr Arg Gln
            20                  25                  30

Arg Tyr

<210> SEQ ID NO 480
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<223> OTHER INFORMATION: N-term BH modified

<400> SEQUENCE: 480

Pro Ala Pro Glu Ala Pro Gly Glu Asp Ala Ser Pro Glu Glu Leu Ala
 1               5                  10                  15

Arg Tyr Tyr Ala Ser Leu Arg Ala Tyr Ile Asn Leu Ile Thr Arg Gln
            20                  25                  30

Arg Tyr

<210> SEQ ID NO 481
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Tyr, or absent
<220> FEATURE:
```

-continued

```
<221> NAME/KEY: MOD_RES
<222> LOCATION: (2)
<223> OTHER INFORMATION: Ile, Pro, or absent
<220> FEATURE:
<221> NAME/KEY: MOD_RES
<222> LOCATION: (3)
<223> OTHER INFORMATION: Ile, Lys, Val, or Pro
<220> FEATURE:
<221> NAME/KEY: MOD_RES
<222> LOCATION: (4)
<223> OTHER INFORMATION: Lys, Ala, Ser, or Arg
<220> FEATURE:
<221> NAME/KEY: MOD_RES
<222> LOCATION: (7)
<223> OTHER INFORMATION: Ala, Gly, or His
<220> FEATURE:
<221> NAME/KEY: MOD_RES
<222> LOCATION: (9)
<223> OTHER INFORMATION: Gly, or Ala
<220> FEATURE:
<221> NAME/KEY: MOD_RES
<222> LOCATION: (12)
<223> OTHER INFORMATION: Ala, or Pro
<220> FEATURE:
<221> NAME/KEY: MOD_RES
<222> LOCATION: (13)
<223> OTHER INFORMATION: Ser, or Pro
<220> FEATURE:
<221> NAME/KEY: MOD_RES
<222> LOCATION: (14)
<223> OTHER INFORMATION: Pro, Ala or Ser
<220> FEATURE:
<221> NAME/KEY: MOD_RES
<222> LOCATION: (16)
<223> OTHER INFORMATION: Glu, or Asp
<220> FEATURE:
<221> NAME/KEY: MOD_RES
<222> LOCATION: (17)
<223> OTHER INFORMATION: Leu or Ile
<220> FEATURE:
<221> NAME/KEY: MOD_RES
<222> LOCATION: (18)
<223> OTHER INFORMATION: Asn, or Ala
<220> FEATURE:
<221> NAME/KEY: MOD_RES
<222> LOCATION: (19)
<223> OTHER INFORMATION: Arg, Lys, Gln, or N(Me)Ala
<220> FEATURE:
<221> NAME/KEY: MOD_RES
<222> LOCATION: (21)
<223> OTHER INFORMATION: Tyr, Ala, Phe, or Lys
<220> FEATURE:
<221> NAME/KEY: MOD_RES
<222> LOCATION: (22)
<223> OTHER INFORMATION: Ala, or Ser
<220> FEATURE:
<221> NAME/KEY: MOD_RES
<222> LOCATION: (23)
<223> OTHER INFORMATION: Ser, Ala, or Asp
<220> FEATURE:
<221> NAME/KEY: MOD_RES
<222> LOCATION: (25)
<223> OTHER INFORMATION: Arg, or Lys
<220> FEATURE:
<221> NAME/KEY: MOD_RES
<222> LOCATION: (26)
<223> OTHER INFORMATION: His, Ala, or Arg
<220> FEATURE:
<221> NAME/KEY: MOD_RES
<222> LOCATION: (28)
<223> OTHER INFORMATION: Leu, or Ile
<220> FEATURE:
<221> NAME/KEY: MOD_RES
<222> LOCATION: (30)
<223> OTHER INFORMATION: Leu, or Met
<220> FEATURE:
<221> NAME/KEY: MOD_RES
<222> LOCATION: (31)
<223> OTHER INFORMATION: Val, Ile, or Leu
```

```
<220> FEATURE:
<221> NAME/KEY: MOD_RES
<222> LOCATION: (35)
<223> OTHER INFORMATION: Lys, or Arg
<220> FEATURE:
<221> NAME/KEY: MOD_RES
<222> LOCATION: (36)
<223> OTHER INFORMATION: Tyr, Trp, or Phe

<400> SEQUENCE: 481

Xaa Xaa Xaa Xaa Pro Glu Xaa Pro Xaa Glu Asp Xaa Xaa Xaa Glu Xaa
1               5                   10                  15

Xaa Xaa Xaa Tyr Xaa Xaa Xaa Leu Xaa Xaa Tyr Xaa Asn Xaa Xaa Thr
            20                  25                  30

Arg Gln Xaa Xaa

<210> SEQ ID NO 482
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Tyr, or absent
<220> FEATURE:
<221> NAME/KEY: MOD_RES
<222> LOCATION: (2)
<223> OTHER INFORMATION: Ile, Pro, or absent
<220> FEATURE:
<221> NAME/KEY: MOD_RES
<222> LOCATION: (4)
<223> OTHER INFORMATION: Lys, Ala, Ser, or Arg
<220> FEATURE:
<221> NAME/KEY: MOD_RES
<222> LOCATION: (6)
<223> OTHER INFORMATION: Glu, Gln, Ala, Asn, Asp, or Val
<220> FEATURE:
<221> NAME/KEY: MOD_RES
<222> LOCATION: (9)
<223> OTHER INFORMATION: Gly, or Ala
<220> FEATURE:
<221> NAME/KEY: MOD_RES
<222> LOCATION: (10)
<223> OTHER INFORMATION: Glu, Ala, Asp, Asn, Gln, Gly, Pro, or Aib
<220> FEATURE:
<221> NAME/KEY: MOD_RES
<222> LOCATION: (11)
<223> OTHER INFORMATION: Glu, Ala, Asp, Asn, Gln, Gly, Pro, or Aib
<220> FEATURE:
<221> NAME/KEY: MOD_RES
<222> LOCATION: (12)
<223> OTHER INFORMATION: Ala, or Pro
<220> FEATURE:
<221> NAME/KEY: MOD_RES
<222> LOCATION: (13)
<223> OTHER INFORMATION: Ser, or Pro
<220> FEATURE:
<221> NAME/KEY: MOD_RES
<222> LOCATION: (14)
<223> OTHER INFORMATION: Pro, Ala or Ser
<220> FEATURE:
<221> NAME/KEY: MOD_RES
<222> LOCATION: (15)
<223> OTHER INFORMATION: Glu, Ala, Asp, Asn, Gln, Gly, Pro, or Aib
<220> FEATURE:
<221> NAME/KEY: MOD_RES
<222> LOCATION: (16)
```

```
<223> OTHER INFORMATION: Glu, or Asp
<220> FEATURE:
<221> NAME/KEY: MOD_RES
<222> LOCATION: (17)
<223> OTHER INFORMATION: Leu or Ile
<220> FEATURE:
<221> NAME/KEY: MOD_RES
<222> LOCATION: (19)
<223> OTHER INFORMATION: Arg, Lys, Gln, or N(Me)Ala
<220> FEATURE:
<221> NAME/KEY: MOD_RES
<222> LOCATION: (21)
<223> OTHER INFORMATION: Tyr, Ala, Phe, or Lys
<220> FEATURE:
<221> NAME/KEY: MOD_RES
<222> LOCATION: (22)
<223> OTHER INFORMATION: Ala, or Ser
<220> FEATURE:
<221> NAME/KEY: MOD_RES
<222> LOCATION: (23)
<223> OTHER INFORMATION: Ser, Ala, or Asp
<220> FEATURE:
<221> NAME/KEY: MOD_RES
<222> LOCATION: (25)
<223> OTHER INFORMATION: Arg, or Lys
<220> FEATURE:
<221> NAME/KEY: MOD_RES
<222> LOCATION: (26)
<223> OTHER INFORMATION: His, Ala, or Arg
<220> FEATURE:
<221> NAME/KEY: MOD_RES
<222> LOCATION: (27)
<223> OTHER INFORMATION: Tyr, or Phe
<220> FEATURE:
<221> NAME/KEY: MOD_RES
<222> LOCATION: (28)
<223> OTHER INFORMATION: Leu, or Ile
<220> FEATURE:
<221> NAME/KEY: MOD_RES
<222> LOCATION: (29)
<223> OTHER INFORMATION: Asn, or Gln
<220> FEATURE:
<221> NAME/KEY: MOD_RES
<222> LOCATION: (30)
<223> OTHER INFORMATION: Leu, or Met
<220> FEATURE:
<221> NAME/KEY: MOD_RES
<222> LOCATION: (31)
<223> OTHER INFORMATION: Val, Ile, or Leu

<400> SEQUENCE: 482

Xaa Xaa Pro Xaa Pro Xaa His Pro Xaa Xaa Xaa Xaa Xaa Xaa Xaa
1               5                   10                  15

Xaa Ala Xaa Tyr Xaa Xaa Xaa Leu Xaa Xaa Xaa Xaa Xaa Xaa Thr
            20                  25                  30

Arg Gln Arg Tyr
```